(12) United States Patent
Schurenberg et al.

(10) Patent No.: US 7,725,331 B2
(45) Date of Patent: May 25, 2010

(54) SYSTEM AND METHOD FOR IMPLEMENTING A GLOBAL MASTER PATIENT INDEX

(75) Inventors: Kurt B. Schurenberg, Roswell, GA (US); Robert C. Yeager, Atlanta, GA (US); Robin D. Johnson, Roswell, GA (US)

(73) Assignee: WebMD Corporation, Atlanta, GA (US)

( * ) Notice: Subject to any disclaimer, the term of this patent is extended or adjusted under 35 U.S.C. 154(b) by 1672 days.

(21) Appl. No.: 10/749,746

(22) Filed: Dec. 31, 2003

(65) Prior Publication Data

US 2005/0004895 A1 Jan. 6, 2005

Related U.S. Application Data

(63) Continuation of application No. 09/734,336, filed on Nov. 30, 2000, now abandoned.

(60) Provisional application No. 60/167,532, filed on Dec. 1, 1999.

(51) Int. Cl.
*G06Q 40/00* (2006.01)
(52) U.S. Cl. .............................. 705/3; 705/2
(58) Field of Classification Search .................. 705/2, 705/3
See application file for complete search history.

(56) References Cited

U.S. PATENT DOCUMENTS

| | | | |
|---|---|---|---|
| 4,315,309 A | 2/1982 | Coli .............................. 705/3 |
| 4,812,994 A | 3/1989 | Taylor et al. ................. 705/410 |
| 4,858,121 A | 8/1989 | Barber et al. .................... 705/2 |
| 4,868,376 A | 9/1989 | Lessin et al. ................. 235/492 |
| 4,882,474 A | 11/1989 | Anderl et al. ............... 235/380 |
| 4,916,611 A | 4/1990 | Doyle, Jr. et al. ............... 705/2 |
| 4,949,251 A | 8/1990 | Griffen et al. .................. 714/20 |
| 4,960,982 A | 10/1990 | Takahira ..................... 235/382 |
| 4,984,272 A | 1/1991 | McIlroy et al. ............... 713/202 |
| 5,150,409 A | 9/1992 | Elsner ......................... 713/177 |
| 5,241,671 A | 8/1993 | Reed et al. ................ 707/104.1 |
| 5,251,152 A | 10/1993 | Notess ....................... 709/224 |
| 5,301,105 A | 4/1994 | Cummings, Jr. ................ 705/2 |
| 5,301,246 A | 4/1994 | Archibald et al. ....... 379/142.06 |
| 5,325,294 A | 6/1994 | Keene ........................... 705/3 |
| 5,327,341 A | 7/1994 | Whalen et al. .................. 705/3 |
| 5,430,875 A | 7/1995 | Ma ............................. 719/318 |
| 5,465,082 A | 11/1995 | Chaco ..................... 340/825.49 |
| 5,491,800 A | 2/1996 | Goldsmith et al. ........... 709/221 |
| 5,550,971 A | 8/1996 | Brunner et al. .............. 395/161 |

(Continued)

*Primary Examiner*—Hani Kazimi
(74) *Attorney, Agent, or Firm*—Wilmer Cutler Pickering Hale and Dorr LLP

(57) ABSTRACT

Separate computer systems may participate in a Health Data Network (HDN) such that the computer systems are linked so as to share various types of healthcare-related information. The shared information may include patient record information. The integration of the patient record information is accomplished by maintaining a Global Master Patient Index (GMPI). Such a GMPI may integrate patient record information used by multiple healthcare organizations, facilities, or businesses. Such a GMPI may also integrate patient record information for a single business having multiple sites or computer systems, e.g., a large hospital. The GMPI preferably provides for performing functions such as locating patient records, locating duplicate records for a selected patient, printing a selected patient record with all its duplicate patient records, reconciling potential duplicate patient records found while searching and retrieving a patient's record final reconciliation (certification) of suspected duplicate patients records, maintaining a persistent relationship between patient records in the GMPI, and maintaining a reconciliation audit trail.

9 Claims, 107 Drawing Sheets

U.S. PATENT DOCUMENTS

| | | | |
|---|---|---|---|
| 5,559,885 A | 9/1996 | Drexler et al. | 235/380 |
| 5,559,888 A | 9/1996 | Jain et al. | 380/25 |
| 5,560,008 A | 9/1996 | Johnson et al. | 713/201 |
| 5,572,422 A | 11/1996 | Nematbakhsh et al. | 705/3 |
| 5,588,148 A | 12/1996 | Landis et al. | 707/1 |
| 5,629,981 A | 5/1997 | Nerlikar | 713/168 |
| 5,664,109 A | 9/1997 | Johnson et al. | 705/2 |
| 5,664,207 A | 9/1997 | Crumpler et al. | 715/505 |
| 5,772,585 A | 6/1998 | Lavin et al. | 600/300 |
| 5,790,785 A | 8/1998 | Klug et al. | 713/202 |
| 5,809,476 A | 9/1998 | Ryan | 705/2 |
| 5,815,665 A | 9/1998 | Teper et al. | 709/229 |
| 5,827,180 A | 10/1998 | Goodman | 600/300 |
| 5,832,488 A | 11/1998 | Eberhardt | 707/10 |
| 5,841,970 A | 11/1998 | Tabuki | 713/201 |
| 5,845,255 A | 12/1998 | Mayaud | 705/3 |
| 5,848,397 A | 12/1998 | Marsh et al. | 705/14 |
| 5,857,190 A | 1/1999 | Brown | 707/10 |
| 5,862,327 A | 1/1999 | Kwang et al. | 709/203 |
| 5,867,821 A | 2/1999 | Ballantyne et al. | 705/2 |
| 5,903,889 A | 5/1999 | De la Huerga et al. | 707/3 |
| 5,905,884 A | 5/1999 | Williams | 709/227 |
| 5,915,240 A | 6/1999 | Karpf | 705/2 |
| 5,953,704 A | 9/1999 | McIlroy et al. | 705/2 |
| 5,960,403 A | 9/1999 | Brown | 705/2 |
| 5,966,715 A | 10/1999 | Sweeney et al. | 707/203 |
| 5,967,789 A | 10/1999 | Segel et al. | 434/236 |
| 5,974,412 A | 10/1999 | Hazlehurst et al. | 707/3 |
| 5,978,842 A | 11/1999 | Noble et al. | 709/218 |
| 6,006,269 A | 12/1999 | Phaal | 709/227 |
| 6,018,619 A | 1/2000 | Allard et al. | 709/224 |
| 6,031,818 A | 2/2000 | Lo et al. | 370/216 |
| 6,070,160 A | 5/2000 | Geary | 707/4 |
| 6,073,106 A | 6/2000 | Rosen et al. | 705/3 |
| 6,073,163 A | 6/2000 | Clark et al. | 709/203 |
| 6,092,196 A | 7/2000 | Reiche | 713/200 |
| 6,112,183 A | 8/2000 | Swanson et al. | 705/2 |
| 6,141,759 A | 10/2000 | Braddy | 713/201 |
| 6,167,523 A | 12/2000 | Strong | 713/201 |
| 6,178,416 B1 | 1/2001 | Thompson et al. | 707/3 |
| 6,189,036 B1 | 2/2001 | Kao | 709/229 |
| 6,253,228 B1 | 6/2001 | Ferris et al. | 709/203 |
| 6,263,330 B1 | 7/2001 | Bessette | 707/4 |
| 6,292,796 B1 | 9/2001 | Drucker et al. | 707/4 |
| 6,334,778 B1 | 1/2002 | Brown | 273/429 |
| 6,347,374 B1 | 2/2002 | Drake et al. | 713/200 |
| 6,362,836 B1 | 3/2002 | Shaw et al. | 345/744 |
| 6,385,611 B1 | 5/2002 | Cardona | 707/6 |
| 6,401,072 B1 | 6/2002 | Haudenschild et al. | 705/3 |
| 6,449,598 B1 | 9/2002 | Green et al. | 705/2 |
| 6,532,459 B1 | 3/2003 | Berson | |
| 6,826,696 B1 | 11/2004 | Chawla et al. | 713/201 |

| First/Middle Name | Last Name/Suffix | Unconfirmed Link | Indirect Link | Confirmed Link | Confirmed Unlink | Certified Link |
|---|---|---|---|---|---|---|
| Thomas A | Folex | 0 | 0 | 1 | 0 | |
| T A | Foley | 0 | 0 | 1 | 0 | |
| Thomas A | Foley | 0 | 0 | 3 | 0 | |
| Tom A | Foley | 0 | 0 | 1 | 0 | |

SYSTEM AND METHOD FOR IMPLEMENTING A GLOBAL MASTER PATIENT INDEX

PRIORITY CLAIM

This application is a continuation of U.S. patent application Ser. No. 09/734,336 filed Nov. 30, 2000 now abandoned, entitled SYSTEM AND METHOD FOR IMPLEMENTING A GLOBAL MASTER PATIENT INDEX, which is hereby incorporated herein by reference in its entirety for each of its teachings and embodiments, and which claims the benefit of U.S. provisional application Ser. No. 60/167,532, filed Dec. 1, 1999, entitled "System and Method Enabling a Distributed Object-to-Relational Application Framework".

FIELD OF THE INVENTION

The present invention relates to the field of healthcare information systems, and more particularly to a system and method for implementing a Global Master Patient Index (GMPI) for managing patient records used by multiple healthcare businesses, sites, or facilities.

DESCRIPTION OF THE RELATED ART

The healthcare industry has historically suffered from information flow and workflow fragmentation. In the past, information was typically exchanged among various parties involved in healthcare, such as physicians, hospitals, insurers, laboratories, employers, and others, using paper-based methods. As is well known in the art, such methods are inherently labor-intensive, inefficient, and error prone. Thus, efforts have been undertaken to improve the healthcare industry through the use of electronic information networks integrating healthcare participants.

There are many difficulties to overcome in implementing such an electronic information network, also referred to herein as a Health Data Network (HDN). One primary difficulty involved is how to integrate and ensure the integrity of data maintained and used by the various healthcare parties. In particular, the integration of patient records that are created and used by the parties has historically been a difficult and important problem.

Duplicate patient records create problems for hospitals, physician practices, and other parties involved in healthcare. Failure to find preexisting records creates duplicate files for the same individual. Duplicate records splinter clinical information and hinder access. Impaired access to complete patient information hinders a clinician's ability to quickly and accurately treat a patient. Duplicate records impact billing processes and decision support for administration.

Causes of incorrect and improper patient entries vary. For example, policies and procedures may be inadequate to support thorough research of patient identities. Lack of training, lack of staff, poor motivation and skill sets all may degrade the quality of data entry and lookup. Variability of patient name spelling, use of nicknames, marriage, divorce, adoption, prefixes, and abbreviations of names all contribute to the problem. Human error is a common factor. Also, a patient's mental status at the time of presentation may preclude obtaining accurate information. All of these factors may impact either the quality of search or the quality of the database.

In the healthcare industry, the index of patients past and current is commonly known by several names, including:
Master Patient Index (MPI)
Master Person Index (MPI)
Master Customer Index (MCI)
Enterprise Master Patient/Person Index, (EMPI)
Global Master Patient/Person Index (GMPI)

The first three names commonly imply one host system. Complex health systems employ the usage of the terms "enterprise" or "global". The term Global Master Patient Index or GMPI is used herein to refer to an index used by multiple sites, facilities, businesses, or other organizations.

Health Data Networks (HDNs) exacerbate the problem of duplicate record creation through consolidation of databases. The HDN environment may link hospital facilities, physician practices, laboratories, health plans, and other organizations together in the provision of patient care. Multiple registration locations, varied data entry processes, and disparate collection systems characterize this network environment. Many categories of personnel may use the GMPI information, including physicians, nurses, health information management staff, registration/admitting office staff, and administrative support staff, among others.

A GMPI helps to streamline vital clinical and payer information. For example, uses of the GMPI may include:
Patient Registration
Claims Payment
Release of Information (Subpoenas, school immunization verification, etc.)
Administrative Review Processes (Peer review, Risk Management, Infection Control, Utilization Management)
Loose Report Processing
Physician Referrals
Routing visitors, flowers, patient mail Thus, it would be desirable to provide a system and method for implementing and successfully maintaining the integrity of a Global Master Patient Index for a Health Data Network.

SUMMARY OF THE INVENTION

According to one embodiment of the invention, separate computer systems may participate in a Health Data Network (HDN). That is, the computer systems may be linked so as to share various types of healthcare-related information. The shared information may include patient record information. The integration of the patient record information is accomplished by maintaining a Global Master Patient Index (GMPI), such as described herein. Such a GMPI may integrate patient record information used by multiple healthcare organizations, facilities, or businesses. Such a GMPI may also integrate patient record information for a single business having multiple sites or computer systems, e.g., a large hospital.

The GMPI preferably provides for performing functions such as locating patient records, locating duplicate records for a selected patient, printing a selected patient record with all its duplicate patient records, reconciling potential duplicate patient records found while searching and retrieving a patient's record final reconciliation (certification) of suspected duplicate patients records, maintaining a persistent relationship between patient records in the GMPI, and maintaining a reconciliation audit trail.

As an example of one function of the GMPI, suppose that a patient visits Physician's Office A for the first time, and this patient has previously visited Physician's Office B, wherein Physician's Office A (Office A) and Physician's Office B (Office B) are both participants (referred to as HDN businesses) in a Health Data Network linked by a GMPI. Thus, the patient may have a patient record that was previously created by a person at Office B, which may be stored on a computer system at Office B or on a server computer to which computers of Office A and Office B are linked. Upon registration at Office A, a clerk may perform a search for previously existing records for the patient, e.g., using a local computer at Office A. As described below, the Office A computer is preferably enabled to retrieve the existing record for the patient that was created by the person at Office B, e.g., either by interfacing directly with the Office B computer or with the server computer described above.

In one embodiment, the computer systems associated with the various HDN Businesses may interface with a middleware server that facilitates the retrieval and update of patient records. For example, in the patient registration situation referred to above, in response to the clerk's request to lookup a record for the patient, an application running on a computer system at Physician's Office A may request the middleware server to retrieve any existing records for the patient, e.g., by specifying one or more identifiers associated with the patient, such as the patient's name, SSN, etc.

The middleware server may then retrieve the record, e.g., from a database associated with Physician's Office B or from another database. In various embodiments, the middleware server may retrieve the patient record in any of various ways. For example, in one embodiment the middleware server may be operable to maintain or interface with an index cross-referencing patient identifier information with the location of corresponding patient records, i.e., the databases or sites at which the records may be found. In another embodiment, the middleware server may query the various sites of the Health Data Network to locate records for the specified patient.

BRIEF DESCRIPTION OF THE DRAWINGS

A better understanding of the present invention can be obtained when the following detailed description of the preferred embodiment is considered in conjunction with the following drawings, in which.

Figure 1:
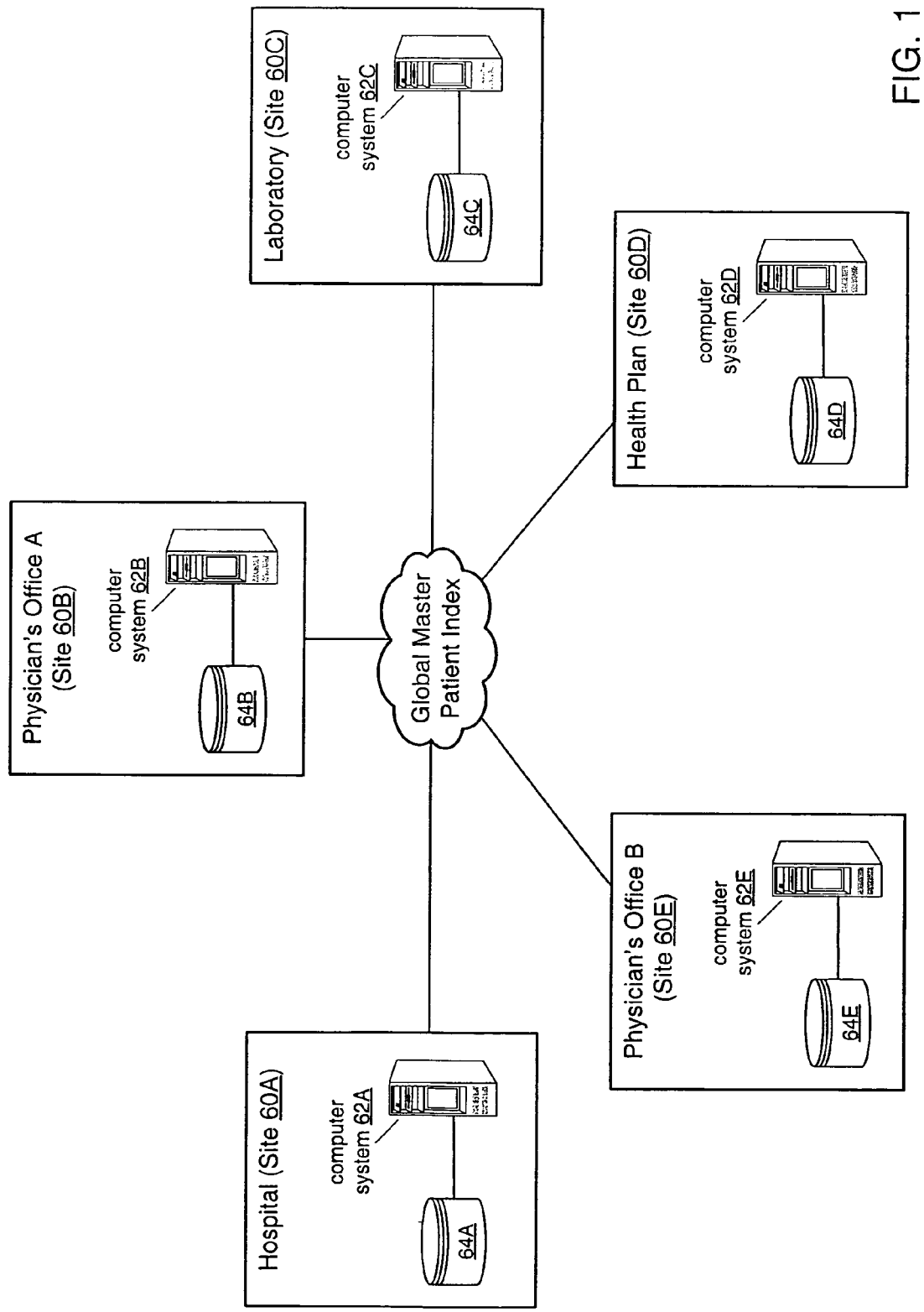
FIG. 1 is a block diagram illustrating the use of a Global Master Patient Index, or GMPI, as enabled by one embodiment of the present invention.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Incorporation by Reference

The following reference is hereby incorporated by reference in its entirety as though fully and completely set forth herein:

U.S. Pat. No. 5,724,575 titled "Method and System for Object-Based Relational Distributed Databases", issued Mar. 3, 1998, whose inventors were Michael K. Hoover, Barrick H. Miller, Kurt Schurenberg, and Richard A. Daigle.

U.S. provisional application Ser. No. 60/167,532 titled "System and Method Enabling a Distributed Object-to-Relational Application Framework", filed Dec. 1, 1999, whose inventors were Robert Yeager, Kurt Schurenberg, and Robin Johnson.

FIG. 1

FIG. 1 is a block diagram illustrating the use of a Global Master Patient Index, or GMPI, as enabled by one embodiment of the present invention. Several exemplary sites 60 are shown. Each site 60 may be associated with a health care organization, facility, or business, such as a physician's office, laboratory, health plan, hospital, etc. The individual sites 60 may be operable to share various types of information with each other, including patient record information, such as patient contact and billing information, patient medical history, etc. In other words, the sites 60 may be associated with a Health Data Network (HDN), and the organization or business associated with each site may be referred to as an HDN Business. It is noted that the sites 60 shown in FIG. 1 represent typical types of businesses found in a typical Health Data Network, and any of various other organizations may be present in other embodiments of a Health Data Network. Also, any number of organizations or businesses may be connected to the HDN.

As shown, each site 60 may utilize a computer system 62 that interfaces to one or more databases 64. Among other types of information, a database 64 may store patient record information The use of patient record information may differ for the various sites. For example, Physician's Office A (site 60B) may primarily use the patient records to view and update clinical information regarding patients' medical history, while the Health Plan (site 60D) may primarily use the patient records to manage insurance information for the respective patients.

According to the preferred embodiment of the present invention, patient record information used by the various sites 60 may be integrated across the Health Data Network, as indicated in FIG. 1 by the Global Master Patient Index (GMPI) interconnecting the various sites. As described above, a GMPI may help to improve patient care and increase the efficiency of healthcare businesses by helping to detect the existence of and avoid the creation of duplicate patient records.

In various embodiments, the system and methods described herein may be used to enable a GMPI for a set of distinct businesses that share information, such as illustrated in FIG. 1. The system and methods may also be employed by a single healthcare business. For example, a healthcare business such as a hospital may have a plurality of departments which utilize the GMPI to integrate patient record information for the various departments. Also, a healthcare business may have multiple physically separated sites that may employ the system and methods described herein to share patient record information among the multiple sites.

As an example of one function of the GMPI, suppose that a patient visits Physician's Office A (site 60B) for the first time, and this patient has previously visited Physician's Office B (site 60E). Thus, the patient may have a patient record that was previously created by a person at Physician's Office B, e.g., by using an application running on computer system 62E. Upon registration at Physician's Office A, a clerk may perform a search for previously existing records for the patient. For example, the clerk may utilize an application running on computer system 62B to perform this search. As described below, the application is preferably enabled to retrieve the existing record for the patient that was created by the person at Physician's Office B.

In various embodiments, the patient record previously created at Physician's Office B may be stored at and retrieved from various locations. For example, this record may be stored in the database 64E at site 60E, and the application running on computer system 62B may be operable to retrieve the record from this database. As another example, the record may be stored in a database not specifically associated with Physician's Office B. For example, when the person at Physician's Office B creates the record, the record may be stored in a central database that stores patient record information for the various HDN Businesses.

In one embodiment, the computer systems associated with the various HDN Businesses may interface with a middleware server that facilitates the retrieval and update of patient records. For example, in the patient registration situation referred to above, in response to the clerk's request to lookup a record for the patient, an application running on computer system 62B at Physician's Office A may request the middleware server to retrieve any existing records for the patient, e.g., by specifying one or more identifiers associated with the patient. such as the patient's name, SSN, etc.

The middleware server may then retrieve the record, e.g., from the database 64E associated with Physician's Office B or from another database. In various embodiments, the middleware server may retrieve the patient record in any of various ways. For example, in one embodiment the middleware server may be operable to maintain or interface with an index cross-referencing patient identifier information with the location of corresponding patient records, i.e., the databases or sites at which the records may be found. In another embodiment, the middleware server may query the various sites of the Health Data Network to locate records for the specified patient.

FIG. 2

Figure 2:
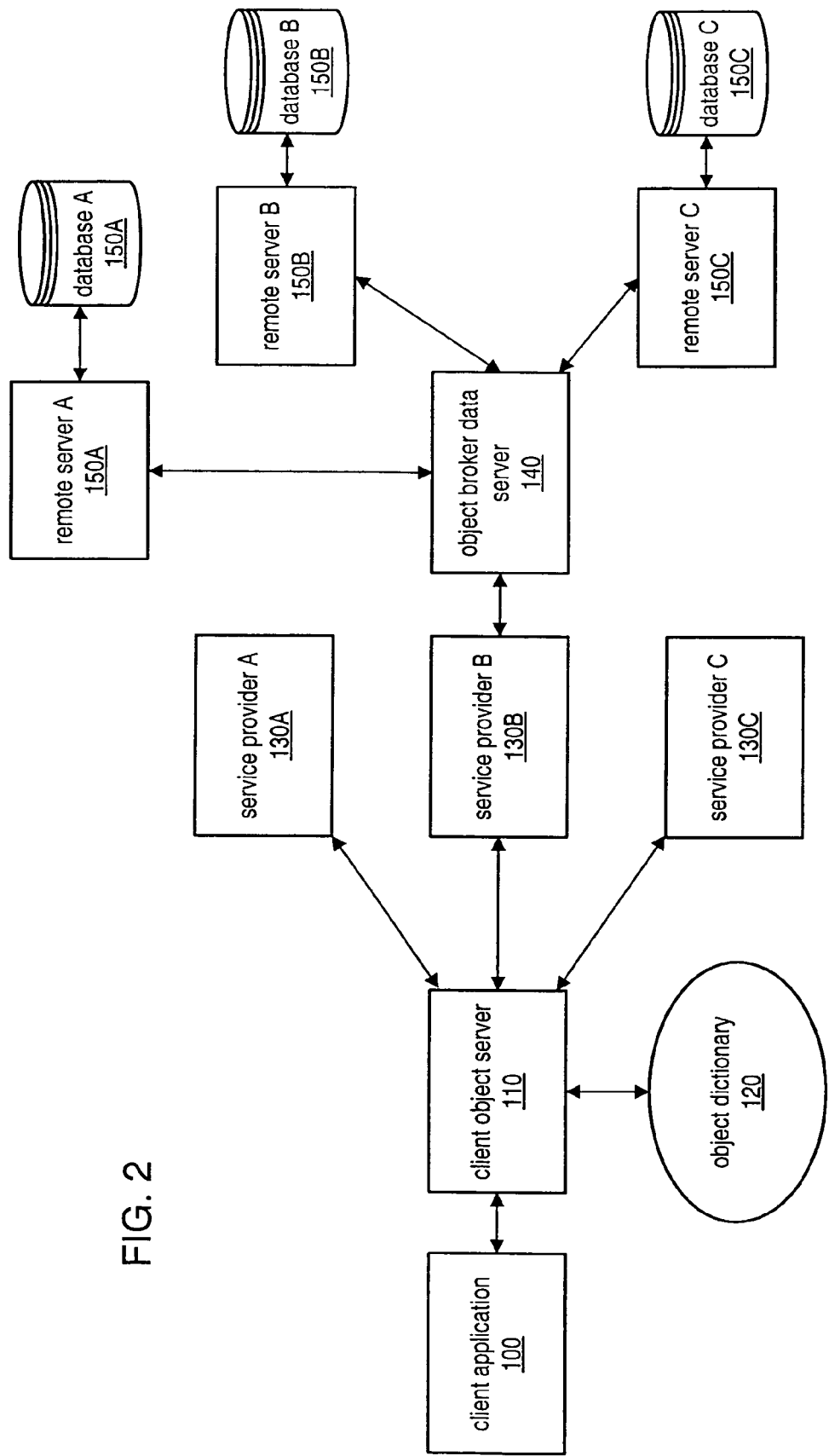
FIG. 2 illustrates one embodiment of a system employing a middleware server to facilitate the integration of patient record information.

FIG. 2 illustrates one embodiment of a system employing a middleware server to facilitate the integration of patient record information. It is noted, however, that any of various systems or architectures may be used to retrieve remote patient records and to maintain the Global Master Patient Index described with reference to FIG. 1.

FIG. 2 illustrates a client application 100 that interfaces with a Client Object Server 110. For example, referring again to the patient registration example given above, the client application 100 may be the application that the clerk at Physician's Office A uses to lookup records for the patient. The client application 100 may also be any of various other types of applications running on any of the other sites 60 shown in FIG. 1. For example, the client application 100 may be a registration application running on computer system 62A at the hospital of site 60A or may be an application associated with managing insurance claims running on computer system 62D at the health plan of site 60D.

The Client Object Server 110 with which the client application 100 interfaces may perform the functions of the middleware server described above. The Client Object Server 110 preferably provides a single standard interface for all of the various client applications running on computer systems 62. The Client Object Server 110 preferably provides an API related to the GMPI which client applications 100 may use to search for patient records, put patient records, delete patient records, etc.

FIG. 2 illustrates a client application 100 that interfaces with a client object server (COS) 110. The client application may be any of various types of computer processes, such as an application that a user interacts with, an application for performing bulk data loading, a communication process associated with another computer system, etc.

The FIG. 2 framework enables a client application to interact with distributed relational databases using a software object model. For example, an application dealing with customer invoices may request a "customer invoice object" from the client object server 110, in order to work with the customer invoice in terms of a software object, such as a C++ or Java object-oriented programming style object. The data for the customer invoice object may be stored in separate tables within a database, or may even be stored in separate databases. The client object server 110 is responsible for managing the retrieval and storage of object data from/to the appropriate locations. In other words, the FIG. 2 framework enables client application logic to be written independently of the data tier(s), and enables data tier(s) to change without requiring client applications to be re-written.

Modern distributed applications often utilize data stored in complex relational models. Enabling client applications to work with the data without requiring knowledge of the complex data model may greatly simplify application programming. Also, data integrity may be increased. For example, when data is added to one table, the data model may specify that a second table should also be updated to reflect the change. However, client application programmers may not know of the need to update the second table, or may forget to do so, resulting in data integrity.

FIG. 2 also illustrates an object dictionary 120. The client object server 110 interfaces with the object dictionary 120 to dynamically determine the data location(s), layout, and retrieval/storage methods. The object dictionary comprises metadata information regarding the data location(s), layout, and retrieval/storage methods for each object that client applications may request from the client object server. For example, the object dictionary may comprise information regarding a customer invoice object, as in the example above. The types of objects that may be defined and managed by the client object server is of course unlimited, and may depend on the purpose of a particular system or application. For example, a healthcare system may define objects representing patients, healthcare providers, etc. The object definitions may be dynamically changed by changing the object dictionary metadata information.

For more information on the interaction of the client object server with the object dictionary and for information on object lifecycle, please refer to the documentation incorporated by reference.

In one embodiment, information is passed between the client application and the client object server via CORBA sequences, e.g., as structured name/value pairs enabling the construction of an "object" on the client-side. Advantageously, this enables client applications to utilize object-oriented style programming without requiring true individual objects, e.g. CORBA objects, to be instantiated and passed to each client application, which could lead to scalability problems for a system with a large number of client applications that communicate with the client object server.

As shown in FIG. 2, the client object server 110 may interface with multiple service provider modules 130. Each service provider module 130 may provide a computing service or interact with another computer system. For example, FIG. 2 illustrates a service provider 130B that interacts with an object broker data server 140, such as the object broker data server described in the above-incorporated documentation. As other examples, a service provider may interact with a file system, a service provider may provide TCP/IP communication abilities, etc. Service providers may also be specific to a particular system or application. For example, an "eligibility" service provider may enable healthcare applications to determine the healthcare insurance eligibility information for a particular patient.

Thus, service providers 130 may add multi-tier aspects to the FIG. 2 framework. The client object server 110, together with the object dictionary 120, may enable client applications to utilize the respective service resources in an object-oriented style, without requiring client applications to possess knowledge of the service implementations. For example, a healthcare application may connect to an external healthcare payer system via an eligibility service provider and query the insurance eligibility status for an individual, using object-oriented methods as described above.

Each service provider may communicate with the client object server via CORBA sequences, similarly as described above, and may communicate with its respective resource in any way appropriate. For example, a service provider may interface with a database resource using a database communication protocol.

Service providers are preferably implemented so that new service providers may easily be incorporated into the framework. In one embodiment, the client object server communicates with each service provider via a common CORBA interface. Thus, a new service provider may be added by simply implementing this interface, as appropriate for the respective resource.

Terminology

The following terms are used herein to describe one embodiment of a Global Master Patient Index.

Unconfirmed link—A link between two records indicating that the records are suspected to correspond to the same person, i.e., indicating that the records are suspected as being duplicates. An unconfirmed link may be automatically created by the system. For example, the existence of an unconfirmed link may indicate that the system has detected two patient records where elements of the records, such as Real World Primary Keys (first name, last name, social security number, date of birth, etc.), have enough similarities for the system to flag the records as possible duplicates. In one embodiment, unconfirmed links are pairwise, i.e., link two patient records. A given patient record may participate in more than one link. An unconfirmed link is non-directional. In other words, neither associated record is thought to be more correct or up-to-date than the other.

Confirmation—A first level of sanctioning a link between a pair of records. For example, confirmation may change an unconfirmed link to a confirmed link or a denigrated link. In the healthcare workflow, confirmation may occur at the point of entry into the system. Confirmation may typically be performed by a clerk or other user who has direct access to the patient. Confirmation may either affirm an association of a pair of records as true (Confirmed Link) or it may reject the association (Denigrated Link).

Confirmed link—A link where a user has confirmed an unconfirmed link detected by the system, or has detected an association between patient records without intervention of the system and has created a link between the records. In the preferred embodiment, a confirmed link is directional, i.e., one record is specified as the most correct, proper, or current record, and the other is thus considered a "trailer" record. The trailer record points or links to the most correct record, which is referred to as a "leader" record.

Certification—A second level of sanctioning a link between a pair of records. For example, certification may change a confirmed link to a certified link or a denigrated link. In the healthcare workflow, certification may be performed by a user responsible for reviewing links between records and supervising and maintaining the integrity of the GMPI. For example, certification may be a privileged operation which only certain users may perform. These users are referred to herein as GMPI administrators.

Certified link—A link where a user has certified two records as being duplicates. In the preferred embodiment, a confirmed link is directional, i.e., one record is specified as the most correct, proper, or current record, and the other is thus considered a trailer record. In one embodiment, when certifying a confirmed link, the user may reverse the direction of the confirmed link if it is determined that the trailer record should actually be the leader record.

Leader record—A "leader" record is a record that has one or more trailer records, but the leader record itself may be a trailer to another record. A "lead" record is a leader record that is not a trailer to any other record.

Trailer record—A record that points or links to a leader record.

Denigrated link—A link where a user has decided that a current link, such as an unconfirmed, confirmed, or certified link is incorrect, e.g., because the linked records do not in fact correspond to the same patient. A denigrated link may thus be created in place of the incorrect link.

Indirect link—In one embodiment, an indirect link may be created when a record has multiple unconfirmed links to different records, and the record is then confirmed as a trailer record to one of these multiple records. For example, suppose that record A has unconfirmed links to records B and C. If the unconfirmed link between A and B is then changed to a confirmed link, where B is chosen as the leader record, then an indirect link between C and B may be created. Indirect links are preferably non-directional links.

It is noted that the descriptions of the terms above refer to one particular embodiment of a Global Master Patient Index, and numerous alternative embodiments are contemplated. For example, the embodiment described above utilizes two levels of review of links, i.e., confirmation and certification. In various embodiments, any number of levels of review may be provided for, as desired. For example, the certification level may not be performed. Also, in one embodiment, an unconfirmed link may be changed directly to a certified link, thus bypassing the confirmation level.

As another example, links are referred to above as being pairwise, i.e., each link may associate two records. In alternative embodiments, links, such as non-directional links, may associate as many records as desired.

As another example, the description above refers to the possible creation of denigrated links, e.g., to replace an incorrect link if it is determined that two records are not in fact duplicates. In alternative embodiments, links may simply be removed if they are discovered to be incorrect, without creating a denigrated link. However, denigrated links may be useful for audit purposes, to track the history of the GMPI, and may also provide for a level of review after a user has denigrated an exiting link.

Also, it is noted that links may be represented and implemented in any of various ways. For example, a link between two records may be represented by including information in each record, wherein this information comprises information such as identifier information specifying the other member of the link, the type of link, the direction of the link (if the link is directional), etc. When operations are performed on patient records, e.g., to lookup or create a new patient record, this information may then be checked to determine the existence of any links. Various methods for the handling of links are described below.

FIG. 3

Figure 3:
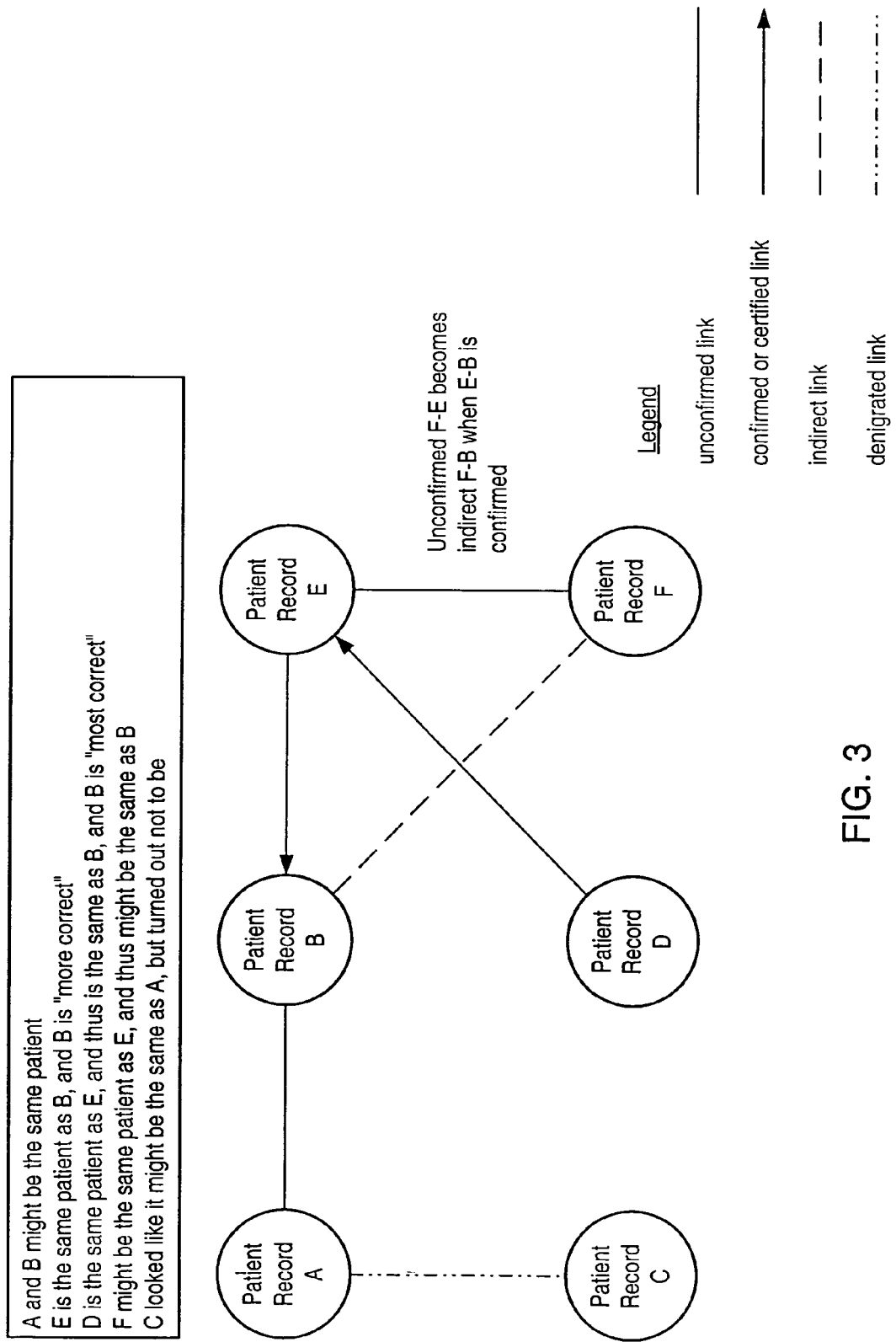
FIG. 3 is a diagram illustrating an example of various types of GMPI links among a set of patient records.

FIG. 3 shows an example illustrating the various types of links described above. In this example, there is an unconfirmed link between patient record F and patient record E. There is a confirmed or certified link from patient record E to patient record B. There is a confirmed or certified link from patient record D to patient record E. There is an indirect link between patient record F and patient record B. There is an unconfirmed link between patient record A and patient record B. There is a denigrated link between patient record A and patient record C.

The unconfirmed link (a non-directional link) between patient record A and patient record B indicates that these two records might correspond to the same person. As described above, the system may have automatically detected that these two records are possible duplicates of each other and may have created the unconfirmed link to indicate this. Various methods for this automatic detection and flagging of possible duplicate records are described below.

The confirmed or certified link (a directional link) from patient record E to patient record B indicates that these two records have been confirmed and/or certified by a user as corresponding to the same person. The link also indicates that record B has been determined to be the most accurate, complete, or up-to-date record of the two. For example, the system may have previously established an unconfirmed link between patient record B and patient record E. A user may have then noticed this link, e.g., in response to performing a search for the person corresponding to patient record B or E. The user may have then inspected the information of records B and E and/or may have consulted with the patient, and may have decided that the information in record B was more current or more complete. Thus, the user may have established a confirmed link from patient record E to patient record B. The user may have also created a confirmed link directly without converting an unconfirmed link to the confirmed link.

The confirmed or certified link from patient record D to patient record E indicates that record D has been confirmed and/or certified by a user as corresponding to the same person as record E. Since record E corresponds to the same person as record B, records D, E, and B all correspond to the same person. Record B is the lead record, and is considered the most accurate or current record for the patient.

It is noted that in alternative embodiments, when multiple records are linked together as in the example of record D, E, and B, links among the records may be adjusted to reduce the degree of chaining. For example, the link from record D to record E could be removed, and a link directly from record D to record B could be created. However, keeping the chain of links in place may have certain advantages. For example, if the link from record E to record B is erroneously certified and has to be removed, the link from record D to record E would still be in place.

The unconfirmed link between patient record E and patient record F indicates that these two records might correspond to the same person, similarly as described above. Since record E corresponds to the same person as record B, records F and B also might correspond to the same person. This is indicated by the indirect link (a non-directional link) between record F and record B. For example, this indirect link may have been created when a previously unconfirmed link between E and B was confirmed as a directional link from E to B.

As described above, the denigrated link between patient record A and patient record C that at one time a link such as an unconfirmed, confirmed or certified link existed between patient record A and patient record C but that link was then denigrated. For example, the system may have automatically detected that patient records A and C were duplicate records and may have established an unconfirmed link between the records. Upon review by a person the person may have determined that records A and C were in fact not matches, were not duplicate, and thus may have requested the system to denigrate a link. As another example, the system may have established an unconfirmed link between the two records and an authorized person may have later confirmed the link based upon information available at the time. However, upon further review another user may have determined that the two records were in fact not duplicates and thus may have requested the system to denigrate the link.

FIG. 4

Figure 4:
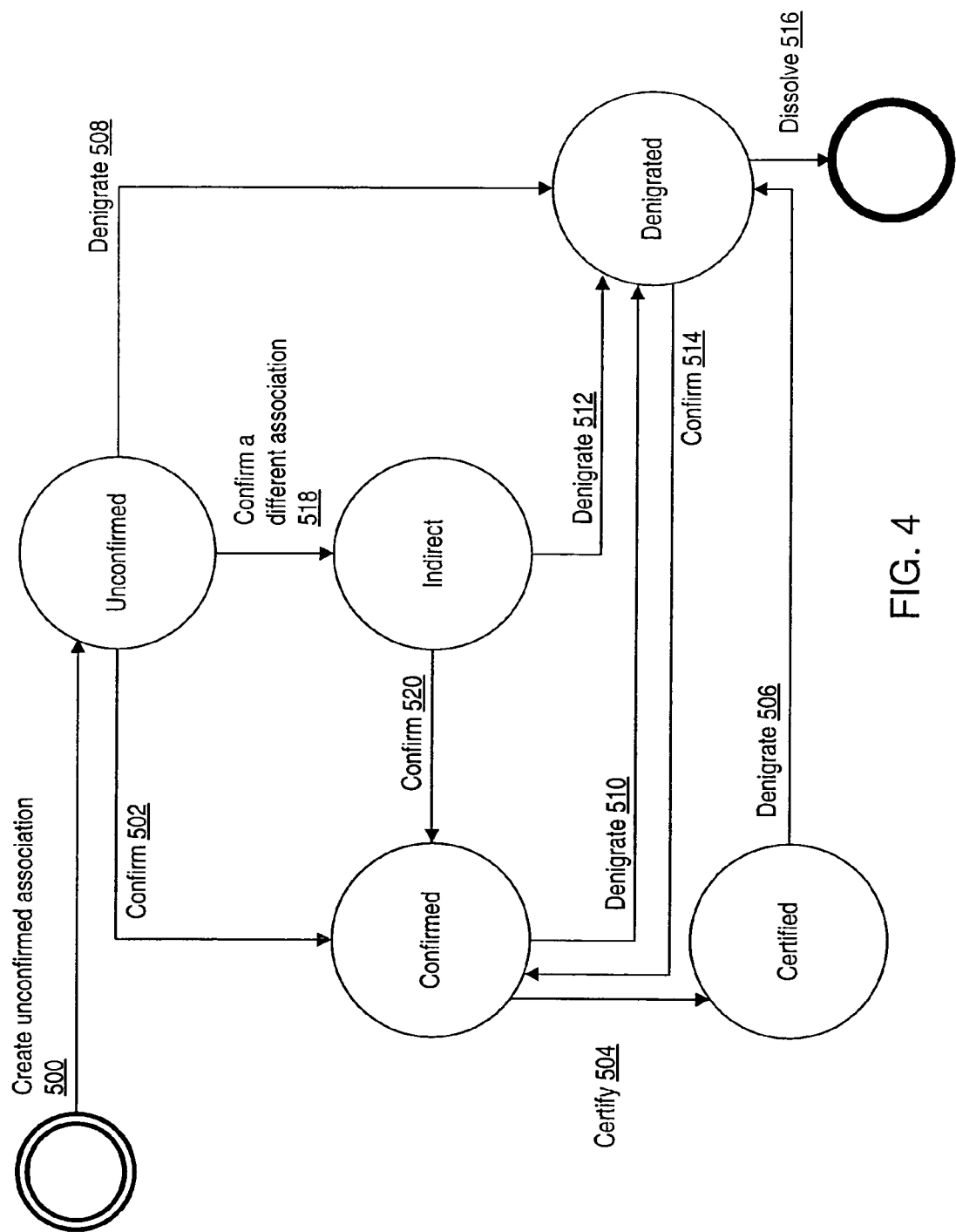
FIG. 4 is a state diagram illustrating various state changes that a GMPI link may undergo, according to one embodiment.

FIG. 4 is a state diagram illustrating various state changes that a link may undergo, according to one embodiment. It is noted that a state change of a link may be implemented in any of various ways. For example, a state change may involve removing an existing link and creating a new type of link, or the state change may involve changing information representing the link, e.g., to indicate that the link is now a different type of link, to specify a direction for a previously non-directional link, etc.

As shown by the arrow 500, a link may begin as an unconfirmed link, e.g., an unconfirmed link that is automatically created by the system in response to detecting two patient records that are possible duplicate records. As indicated by the arrow 502, this unconfirmed link may then become a confirmed link, e.g., in response to user input confirming the link and specifying a direction for the link. As indicated by the arrow 504, a confirmed link may then be certified.

Referring now to arrow 508, an unconfirmed link may also be denigrated. For example, as described above, a user may specify that the two records associated by the link do not actually correspond to the same patient. As indicated by arrows 510 and 506, confirmed and certified links may also be denigrated, e.g., if the confirmed or certified link is discovered to be erroneous. As indicated by arrow 516, a denigrated link may be dissolved. For example, information representing the link may be removed entirely. It is noted that in alternative embodiments, links in various other states, such as confirmed links, may also be dissolved directly if desired, without first being denigrated. However, arrow 514 illustrates one reason why a denigrated state may be useful. This arrow indicates that a denigrated link may become a confirmed link. For example, a GMPI administrator may review links that were recently denigrated and may discover that another user denigrated the link in error and may confirm (or certify) the link.

Arrow 518 indicates that indirect links may also be created. Indirect links are described above. In this case, the creation of the indirect link may involve the addition of a new link to a new record, rather than a state change of the existing link. For example, if record A has unconfirmed links to records B and C, and the link from A to B is confirmed, then an indirect link from C to B may be created, and the unconfirmed link between C and A may remain. However, the unconfirmed link between C and A may also be removed, if desired.

An indirect link may be confirmed, as indicated by arrow 520 or denigrated, as indicated by arrow 512.

It is noted that the state diagram of FIG. 4 illustrates one embodiment of state changes a link may undergo. In alternative embodiments, various additional states may be possible, various of the states shown may not be possible, or paths between the states may be different. For example, in one embodiment, an "unresolved" state is also possible. For example, in addition to confirming or denigrating an unconfirmed link, a user may also specify that the link is unresolved, e.g., indicating that the user does not know whether the link should be confirmed or denigrated.

FIG. 5

Figure 5:
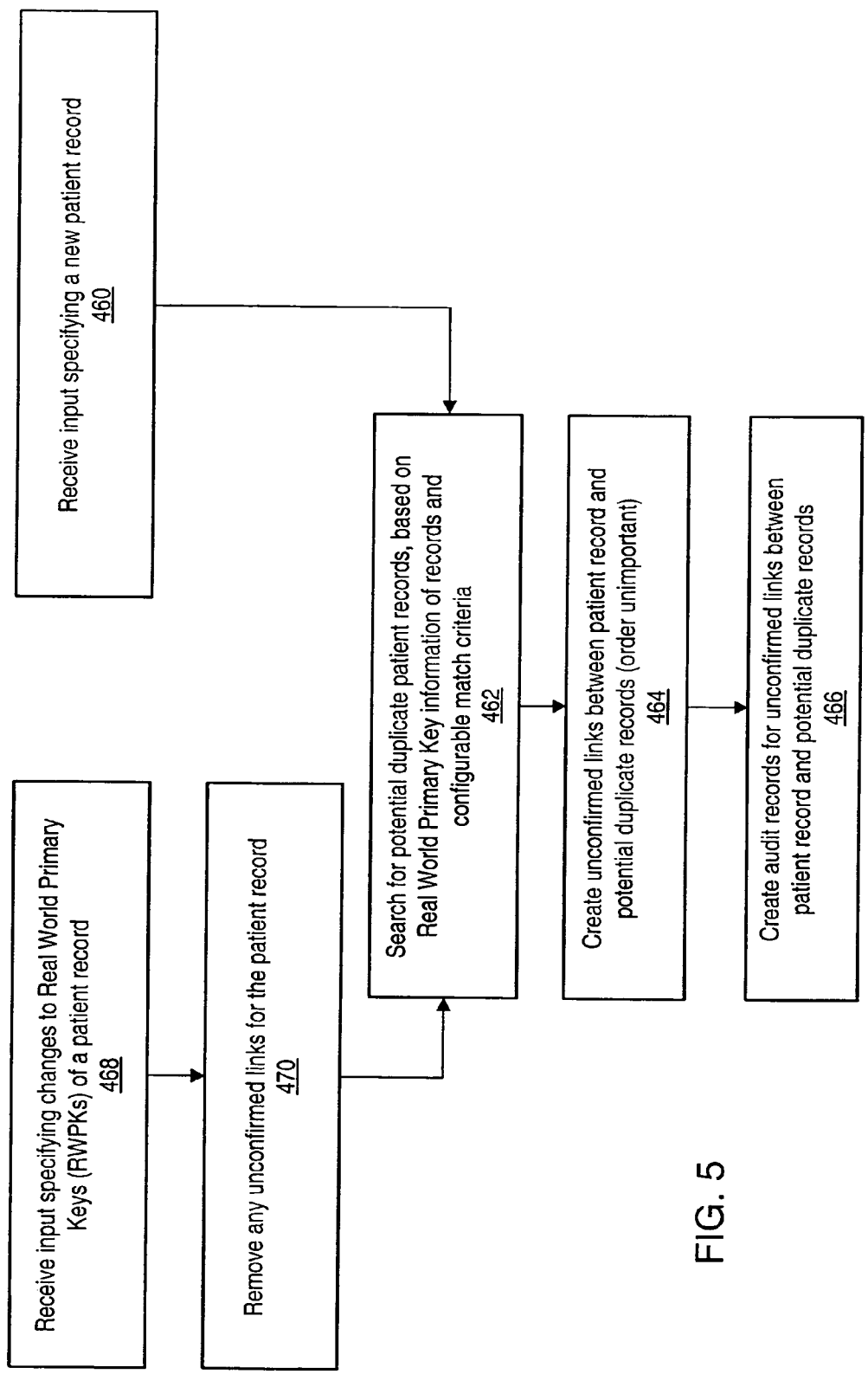
FIG. 5 is a flowchart diagram illustrating one embodiment of a method for automatically creating an unconfirmed link between two patient records.

FIG. 5 is a flowchart diagram illustrating one embodiment of a method for automatically creating an unconfirmed link between two patient records.

In step 460 user input specifying a new patient record is received. For example, a hospital clerk using a registration application may create a new patient record when a patient checks in to the hospital.

In step 462, a search for potential duplicate patient records of the new patient record is performed. It is noted that this search may be performed offline or in the background. In other words, the new patient record may be created and may be ready for immediate use by the application. As illustrated in FIG. 1, patient record information may be distributed among different databases at different sites in a Health Data Network. The search may comprise searching patient records stored on a local system as well as searching for patient records located on systems in other organizations. For example, the local computer system may interface with the client object server, as described above, to search for potential duplicate records. Thus, it may be desirable to perform the search for potential duplicate records as a background task, without forcing the user to wait for the search to be completed.

The determination of possible duplicate records may be performed in any of various ways. In one embodiment, Real World Primary Key (RWPK) information of the new patient record and the existing records is used. Real World Primary Key information may include information such as first name, last name, social security number, gender, date of birth, etc. Any of various criteria may be used in determining whether the RWPKs of two records match each other sufficiently closely for the records to be flagged as potential duplicate records. The match criteria used may be configurable by the user or by an administrator of the system.

In one embodiment the five RWPKs listed above may be used in the match, and the match may be determined as follows:

Case 1: If two records match exactly on all five elements then the records are considered matches. It is noted that blank entries do not match blank entries in the other record.

Case 2: Exact match on first name, last name, and social security number and either gender or date of birth, but only when the gender or date of birth in the matching record in the database is NULL.

Case 3: Exact match on first name, last name, gender, and date of birth, but only when the social security number in the database is NULL.

This algorithm is of course exemplary, and any of various types of match criteria or algorithms may be used. For example, the match algorithm may attempt to take possible typographic errors into account.

In step 464, if potential duplicate records were found in step 462, then the system creates unconfirmed links between the new patient record and each potential duplicate record. As described above, these unconfirmed links are preferably not directional links. The creation of the unconfirmed links may be performed in any of various ways, depending on a particular implementation.

In one embodiment, the system may be operable to maintain audit information enabling users to track the history of the Global Master Patient Index. Thus, in step 466 audit records indicating the unconfirmed links between the new patient record and the potential duplicate records may be created.

Once the unconfirmed links between the new patient record and the potential duplicate records are established, the links may be resolved in various ways. For example, the next time a user looks up the new patient record or one of the potential duplicate records, the user's application may indicate that the record has unconfirmed links and may display a user interface enabling the user to resolve the links, e.g., by confirming or denigrating the links. Also, a user, such as a GMPI administrator, may utilize an application enabled to perform a search for records with unconfirmed links and may then resolve the links.

In addition to creating unconfirmed links for a new patient record, FIG. 5 also illustrates a method for creating unconfirmed links between two previously existing patient records. For example, in step 468 input specifying changes to the RWPKs of an existing patient record may be received. For example, if a patient's SSN is discovered to be incorrectly listed in the patient record, the SSN may be corrected.

In response to the specified RWPK changes, in step 470, any unconfirmed links for that patient record may be removed. Steps 462 through 466 may then be performed similarly as described above, to search for potential duplicates of the record and create unconfirmed links to these potential duplicates.

FIG. 6

Figure 6:
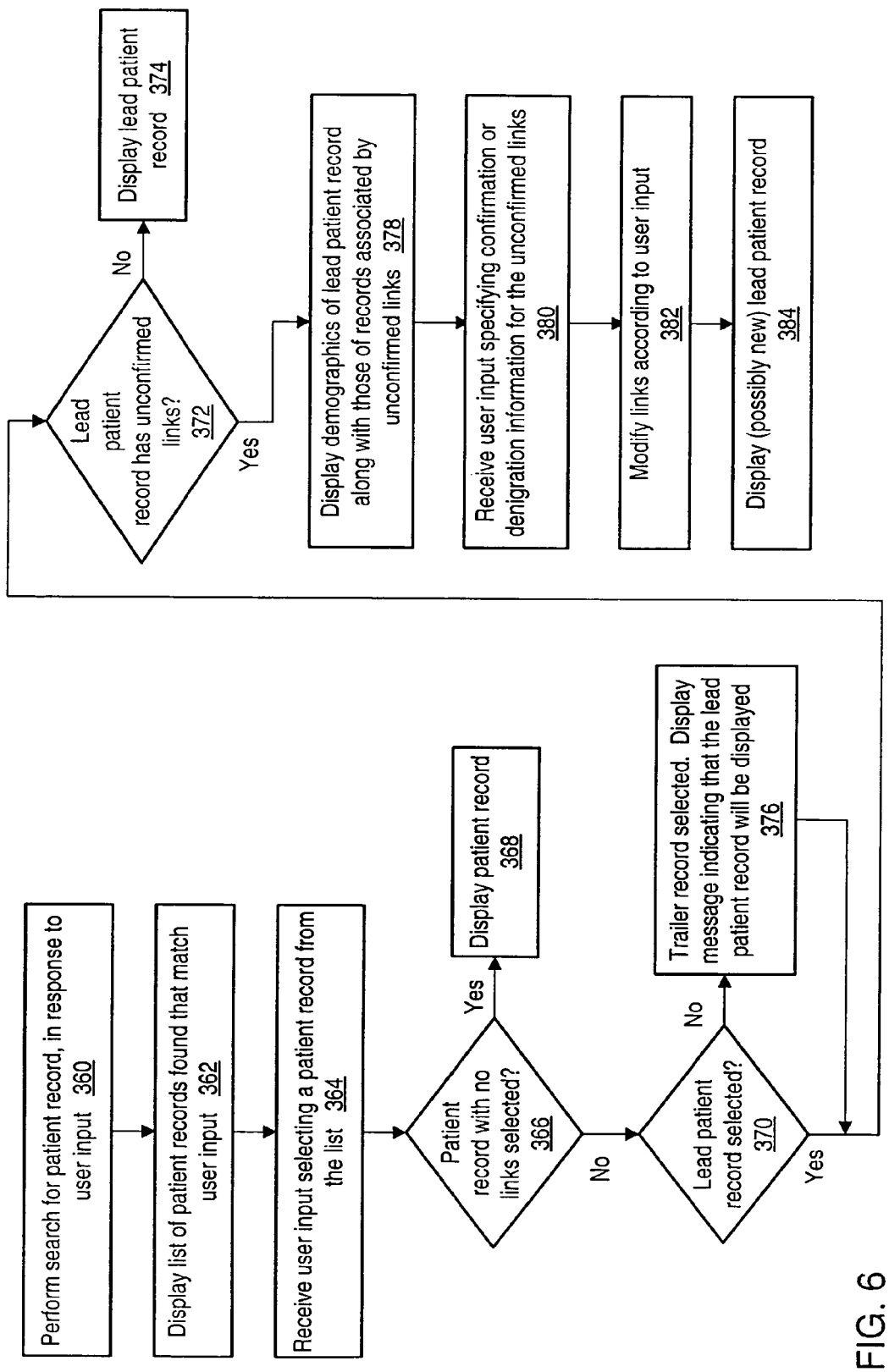
FIG. 6 is a flowchart diagram illustrating one embodiment of a method for looking up patient records in the GMPI in response to user input.

Applications that process patient records may be operable to determine when a patient record has links and may use this information in various ways. One situation when this information may be used is when a user performs a lookup of a patient record. FIG. 6 is a flowchart diagram illustrating one embodiment of a method for looking up patient records in the GMPI, in response to user input.

In step 360, a patient record search is performed in response to user input. This user input may specify any of various types of information that can be used to search for patient records, such as RWPK information or other information identifying a specific patient record. The search performed in step 360 may comprise searching for patient records on the user's local site as well as searching for patient records stored on remote sites. For example, the user's application may interface with the Client Object Server discussed above to perform the search.

In step 362, a list of patient records that were found that matched the specified user input may be displayed.

In step 364, user input selecting a patient record from the displayed list may be received.

In step 366, the method may determine whether the selected patient record has links to other records. If not, then the selected patient record may be displayed, as shown in step 368.

Otherwise, the method may determine whether the selected patient record is a lead record. If the selected patient record is not a lead record, then the selected record is a trailer record. In the preferred embodiment, when a trailer record is selected then the lead patient record for that trailer record is displayed instead of the selected trailer record. As shown in step 376, a message may be displayed to indicate to the user that this has occurred. It may be desirable to display the lead record since, as described above, the trailer record was determined to be less accurate or current than the lead record, for any of various reasons.

In step 372, the method determines whether the selected lead patient record or the lead patient record of the selected trailer record has unconfirmed links. If not, then the lead patient record may be immediately displayed, as shown in step 374.

Otherwise, in step 378, demographic information of the lead patient record along with the demographic information of records associated with the lead patient record by unconfirmed links may be displayed. A user interface enabling the user to enter confirmation information for the associations may also be displayed.

In step 380, user input specifying resolution information for the unconfirmed links of the lead patient record may be received. For example, the user may specify that a confirmed link should replace one of the unconfirmed links and may specify the appropriate direction for this confirmed link. A user may also denigrate an unconfirmed link or specify that he does not know whether the link should be confirmed or denigrated, thus changing the unconfirmed link to an unresolved link. Unresolved links may subsequently be treated similarly as unconfirmed links.

In step 382, the links among the records may modified as appropriate in response to the user input received in step 380. Various embodiments of methods to perform these modifications are described below.

Once the unconfirmed associations have been resolved, the lead patient record may be displayed, or if the lead patient record was confirmed as a trailer to another record, this new lead record may be displayed, as shown in step 384.

It is noted that FIG. 6 represents one embodiment of a method for looking up patient records, and in other embodiments various steps may be added, combined, altered, removed, reordered, etc. For example, instead of entering resolution information via a user interface, the user may have the option of skipping this process to immediately view the selected patient record. Also, this user interface may only be displayed for certain users that have permission to modify patient record links.

FIG. 7

Figure 7:
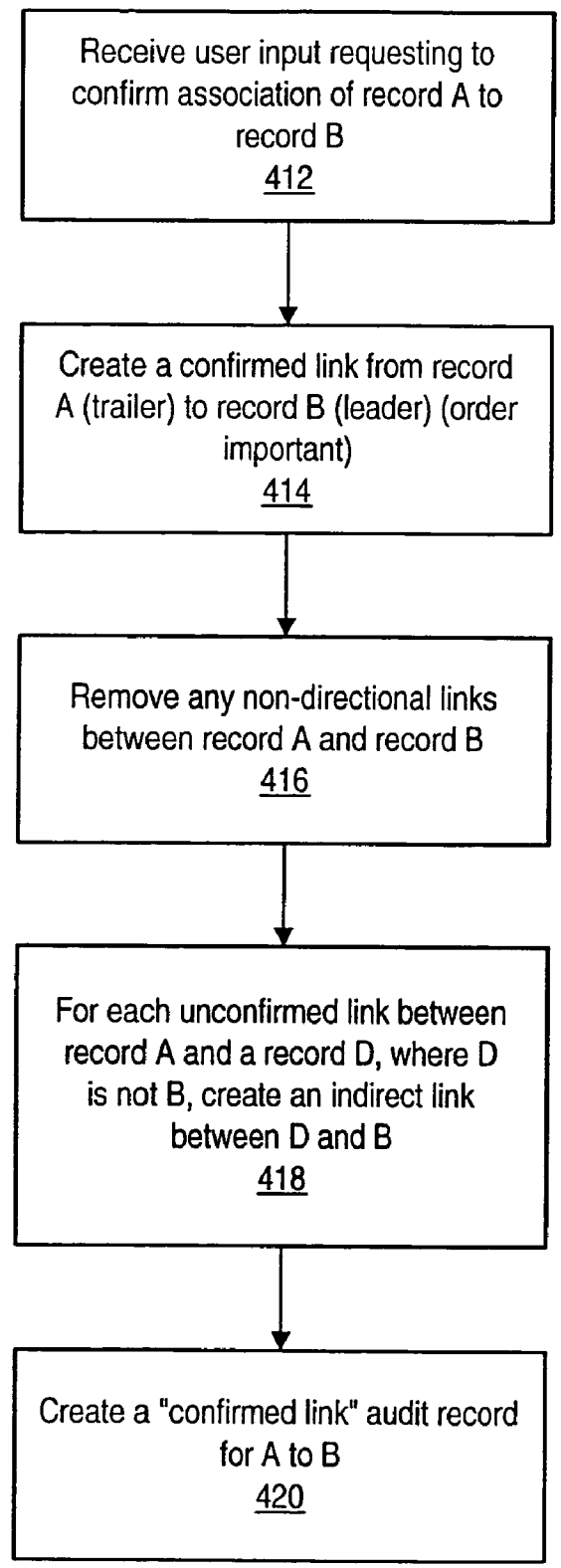
FIG. 7 is a flowchart diagram illustrating one embodiment of a method for confirming a link from a record A to a record B, wherein a non-directional link, such as an unconfirmed or denigrated link, exists between A and B.

FIG. 7 is a flowchart diagram illustrating one embodiment of a method for confirming a link from a record A to a record B, wherein a nor-directional link, such as an unconfirmed or denigrated link, exists between A and B.

In step 412, user input requesting to confirm the link is received. For example, as described above, when the user requests a patient record with unconfirmed links to be displayed, a user interface enabling the user to specify confirmation information for the patient record may be displayed, and the user may request to confirm an unconfirmed link via this user interface. Also, a user may confirm a link between A and B that was previously denigrated.

In step 414, a confirmed link from record A to record B may be created. As shown in FIG. 7, this confirmed link is preferably a directional link linking record A, i.e., the trailer record, to record B, i.e., the leader record. In various embodiments, this confirmed link may be represented or implemented in any of various ways.

In step 416, any non-directional links between record A and record B may be removed. Although steps 414 and 416 are shown as two separate steps in FIG. 7, it is noted that in alternative embodiments the steps may be combined, e.g., by changing information specifying a link type between record A and record B.

As shown in step 418 and described above, when a link between two records is confirmed, indirect links may also be created. For example, as indicated in step 418, for each unconfirmed link between record A and a record D, where D is not B, an indirect link between D and B may be created.

In one embodiment the system may be operable to maintain audit information for the GMPI. This audit information may enable GMPI administrators to track the history of the GMPI as well as to view a specific user's actions affecting the GMPI. Thus, in step 420 an audit record indicating the confirmed link from record A to record B may be created.

In one embodiment, once a trailer record is confirmed into a leader record, the leader record may be modified to include information of both the trailer and the leader record. For example, the leader record may include employment data, medical data, insurance data, documents, contact data, consent data, lab orders data, lab result report data, diagnosis codes, etc., of both the leader and the trailer records.

FIG. 8

Figure 8:
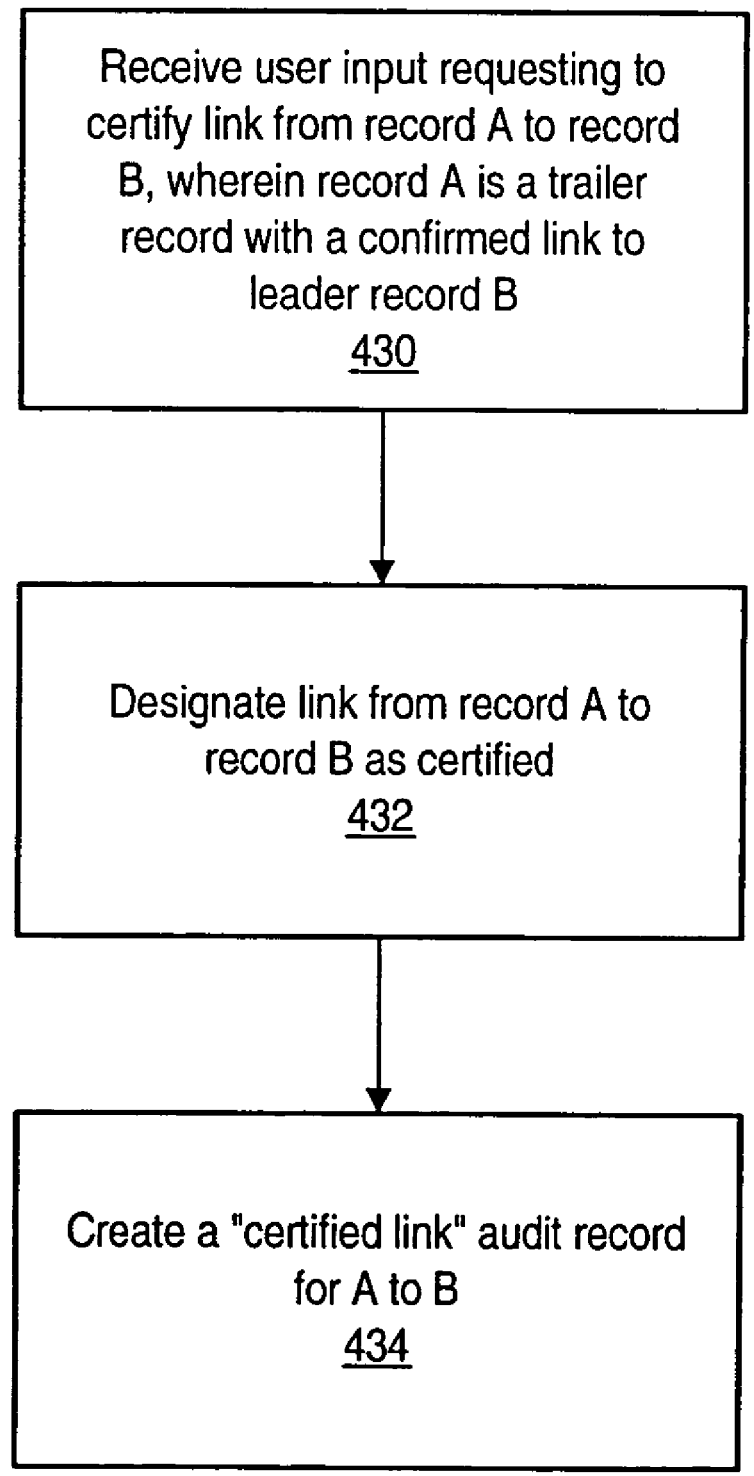
FIG. 8 is a flowchart diagram illustrating one embodiment of a method for certifying a link from a record A to a record B, wherein record A is a trailer record with a confirmed link to a leader record B.

FIG. 8 is a flowchart diagram illustrating one embodiment of a method for certifying a link from a record A to a record B, wherein record A is a trailer record with a confirmed link to a leader record B.

In step 430, user input requesting to certify the link from A to B is received. For example, GMPI administrators responsible for reviewing confirmed links may utilize an application to display records having confirmed links and may certify one or more of these links.

In step 432, the link from record A to record B may be designated as certified. For example, step 432 may involve storing information indicating that the link has been certified. In alternative embodiments, step 432 may involve separate steps of removing the existing confirmed link and creating a new certified link from A to B.

In step 434, an audit record for indicating the action of certifying the link from A to B may be created.

FIG. 9

Figure 9:
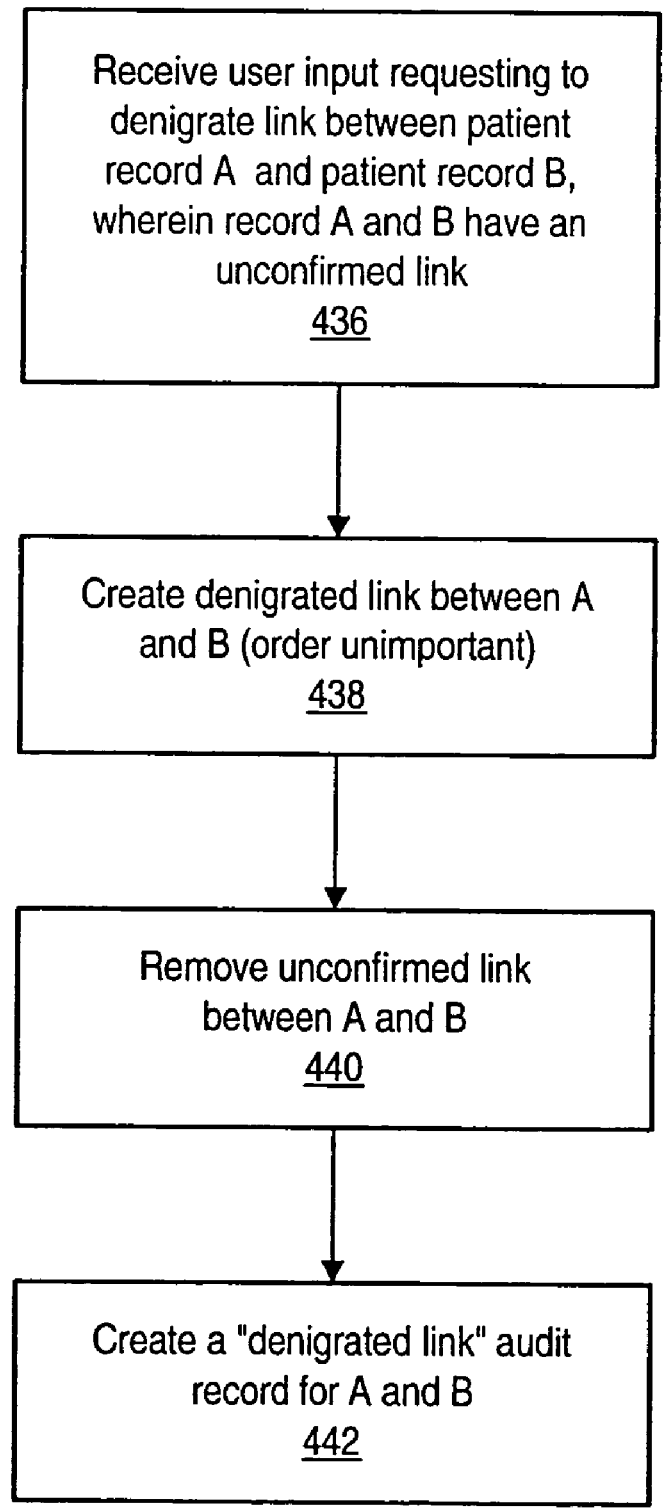
FIG. 9 is a flowchart diagram illustrating one embodiment of a method for creating a denigrated link between a patient record A and a patient record B, wherein there is an existing unconfirmed link between A and B.

FIG. 9 is a flowchart diagram illustrating one embodiment of a method for creating a denigrated link between a patient record A and a patient record B, wherein there is an existing unconfirmed link between A and B. Denigrating an unconfirmed link may be desirable, for example, if the system automatically creates an unconfirmed link between two records determined to be potential duplicate records, but a user then determines that the records are not actually duplicates.

In step 436, user input requesting to denigrate the link may be received.

In step 438, a denigrated link between A and B may be created. This denigrated link is preferably a non-directional link, i.e., the order of the link is not important.

In step 440, the existing unconfirmed link between record A and record B may be removed.

In step 442, an audit record indicating the creation of the denigrated link between A and B may be created.

FIG. 10

Figure 10:
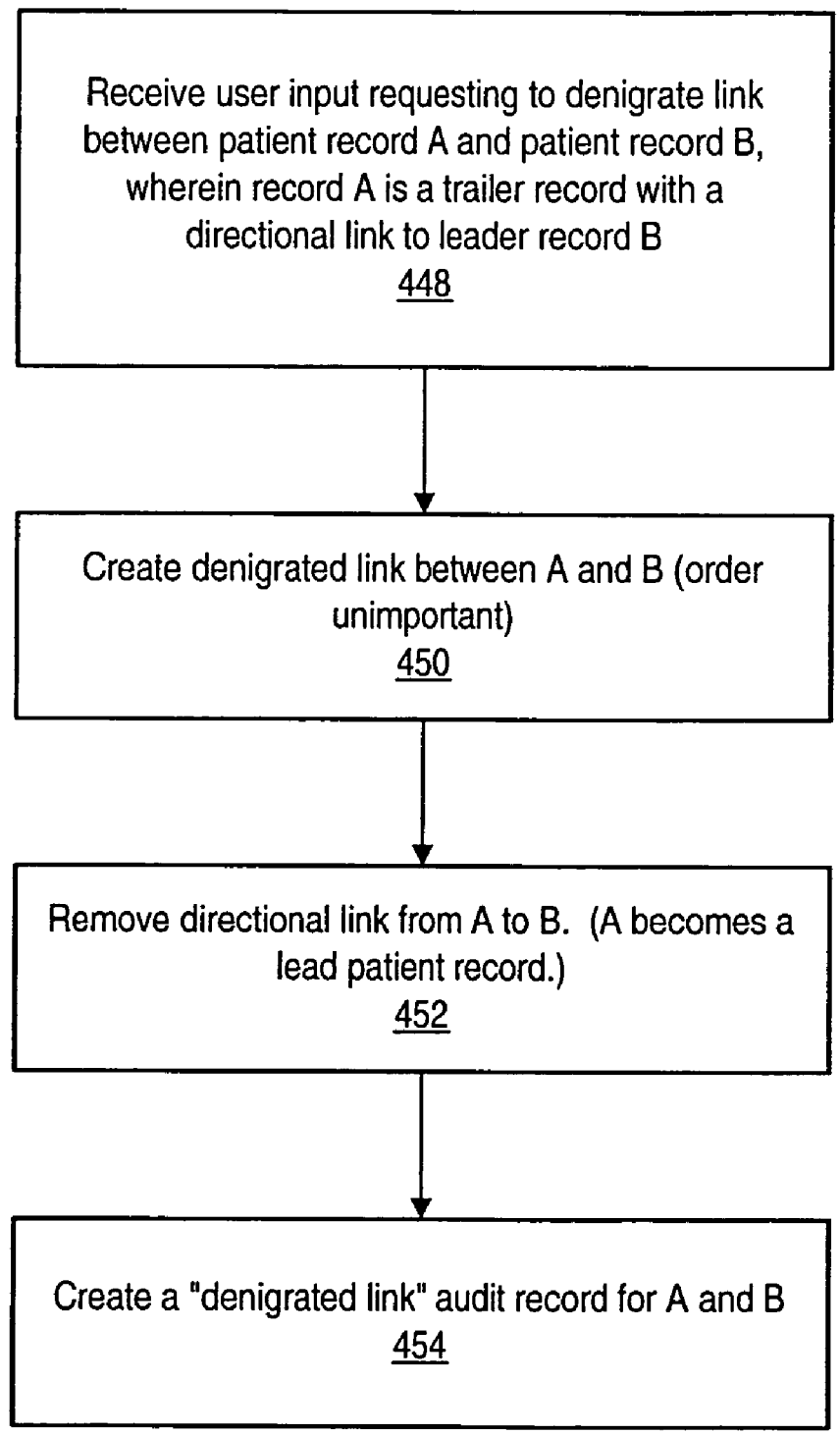
FIG. 10 is a flowchart diagram illustrating one embodiment of a method for denigrating a link between a record A and a record B, wherein record A is a trailer record with a directional link to leader record B.

FIG. 10 is a flowchart diagram illustrating one embodiment of a method for denigrating a link between a record A and a record B, wherein record A is a trailer record with a directional link to leader record B. For example, the directional link from A to B may be a confirmed or certified link, and it may be discovered that this link was confirmed or certified in error.

In step 448, user input requesting to denigrate the directional link is received.

In step 450, a denigrated link between A and B may be created. This denigrated link is preferably a non-directional link.

In step 452, the directional link from A to B may be removed. Thus, the trailer record A may become a lead patient record.

In step 454, an audit record indicating the creation of the denigrated link may be created.

Laboratory Application

As discussed above, any of various types of applications used by any of various types of healthcare organizations may use GMPI patient record information. The remainder of this disclosure describes one particular application, i.e., a laboratory application, enabled to utilize a GMPI. This application enables various healthcare sites, such as physician offices or hospitals, to connect to clinical laboratories, e.g., to electronically place lab orders and receive lab results.

This lab application includes several user interface displays related to managing patient records and maintaining a GMPI. In particular, FIGS. 52-61 illustrate user interface screens related to one embodiment of a GMPI.

Laboratory Orders and Results Application

Figure 11:
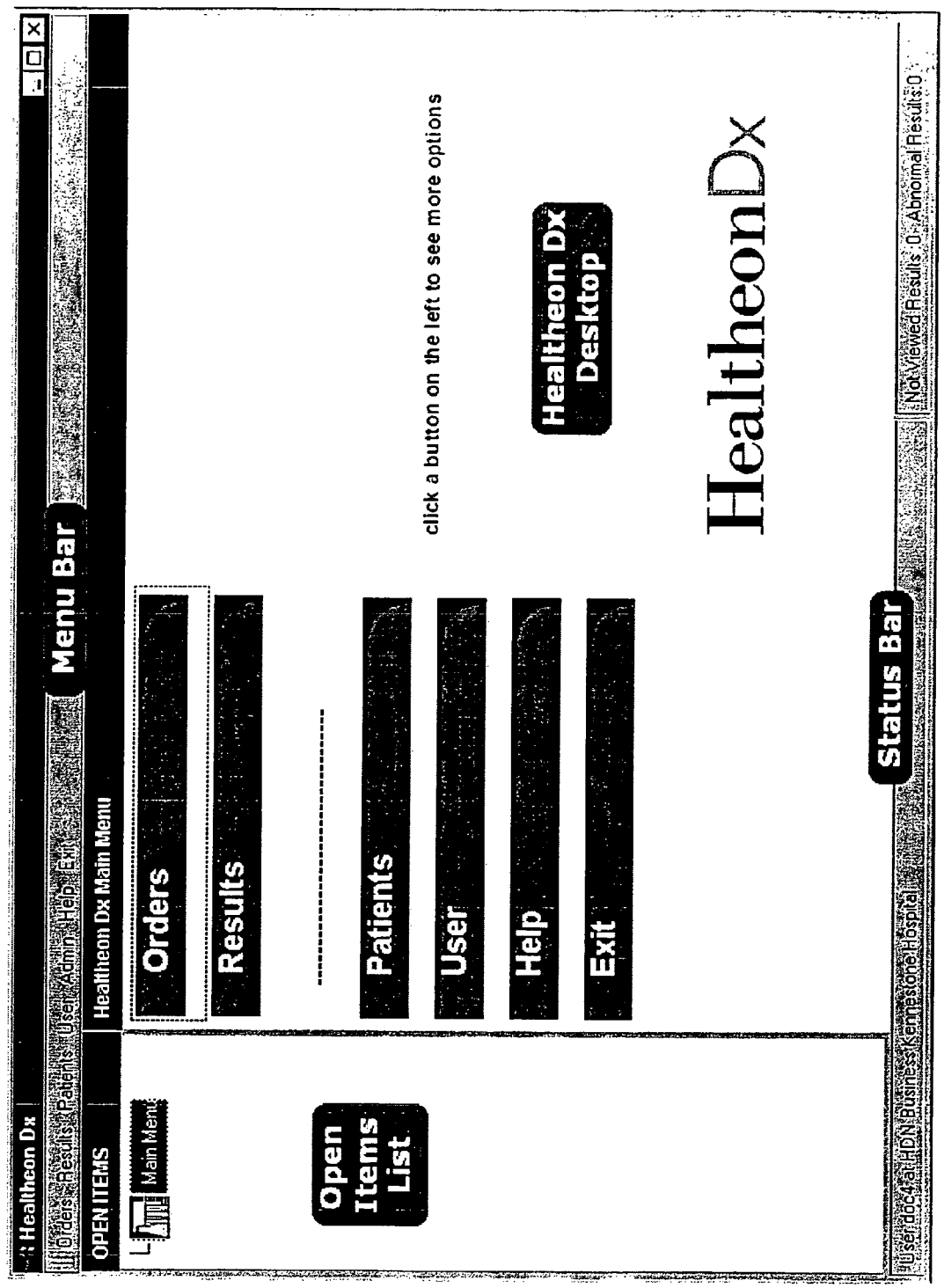
FIGS. 11-107 describe an exemplary laboratory application operable to use a GMPI to integrate patient information across healthcare businesses.

After the user has successfully logged on to the lab orders and results system, the main window appears, as shown in FIG. 11. In addition to standard user interface window components, the system main window has several application-specific components, including drop-down menus, an open items list, a desktop area, and a status bar.

Drop-down menus: The menu bar, located across the top of the system main window, provides access to all functions needed to use and maintain the system. Various menu items are described below.

Figure 12:
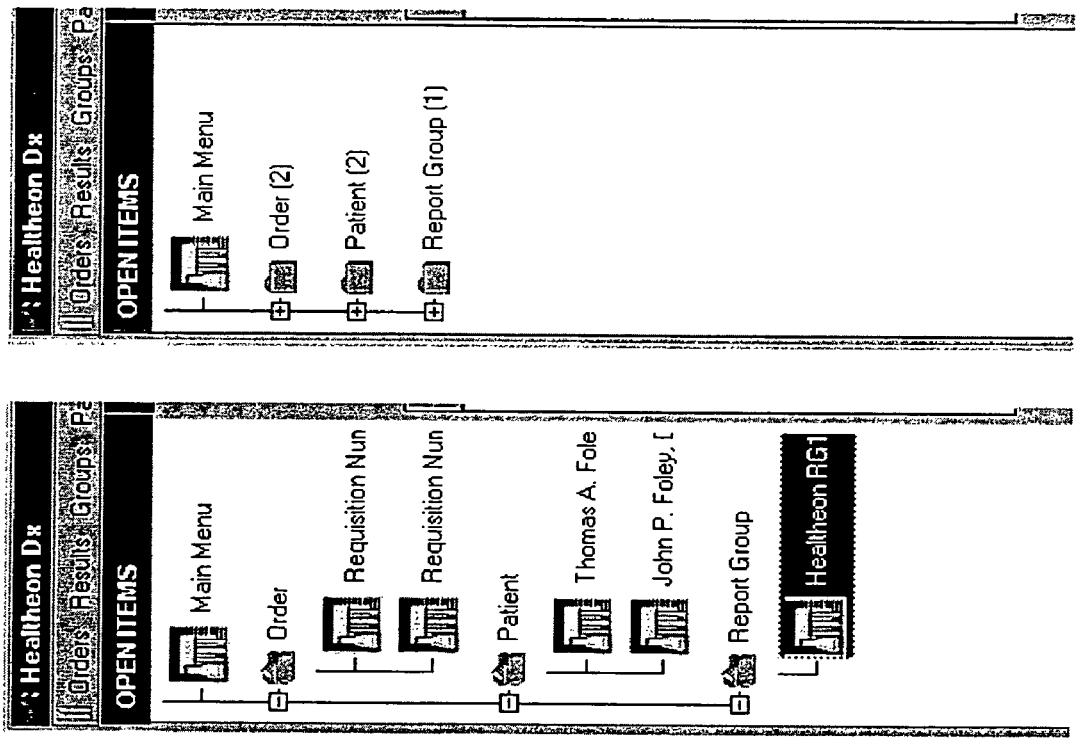

Open Items list: The Open Items list, located on the left side of the system window, shows all items that are open. As the user works with various items, such as lab requisitions, patient records, etc., the items appear in the Open Items list. This feature allows the user to switch back and forth between different items without having to close the one the user is currently working on. FIG. 12 illustrates an exemplary Open Items list. In this illustration, the following items are open: two requisitions under the Order section, two patient records under the Patient section, and one patient group under the Report Group section. When the user log on to the system, the default item in the Open Items list is Main Menu. At the bottom of the list, there is a horizontal scroll bar that lets the user expand the view. To view an item from the Open Items list, the icon next to the item is clicked. The dark box around the item indicates that this is the item currently displayed on the system desktop.

Desktop: The desktop area, the large area located on the right side of the window, is where all screens of the application appear. When the application first opens, the system desktop is occupied by the Main Menu desktop menu, as shown in FIG. 11. This desktop menu provides a graphic means of accessing the most frequently used functions of the application.

Status bar: The status bar, located at the bottom of the desktop area, has two message panels. On the left side is the log on status, which displays the username used to log on at the workstation and the name of the active Health Data Network (HDN) Business. In the example of FIG. 11, the user doc4 is logged on at the workstation and Kennestone Hospital is the active HDN Business. On the right side is the lab results status, which displays the number of lab results that have not been viewed, i.e., new results electronically received from various labs but not yet reviewed, and the number of those results that are abnormal.

Functional Architecture

In one embodiment the system includes the following functional modules: Orders, Results, Patients, User, and Admin. Each of these modules is described below.

Orders Module

Figure 13:
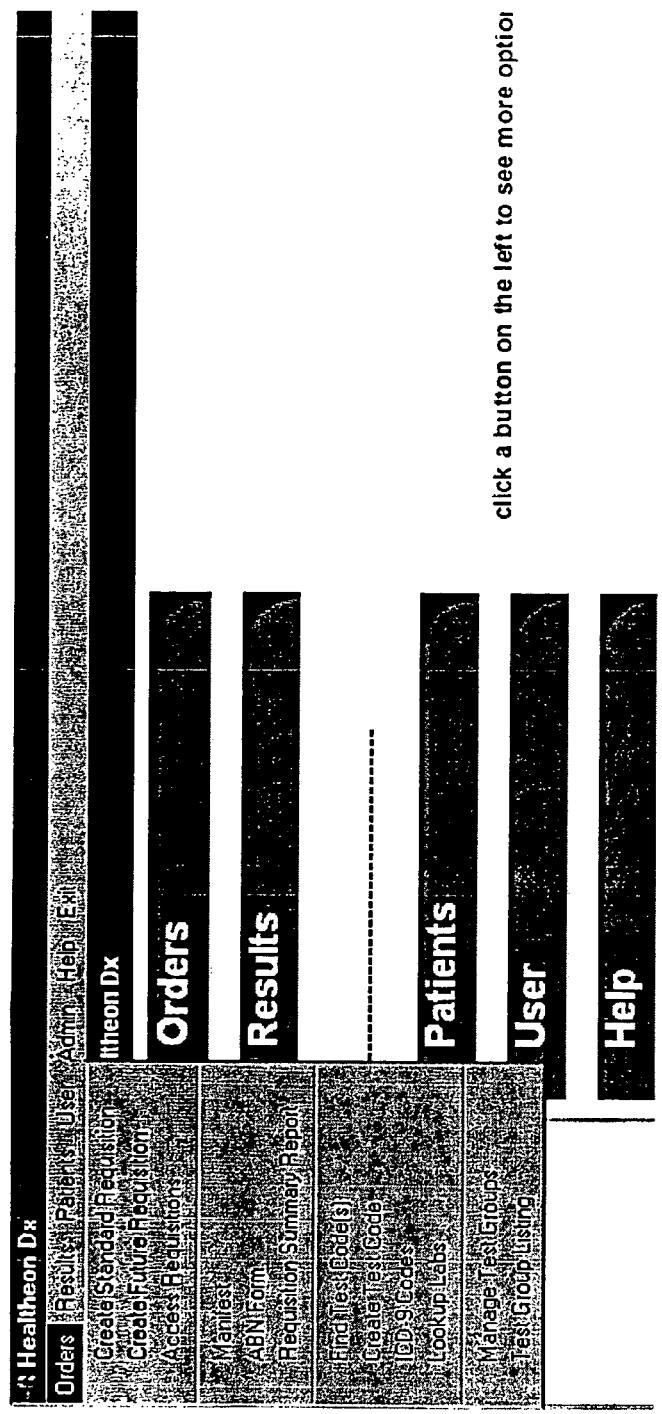
Figure 14:
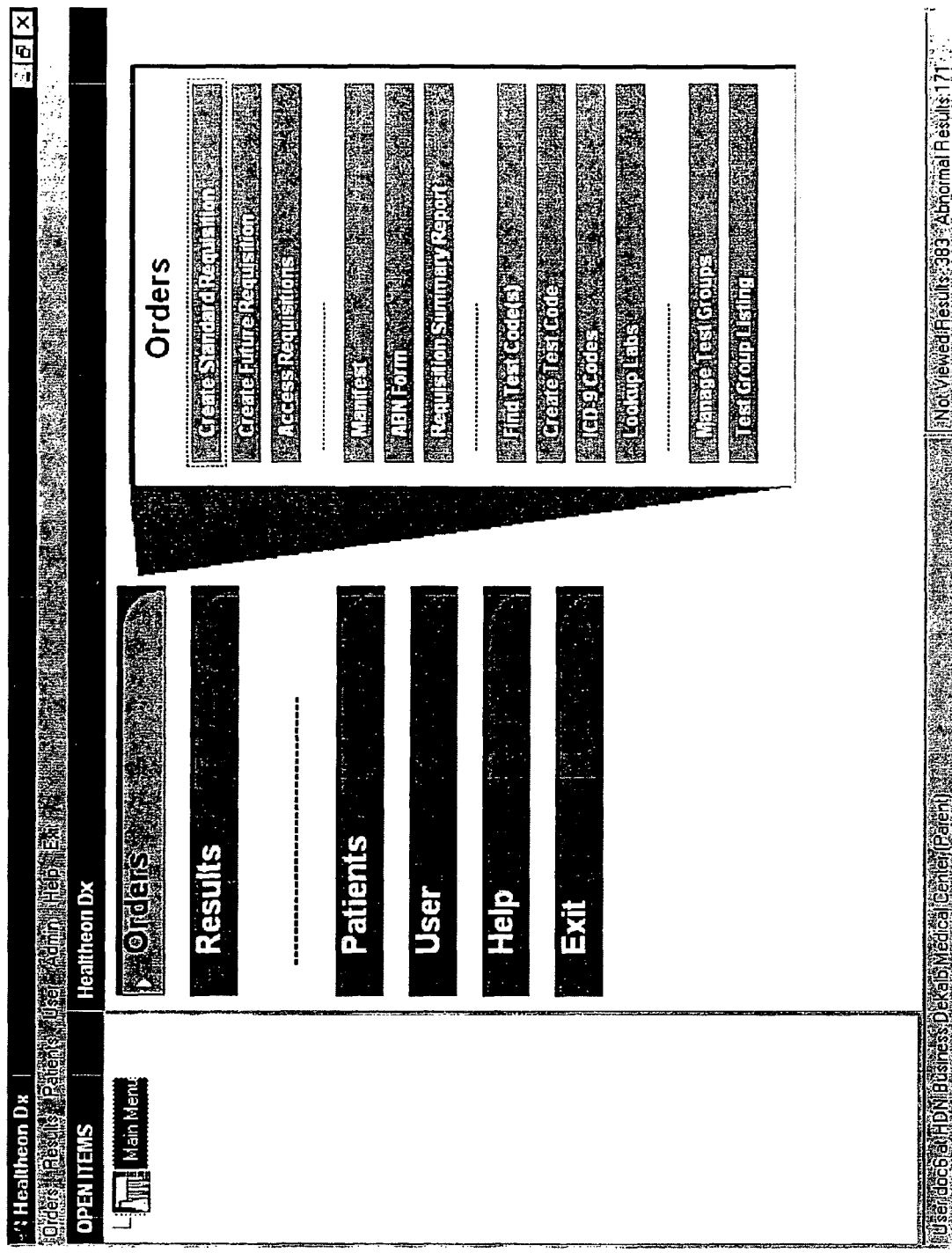

In one embodiment, there are twelve basic functions to the Orders module of the system:
  Create Standard Requisition
  Create Future Requisition
  Access Requisitions
  Manifest
  ABN Form
  Requisition Summary Report
  Find Test Codes
  Create Test Code
  ICD-9 Codes
  Lookup Labs
  Manage Test Groups
  Test Group Listing These functions may be accessed from the Orders drop-down menu, as shown in FIG. 13 or from the Orders desktop menu, as shown in FIG. 14. The Orders functions pertain to creating and managing lab orders. The Orders functions are described below.

Orders: Create Standard Requisition

The user creates a "standard" requisition when the patient is on site and a specimen can be obtained right away. Once the requisition is completed, it can be sent to the lab. When the user creates a standard requisition, a requisition number may automatically be generated by the system. If the user's system is configured for entering manual requisition numbers, the system may also generate a requisition number every time the user creates a new requisition, but the user has the option of changing the requisition number.

The Create Standard Requisition menu option enables the user to:
  Create a standard requisition for an existing patient.
  Create a standard requisition for a new patient.

Print or preview the requisition.

Delete the requisition.

Each standard requisition is divided into four pages of information as shown in the following table:

| Page Name | Includes... |
| --- | --- |
| General | Bill Type, patient demographics, and guarantor |
| Billing | Lab, primary care and referring physicians, ordering client information, collection date and time, and insurance |
| Test Codes | Diagnosis and test codes |
| Additional Info | Specimen information, lab instructions, comments, and a "Copy To" list. |

Figure 15:
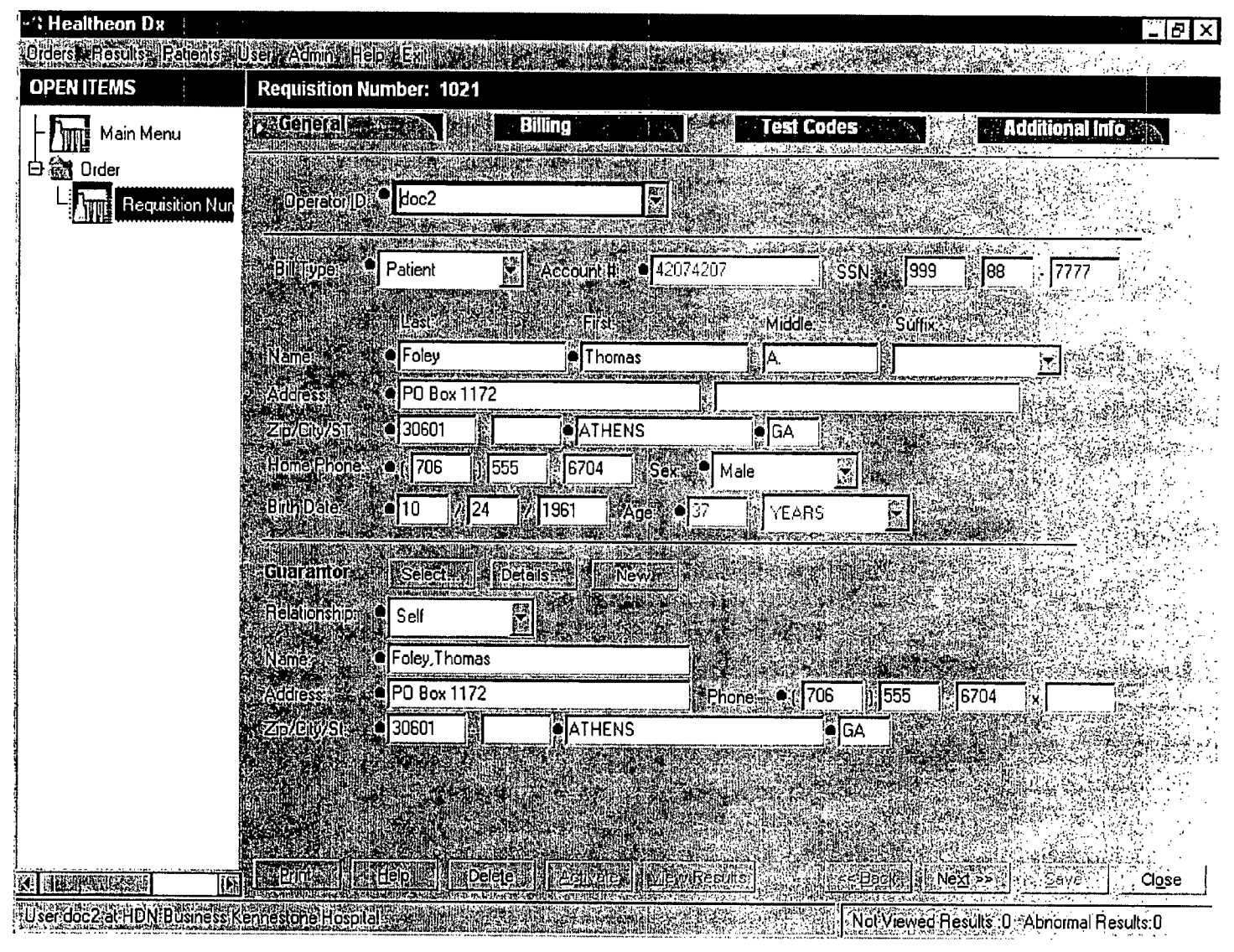

FIG. 15 illustrates the General page of the Requisition window. Each page may be accessed by clicking on the appropriate tab at the top of the window.

Creating a Requisition

Figure 16:
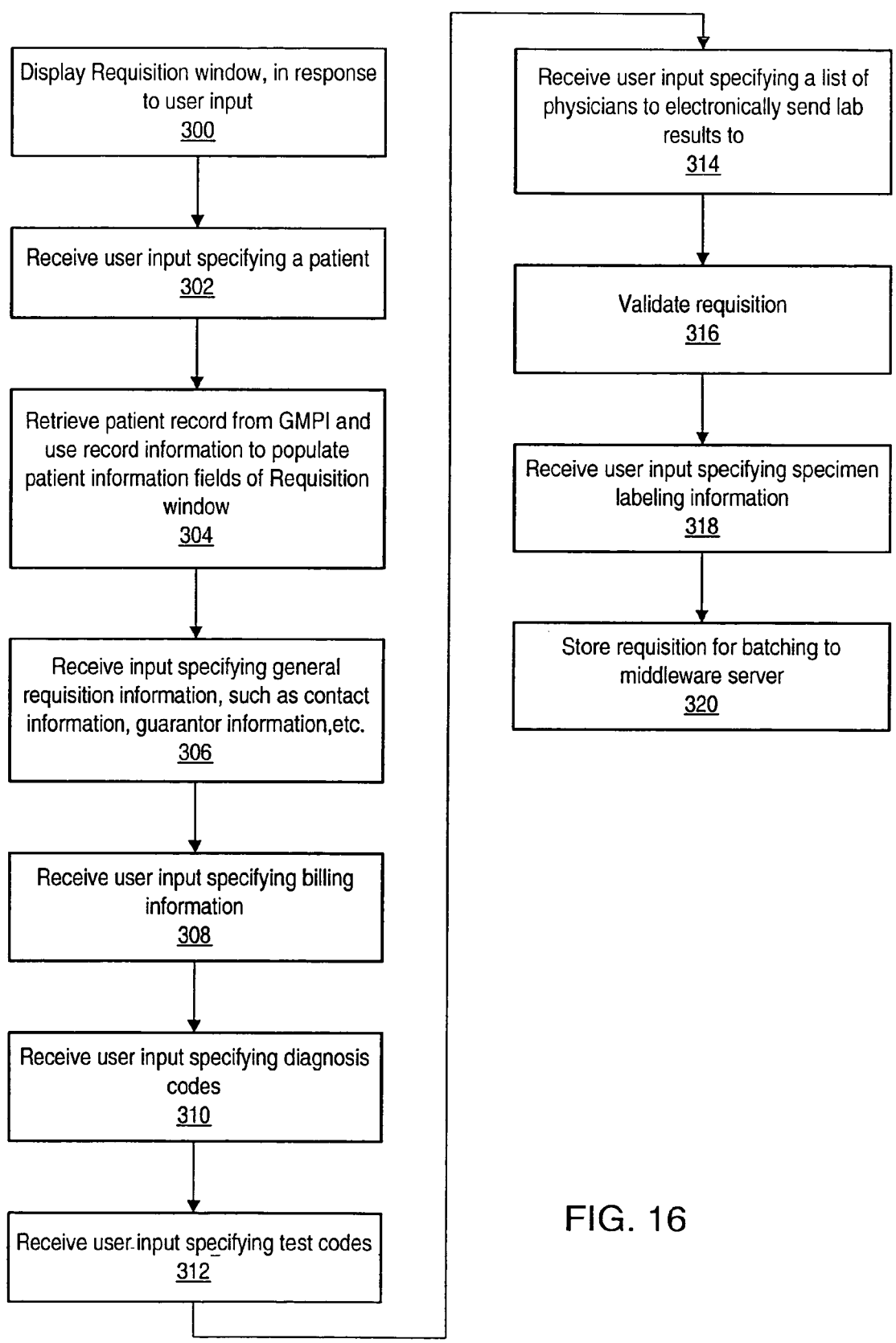

FIG. 16 is a flowchart diagram illustrating one embodiment of a method for creating a standard requisition.

In step 300 a Requisition window is displayed. The Requisition window includes fields for receiving user input specifying requisition information. In one embodiment, the Requisition window includes tabs for accessing a General page, a Billing page, a Test Codes page, and an Additional Info page, as described above.

Figure 17:

In step 302 user input specifying a patient is received. For example, FIG. 17 illustrates a Finding a Patient window. The patient may be found by various identifiers, such as the name or social security number, or a recently viewed patient may be chosen. If a requisition is to be created for a patient who does not yet have a patient record, then the user may create a new patient record. In one embodiment, the Finding a Patient window appears automatically in response to a request to create a requisition, before the Requisition window is displayed in step 300.

In step 304, the record for the specified patient is received, and the record information is used to populate patient information fields of the Requisition window. In one embodiment, the system may be operable to maintain a Global Master Patient Index (GMPI) that integrates patient record information for multiple Health Data Network Businesses. Thus, this GMPI information may be used in retrieving the appropriate patient record.

In step 306, user input specifying general requisition information is received, such as contact information for the patient, guarantor information, etc. FIG. 15 illustrates an exemplary user interface for receiving this general information, i.e., the General page of the Requisition window displayed in step 300.

The FIG. 15 user interface also includes a field for specifying a Bill type, such as client, patient, or third party. If a requisition was previously created for the specified patient, relative information from that requisition, such as the Bill Type, also populates the appropriate fields. Otherwise, the remaining fields are populated with the default values.

Figure 18:
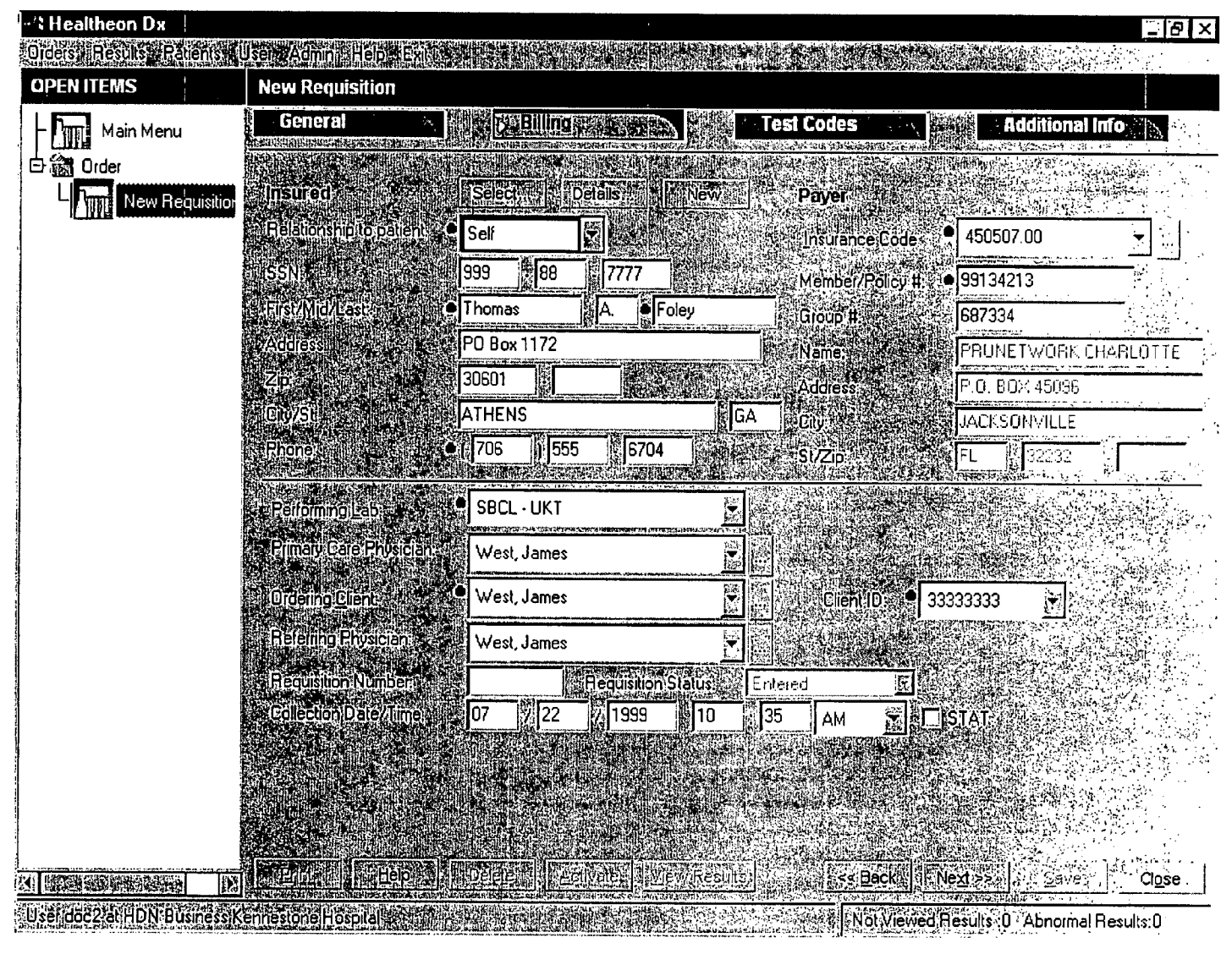

In step 308, user input specifying billing information for the requisition is received. FIG. 18 illustrates an exemplary user interface for receiving this billing information, i.e., the Billing page of the Requisition window displayed in step 300. In one embodiment, when the user moves from the General page to another page, such as the Billing page, any data the user has entered in the patient information fields is automatically saved in the patient's record. A message may appear, advising the user that all requisitions will now use the new patient information. In one embodiment, the user may be able to choose whether or not to modify the patient record in this way. It is noted that the fields included in the user interface that is displayed in step 308 may depend on the Bill Type chosen by the user.

Figure 19:
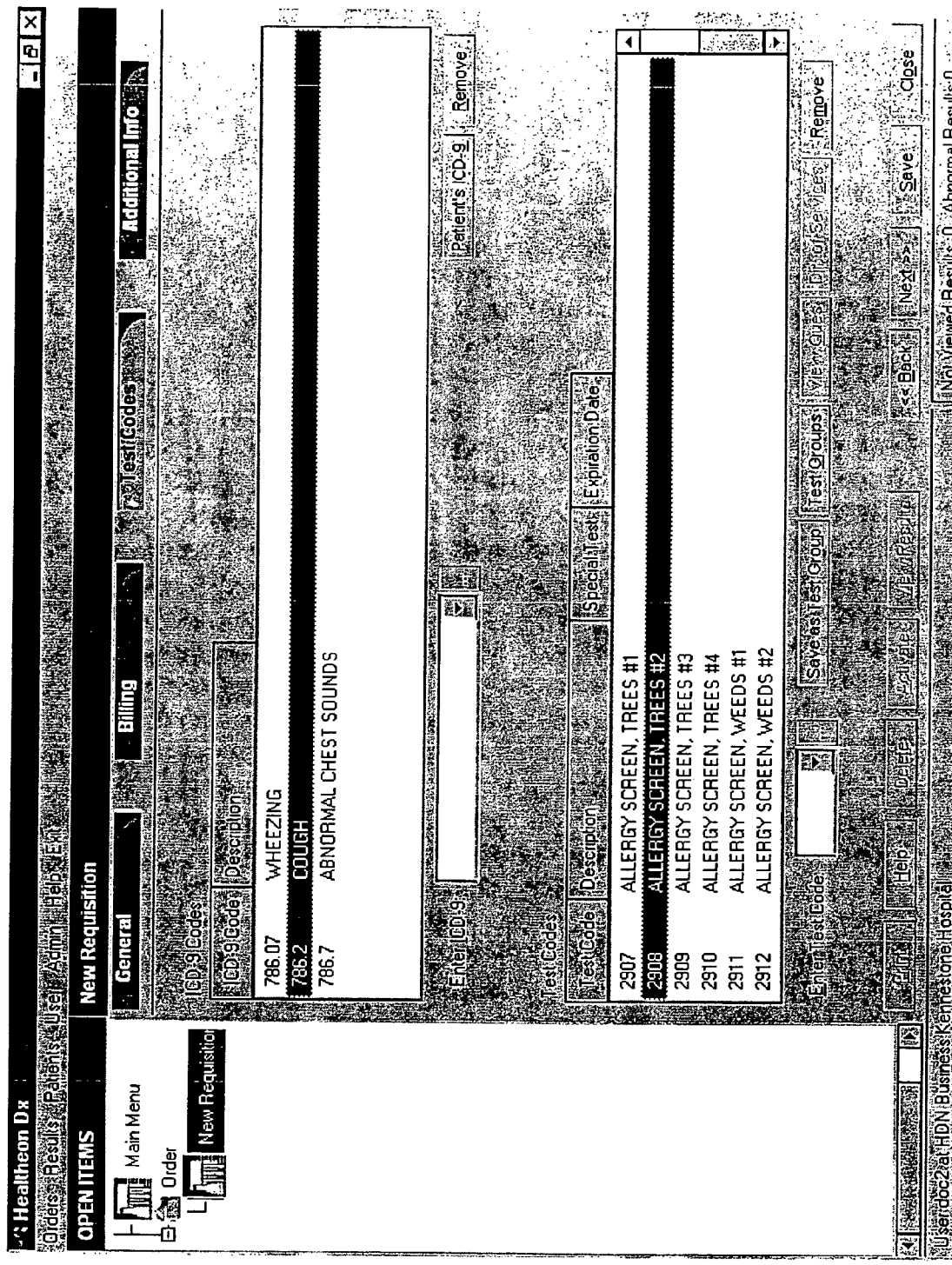

In step 310, user input specifying diagnosis codes for the requisition is received. FIG. 19 illustrates an exemplary user interface for receiving this diagnosis code information, i.e., the Test Codes page of the Requisition window displayed in step 300. The user may enter a list of diagnosis codes, such as ICD-9 codes that specify the caregiver's diagnosis for the patient.

In step 312, user input specifying test codes for the requisition is received. FIG. 19 illustrates an exemplary user interface for receiving this test code information, i.e., the Test Codes page of the Requisition window displayed in step 300. The user may enter a list of test codes specifying the desired lab tests to perform on the patient specimen(s).

Figure 20:
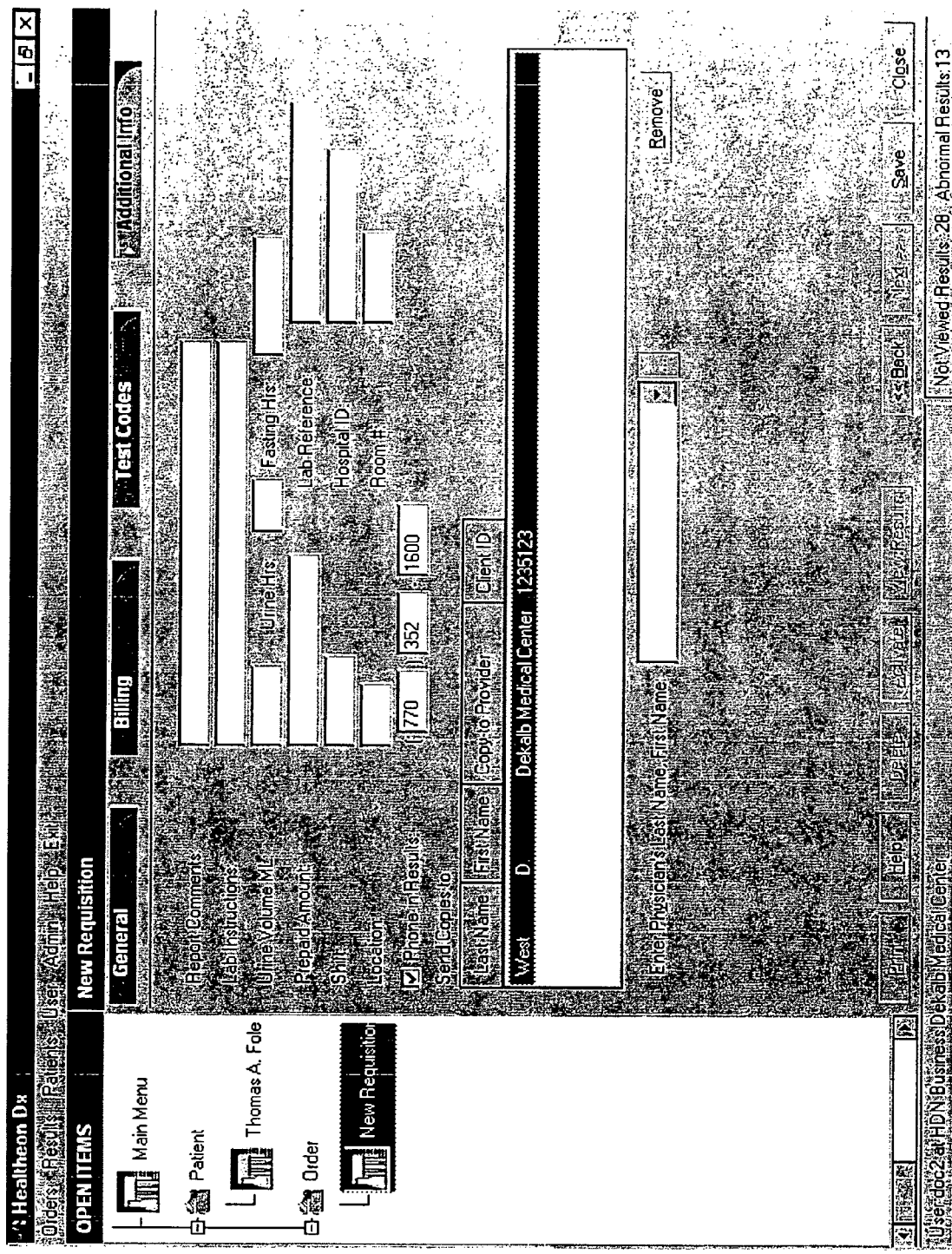

In step 314, user input specifying a list of caregivers to whom to electronically send the results of the lab tests is received. FIG. 20 illustrates an exemplary user interface for receiving this information, i.e., the Additional Info page of the Requisition window displayed in step 300.

As shown in the user interface of FIG. 20, user input specifying other information for the requisition may also be received, such as lab instructions, information regarding the patient specimens collected, etc.

In step 316, the requisition is validated by the system, e.g., in response to receiving user input specifying that the user is done entering information. If there are errors in the information entered for the requisition, an error message may appear, and the user may be required to correct the errors.

In one embodiment, when the bill type chosen is Third Party and the patient insurance is for a Medicare payer and the user selected a test code that is not LCP-compliant or FDA-approved, the ABN Dialog box appears.

If the patient has already signed an ABN Form, the user selects Yes next to The Patient has signed an ABN Form. The Patient Acknowledgment of Non-Covered Services statement will print at the bottom of the requisition.

If the patient has not already signed an ABN Form, the user selects No next to The Patient has signed an ABN Form. If the patient is in the user's office and can sign an ABN Form, the user selects Yes next to Patient Is Here to Sign an ABN form. The Patient Acknowledgment of Non-Covered Services statement will print at the bottom of the requisition. The user should then have the patient sign the statement.

Otherwise, the user selects No next to Patient Is Here to Sign an ABN form. If there are other medically appropriate diagnosis codes in the patient's chart for this date of service, then the user may specify Yes, and the requisition window appears, allowing the user to click on the Test Codes page and select appropriate ICD-9 Diagnosis Codes for the selected tests. Otherwise, the user specifies No, and an ABN Warning appears.

In step 318, user input specifying a number of specimen labels to print may be specified, and the system may then print the specimen labels. The specimen labels may include information from the requisition that facilitates efficient handling of the specimen.

In step 320, the requisition information may be stored. The user may later use the Access Requisitions option of the Orders menu to select and electronically send the requisitions, e.g., by interfacing with the middleware COS server 110 illustrated in FIG. 2.

Requisition Window Fields

The following sections describe fields for the four pages of the exemplary Requisition Window described above (i.e., the General page, Billing page, Test Codes page, and Additional Info page).

The procedure for entering the information on the pages of the Requisition window is determined by the bill type selected on the General page. In one embodiment, there are three possible bill types, as shown in the following table:

| Bill Type | The lab will bill . . . |
|---|---|
| Client | The client (provider or physician) ordering the tests |
| Patient | The patient's guarantor |
| Third Party | The patient's insurance |

If the user has previously created a requisition for the selected patient, the Bill Type field may be populated with the selection made on the last requisition. If the user has not previously created a requisition for the selected patient, the field may be populated with the default value for the HDN Business the user is logged into.

A bill type of Client means that the client will be billed for services rendered. No additional billing information will be required.

A bill type of Patient means that the patient will be billed for services rendered. The user will need to enter guarantor information for the patient on the Billing page.

A bill type of Third Party means that an insurer will be billed for services rendered. The user will need to enter insured and payer information on the Billing page.

Requisition—General Page

The General page includes basic patient demographic information, as well as a field for the Bill Type. As shown in FIG. 15, The following fields may be included on the General page: Account # (The patient's account number); Address; Age; Birth Date; City; First Name; Home Phone; Last Name; Middle Name; Operator ID (The identifier for the operator creating the requisition); Sex; SSN; State; Zip.

For various of the above fields, if the user selects an existing patient and the information exists in their record, the field may be automatically populated. Changes made to the field may also change the patient's existing record.

The General page also includes a set of fields for entering Guarantor information, e.g., for the name and contact information for the Guarantor. The fields are only active if the value in the Bill Type field is Patient. If the user has previously created requisitions for the selected patient where the Bill Type was set to Patient, the guarantor information from the last requisition may populate the fields. If the user has not previously created requisitions for the selected patient or if this is a new patient, the fields are blank. If the user selects an existing guarantor and the information exists in their record, the fields are automatically populated.

Requisition—Billing Page

The Billing page (see FIG. 18) includes a set of fields for entering patient insurance information. These fields are only active if the value in the Bill Type field on the General page is set to Third Party. If the user has previously created requisitions for the selected patient, the insurance information from the last requisition populates the fields. If the user has not previously created requisitions for the selected patient, these fields are blank.

Insured information fields—The Billing page may include a set of fields for information related to the Insured, such as: address, city, first name, last name, phone number, relationship (for specifying the patient's relationship to the insured), etc.

Payer information fields—The Billing page may include a set of fields for information related to the Payer, such as: address, city, group number (the group number of the policy for the selected patient insurance), insurance code (The identifying code for the payer), member/policy number (The member or policy number for the selected patient insurance), name (he name of the payer for the selected patient insurance), state, zip, etc.

Order information fields—The Billing page may also include selected order information, including Performing Lab, Requisition Status, Ordering Client, Client ID, and Referring Physician. If the user has previously created requisitions for the selected patient, the order information from the last requisition may populate the fields. If the user has not previously created requisitions for the selected patient, the fields are blank.

Before a physician or provider can order a test, they must be setup in the system. The Health Data Network (HDN) Business that is associated with the physician or provider must also be setup to do electronic transactions. Otherwise, when the user tries to find the name of the ordering physician, the system will not be able to locate it and a pop up window with the message "No records were found" will appear.

The ordering physician may or may not have a Client ID number. If the physician has a Client ID number, the system automatically displays that number in the Ordering Physician Client ID field. Otherwise, it displays the HDN Business Client ID. An administrator may be responsible for setting up the links between providers and caregivers and assigning Client IDs to those caregivers. These assignments are made through the Manage Security/HDN Businesses and Manage Businesses/Providers functions, which are accessed through the Admin menu, as described below.

The system may automatically generate and assign a unique requisition number to each new requisition. If the user's system is configured for entering manual requisition numbers, the user has the option of changing the requisition number. This requisition number appears displayed on the title bar of the patient window.

The billing information fields may include the following fields, as shown in FIG. 18:

| Field | Description |
|---|---|
| Client ID | The ordering physician lab client identifier. If the ordering physician does not have a specific lab client ID, the default client ID of the active HDN Business is used. |
| Collection Date/Time | The date and time when the sample was collected. |
| Ordering Client | The physician ordering the tests. The physician must be a lab client or associated with a provider who is a lab client. If the patient's Primary Care Physician is a lab client, this field is populated with that physician's name. |
| Performing Lab | The lab that will perform the tests. This field is automatically populated with the default lab set up for the active HDN Business. |
| Primary Care Physician | The Primary Care Physician for the patient. If the user selects a client physician as the patient's Primary Care Physician, that physician will be used as the default Ordering and Referring physician on the Order Info page. |

-continued

| Field | Description |
| --- | --- |
| Referring Physician | The physician that referred the patient to the ordering physician. The ordering physician is automatically used for this field. The referring physician does not have to be a client of the lab. |
| Requisition Number | The number assigned by the system for the requisition. |
| Requisition Status | The status of the requisition. The default status for a standard requisition is "entered". The default status for a future requisition is "inactive". |
| STAT | Checking this field indicates that the ordering physician wants STAT processing of this order |

Requisition—Test Codes Page

The Test Codes page (see FIG. 19) includes fields for entering laboratory test code information for the requisition, such as ICD-9 diagnosis codes and test codes.

ICD-9 stands for International Classification of Diseases version 9. ICD-9 coding is recommended for use in all clinical settings and is required for reporting diagnoses and diseases to all U.S. Public Health Service and Health Care Financing Administration programs. The user can retrieve ICD-9 and test codes from the user's Preferred List of codes by selecting Preferred List from the field control menu located next to the each input field.

The ICD-9 code list may include the following columns, as shown in FIG. 19:

Description The description of the ICD-9 Diagnosis Code

ICD-9 Code The ICD-9 Diagnosis Code

User Description A user-defined description for the ICD-9 Diagnosis Code

Test codes are used to specify what tests to perform on a patient. When the user prints or previews a requisition, the user will see the tests codes listed under the heading PROFILE/TESTS.

If a selected test code includes Ask-at-Order-Entry (AOE) questions, the first question in a series appears on the screen. The user may then answer the question and click Continue. Questions continue to appear until the user has answered them all. After the last question is answered, the Test Codes page appears.

If the user selects a PAP test, the PAP Information window appears. The user enters the appropriate information in each of the fields.

If the user attempts to add a test code that is already on the list, the Duplicate Found dialog box appears.

The test code list may include the following columns, as shown in FIG. 19:

| | |
| --- | --- |
| Description | The description of the test code |
| Expiration Date | The expiration date of the test code |
| Special Test | Indicates whether or not the specimen for the test code requires special handling |
| Test Code | The test code |

Requisition—Additional Info Page

The Additional Info page (see FIG. 20) includes fields for entering additional information regarding the requisition. The test codes the user selects on the Test Codes page, the Bill Type setting on the General page and the type of the active HDN Business (e.g., "physician practice" or "hospital") determines which of these fields is required For example, when the user orders a test that requires 24 hour urine samples, the user is asked a series of questions such as the patient's height, weight and urine volume. In this case, the user would complete these fields: Lab Instructions, Urine Volume ML, and Urine Hrs, and any other information relevant to the patient or test being performed.

The Additional Info page may include the following fields, as shown in FIG. 20:

| Field | Description |
| --- | --- |
| Fasting Hrs | The number of hours the patient fasted before the specimen was collected |
| Hospital ID | If the active HDN Business is a hospital, this is the hospital's identifier |
| Lab Instructions | These are specific instructions from the ordering physician to the lab for tests ordered |
| Lab Reference | The lab reference |
| Location | If the active HDN Business is a hospital and the patient has been admitted, this is the patient's location |
| Phone in Results | Selecting this field indicates that the ordering physician wants the lab to phone in the results, as well as return them electronically. In this field, the user must enter the phone number that the user wants the lab to call |
| Prepaid Amount | The amount the patient has prepaid for the tests ordered |
| Report Comments | This field is for any comments from the ordering physician that need to accompany the tests ordered |
| Room # | If the active HDN Business is a hospital and the patient has been admitted, this is the patient's room number |
| Send Copies to | This is a list of physicians that should be copied on the results. All physicians on this list must be a lab client or associated with an HDN Business that is a lab client |
| Shift | If the active HDN Business is a hospital and the patient has been admitted, this is the shift which collected the specimen |
| Urine Hrs | This is the number of hours for urine specimens |
| Urine Volume ML | This is the number of milliliters of urine collected for the tests |

Orders: Create Future Requisition

The Create Future Requisition menu option of the Orders menu enables the user to prepare a requisition before the patient arrives or the specimen is received. A future requisition can also be printed and given to a patient to take to a lab.

Future requisitions are stored in the system until the specimen is collected. When the user creates a future requisition, a requisition number is automatically generated by the system. If the user's system is configured for entering manual requisition numbers, the user has the option of changing the requisition number.

The distinction between standard and future requisition types exists to keep track of those requisitions whose specimens have not been collected yet. The system accomplishes this by assigning a different status to each type. When a standard requisition is created it has an Entered status. When a future requisition is entered its status is Inactive.

The Create Future Requisition menu option enables the user to:

Create a future requisition for an existing patient

Create a future requisition for a new patient

Print or preview the requisition

Delete the requisition

Activate the requisition, which tells the system that a future requisition can be sent to the lab for processing Each future requisition is divided into four pages of information, similar to the four pages described above with reference to standard requisitions. The procedure for entering the information on these pages is determined by the bill type selected on the Patient page. There are three possible bill types: Client, Patient, and Third Party.

At the bottom of every page in the Create Future Requisition function there is a row of buttons which correspond to the following functions:

| Button Names | Function |
| --- | --- |
| Print | Opens the Print dialog, allowing the user to print the requisition and specimen labels. |
| Help | Opens the help topic for the current active page. |
| Delete | Deletes the requisition. |
| Activate | Activates the requisition (changes the status from "inactive" to "entered") so that it may be sent. |
| <<Back | Moves to the previous page of the requisition. |
| Next>> | Moves to the next page of the requisition. |
| Save | Saves the requisition. The user cannot save a requisition until all the required fields are complete. |
| Close | Closes the requisition. |

Creating a future requisition follows a similar procedure as described above for creating standard requisitions. As needed, the user activates future requisitions through the Access Requisitions option of the Orders menu.

Orders: Access Requisitions

The Access Requisitions menu option of the Orders menu enables the user to keep track of all the requisitions generated from the user's office and their current status. From the Access Requisitions menu option the user can:
  View a list of requisitions
  View all details of a requisition
  Modify a requisition
  Print a list of requisitions
  Print details of a requisition
  Delete a requisition if it has not been sent to a lab
  Send one or more requisitions
  Send all requisitions The user can find requisitions by using requisition information or by using patient information. Each method enables the user to use different parameters to narrow down the results of the user's search. For example, the user may want to generate a list of all the entered requisitions whose specimens were collected within a certain time period, or the user may want to obtain a list of all the requisitions that were ordered by a physician for a patient. Also, there may be times when the user needs to add more information to an existing requisition that has not been transmitted to a lab yet, as in the case where a doctor requests an additional test for a patient or the user needs to change information on the patient's insurance coverage. In both cases, the user would search for the requisition, make the required changes to it and then save it. A doctor may also decide to cancel a requisition, in which case, the user would delete that requisition because it is no longer needed.

Figure 21:
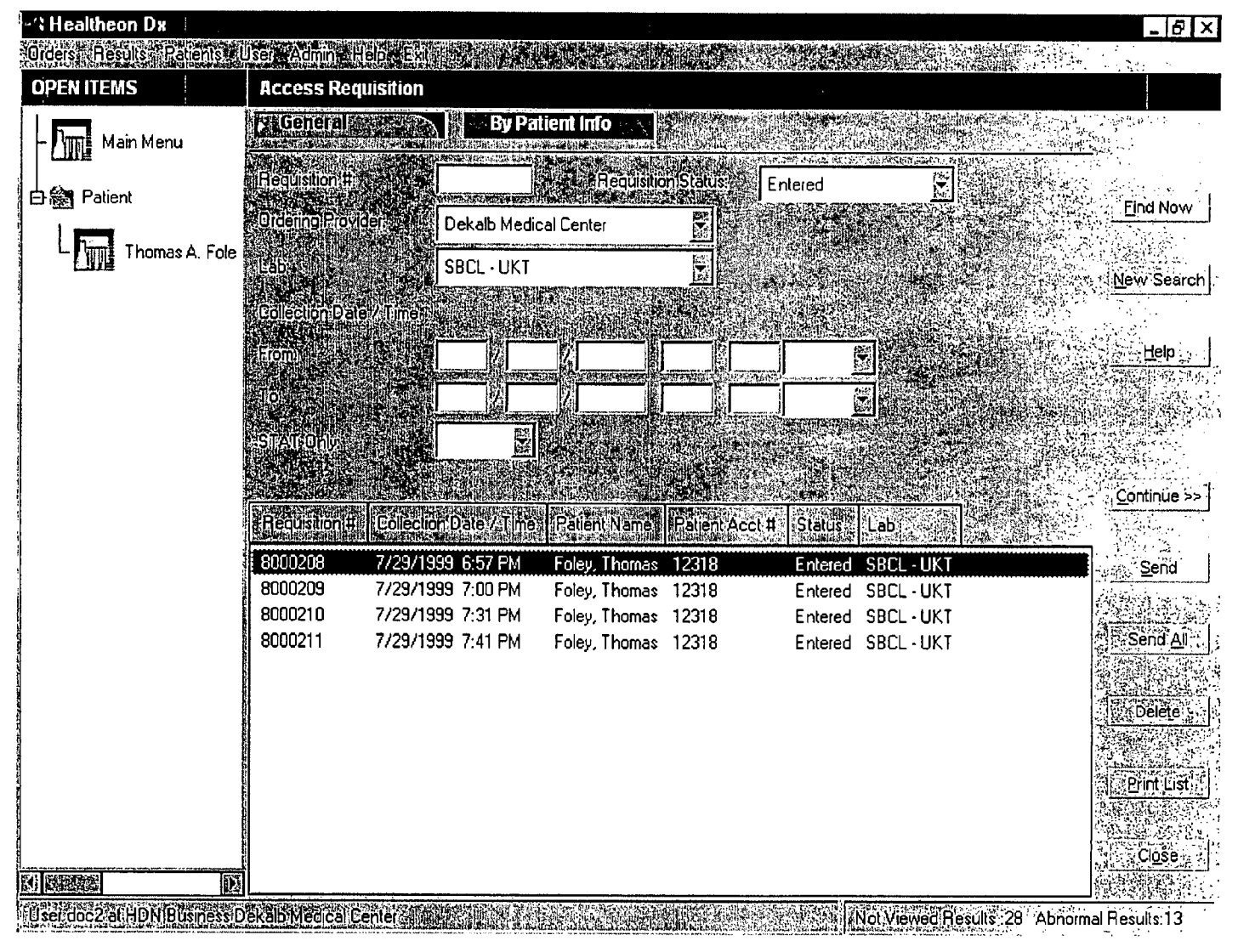

From the General page, the user can find a requisition using one or more of the following search criteria: Requisition #; Requisition Status; Ordering Provider, Lab; Collection Date Range; and Stat Only. FIG. 21 illustrates the General page of the Access Requisitions window.

From the page labeled By Patient Info, the user can find a requisition using one or more of the following search criteria: Patient; Ordering Physician; Referring Physician; Bill Type; Client ID; and Anonymous Requisition.

The user can generate a list of requisitions stored in the system by specifying at least one of the search parameters in the Access Requisition window. Requisitions can be modified and/or deleted as long as they have not been sent to the lab for processing. The requisition status indicates whether a requisition has already been transmitted.

Orders: Manifest

The Manifest menu option of the Orders menu enables the user to generate a manifest manually for those cases where the original manifest may be misplaced or if the user just wants to have an extra copy of the manifest for the user's records. A manifest is used by the submitting client to verify that all specimens are accounted for. The manifest lists all the tests ordered on each requisition, and it provides a convenient means for both the courier, who picks up the specimens, and the receiving laboratory to verify that the correct number of specimens and requisitions is received.

Figure 22:
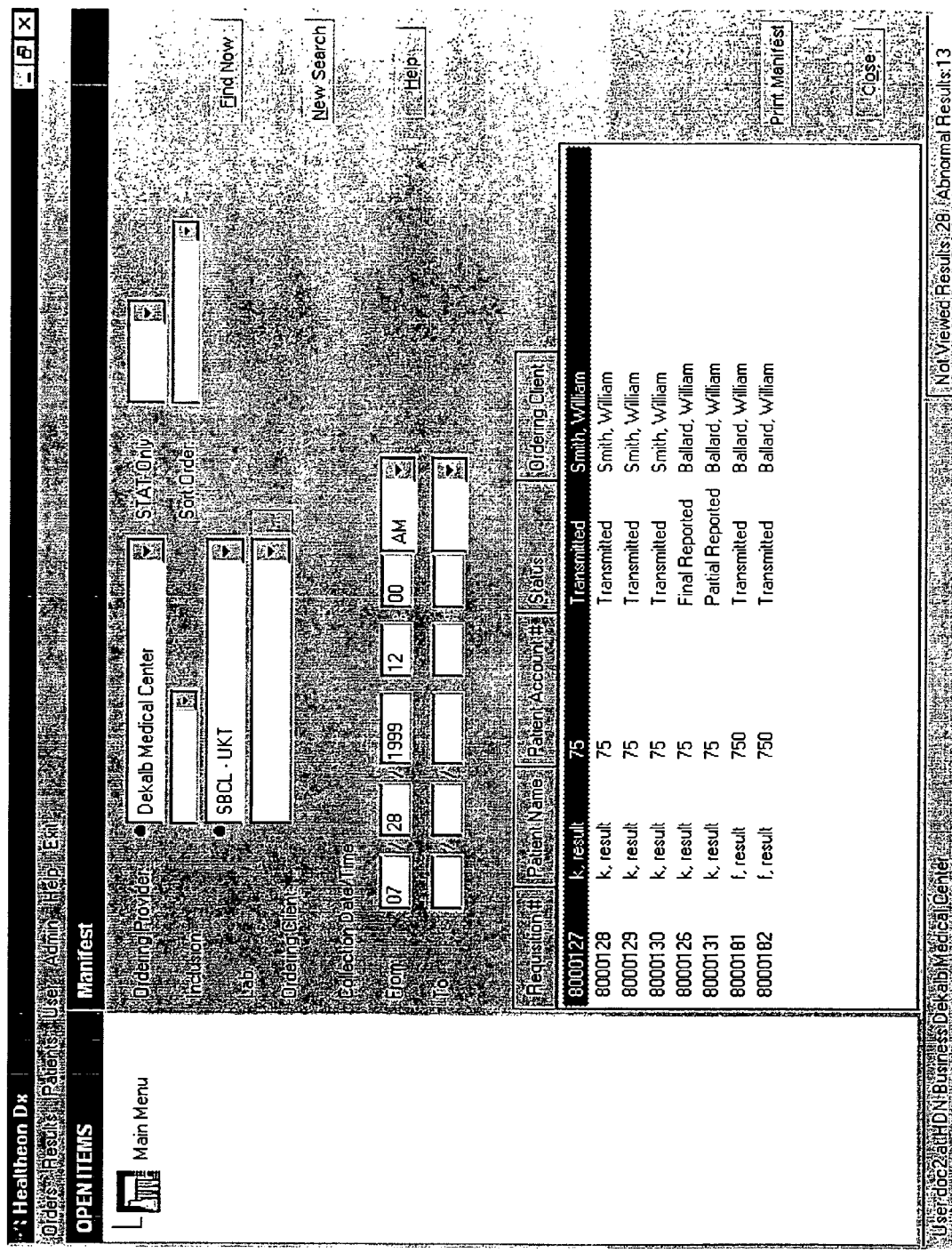

The Manifest window is shown in FIG. 22. Clicking the Find Now button on the Manifest window without specifying any search criteria generates a listing of all requisitions with a 'Transmitted' status in the user's active HDN Business. The user can narrow down the results list by specifying one or more of the following search criteria: Stat Only; Inclusion; Sort Order; and Collection Date/Time Range.

The search results appear listed under the following column headings: Requisition No.; Patient Name; Patient Account #; Status; and Ordering Client. When the results of the user's search appear on the Manifest window, the user can selectively highlight those requisitions the user wants to include on the manifest. A manifest can be previewed or printed. The first page of the report is a header page that shows the name of the ordering provider and the search criteria that were used to generate the manifest. The rest of the report displays a list of all the requisitions in the manifest under the following column headings:
  Control #
  Pat. Account
  Patient Name
  Age
  Sex
  Hosp ID
  Lab Ref.
  Collection Date/Time
  Urine Vol. & Hrs.
  Test
  Operator ID
  Results Received Orders: ABN Form The ABN Form menu option enables the user to access an Advanced Beneficiary Notice (ABN) Form. An Advanced Beneficiary Notice is a printed statement that contains a list of tests not covered by the payer. By signing an ABN form, the patient or the insured accepts financial responsibility for those tests that are not covered by the payer. For example, Medicare has limited coverage. An ABN form is generated when the user enters information on the Requisition Test Codes page. If the test code the user enters is for a limited coverage test and the diagnosis code is not approved to cover that test, the system prompts the user to answer questions pertaining to the ABN and have the patient sign the statement that is printed at the bottom of the requisition.

The only search criteria required to generate this form is the payer or insurance company name. An optional header page can be included as the first page in the report showing:
- Date and time when the form is printed
- Name of the user generating the form
- Comment line
- Search criteria used to generate the form Once the ABN form is complete and signed by the patient, a copy of it can be sent to the lab along with the accompanying requisition and specimen.

Figure 23:
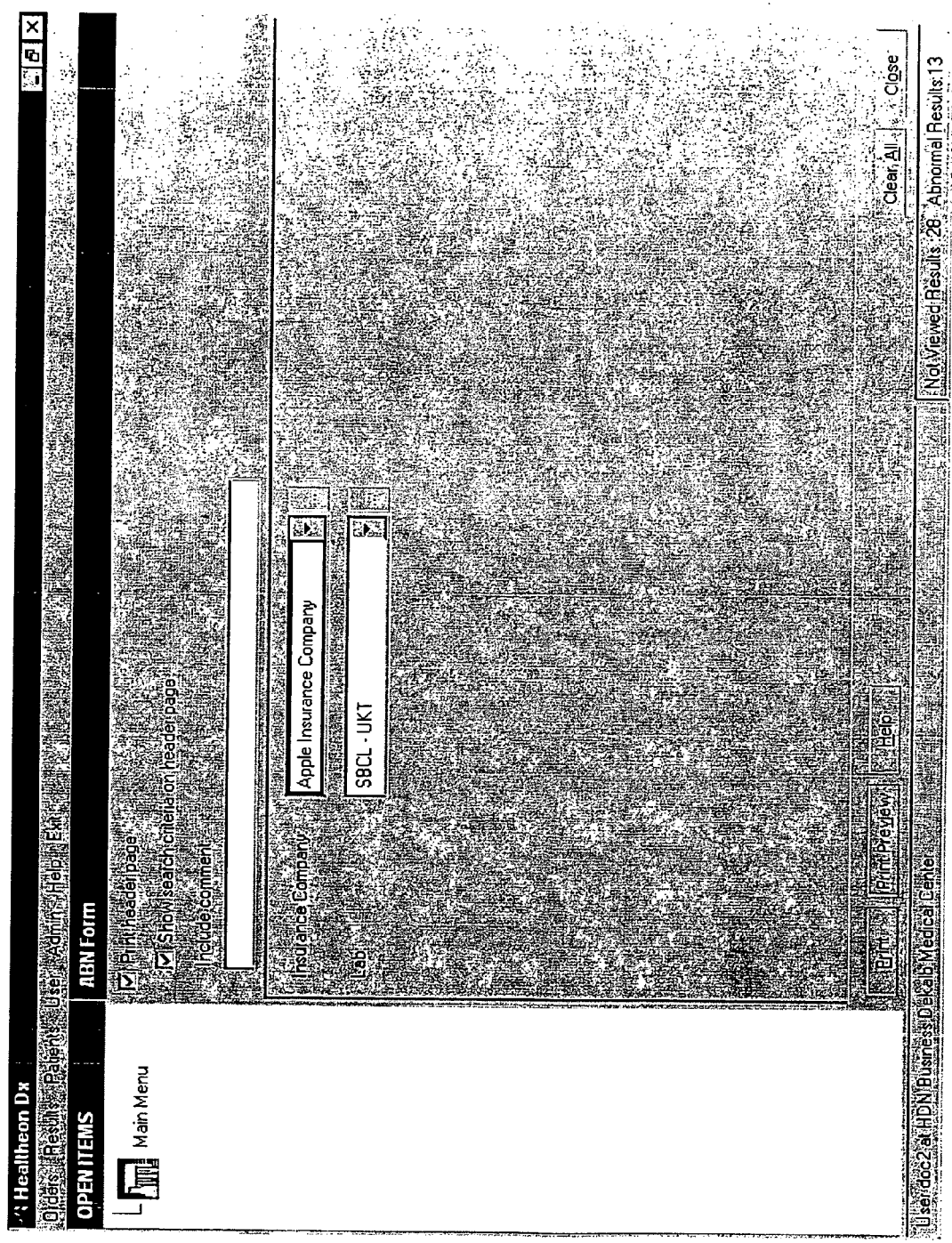
Figure 24:
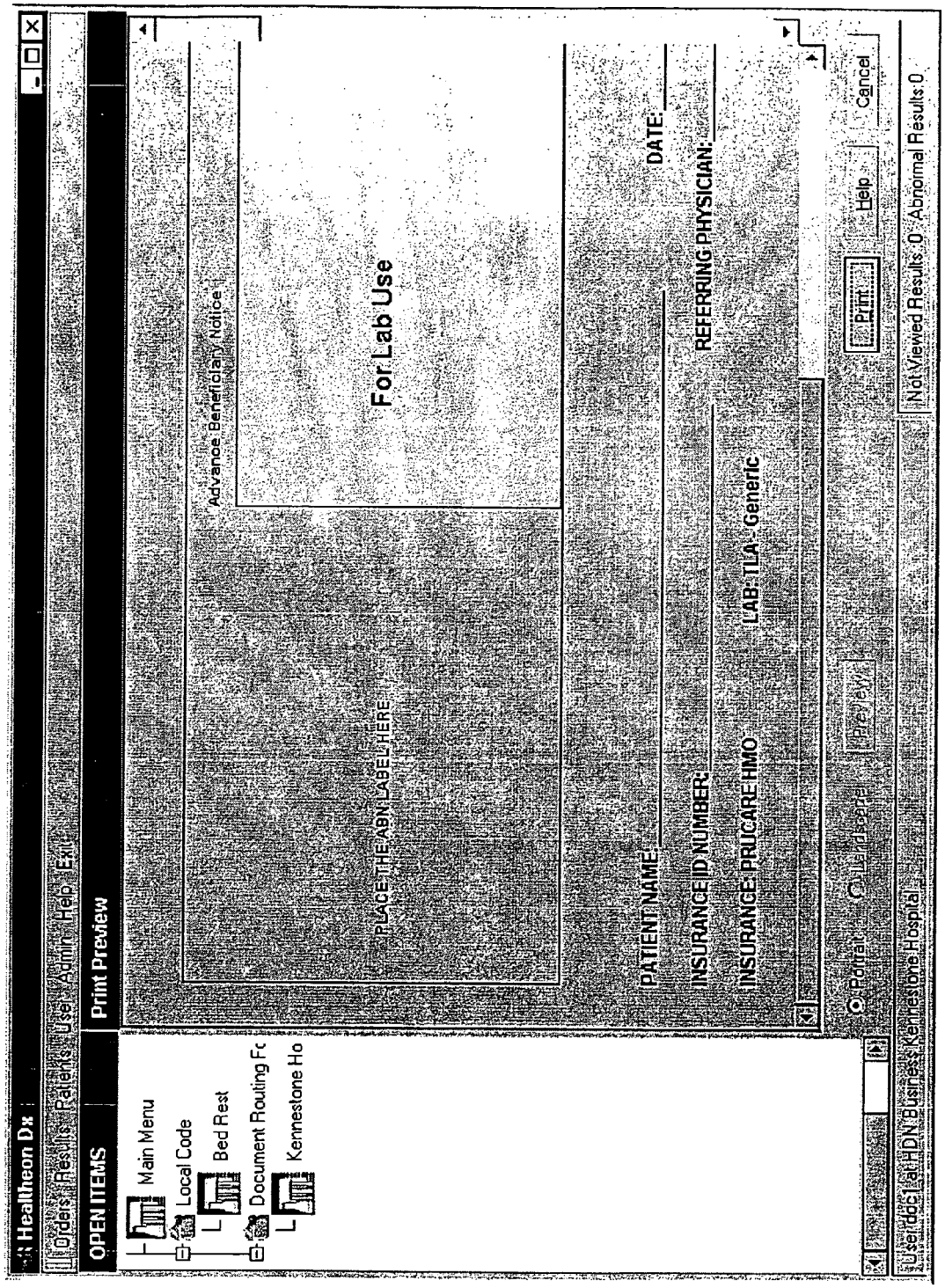

FIG. 23 illustrates the ABN Form window. A print preview of the ABN form may be displayed. FIG. 24 illustrates the ABN Form Print Preview window.

Orders: Requisition Summary Report

The Requisition Summary Report menu option of the Orders menu enables the user to generate a list of requisitions for any date range, patient, ordering physician and requisition status The user can also get a listing of all requisitions by just running the report without specifying any of these search parameters. However, without specifying some search criteria the report may be very large.

Figure 25:
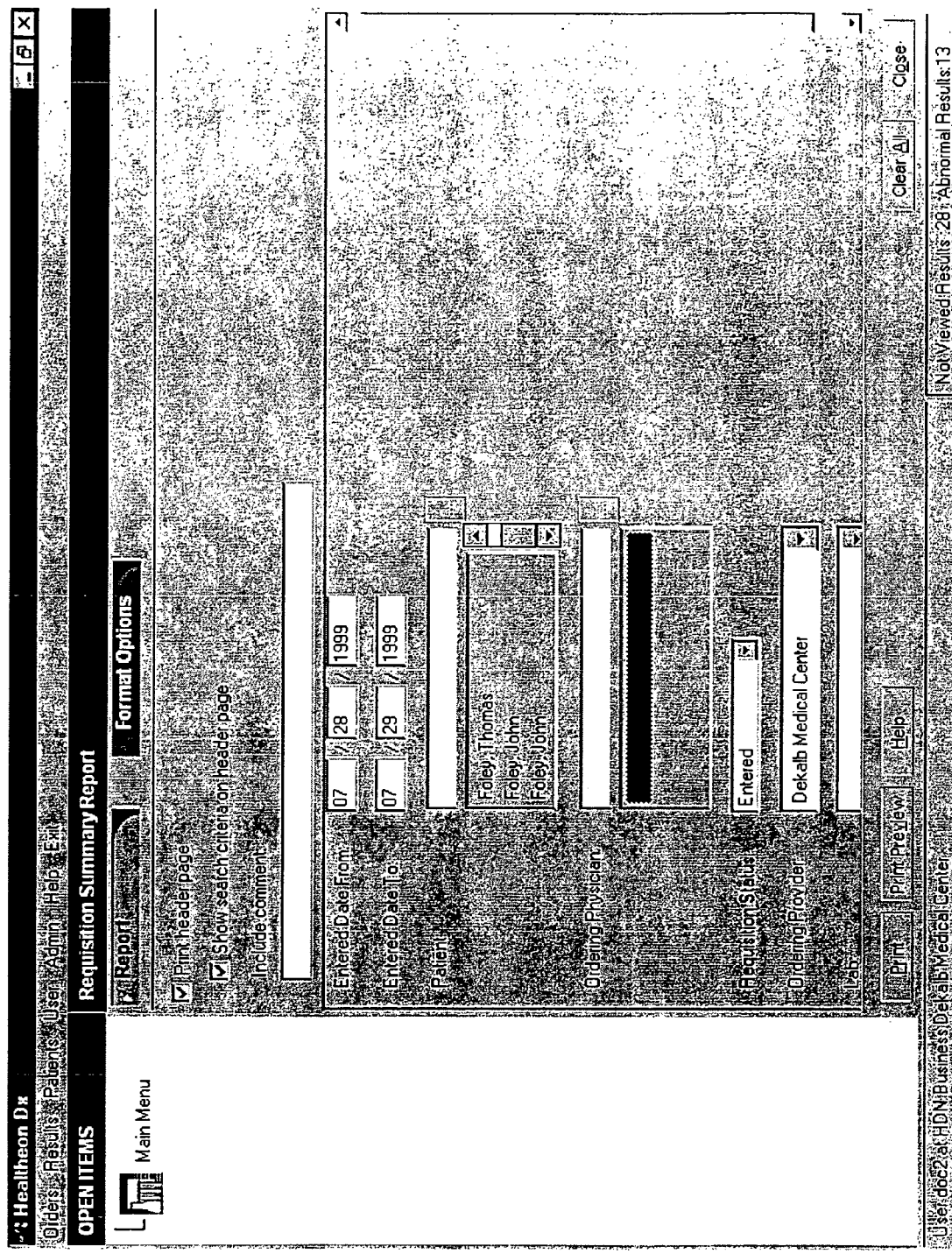
Figure 26:
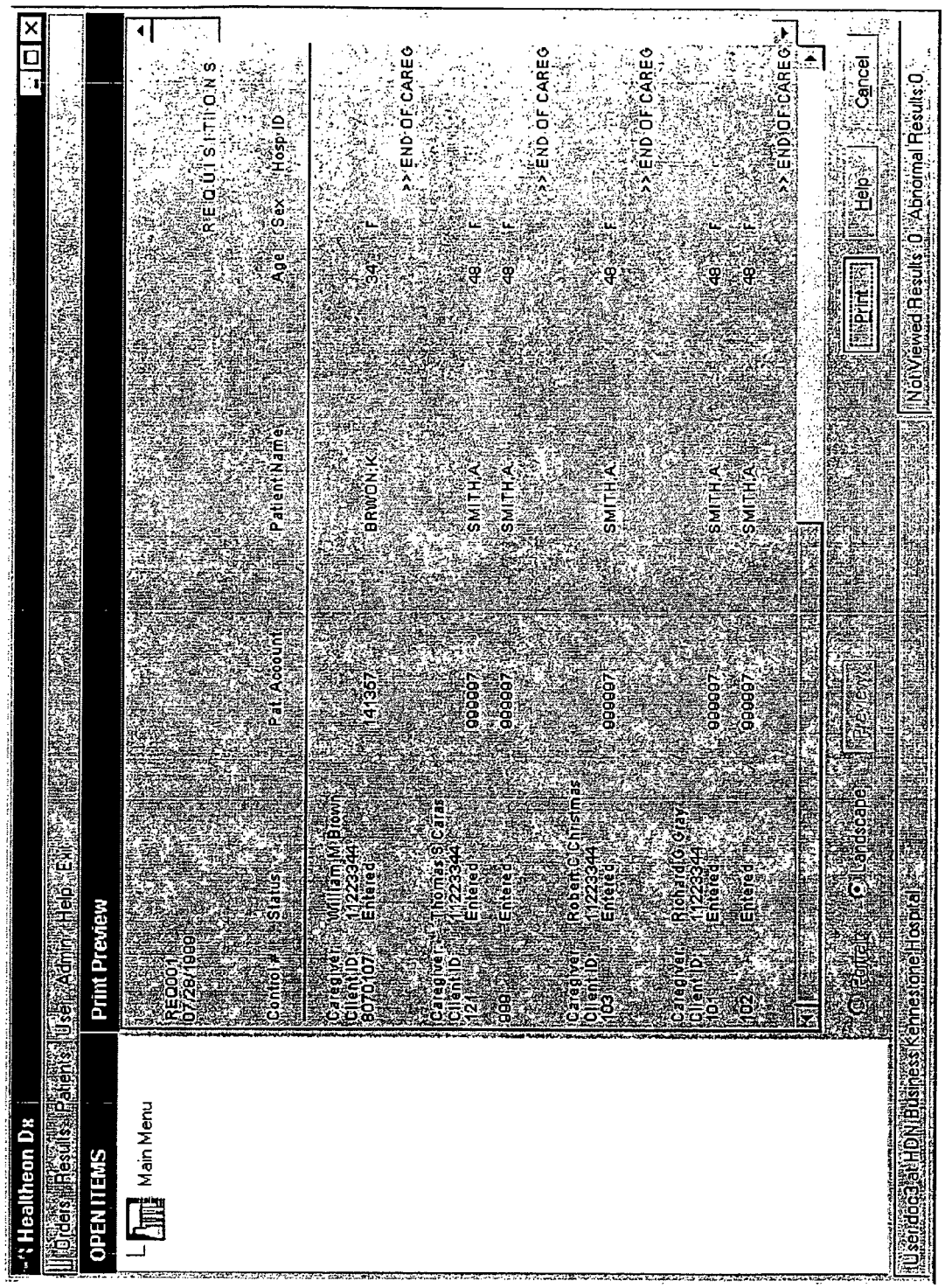

The Report page, shown in FIG. 25, lets the user specify a header page as a configurable option. The header pages shows:
- Date and time of the report
- Name of the user running the report
- Comment line
- Search criteria used to generate the report The Format Options page lets the user specify how the user want the report to be sorted. The report can be sorted by:
- Patient Last Name
- Requisition Number
- Patient Account Number The Requisition Summary Report can be either previewed or printed. FIG. 26 illustrates the Requisition Summary Print Preview window. The report is printed and displayed in landscape mode with the following column headings:
- Control # (same as Requisition #)
- Status
- Pat. Account
- Patient Name
- Age
- Sex
- Hospital ID
- Lab Reference
- Collection Date/Time
- Test
- Description In addition, the system prints each ordering physician's full name and Client ID at the beginning of each page in the report.

Orders: Find Test Codes

Figure 27:
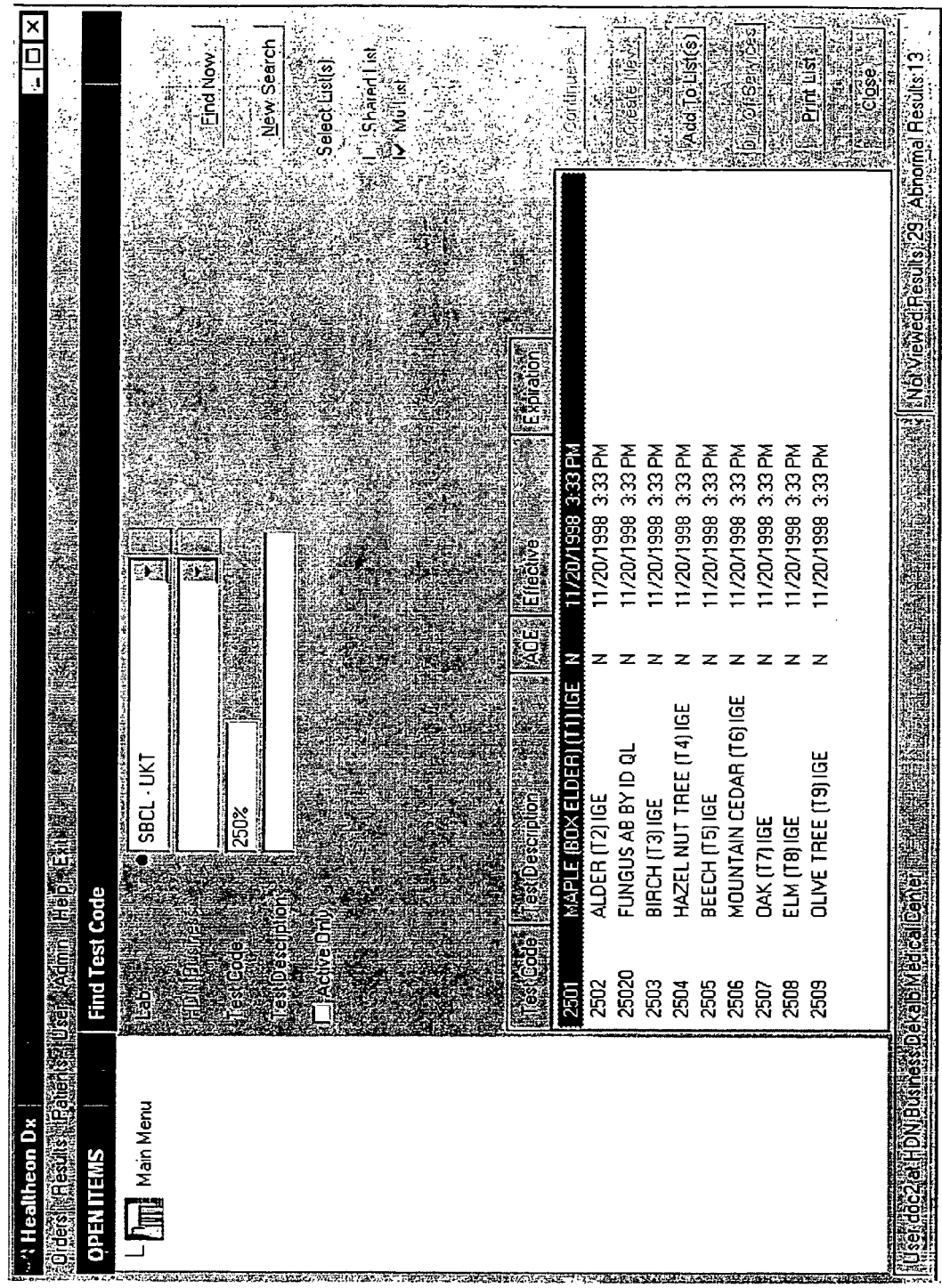

The Find Test Codes menu option of the Orders menu allows the user to locate test codes for labs. When selected, the Find Test Codes window appears, as shown in FIG. 27. The user can enter the search criteria needed to best locate the test code the user wants to find and click Find Now to perform the search. The results appear in the list at the bottom of the window. The user can then locate and select the test code(s) the user wants to use. The user can also add test codes to a Preferred List of Test Codes.

Orders: Create Test Code

Figure 28:
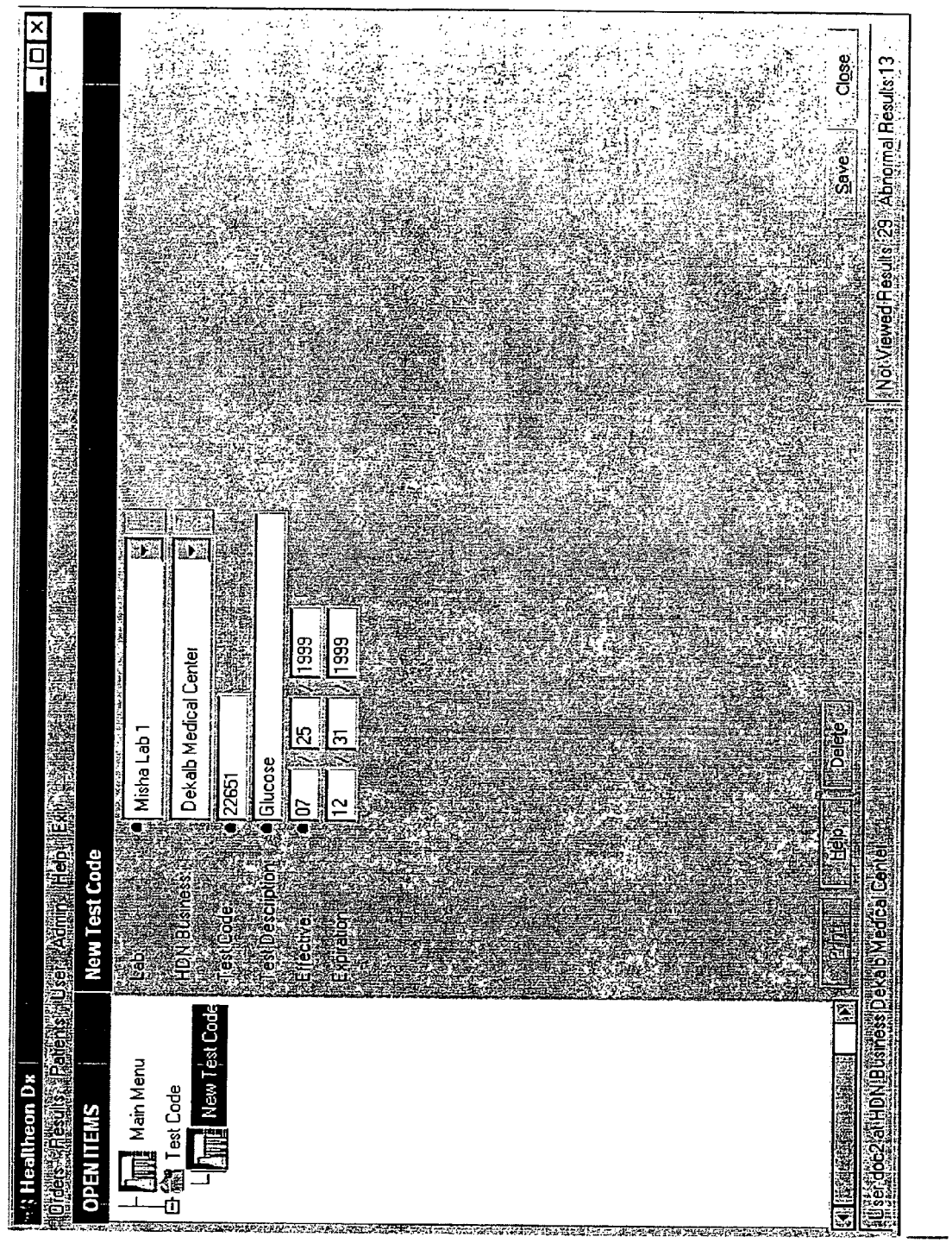

The Create Test Code menu option of the Orders menu allows the user to create new test codes for labs. When selected, a blank Test Code Details window appears, as shown in FIG. 28, allowing the user to fill in the fields to create a new test code.

Orders: ICD-9 Codes

Figure 29:
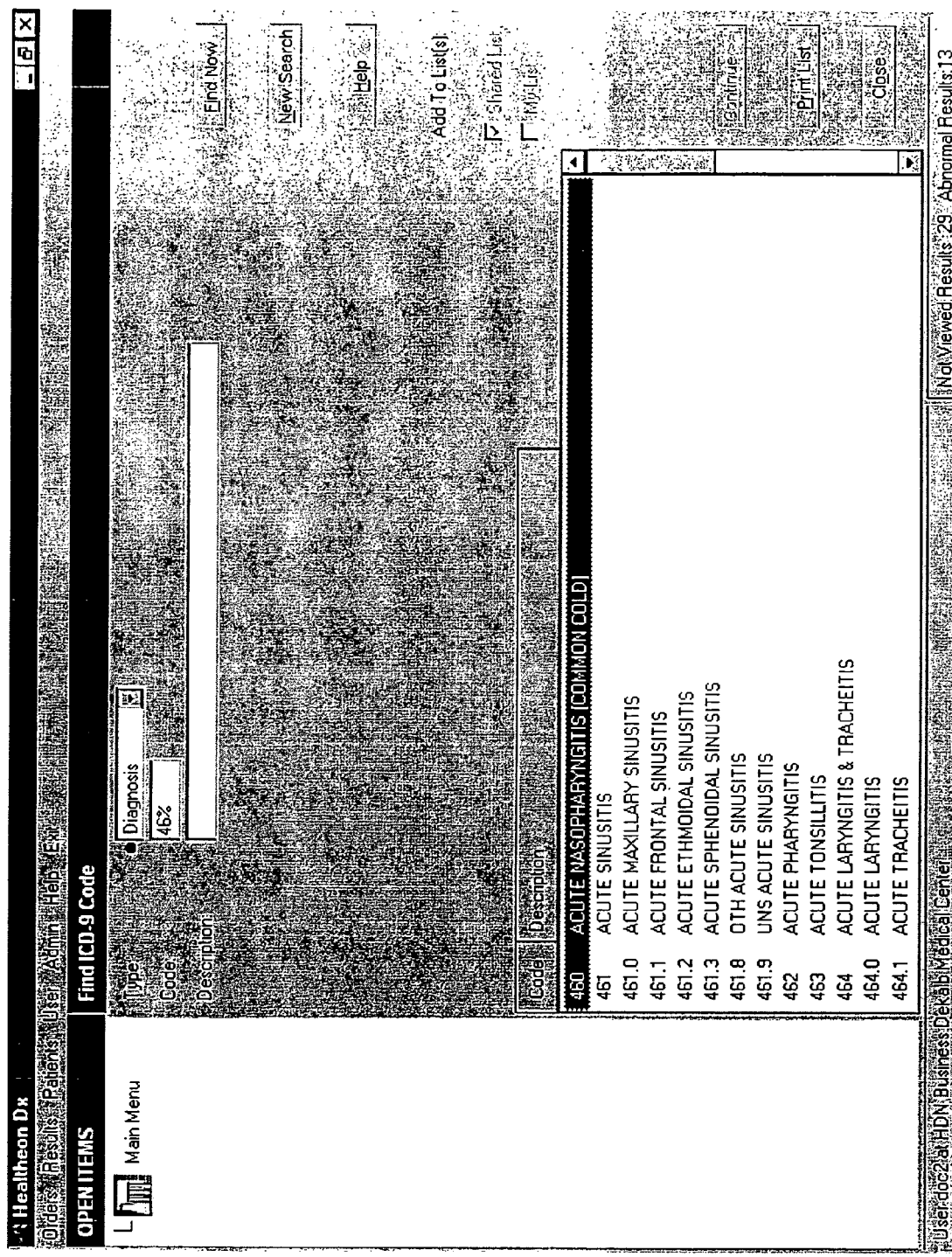

The ICD-9 Codes menu option of the Orders menu allows the user to locate ICD-9 codes. When selected, the Find ICD-9 Code window appears, as shown in FIG. 29. The user can enter the search criteria needed to best locate the ICD-9 code(s) the user wants to find and click Find Now to perform the search. The results appear in the list at the bottom of the window. The user can then locate and select the ICD-9(s) the user wants to use. The user can also add ICD-9 codes to a Preferred List of ICD-9 Codes.

Orders: Lookup Labs

Figure 30:
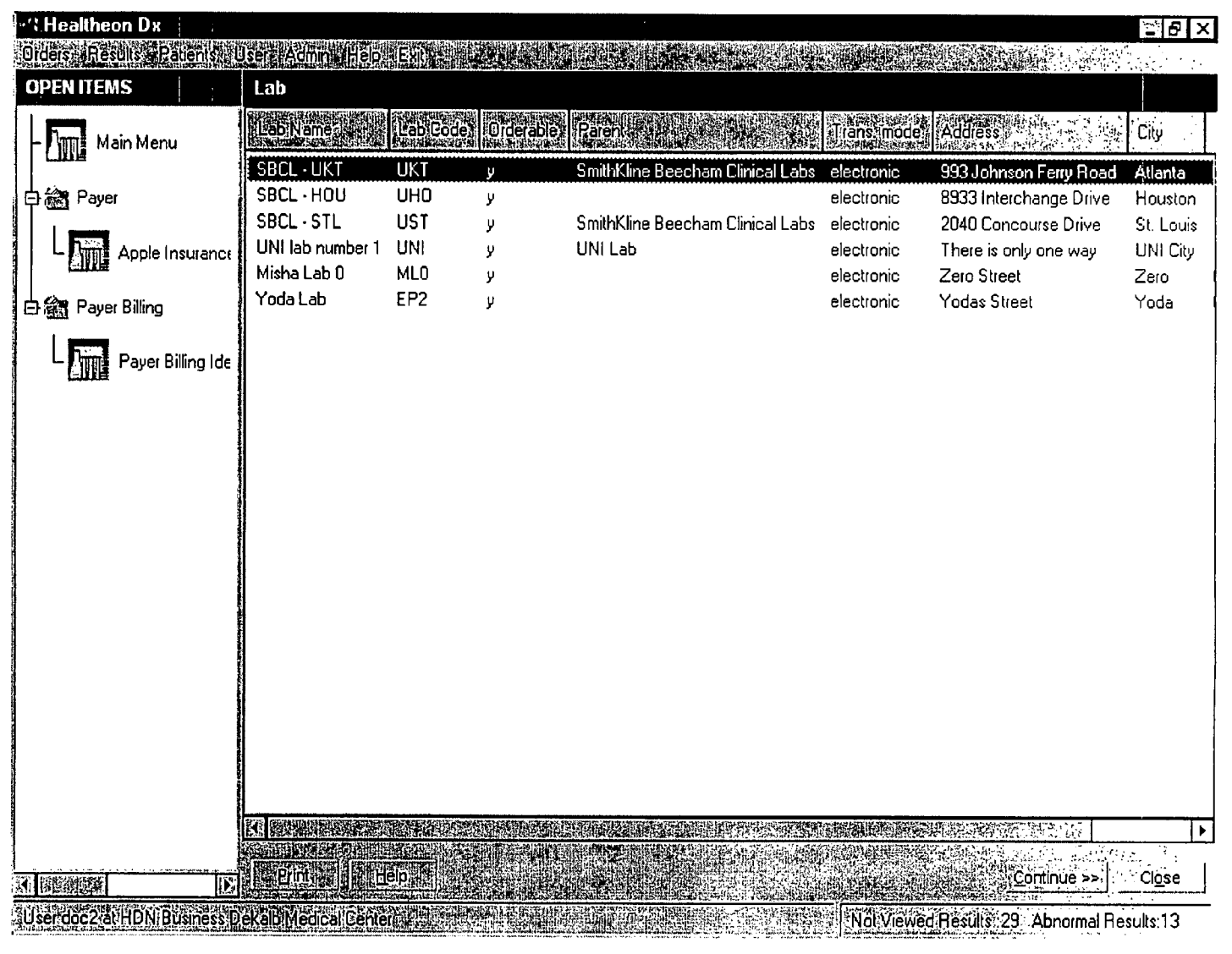

The Lookup Labs menu option of the Orders menu allows the user to locate and select labs available for the user's use, e.g., to electronically send requisitions to the labs. When selected, the Lookup Labs window appears, as shown in FIG. 30. The user can click the Lab field control button and choose Select to display a list of available labs.

Orders: Manage Test Groups

The Manage Test Groups menu option of the Orders menu allows multiple tests to be grouped together for the purpose of ordering. Each test group is identified by a code and includes multiple tests. Being able to enter test group codes instead of individual test codes saves the user time and promotes accuracy when creating a requisition, e.g., by preventing erroneous test code from being entered and ensuring that required codes are not forgotten.

Test Groups also help the user simplify the task of creating requisitions by enabling the user to work with only those test codes that are specific to a group of patients in the user's practice. For example, the tests performed in an allergy/immunology practice will more than likely differ from those performed at an office specializing in cardiovascular diseases. Also, there may be multiple physicians in a practice, and each physician may handle specific types of patients who require different types of tests.

Figure 31:
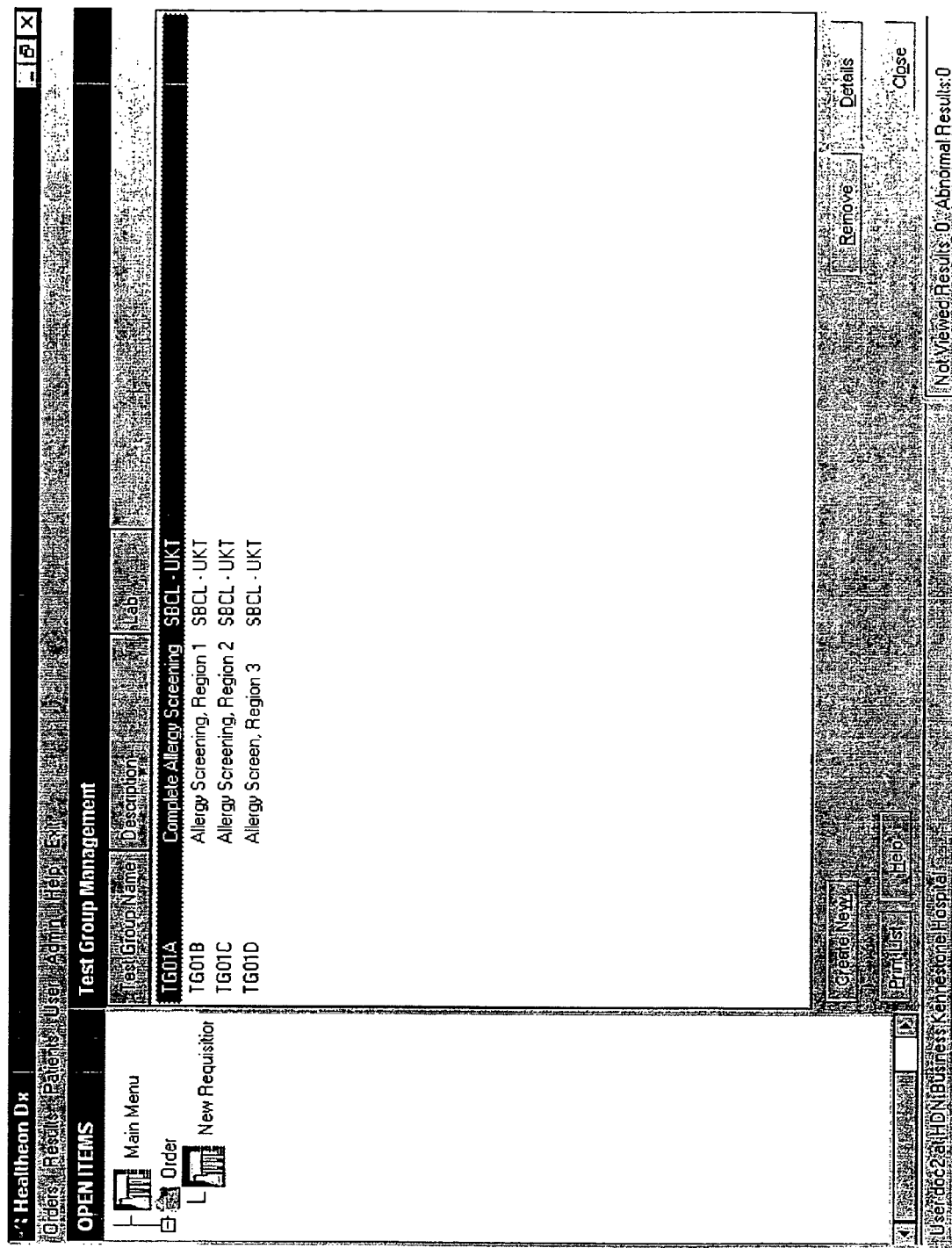
Figure 32:
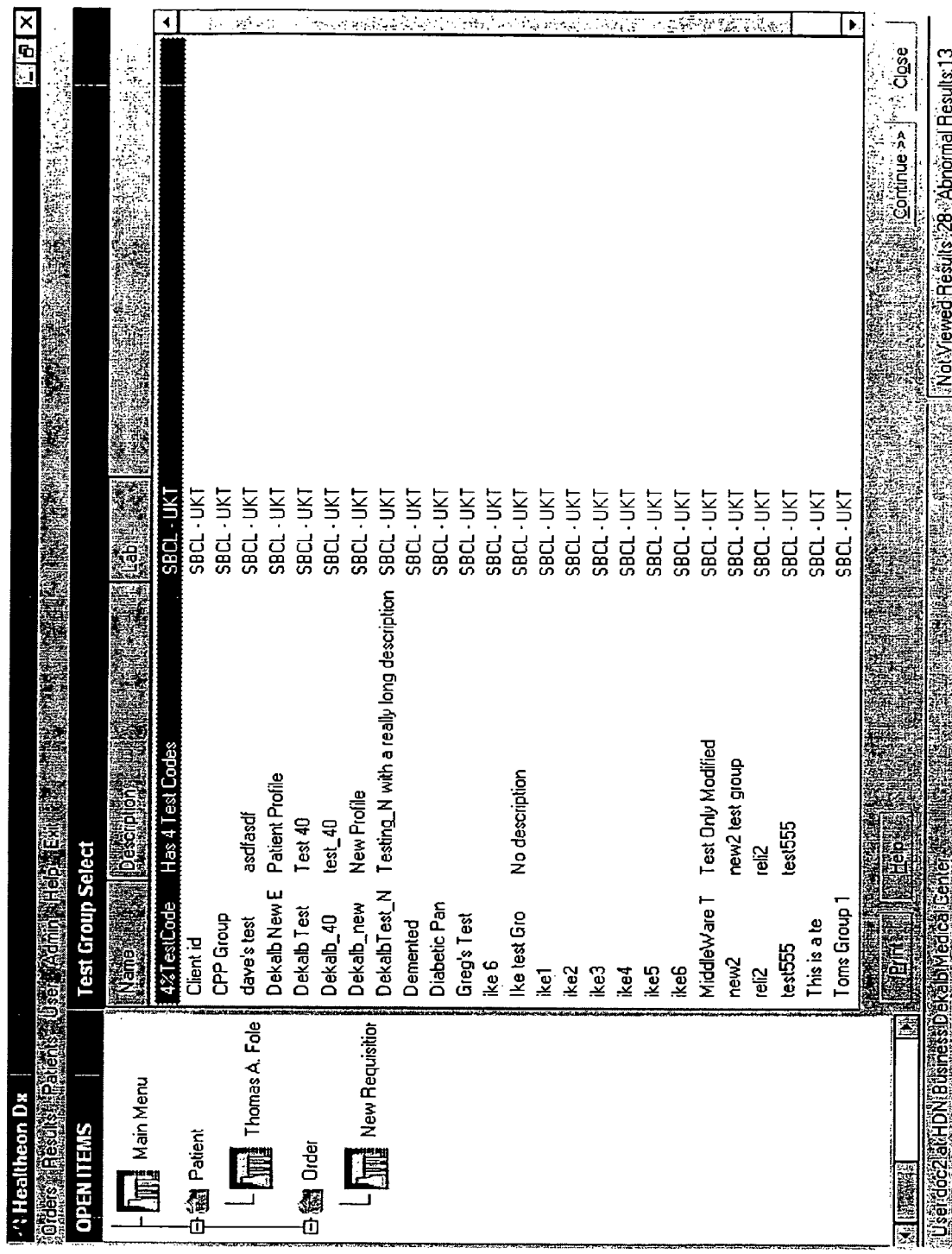

When the user chooses Manage Test Groups from the Orders menu, the Test Group Management window appears, as shown in FIG. 31. From this window, the user can:
- List all test groups
- List all the test codes in a test group
- Create New test groups
- Add a new code to a test group
- View/Modify details in a test group
- Remove a test group
- Remove a test from a test group
- Print a list of all test groups
- Print details on a specific test group Orders: Test Group Listing The Test Group Listing menu option of the Orders menu allows the user to preview or print a list of all the test groups for each provider that are created through the Manage Test Groups function. The items on the list appear sorted in alphabetical order. A header page is a configurable option. The header pages shows:
- Date and time of the report
- Name of the user running the report
- Comment line
- Search criteria used to generate the report FIG. 32 illustrates the Test Group Listing window.

Results Module

Figure 33:
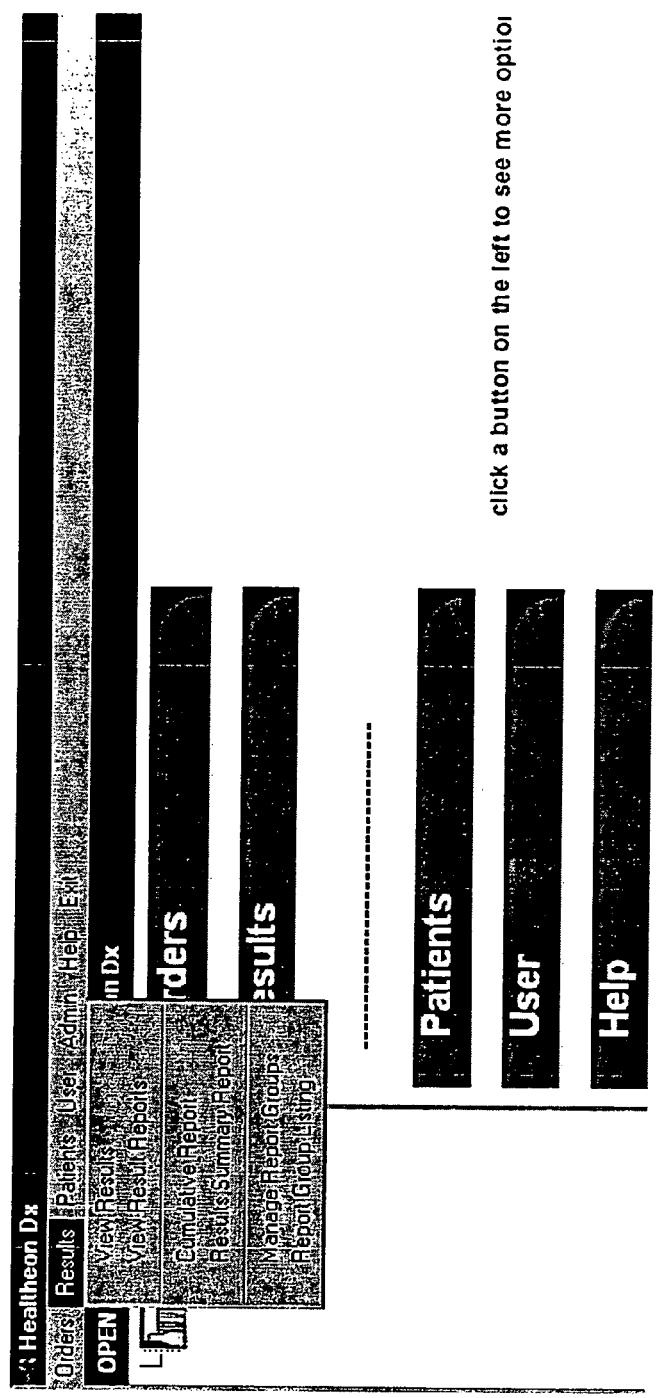

In on embodiment, there are six basic functions to the Results module of the system:
- View Results
- View Result Reports
- Cumulative Report
- Results Summary Report
- Manage Report Groups
- Report Group Listing These functions may be accessed through the Results drop-down menu, as shown in FIG. 33, or the Results desktop menu (not shown). The Results functions pertain to reviewing and managing lab results. The Results functions are described below.

Results: View Results

Figure 34:
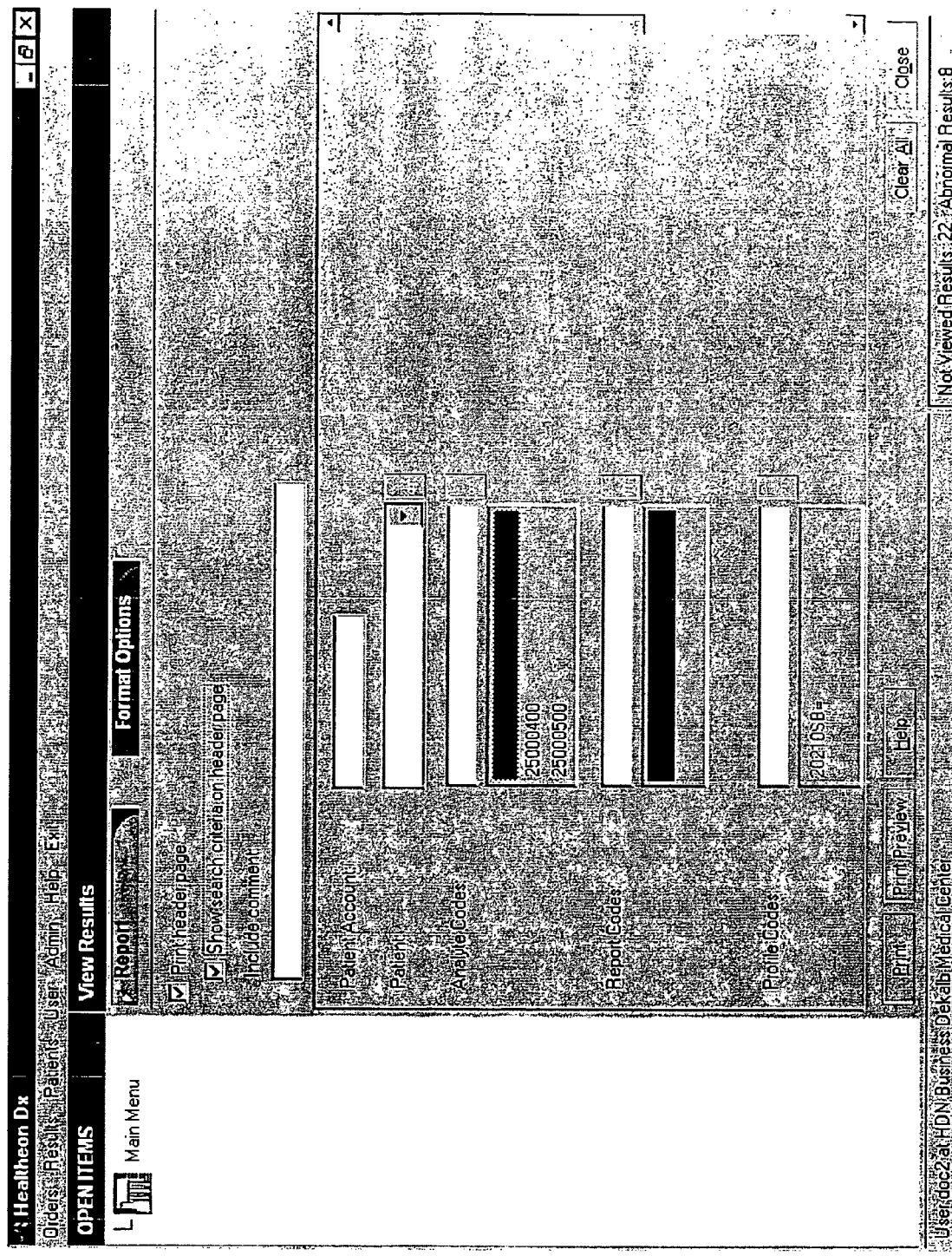

The View Results menu option of the Results menu provides flexible, on-demand reporting capability for current and historical test data. This reporting feature enables a physician to track a patient's progress over a period of time. The View Results window is shown in FIG. 34. This window enables the user to generate a listing of results based on the following search criteria: Patient Account; Patient; Analyte Codes; Report Codes; Profile Codes; Collection Date Range; and Result Date Range. The user may be required to enter The Format Options page of the View Results window lets the user specify how the user want the results to be sorted. The report can be sorted in reverse chronological order or in chronological order.

Figure 35:
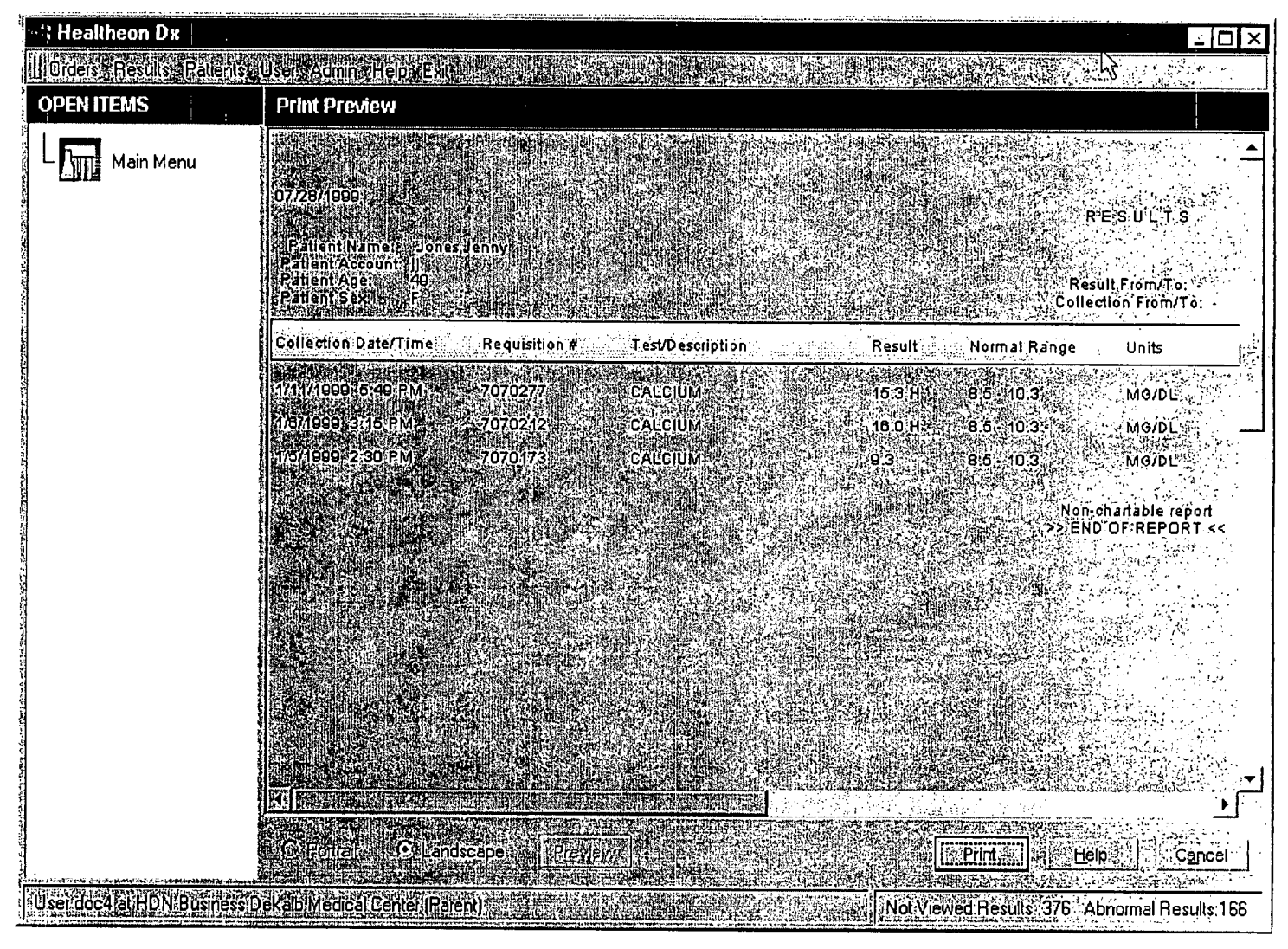

The Results Report can be previewed or printed. The report may be printed and displayed in landscape mode with the following column headings:
- Collection Date/Time
- Requisition #
- Test/Description
- Result
- Normal Range
- Units
- Specimen Type
- Reported Date/Time A header page is a configurable option for a Results Report. The header page shows:
- Date and time of the report
- Name of the user running the report
- Comment line
- Search criteria used to generate the report In addition, the system prints detailed information on the selected patient at the top left hand corner of the report which includes patient name, patient account, patient age and sex. FIG. 35 illustrates a Results Report Print Preview Window.

Results: View Result Reports

As described above, the user interface windows of the application display a status message at the bottom right corner of the screen showing "Not Viewed Results" and "Abnormal Results". This status message tells the user if any new test results have been electronically received. It also tells the user if any of those test results are abnormal.

The View Result Reports function enables the user to preview and print electronic reports of lab results. The user can use a variety of search criteria to narrow down the results of the user's search.

Figure 36:
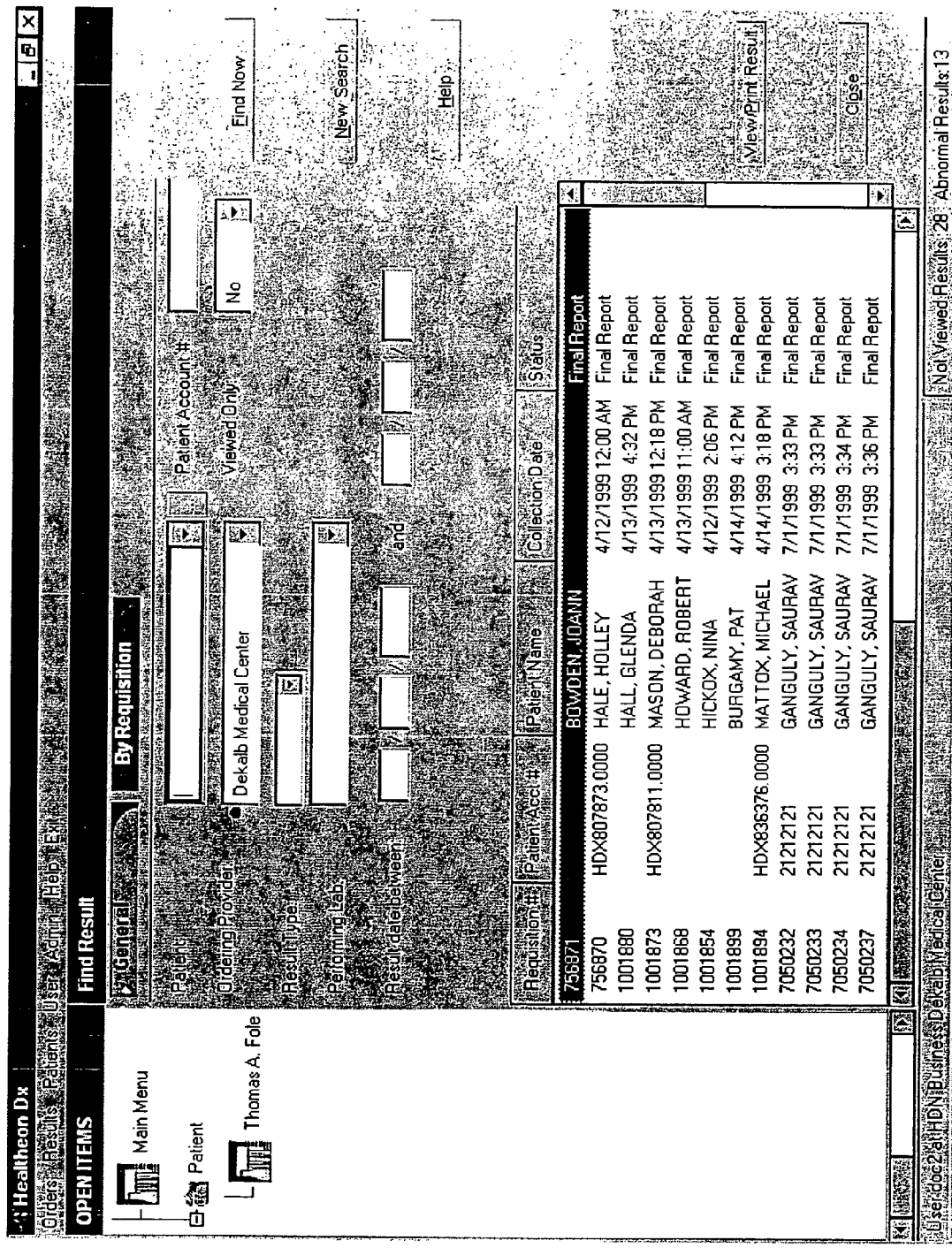
Figure 37:
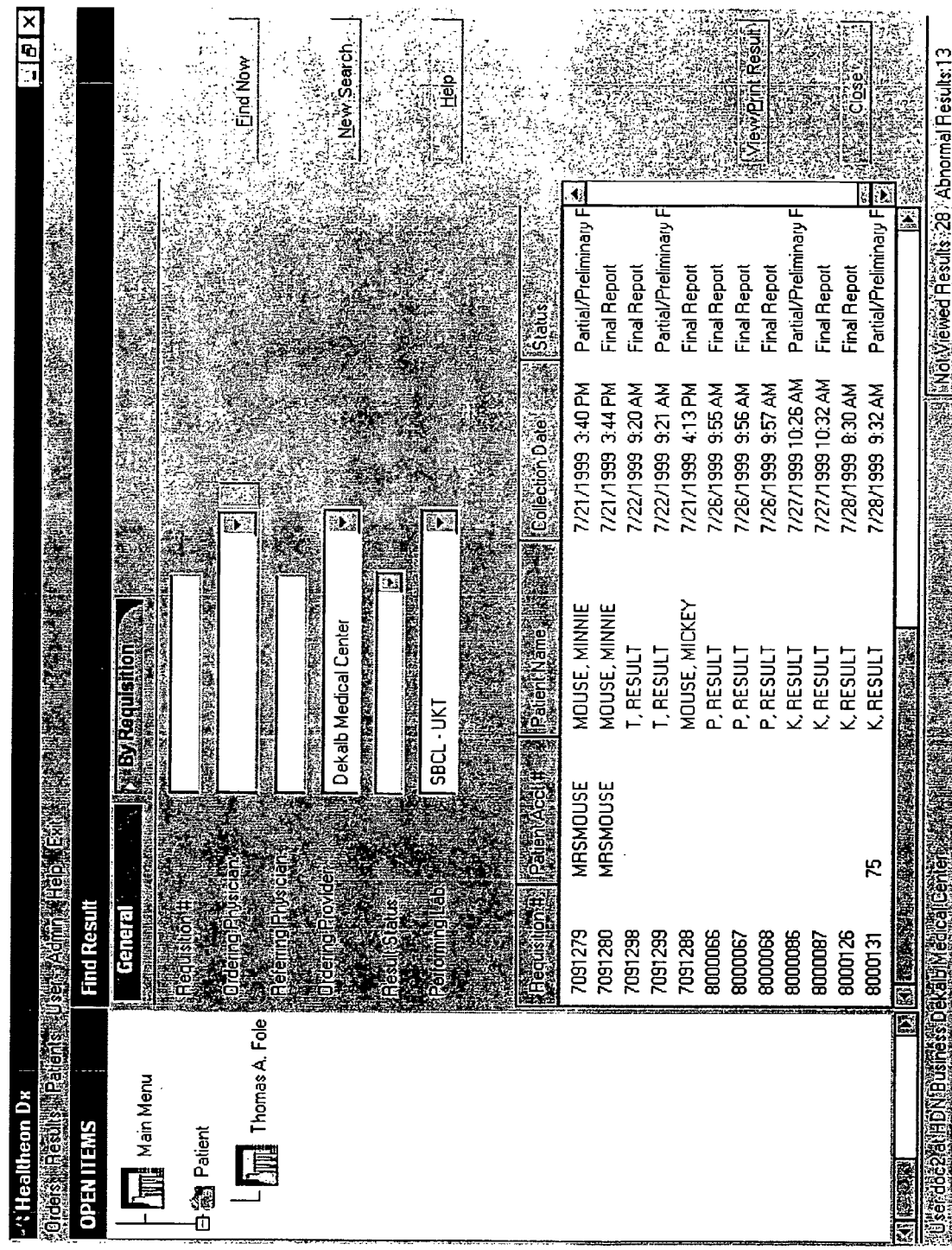

FIG. 36 illustrates the General page of the Find Result Reports window. From the General page the user can specify one or more of the following:
- Patient
- Result Type
- Performing Lab
- Performing Lab Type
- Result Date Range
- Accession #
- Viewed Only FIG. 37 illustrates the By Requisition page of the Find Result Reports window. From the By Requisition page the user can specify one or more of the following:
- Requisition #
- Ordering Physician
- Referring Physician
- Ordering Provider (this field is populated by the system with the name of the currently active HDN Business)
- Result Status The results of the user's search are displayed under the following column headings:
- Req. #
- Acc. #
- Patient Name
- Collection Date
- Status
- Abnormal
- Result Date
- Ordering Physician Name
- Provider
- Lab
- Viewed Once a list of result reports appears on the screen, the user can select one or more of the results to view or print them, e.g., by highlighting the desired result(s) and clicking the View/Print Result button. When the user clicks the View/Print Result button, a Print Options window appears. This is where the user specifies whether the report should show abnormal high/abnormal low flags next to each result and whether the user wants to preview or print the report.

Results: Cumulative Report

The Cumulative Report menu option of the Results menu allows the user to review and print analyte results for a patient over a specified period of time. This reporting tool provides a physician the ability to examine a patient's progress over a period of time and simplifies the collecting, organizing and filing of test results for a patient or patients. The main difference between Cumulative Reports and View Results Reports is in the way information is displayed. In a Cumulative Report the results for a single analyte appear listed horizontally over several date/time column headings. Also a Cumulative Report does not show requisition numbers or additional information on a test such as normal range, units and specimen type.

Figure 38:
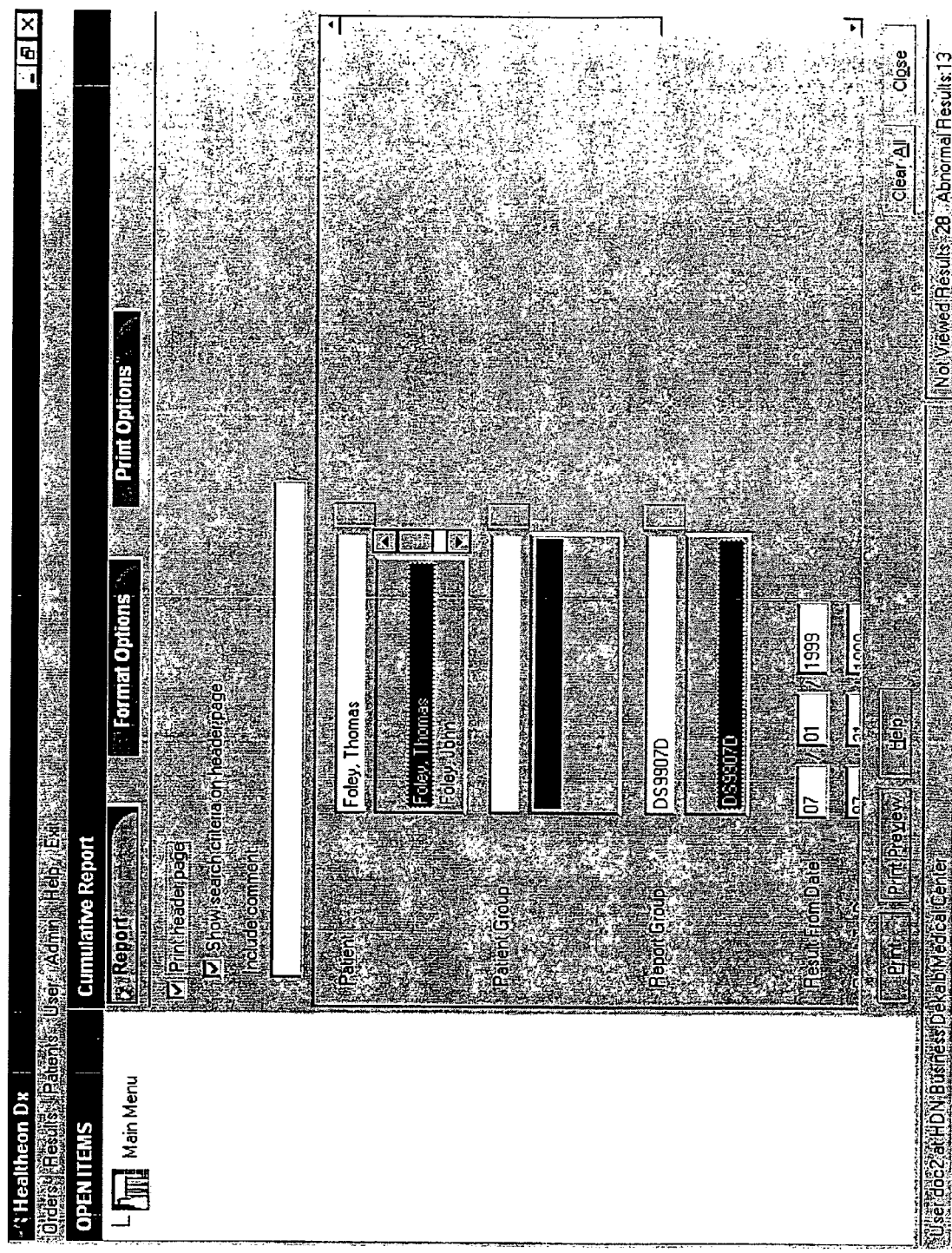
Figure 39:

FIG. 38 illustrates the Report page Cumulative Reports window. The user can specify the following criteria to narrow down the results of the search:
- Date Range
- Patient
- Patient Group
- Shift
- Location
- Ordering Physician
- Report Group FIG. 39 illustrates the Format Options page of the Cumulative Report window. In the Format Options page, the user can select the following options to display a Cumulative report:
- Display Date/Time horizontally and Analyte Code vertically or vice versa
- Display results in chronological order or reverse chronological order Title (An optional free text field where the user can enter a report title)

Figure 40:
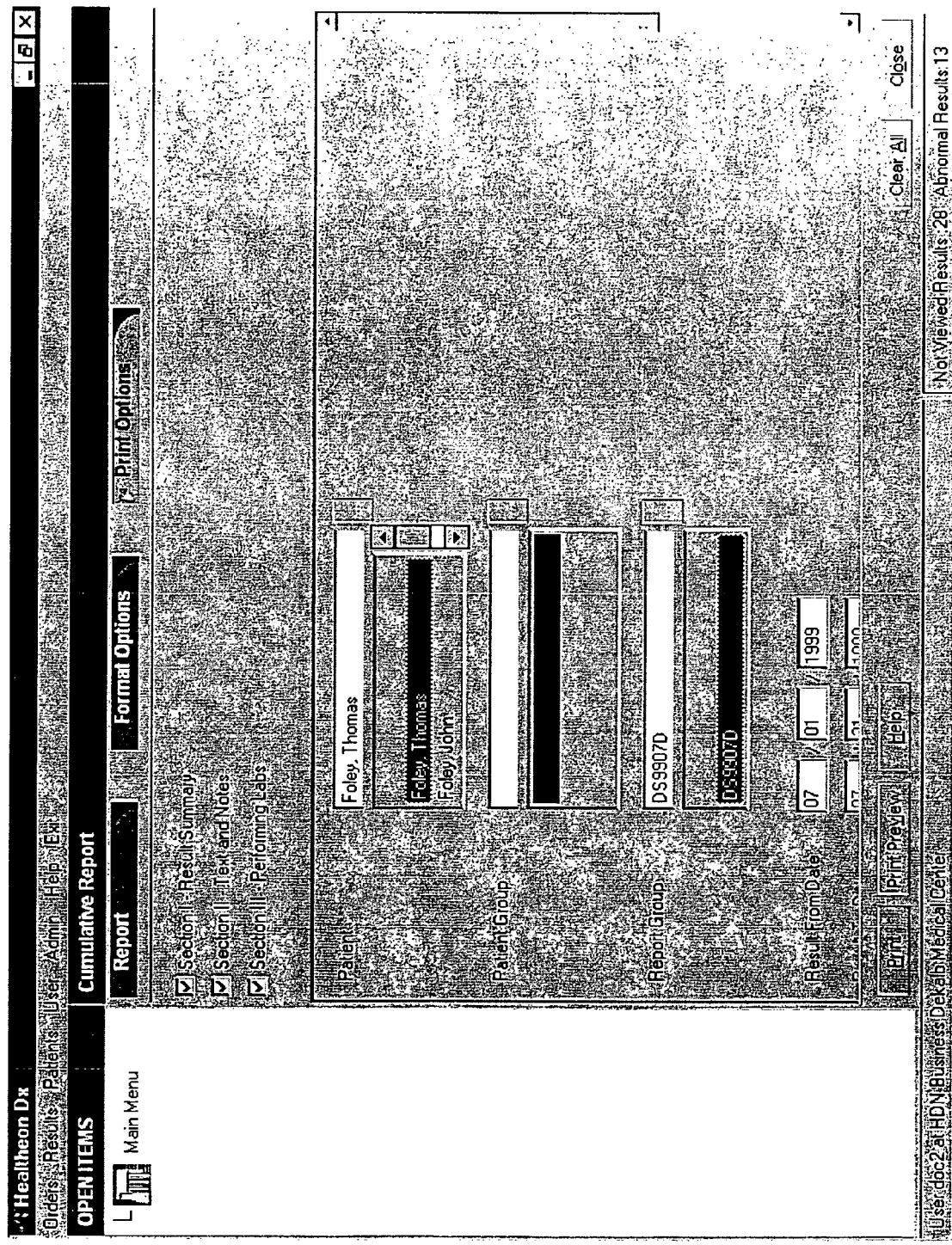

FIG. 40 illustrates the Print Options page of the Cumulative Report window. In the Print Options page, the user specifies what additional supplemental information to include in the report. The user may select from the following three sections to include in the report.

Section I—Results Summary
Section II—Text and Notes
Section III—Performing Laboratories The Results Summary section shows a listing of analyte results for a patient over a period of time. This is the most important component in a cumulative report. Results appear under their corresponding collection date/time column headings. Abnormal results are flagged with an H for high or L for Low.

The Text and Notes section of the report displays miscellaneous notes and remarks associated with test results. Text and notes can originate from report comments the user enters on the Additional Info page of a requisition or from an authorized user at the lab such as a lab director, medical technologist, pathologist or microbiologist. Non-numeric results such as "positive" or "abnormal" appear in the Text and Notes section. For example, if the results of a CBC test reveal a low red blood cell count, the lab technician may include a message along with the results such as: "R/O anemia. A complete blood count is used as a screening test for various states such as anemia, leukemia and inflammatory disease".

The Performing Laboratories section lists the names and addresses of all the laboratories from which the test results were obtained.

Figure 41:
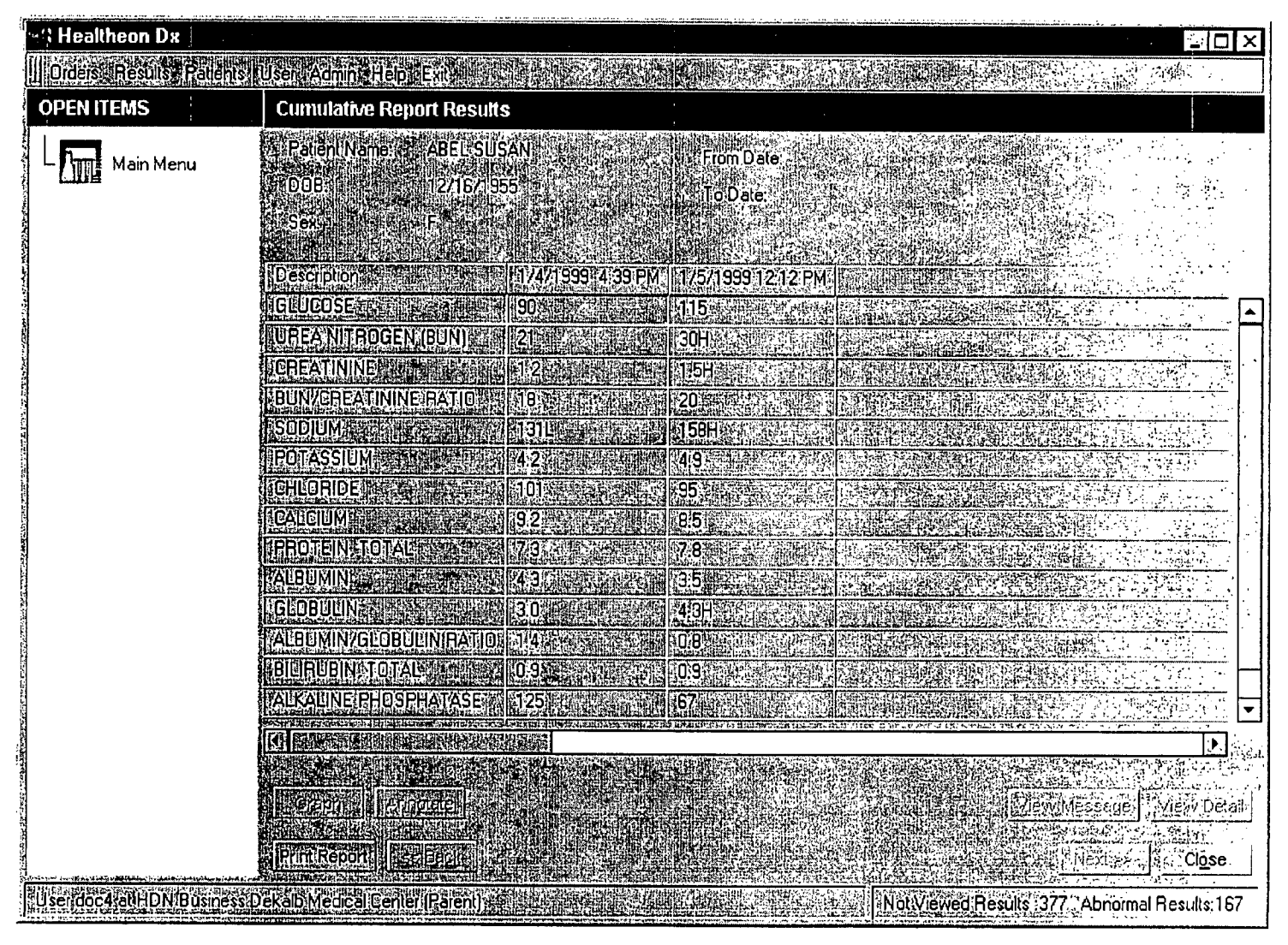

After selecting the report search criteria, format options and print options, the results can be previewed or printed. When the results are previewed, an Analyte Result window appears, as shown in FIG. 41. Results are displayed one patient at a time. The top part of the display shows a heading with the patient's name, date of birth, sex and date range. Below the heading are the results for each analyte displayed over a period of time. The bottom part of the display contains the following set of buttons:

| | |
|---|---|
| Graph | This button displays analyte results in a graph. The graph can be previewed and printed. |
| Annotate | This button opens a free text window where the user can enter comments. Comments can be viewed, modified and deleted. |
| View Message | This button displays a window with text messages that originate from TopLab. If there are no messages from TopLab, the message results window box appears empty. |
| View Detail | This button displays an Analyte Result Detail window that shows detailed information on the analyte result selected. |
| Print Report | This button prints the Analyte Result report that appears on the screen. |
| <<Back | This button displays the results of the previous patient. |
| Next>> | This button displays the results of the next patient. |
| Close | This button closes the Analyte Result window. |

Results: Results Summary Report

Figure 42:
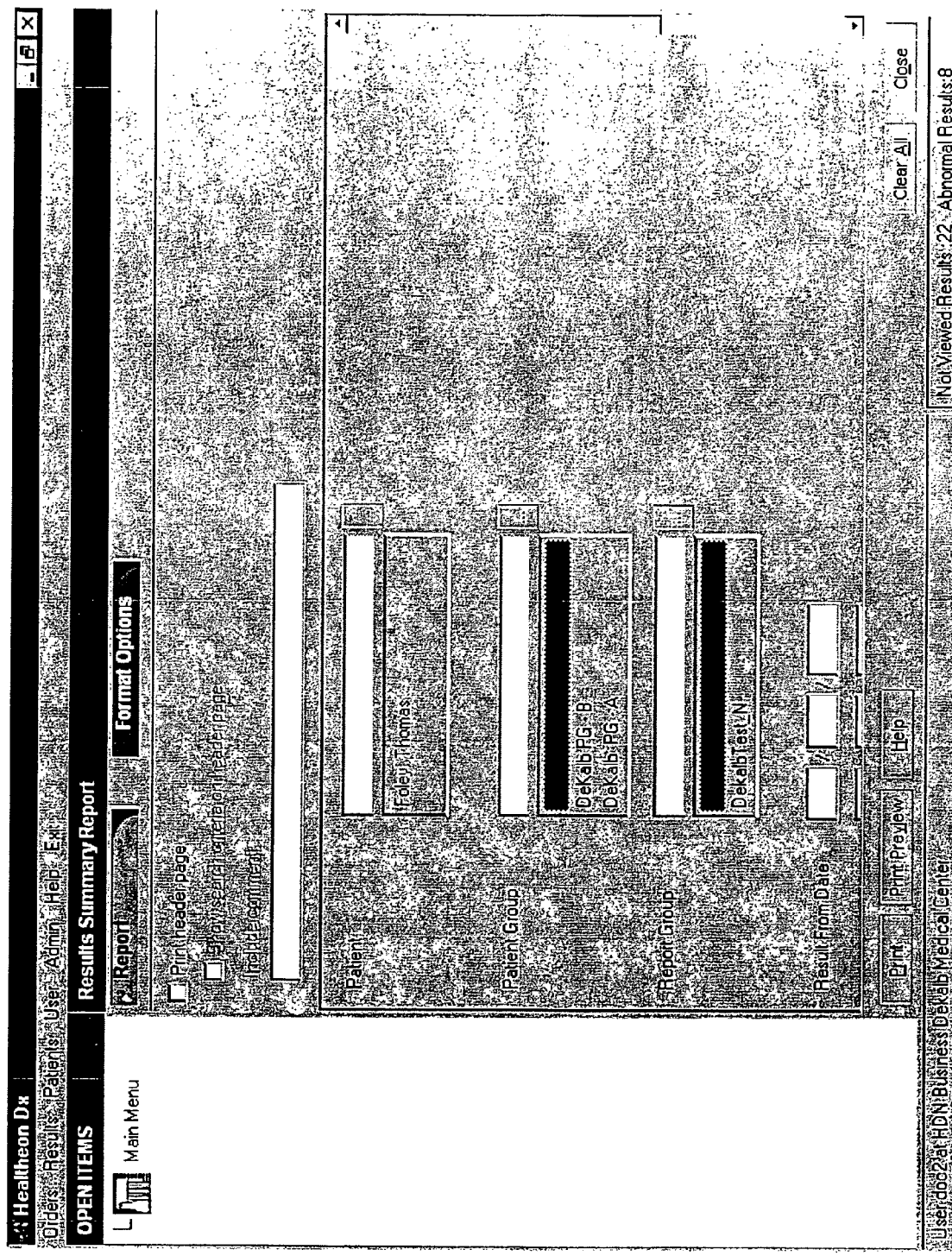

The Results Summary Report menu option of the Results menu allows the user to generate a multiple patient report designed to present a one time summary of any results received that meet a certain criteria FIG. 42 illustrates the Results Summary Report window. The user can customize the search criteria to produce only the results that best meet the user's practice requirements. For example, the user can generate a listing of all the patients who had abnormal or high HDL cholesterol readings over a period of time.

The user can specify the following criteria to narrow down the results of the user's search:

Date Range (dates of the first and last results to include in the report)
Patient (a list of patients whose to include in the report.)
Patient Group (a list of patient groups whose results to include in the report.)
Shift (the shift that collected the specimen for the results to be included in the report)
Location (the location where the specimen was collected for the results to include in the report.)
Ordering Physician (a list of ordering physicians of the requisitions corresponding to the results to include in the report.)
Report Group (a list of report groups to include in the report)

Figure 43:
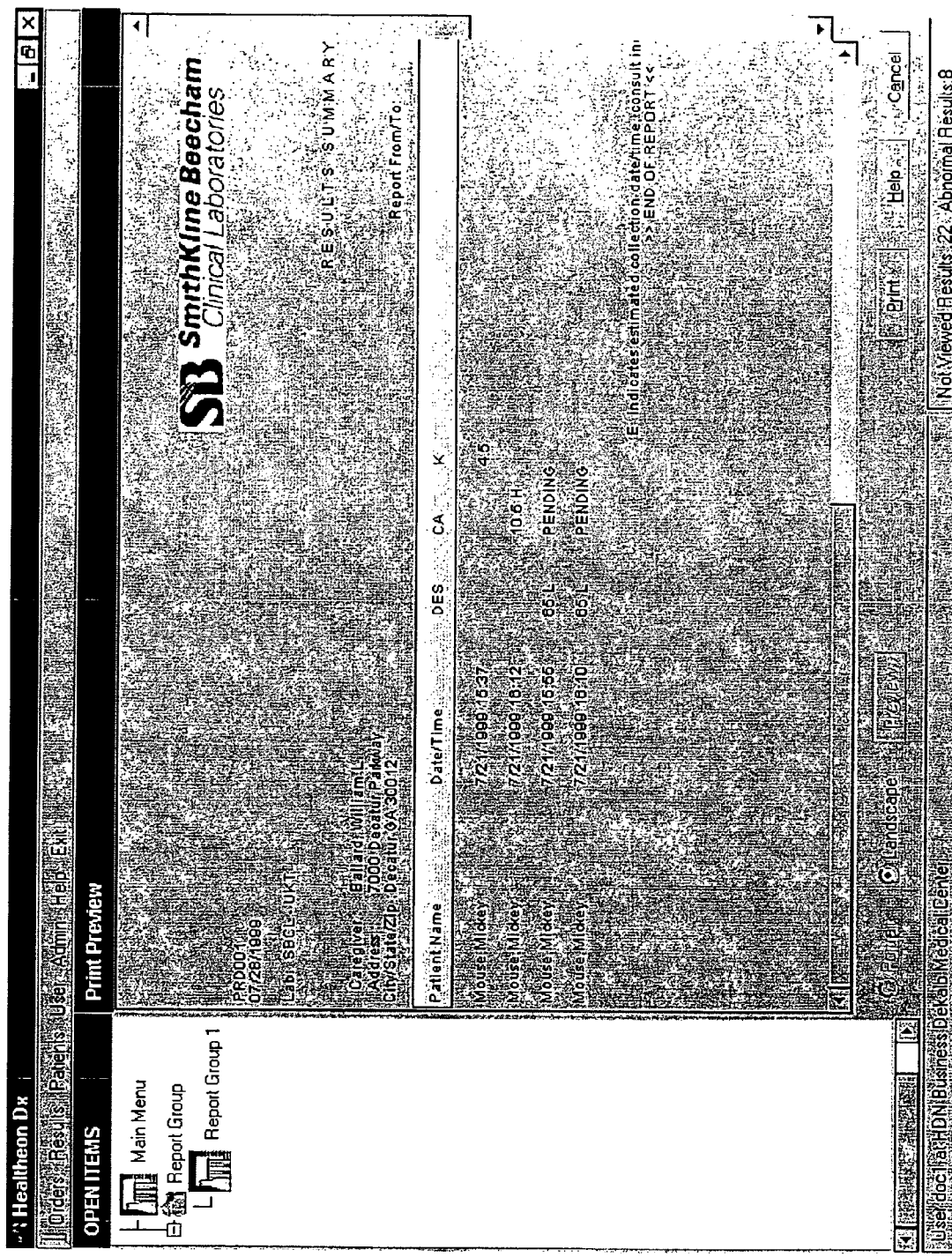

Results are printed per patient. The selection of analytes for the report is done using the report groups. A header page is a configurable option. The header pages shows:

Date and time of the report
Name of the user running the report
Comment line
Search criteria used to generate the report FIG. 43 illustrates a Results Summary Report Print Preview window.

In the Format Options page of the Results Summary Report window, the user can select the following options to display a Results Summary report:

Format Style (Tabular or List)
Clinical Status (Normal, Abnormal or Both)
Sort Order (Patient Name or Account Number)
Title (An optional free text field where the user can specify a report title)

Results: Manage Report Groups

Report Groups are user-defined collections of analyte codes, report codes and profile codes. The Manage Report Groups menu option of the Results menu allows the user to create and maintain these report groups.

Report Groups are used to generate Results Summary Reports and Cumulative Reports. Information obtained from these reports can be used to schedule patient visits in advance, gather valuable statistical information, and identify trends in a patient population. A Results Summary Report is a listing of all the test results that meet a certain criteria such as date range, patient, patient group, shift, location, ordering physician and report group. A Cumulative Report allows the user to review and print information on any analyte or group of analytes, for a particular patient or group of patients over a specific time period.

Figure 44:
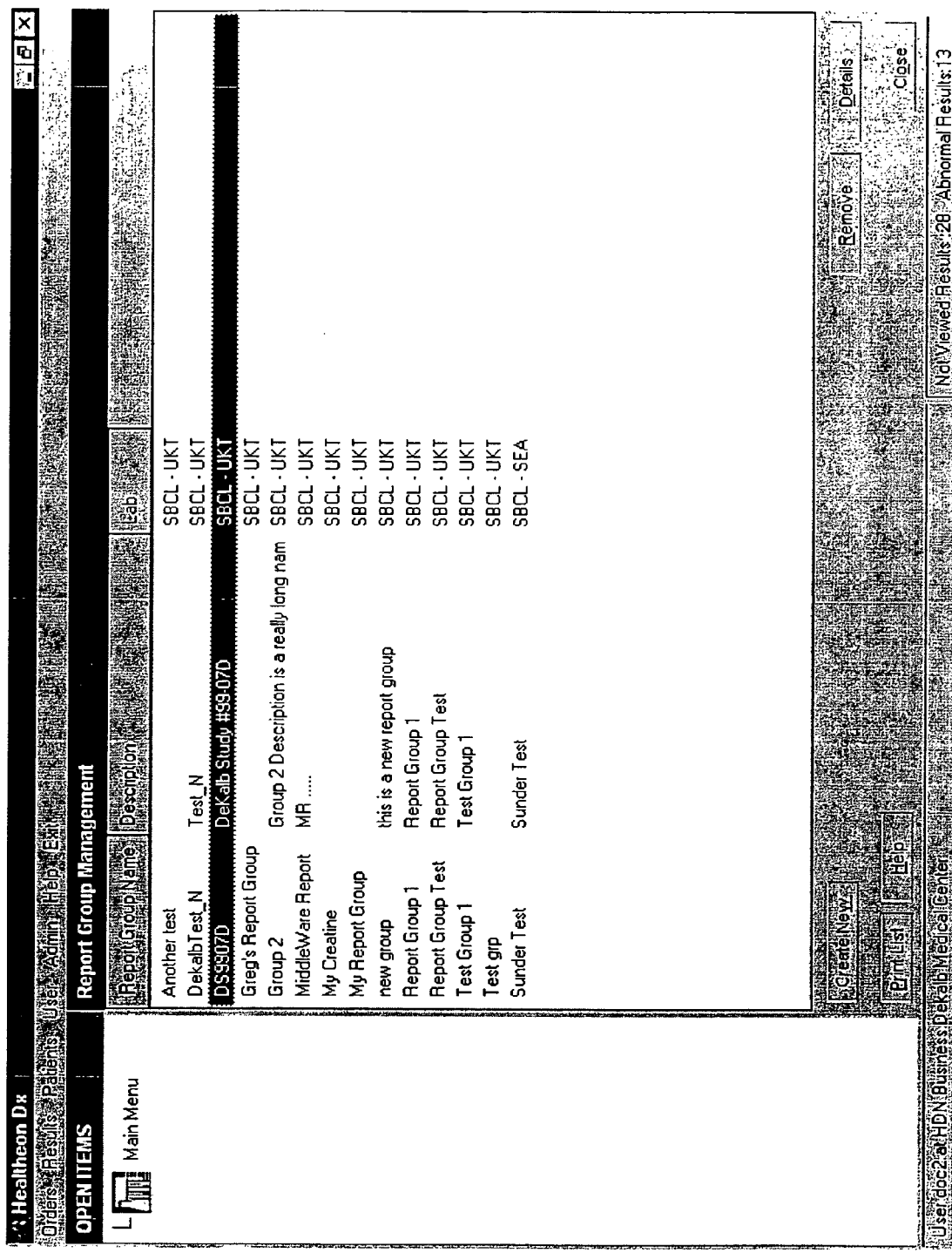

When the user chooses Manage Report Groups from the Results menu, the Report Group Management window appears, as shown in FIG. 44. From this window, the user can:

List all report groups
List all the analyte codes in a report group
Create New report groups
Add a new code to a report group
View/Modify details in a report group
Remove a report group
Remove an analyte code from a report group.
Print a list of all report groups
Print details on a specific report group The user can build a report group by selecting any combination of one or more profiles, report codes or analyte codes. Once a Report Group has been defined and given a name, it appears listed in the Report Group Management window. Regardless of what method the user uses to build a report group (by profile, report or analyte code), the report group always shows the individual analyte codes that make up the report group along with their individual name and description.

Results: Report Group Listing

Figure 45:
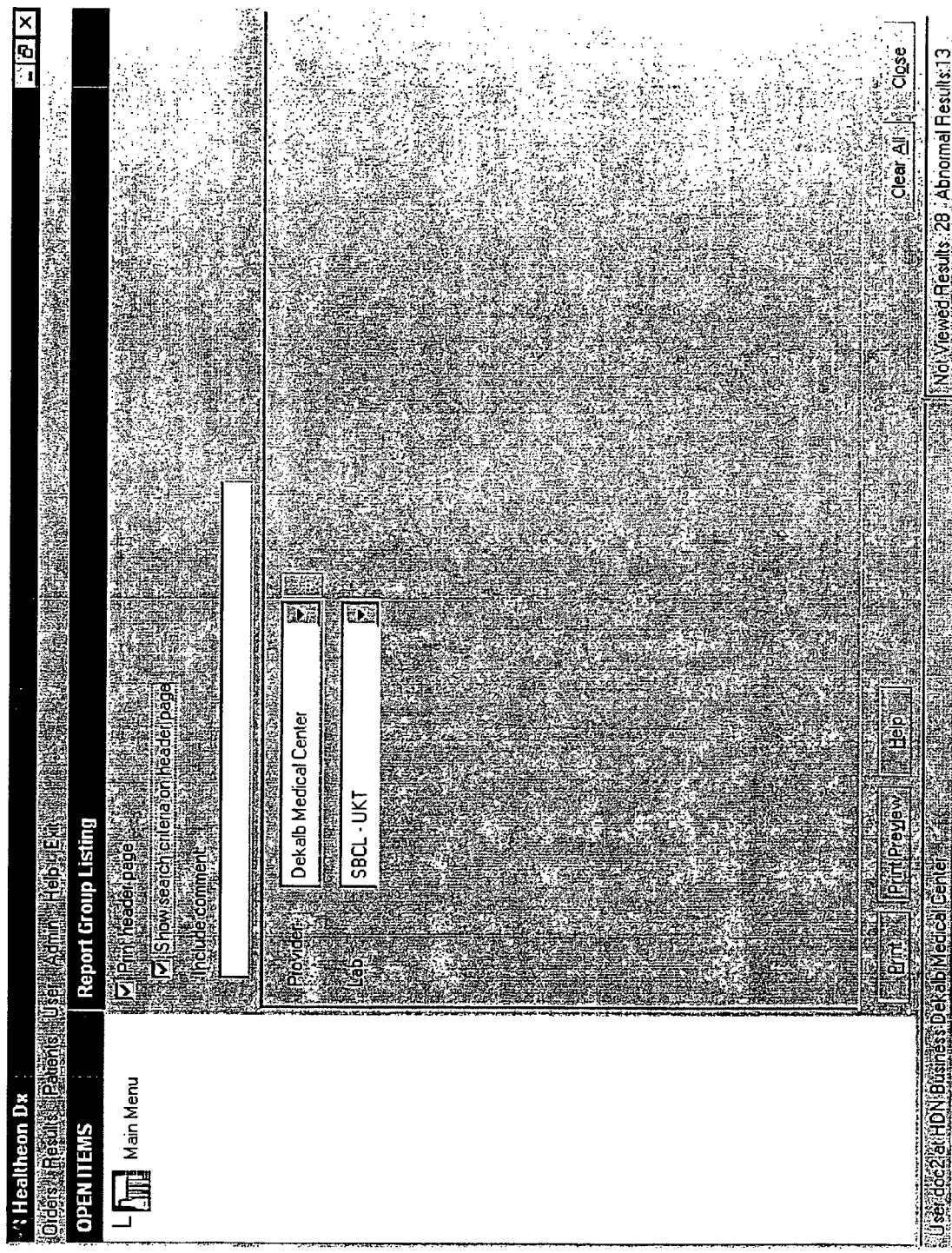
Figure 46:
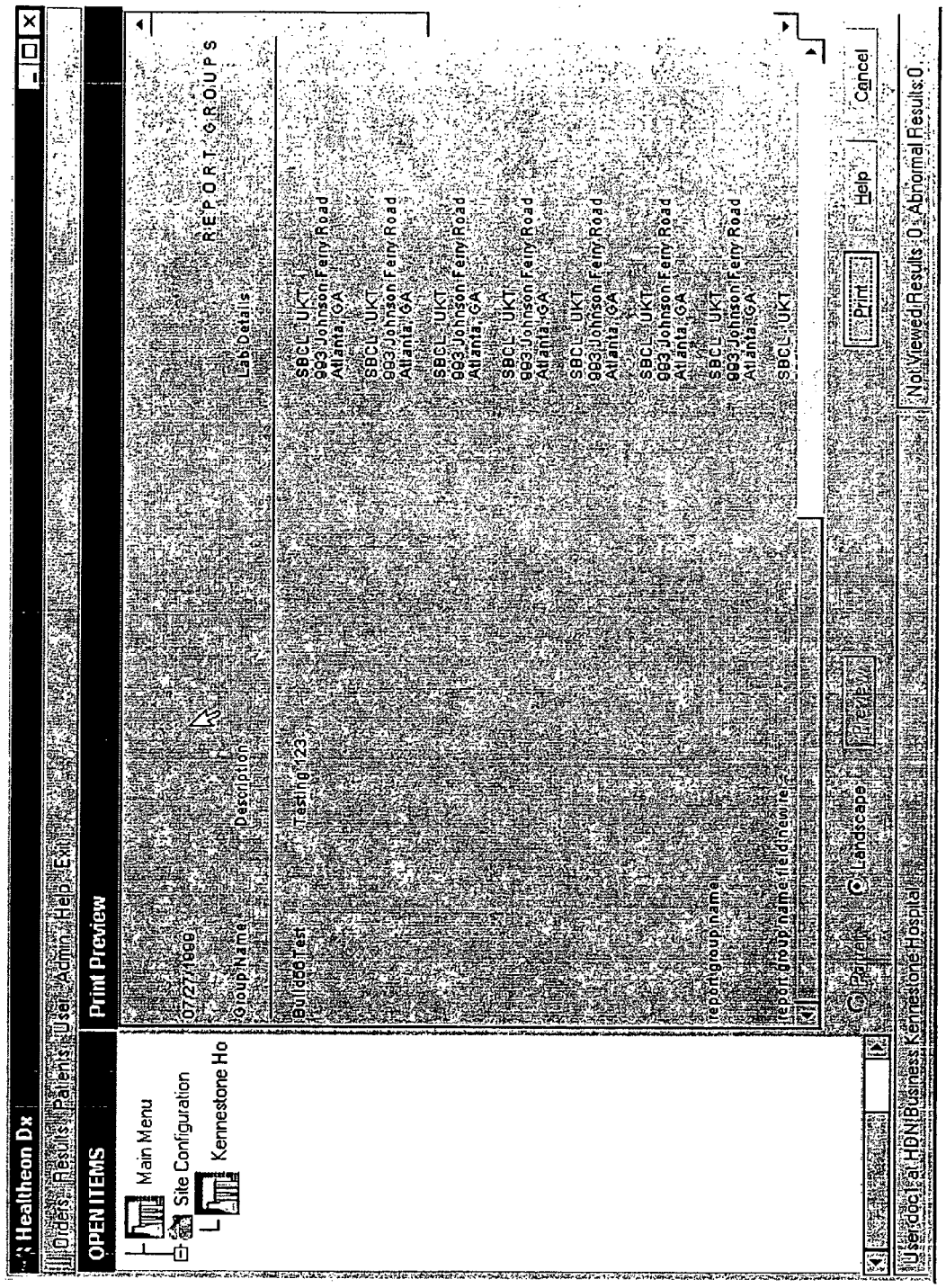

The Report Group Listing menu option of the Results menu allows the user to preview or print a list of all the report groups for each provider that are created through the Manage Report Groups function. The items on the list appear sorted in alphabetical order. A header page is a configurable option. The header pages shows:
- Date and time of the report
- Name of the user running the report
- Comment line
- Search criteria used to generate the report FIG. 45 illustrates the Report Group Listing window, and FIG. 46 illustrates a Report Group Listing Print Preview window.

Patients Module

Figure 47:
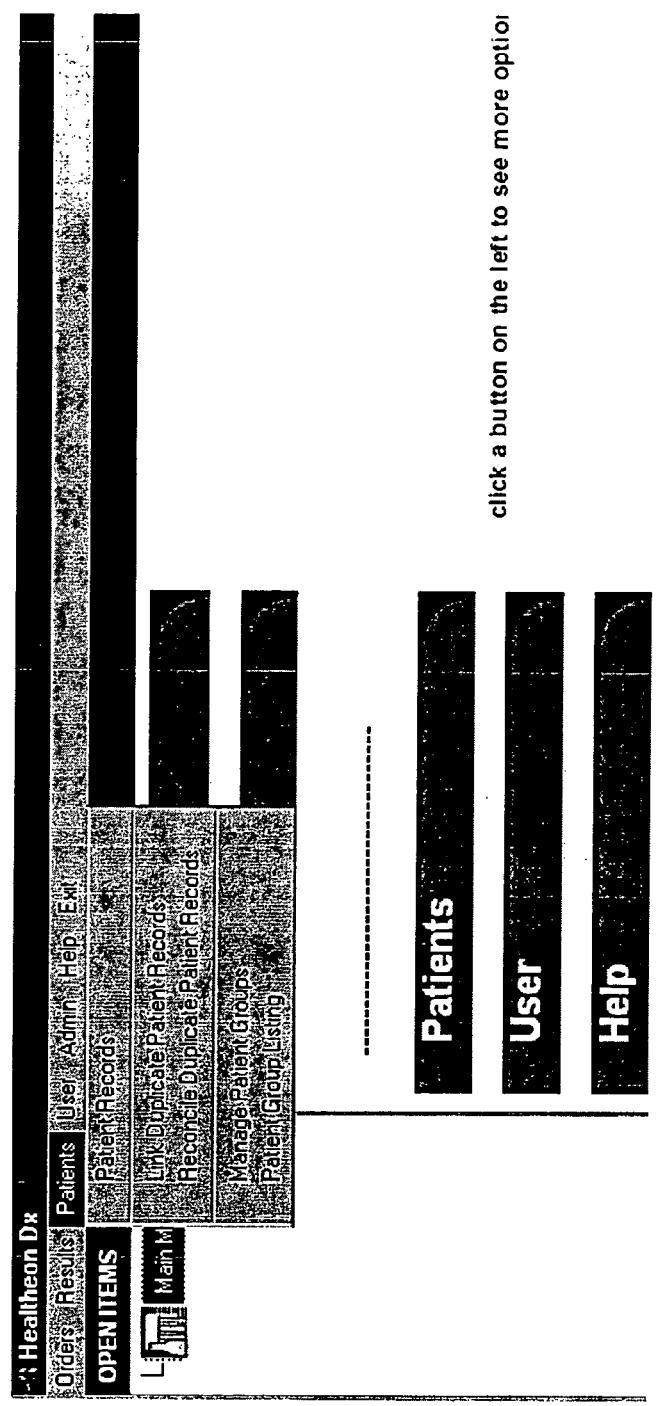

In one embodiment, there are five basic functions to the Patients module of the system:
- Patient Records
- Link Duplicate Patient Records
- Reconcile Duplicate Patient Records
- Patient Group Listing
- Manage Patient Groups These functions may be accessed through the Patients drop-down menu, as shown in FIG. 47, or the Patients desktop menu. The Patients functions pertain to managing patient records. The Patients functions are described below.

Patients: Patient Records

The Patient Records menu option of the Patients menu allows the user to:
- Create new patient records
- Find existing patient records
- View details of existing patient records
- Modify details of existing patient records
- Print existing patient records Each patient record may include the following types of information:
- Demographics information, such as:
  - Account #
  - Patient's Name
  - Home address
  - Home, work, and fax phone numbers
  - General identification, such as Social Security Number and driver's license number
  - Birth date, birth place, and death date
  - General profile information such as sex, marital status, and ethnic group
  - Religious information including religion, place of worship and religious contact
- Name Aliases (other names by which the patient has been or is known)
- Identifier information. The system allows the user to link to a single patient record multiple identifiers that the user's organization and other organizations use to track the patient record, such as chart number, record number, test number and account number. For example, one facility may use Medical Record Numbers (MRNs) to keep track of its patients while another facility may use Patient Identification Numbers (PIDs) for the same purpose.
- Employment information, both past and present, including employer name, address, phone numbers, employment period and position.
- Guarantor information, which lists the person(s) responsible for any medical procedures not covered by a payer or a third party. A guarantor can be any of the following:
  - the patient
  - a parent
  - the patient's spouse
  - the patient's employer
  - any other person financially responsible for the patient's medical expenses
- Medical Data, which the user's office and other organizations maintain for a patient.
- Insurance information, which includes insurance code, payer, insured name, policy/member number, and effective dates.
- Documents, which is a list of all documents, such as X-rays, lab reports, and medical notes, etc., that have been added to the patient's file either through the user's organization or other organizations.
- Contacts, which is a list of all persons who are contacts for the patient and includes the person's name, address, phone numbers and relationship to the patient.
- Consent information, which indicates if there is a valid patient consent form on file for a particular patient record.
- Orders, which lists all laboratory tests performed on a patient.
- Result Reports, which lists the results of all laboratory tests performed on a patient.
- Diagnosis Codes, which includes a patient's diagnosis codes and their description.

Patient information is used by many other modules in the system and is shared within the user's organization as well as other organizations participating in the care of the patient. Therefore, great care should be taken to maintain the accuracy and integrity of this information. The system includes various features for helping to maintain data integrity, as described below.

Figure 48:
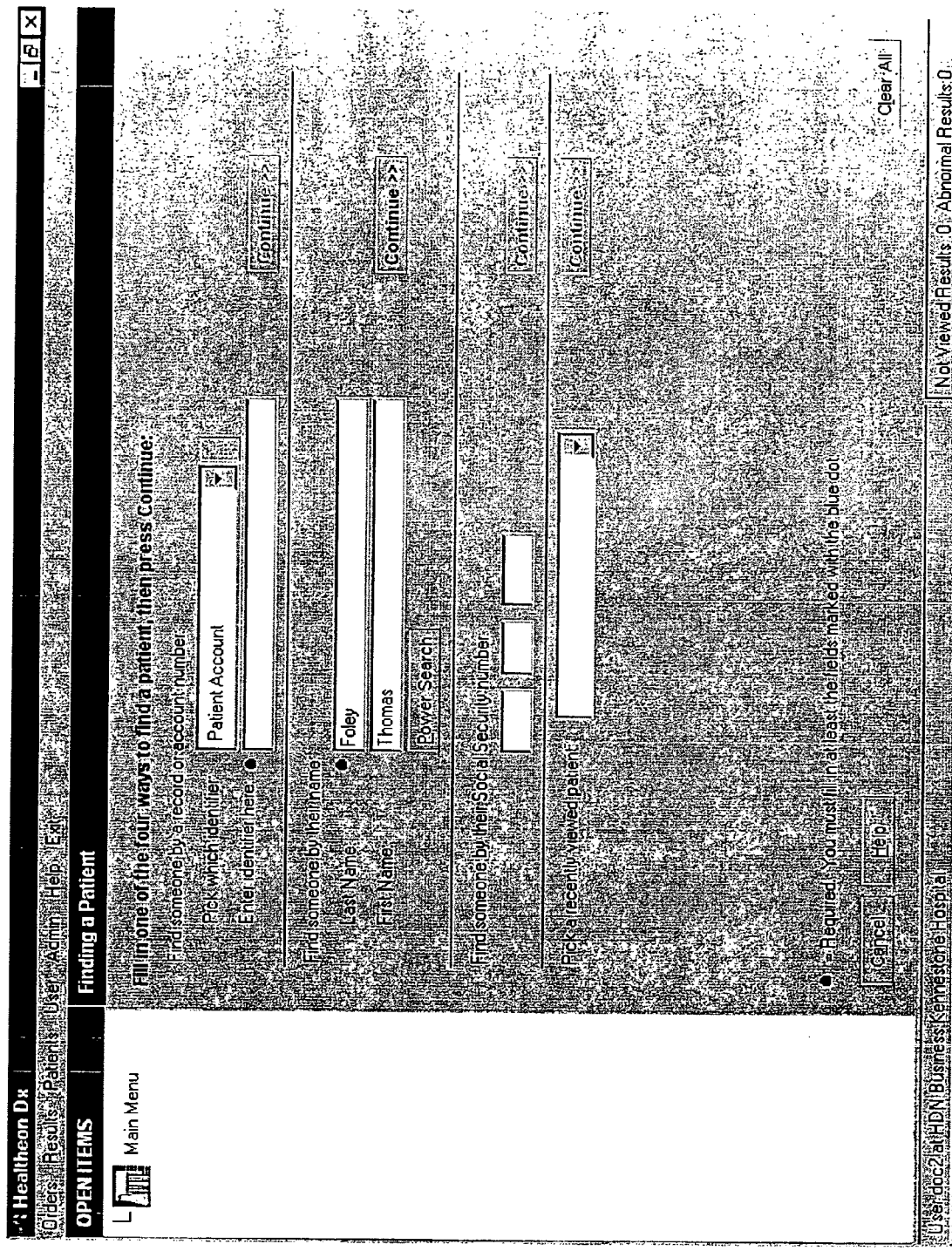

Assuming the user has the proper security clearance, the Patient Records function of the system allows the user to carry out the following within each patient record:
- Enter and modify demographic information in a patient record
- Add, modify and remove name aliases in a patient record
- Add, modify and remove identifiers in a patient record
- Add, modify and remove employment records in a patient record
- Add, modify and remove guarantor information in a patient record
- Add, modify and remove medical data in a patient record
- Add, modify and remove insurance information in a patient record
- View, link and forward documents linked to a patient record
- Add, modify and remove contacts in a patient record
- Add, modify and remove consent information in a patient record
- Add, modify and remove lab orders from a patient record
- View and print lab result reports in a patient record
- Add and remove diagnosis codes in a patient record Finding Patient Records:

Patient records may be looked up in various ways, including by name, by identifier, or by social security number. The user may also perform a "power search" to lookup patient records. FIG. 48 illustrates the Finding a Patient basic search window. This window may appear after selecting the Patient Records menu option from the Patients menu or in other contexts, such as in response to selecting Create Standard Requisition from the Orders menu.

In one embodiment, the system may be enabled to interface with a Practice Management System (PMS). If the user's system has a PMS interface and the user searched by Patient Account identifier type, the system may search the PMS first. If a record is not located in the user's PMS with the matching account identifier, the PMS Search dialog box appears. The patient index maintained by the system may then be searched for a matching record.

Figure 49:
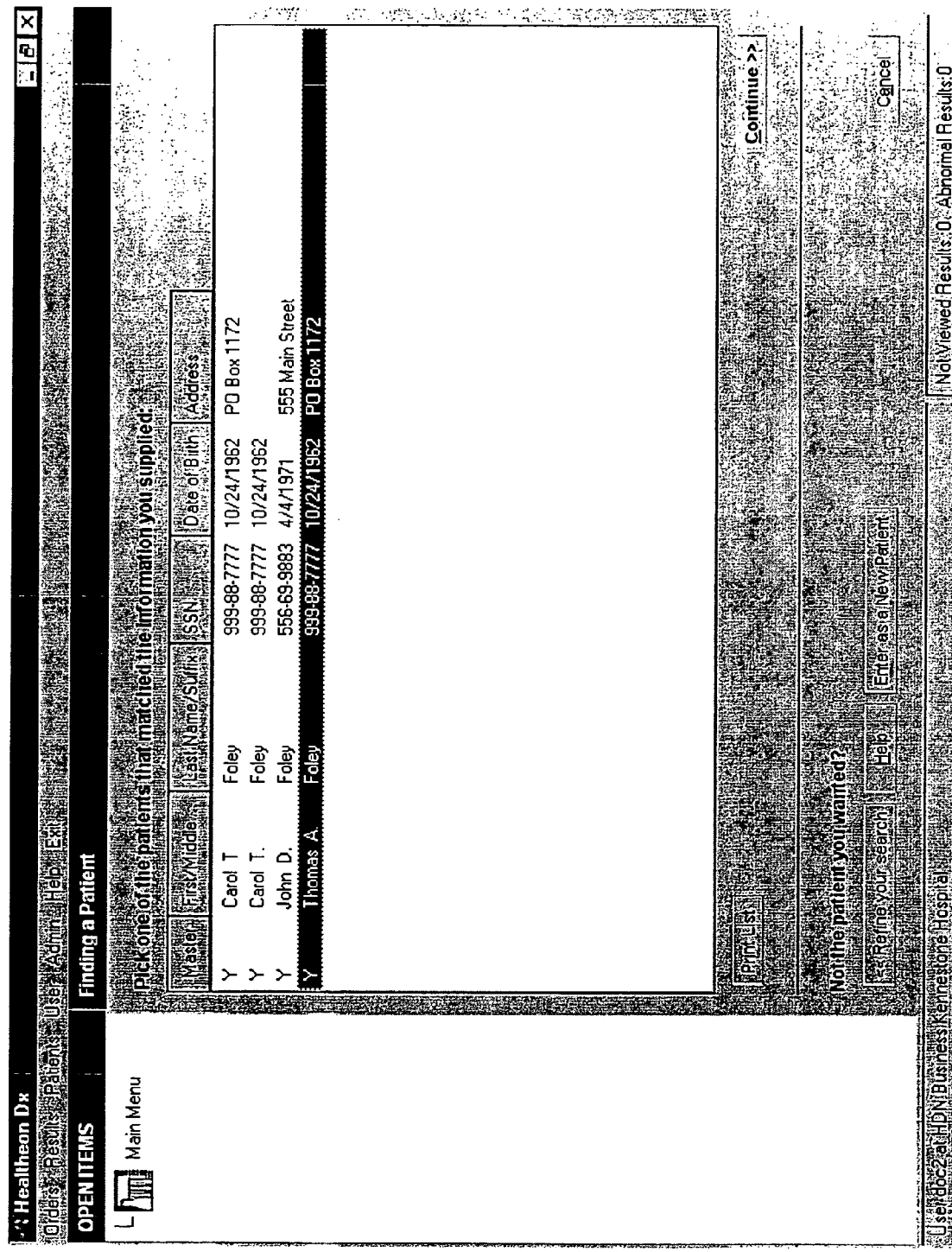
Figure 50:
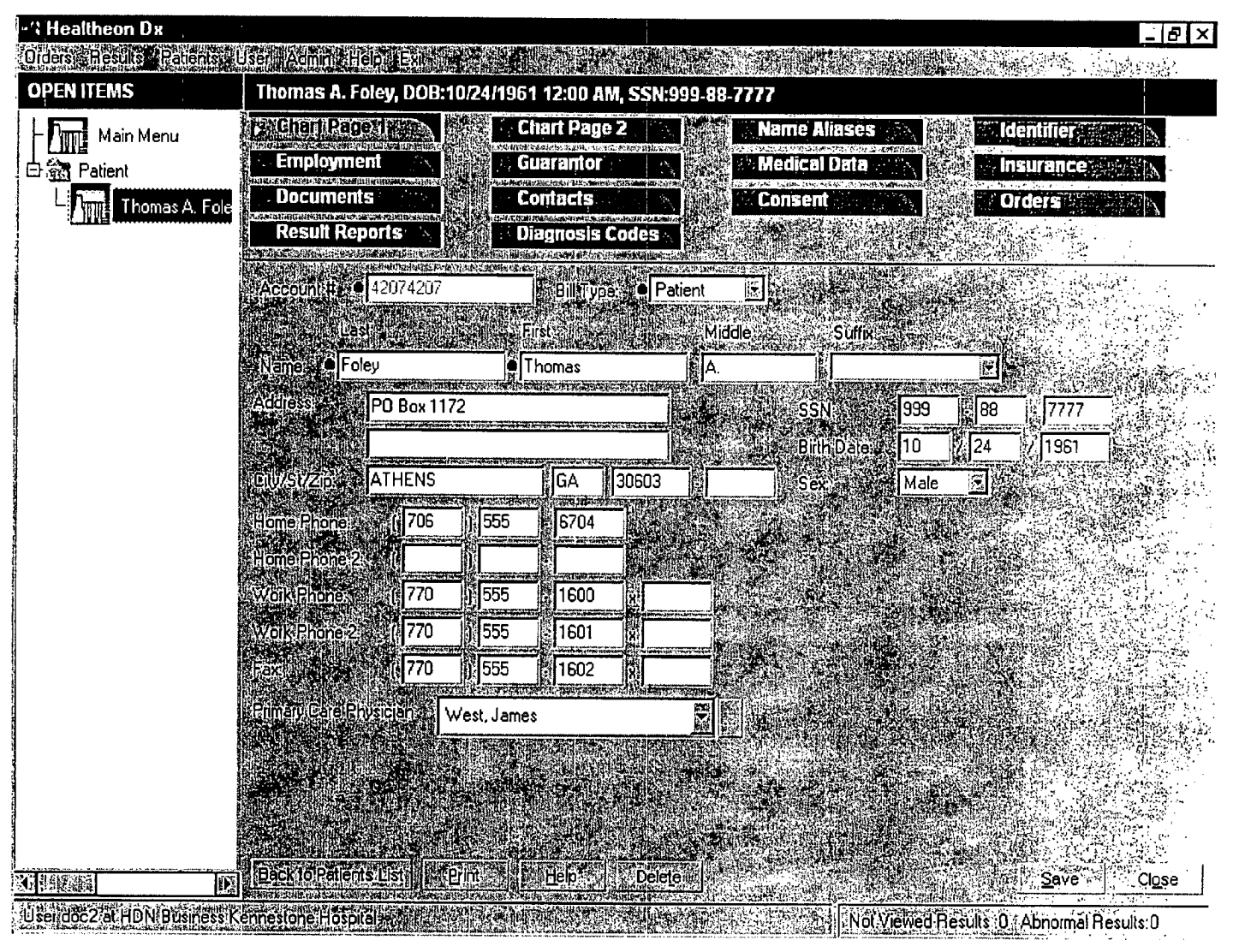
Figure 51:
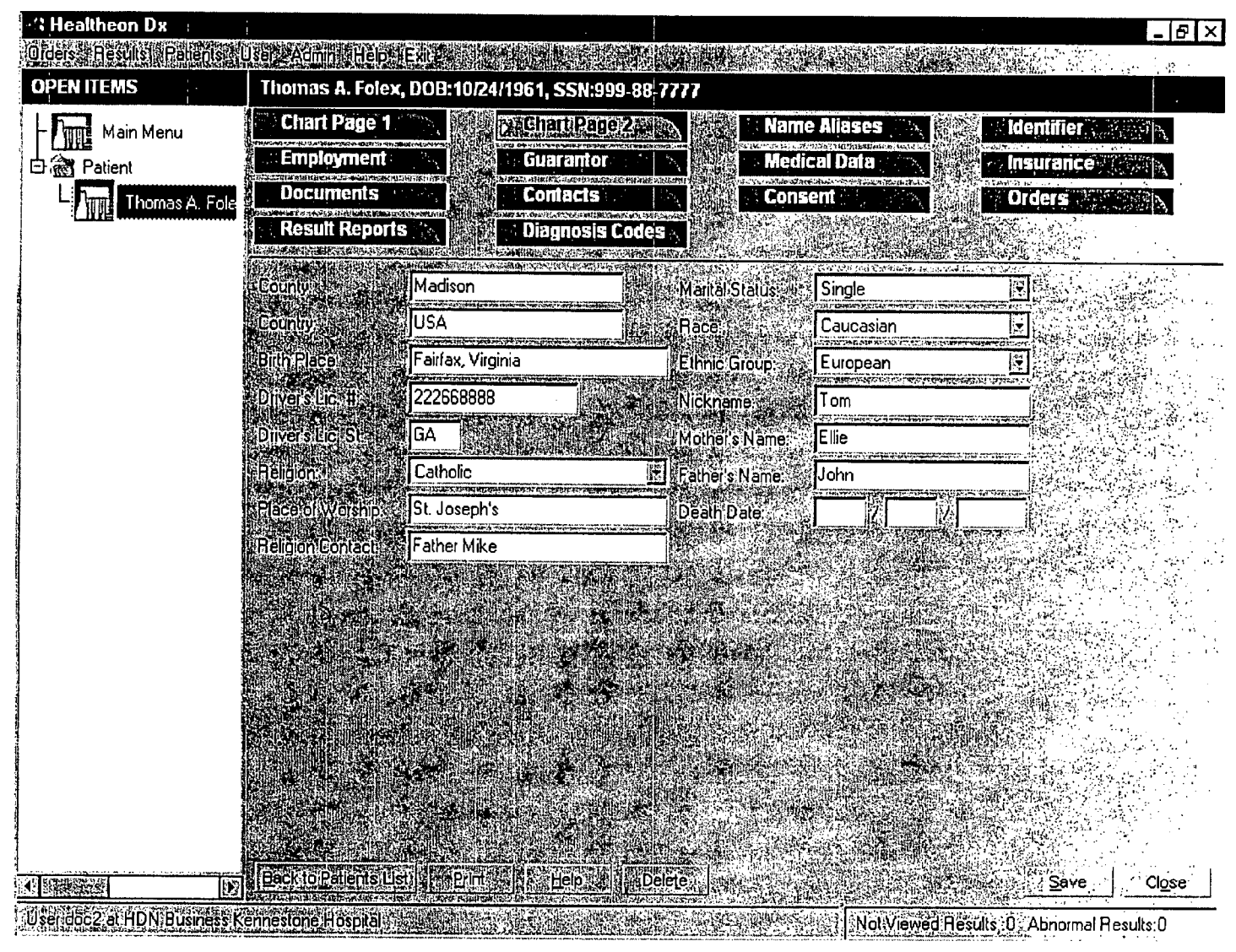
Figure 53:
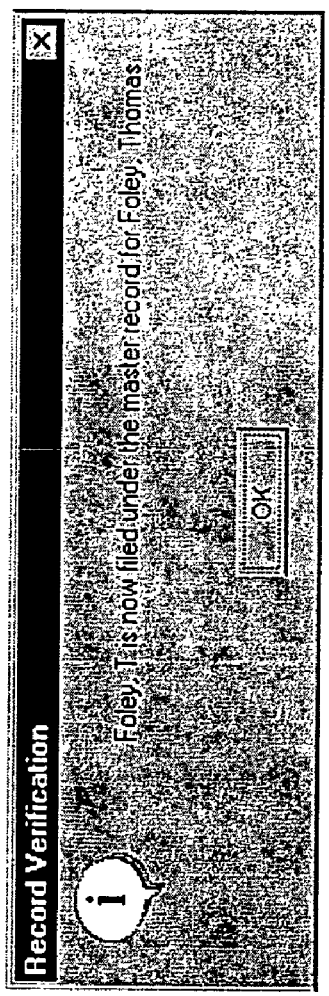

After performing a search, the search results appear in the Finding a Patient window, as shown in FIG. 49. The patient record of interest may then be selected, and the appropriate window appears. For example, if the Finding a Patient window was opened through the Create Standard Requisition or Create Future Requisition options of the Orders menu, the Requisition window appears with the General page active, as shown in FIG. 15. If the Finding a Patient window was opened through the Patient Records option of the Patient menu, the Patient Details window opens with Chart Page 1 active, as shown in FIG. 50. FIG. 51 illustrates Chart Page 2 of the Patient Details window.

Figure 52:
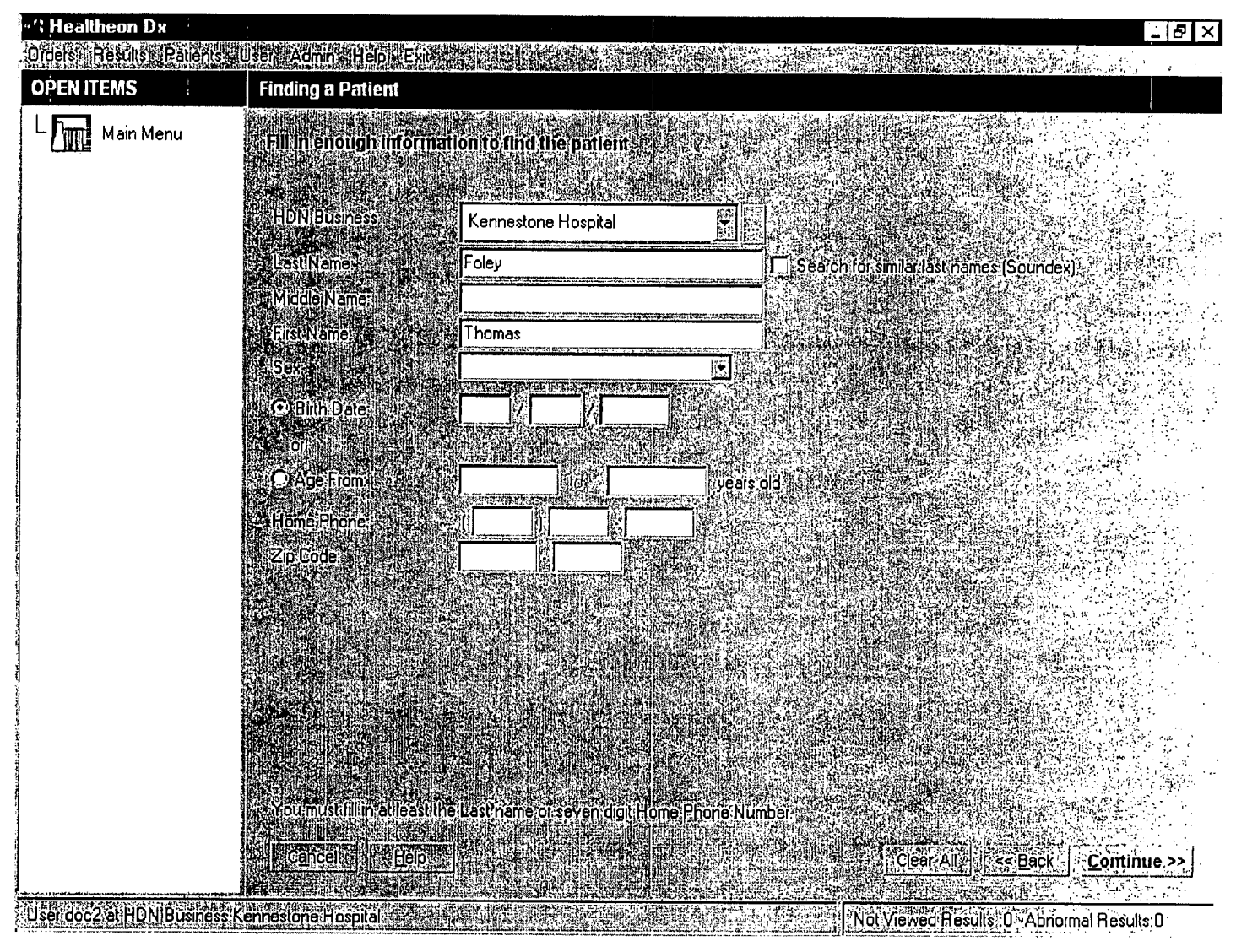

FIG. 52 illustrates the Finding a Patient power search window, which may also be used to lookup patient records.

Working with Patient Records: Patient Name Aliases

The Name Aliases page of the Patient Details window (not shown) lists other names by which the patient has been or is known. This page may be used to view or enter new name aliases for the patient.

Working with Patient Records: Patient Identifiers

The Identifiers page of the Patient Details window (not shown) lists identifiers which have been associated with the patient and allows the user to associate new identifiers with the patient. The system allows the user to link to a single patient record multiple identifiers that the user's organization and other organizations use to track the patient record, such as chart number, record number, test number and account number. For example, one facility may use Medical Record Numbers (MRNs) to keep track of its patients while another facility may use Patient Identification Numbers (PIDs) for the same purpose.

Working with Patient Records: Patient Employment Records

The Employment page of the Patient Details window (not shown) lists employment information for the patient, both past and present, and includes employer name, address, phone numbers, employment period and position. This page may be used to edit or enter new employment information for the patient.

Working with Patient Records: Patient Guarantors

The Guarantors page of the Patient Details window (not shown) lists the person(s) responsible for payment for any medical procedures not covered by a payer or a third party. A guarantor can be the patient, a parent/guardian, the patient's spouse, the patient's employer, or any other person financially responsible for the patient's medical expenses. This page may be used to edit or enter guarantor information for the patient.

Working with Patient Records: Patient Medical Data

The Medical Data page of the Patient Details window (not shown) lists data which the user's office and other organizations maintain for a patient. This page may be used to edit or enter medical data for the patient.

Working with Patient Records: Patient Insurance

The Insurance page of the Patient Details window (not shown) lists insurance information, both current and expired, for the patient, and includes insurance code, payer, insured name, policy/member number and effective dates. This page may be used to edit or enter insurance information for the patient.

Working with Patient Records: Patient Documents

The Documents page of the Patient Details window (not shown) lists all documents, such as X-rays, lab reports, and medical notes, that have been added to the patient's file either through the user's organization or other organizations. This page may be used to view the documents, change document links, or forward documents to different users.

Working with Patient Records: Patient Contacts

The Contacts page of the Patient Details window (not shown) lists persons who are contacts for the patient, and includes the contact's name, address, phone numbers and relationship to the patient. This page may be used to edit or enter contact information for the patient.

Working with Patient Records: Patient Consent

The Consent page of the Patient Details window (not shown) indicates whether there is a valid patient consent form on file for a particular patient record. This page may be used to edit or enter consent information for the patient.

Working with Patient Records: Patient Orders

The Orders page of the Patient Details window (not shown) lists all laboratory requisitions that have been prepared for the patient. To create a new standard requisition, the user can click Create New. The Requisition window appears with the General page active and the patient information populating the fields. This page may also be used to edit order information for the patient.

Working with Patient Records: Patient Result Reports

The Result Reports page of the Patient Details window (not shown) lists all result reports which have been received for the patient.

Working with Patient Records: Patient Diagnosis Codes

The Diagnosis Codes page of the Patient Details window (not shown) lists diagnosis codes which have been associated with the patient, either manually through this page or automatically when a requisition is created for the patient. This page may be used to edit or enter diagnosis code information for the patient.

Duplicate Patient Records and GMPI Overview

Because patient records are setup and maintained by multiple users at multiple facilities in the Health Data Network, it is possible that a patient will have multiple patient records. This can create problems when determining which record to maintain. Duplicate records can splinter clinical data and hinder access to patient information.

For this reason, the system implements a Global Master Patient Index (GMPI). The GMPI can link multiple records together for the same patient. Thus, the GMPI gathers patient information together under a single umbrella. In the preferred embodiment, GMPI functionality within the system includes:
  Locating patient records
  Locating duplicate records for a selected patient
  Printing a selected patient record with all its duplicate patient records Reconciling potential duplicate patient records found while searching and retrieving a patient's record Final reconciliation (certification) of suspected duplicate patients records Maintaining a persistent relationship between patient records in the GMPI Maintaining a reconciliation audit trail Patients: Link Duplicate Patient Records The Link Duplicate Patient Records menu option of the Patients menu enables the user to link two patient records that are suspected of being duplicates of each other. When linking the records, one is designated as the lead record (also called a master record) and the other the trailer of the lead record. Once linked, if the user selects the trailing patient record, the lead patient record will be opened instead. The dialog box shown in FIG. 53 appears in order to notify the user that this has occurred.

The link established between the two records using the Link Duplicate Patient Records menu option may be referred to as a confirmed link. This confirmed link may then be certified, e.g., by a GMPI administrator.

Figure 54:
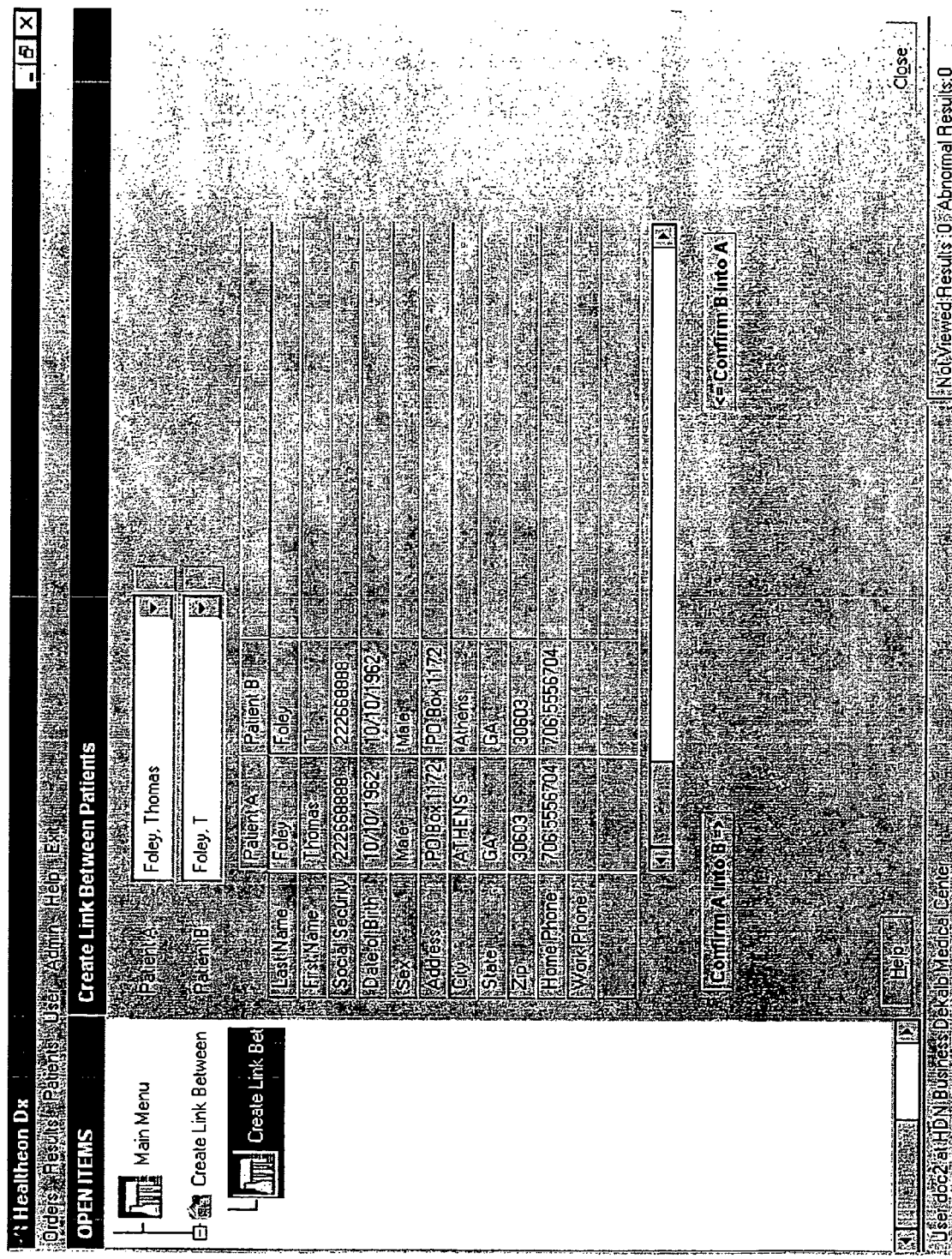
Figure 55:
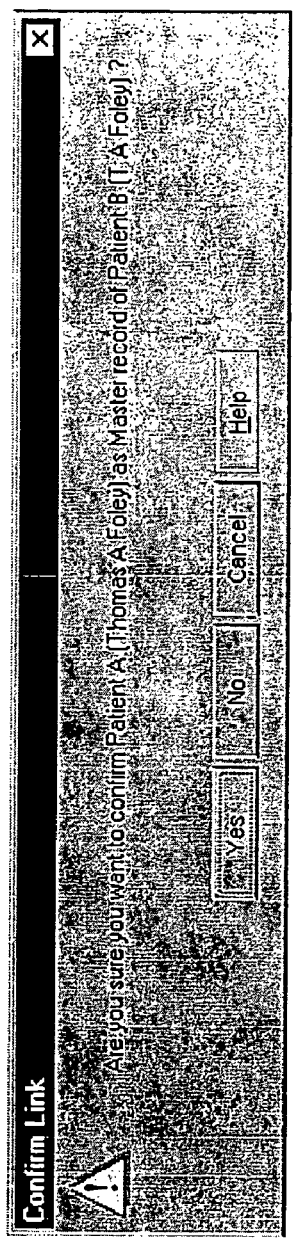

When the user selects the Link Duplicate Patient Records menu option, the Create Link Between Patients window appears, as shown in FIG. 54. In the Patient A field, the user selects the first patient of the duplicate pair. In the Patient B field, the user selects the second patient of the duplicate pair. If the user wants Patient A to be the lead record, the user clicks Confirm B into A. If the user wants Patient B to be the master record of Patient A, the user clicks Confirm A into B. The Confirm Link Dialog Box then appears, as shown in FIG. 55. The user clicks Yes to confirm the link as described in the dialog box. A confirmed (directional) link between the records is then created, and the Created a Link dialog box appears.

An unresolved link occurs when a user is reconciling a duplicate pair through the Link Duplicate Patient Records and selects the "I do not know option". In this case, the link status changes from an unconfirmed link to an unconfirmed unresolved link. This link status is not visible to the user, but it will appear in the Suspected Duplicate Log under the Unconfirmed Link column. If the user selects a patient record with an unresolved link during the reconciliation process, the first column of the reconciliation grid on the LINK row will display the unresolved link status. If the link has been reconciled with the "I do not know" option meaning it is an unresolved link, the user line will display the name of the user who carried out the reconciliation action. Unresolved links do not appear displayed on any of the application screens, but the GMPI system keeps track of them in an audit trail log that can be viewed or printed by administrators.

Patients: Reconcile Duplicate Patient Records

The Reconcile Duplicate Patient Records menu option of the Patients menu is used to provide official certification of patient record links. This function is typically used by administrators who are responsible for the oversight and maintenance of the Global Master Patient Index (GMPI).

When the user selects the Reconcile Duplicate Patient Records menu option, a list of patient records that have links to other records appears, as illustrated in the Finding a Patient with Links window (FIG. 56). As shown in FIG. 56, the system provides filters enabling the user to filter the patient records that appear in the list. For example, the filter may be based on the system time stamp: e.g., 24 hours, 48 hours, 72 hours, 7 days, 30 days, etc. Also, a custom filter may be applied. For example, the custom filter may enable the user to search for patient records by link status, such as Unconfirmed Link, Indirect Link, Confirmed Link, Confirmed Unlink, Certified Link, and All.

The Certified Link column indicates the number of certified links for the patient. The Confirmed Link column indicates the number of confirmed links for the patient. The Confirmed Unlink column indicates the number of confirmed unlinks (or denigrated links) for the patient. The Indirect Link column indicates the number of indirect links for the patient. The Unconfirmed Link column indicates the number of unconfirmed links for the patient.

Assuming the user has the proper security clearance, the Reconcile Duplicate Patient Records function of the system enables the user to:

Retrieve and View the selected patient record and all its potential duplicates. The selected patient's demographics along with all its links appear in columnar format.

View a graphical representation of the selected patient record and all its potential duplicates.

Print demographics information for the selected patient record and its suspected duplicate records.

View details of the selected patient record or any of its duplicate records on the grid.

Reconcile a link between duplicate patient records. Reconciling a duplicate record pair involves one or more of the following tasks:

Denigrating a link between two records.

Certifying a confirmed or unconfirmed link. This creates a certified link between two records.

Certifying a denigrated link

Denigrating a certified or confirmed link. When a certified or confirmed link is denigrated, it ceases to be directional.

Examine the Link Path of any potential duplicate records. This means that the user can select one of the duplicate records and make it the new selected patient record to view all of its links.

Figure 57:
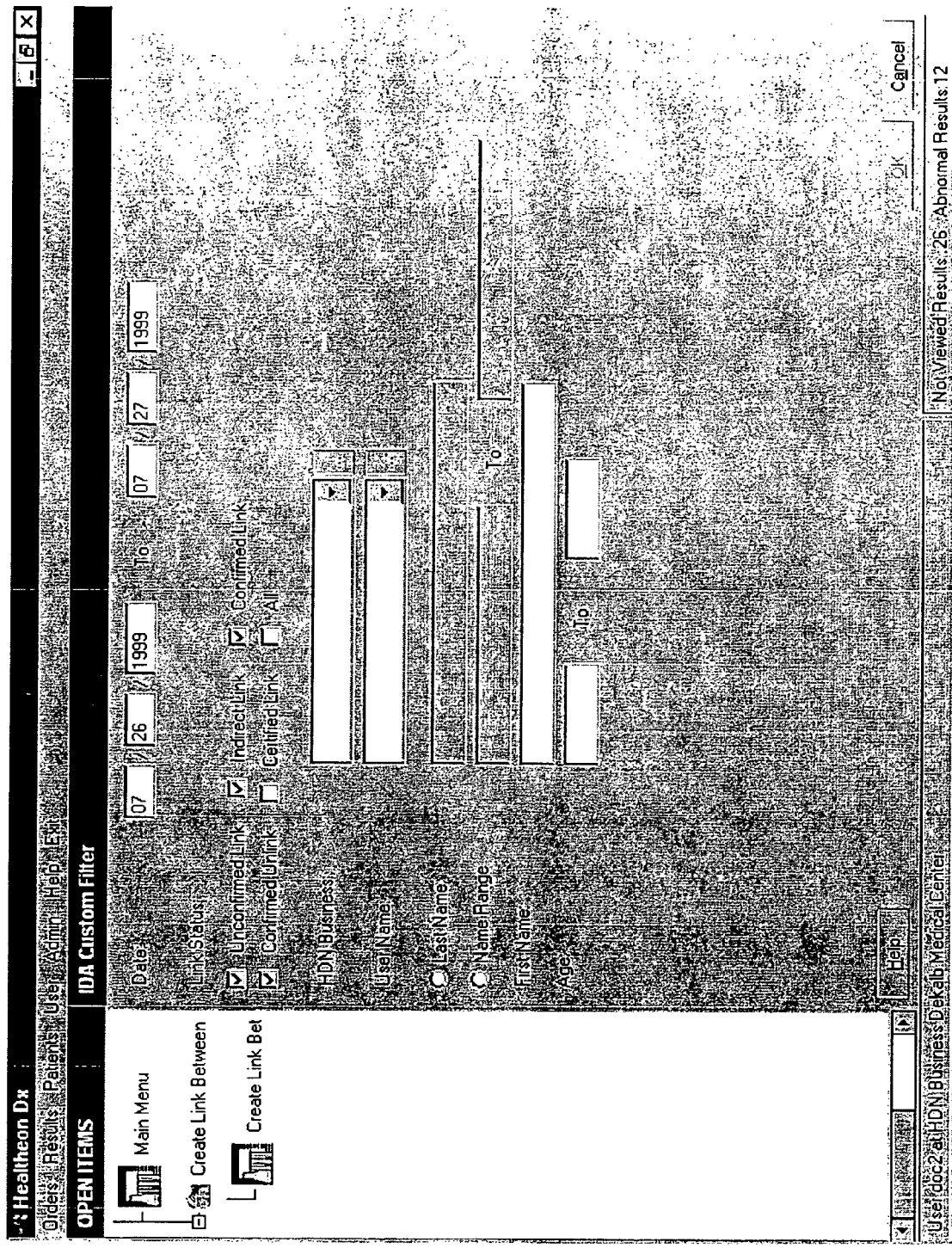

To find a patient record with links, the user chooses Reconcile Duplicate Patient Records from the Patients menu. The Finding a Patient with Links window appears, as shown in FIG. 56. The user may select a pre-defined filter from the drop-down list next to the Filter field. The user may apply a custom filter by clicking Custom. The Custom Filter window appears, as shown in FIG. 57. The user may then enter the filter criteria in the fields and click Apply to apply the filter and return to the Finding a Patient with Links window.

The result list appears, as shown in FIG. 56. To sort the list, the user can move the mouse pointer over the heading of the column to sort on and click. The search results list is sorted in ascending order using the selected column as the sort criteria.

Figure 58:
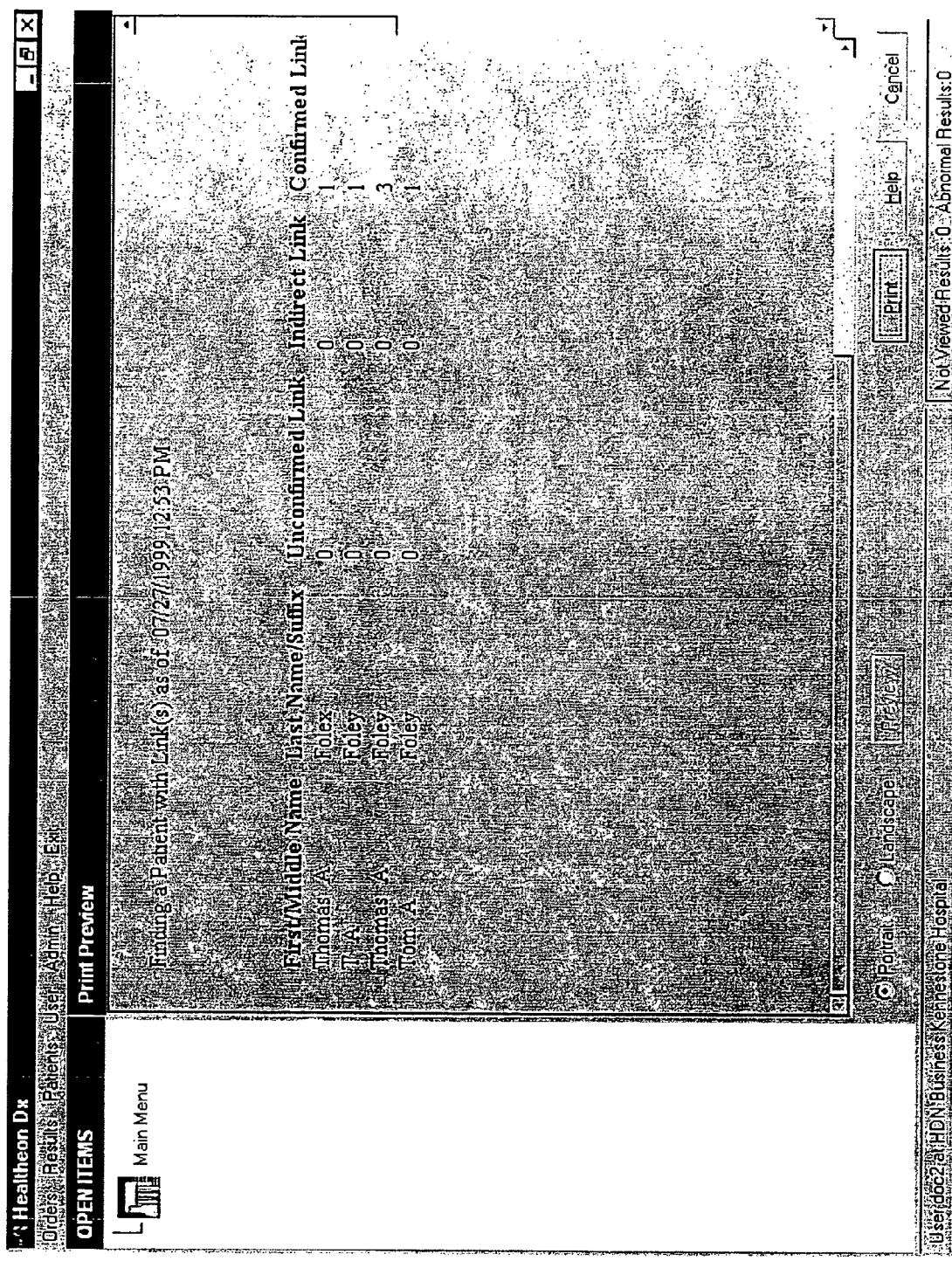

To print the list, the user clicks Print List. FIG. 58 illustrates a Print Preview window.

Figure 59:
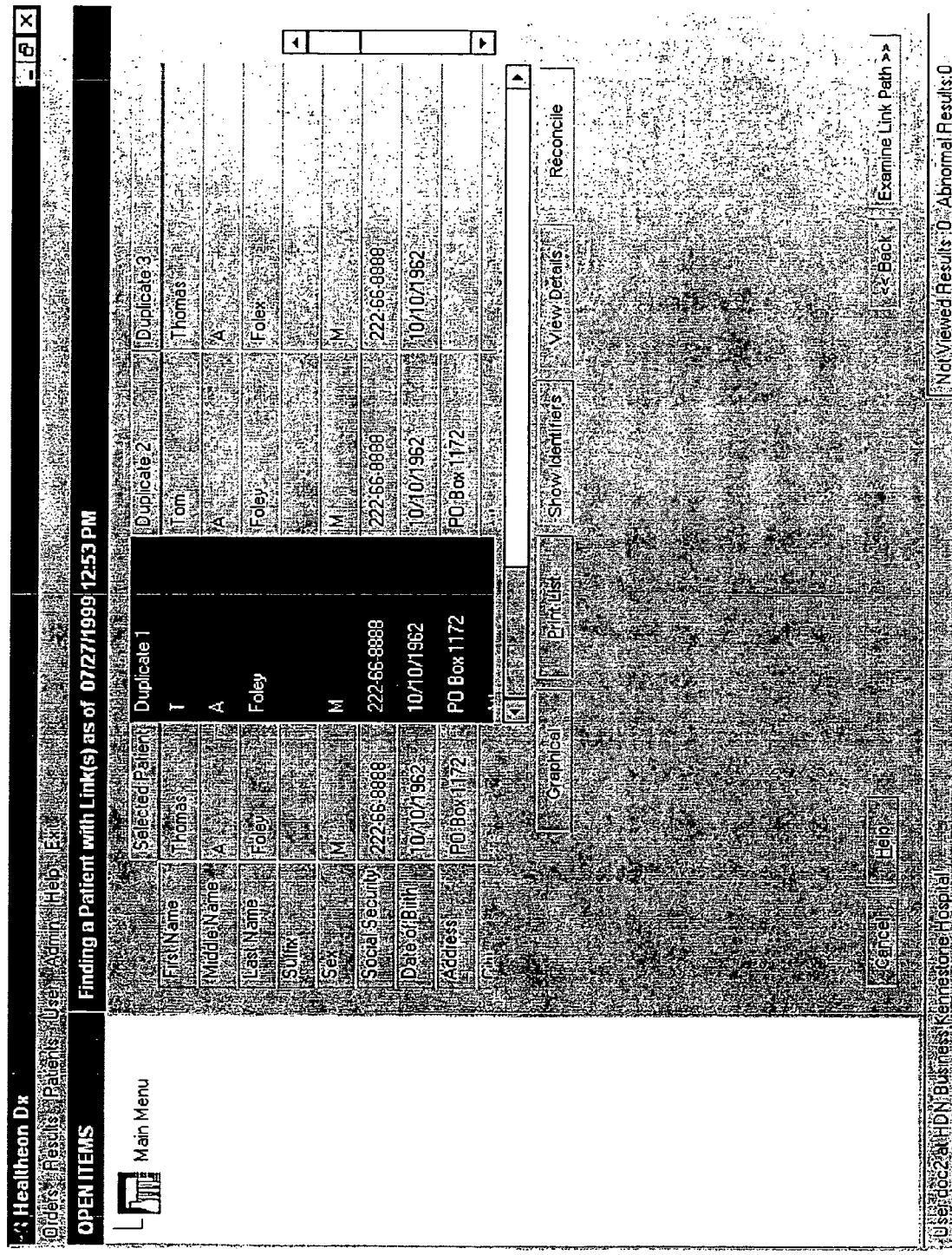

To reconcile a patient record, the user highlights the desired record and clicks Continue. The Finding a Patient with Links table appears, as shown in FIG. 59. To reconcile duplicate patient records, the user highlights a Duplicate patient record to reconcile with the selected patient record and clicks Reconcile.

Figure 60:
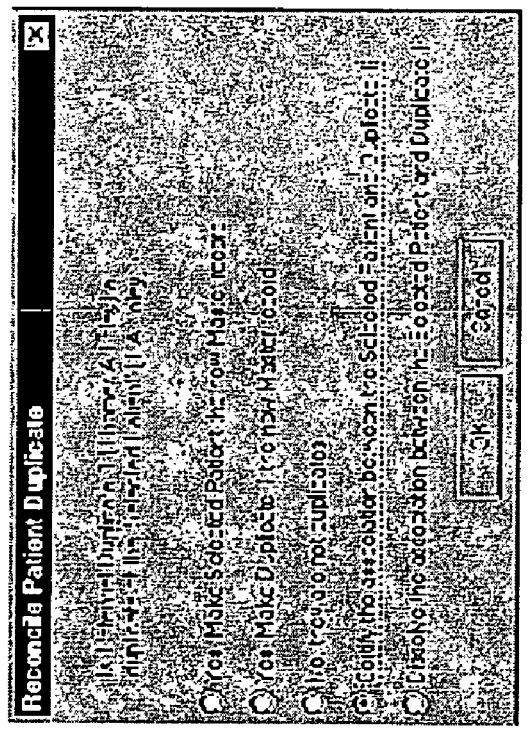

In response, the Reconcile Patient Duplicate dialog box appears, as shown in FIG. 60. The dialog box includes a statement at the top indicating which patient record is currently designated as the Potential Duplicate and which patient record is designated as the Selected Patient.

To make the Selected Patient the leader record of the Potential Duplicate, the user chooses "Yes. Make Selected Patient the new Master record".

To make the Potential Duplicate the leader record of the Selected Patient, the user chooses "Yes. Make Duplicate # the new Master record".

If the records are not duplicates, the user chooses "No. they are not duplicates".

To certify the association between the Selected Patient and the Potential Duplicate, the use chooses "Certify the association between the Selected Patient and the Duplicate #."

To denigrate the association between the Selected Patient and the Potential Duplicate, the user chooses "Dissolve the association between the Selected Patient and the Duplicate #".

To terminate reconciling the two patient records, the user clicks Cancel.

To view the details of a patient, the user highlights the column containing the patient to view and clicks View Details. The Patient Details window appears.

To show the identifiers for each patient, the user clicks Show Identifiers. The list "jumps" to the fields containing the identifiers for the patients.

Figure 61:
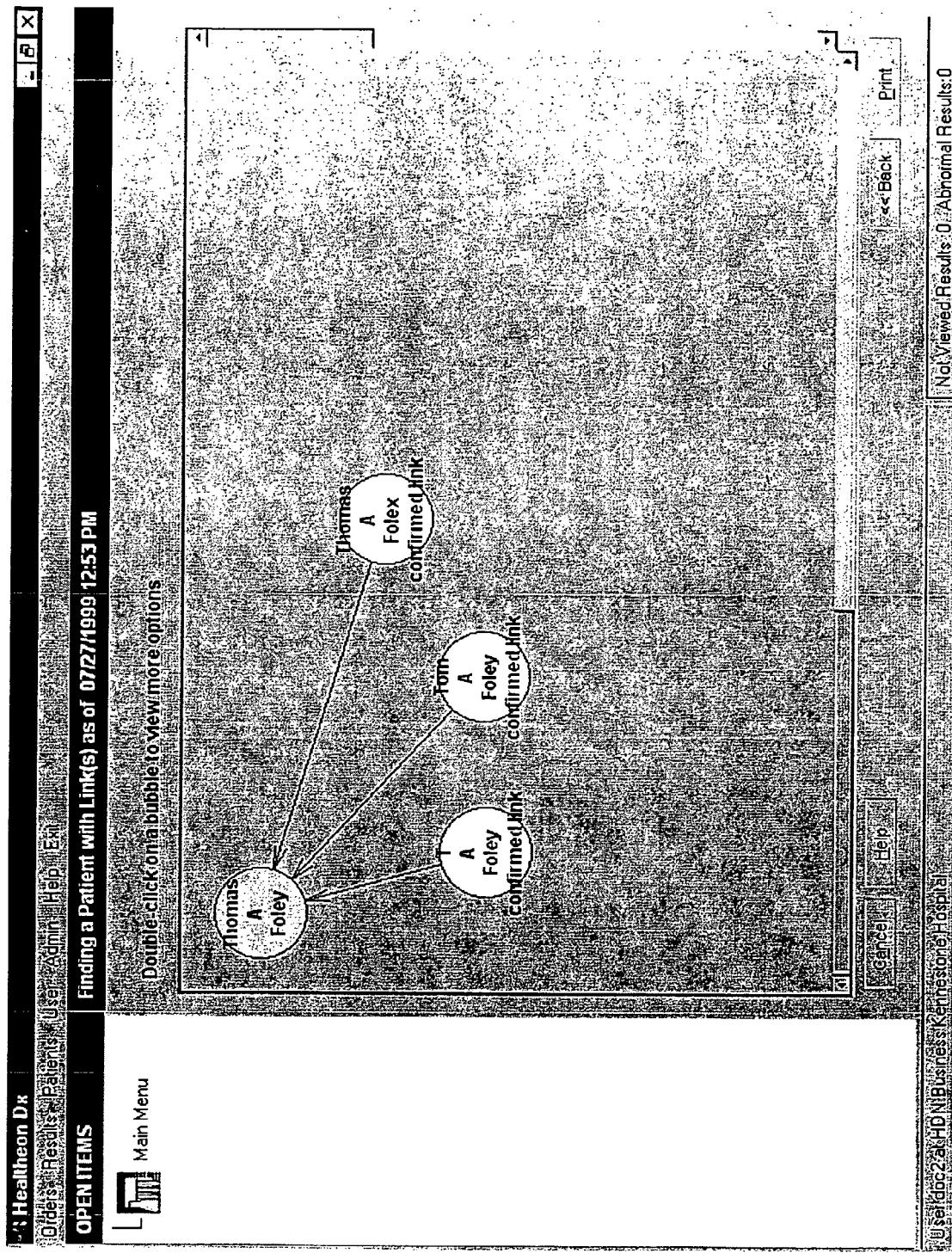

To view a graphical representation of the table, the user clicks Graphical. In response, a graphical representation window appears, as shown in FIG. 61. The user can click and drag a patient-bubble across this window. To view details of the patient record, the user can double-click on a patient-bubble and select View Details from the menu that appears. To reconcile a patient record, the user can double-click on a patient-bubble and select Reconcile from the menu that appears. To return to the Finding a Patient with Links table window, the user clicks Back. To print the Finding a Patient with Links table window, the user clicks Print.

Patients: Manage Patient Groups

The Manage Patient Groups menu option enables the user to create patient categories that are identified by a code and to sort patients into these various categories. Examples of patient groups are "High HDL Cholesterol Group", "Diabetes Control Group", and "*E. Coli* Testing". Patient Groups with Report Groups are used to generate Results Summary Reports and Cumulative Reports. Information obtained from these reports can be used to schedule patient visits in advance, gather valuable statistical information and identify trends in a patient population.

Figure 62:
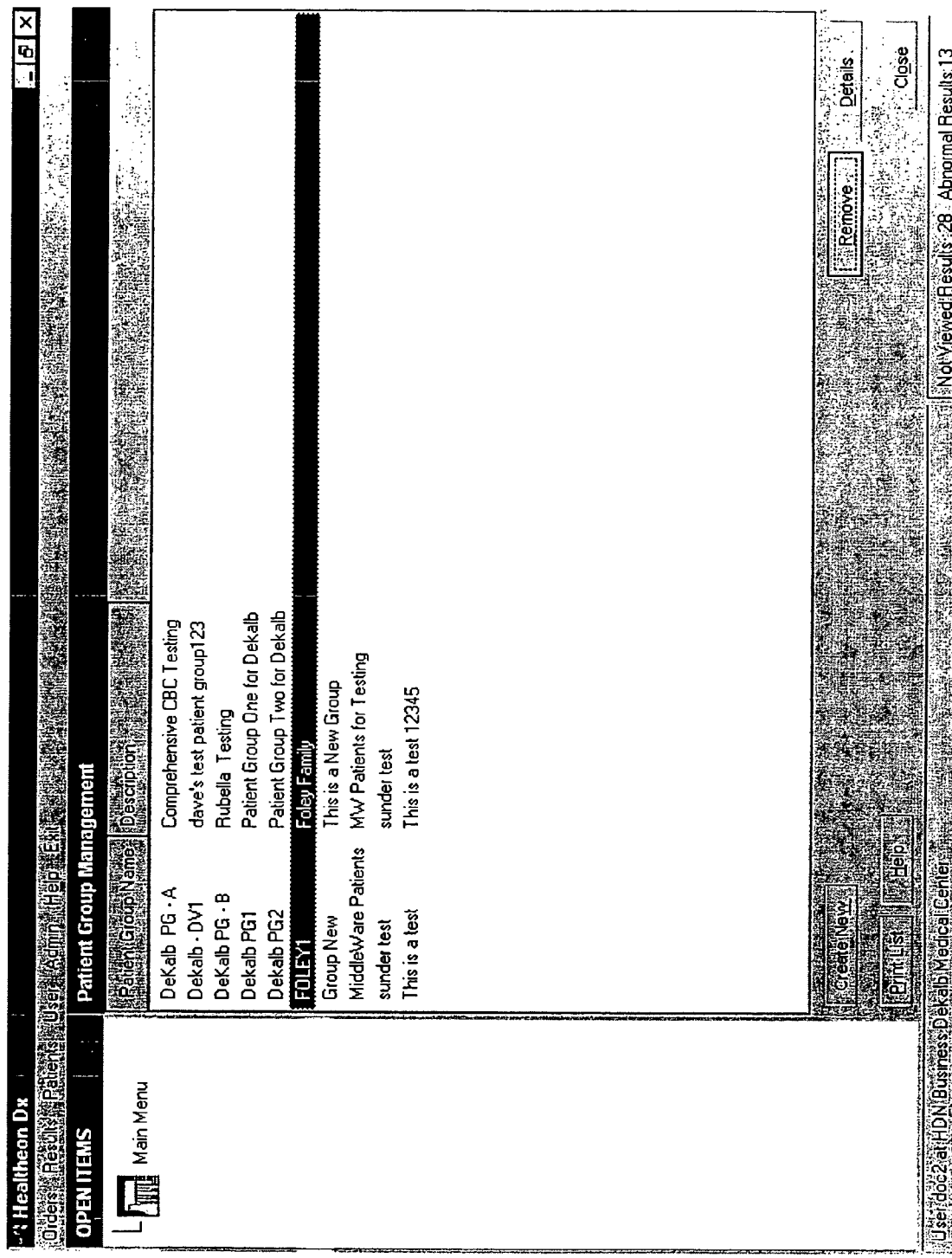

When the user choose Manage Patient Groups from the Patients menu, the Patient Group Management window appears, as shown in FIG. 62. From the Manage Patient Groups menu option the user can:

List all patient groups
List all the patients in a patient group
Create New patient groups
Add a new patient to a patient group
View a patient group
View details of each patient in a patient group
Modify details in a patient group
Remove a patient group
Remove a patient from a patient group
Print a list of all the patient groups
Print details on a specific patient group The user can follow the following procedures to view or modify an existing patient group from the Patient Groups Management window.

Figure 63:
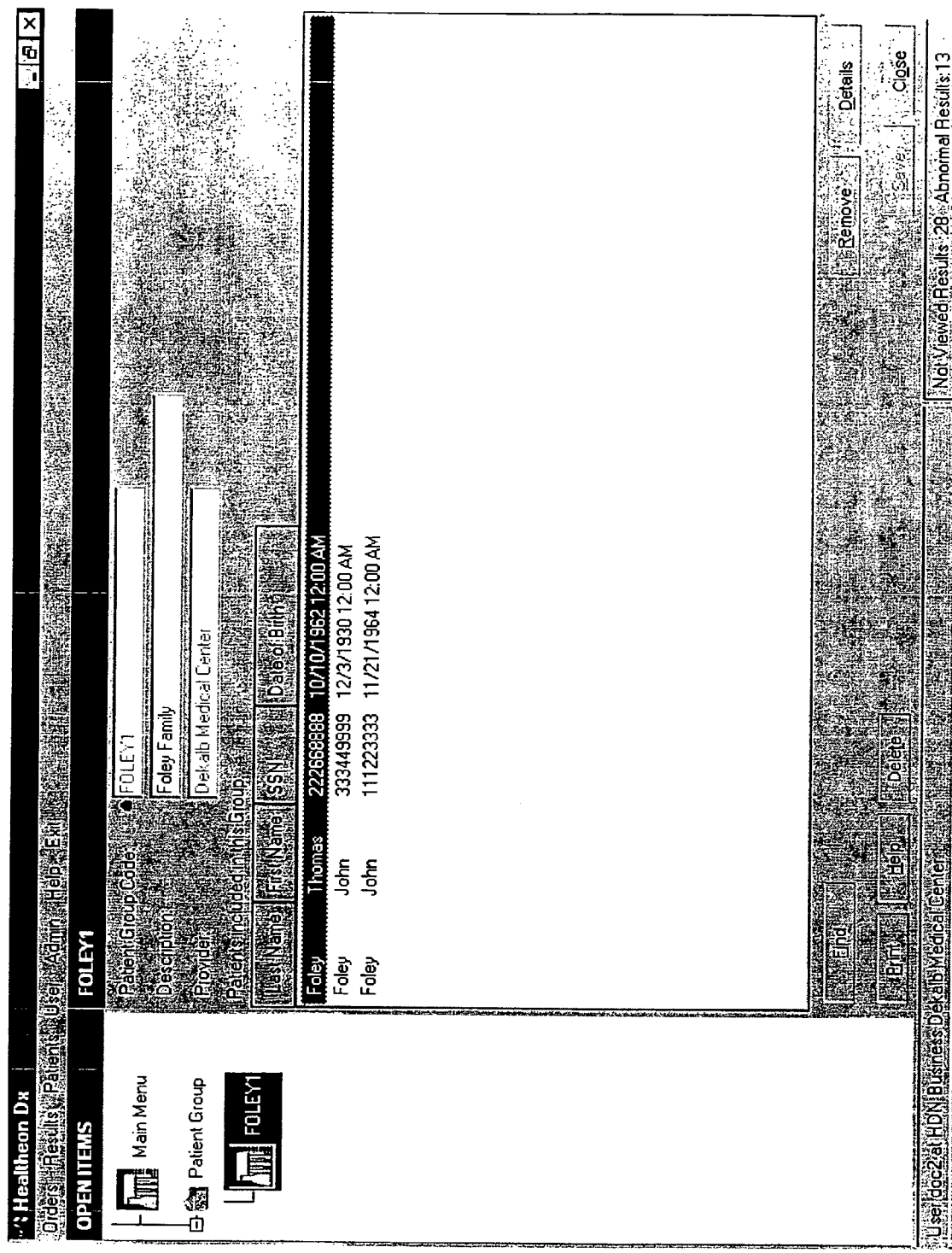

1. On the Patient Groups Management, highlight the patient group to view or modify and click Details. The Patient Group Details window appears for the selected patient group, as shown in FIG. 63. The Description field is a description of the patient group. The Patient Group Code field is the patient group code. The Provider field is the provider for which the patient group was created. The default value for this field is the active HDN Business.

2. View or modify the fields at the top of the screen.

3. Add and/or remove patients on the Patients included in this Group list. To add a patient to the group, click Find. The Finding a Patient window appears. Find an existing patient or create a new patient to add to the patient group. The patient is added to the group. To get details of a patient previously added to the group, highlight the patient and click Details. The Patient Details window appears with the Chart Page 1 page active and the information last entered for the patient populating the fields.

Patients: Patient Group Listing

The Patient Group Listing menu option of the Patients menu enables the user to preview or print a list of all the patient groups for each provider that are created through the Manage Patient Groups function. The items on the list appear sorted in alphabetical order. A header page is a configurable option. The header pages shows: Date and time of the report, Name of the user running the report, Comment line, and Search criteria used to generate the report.

Figure 64:
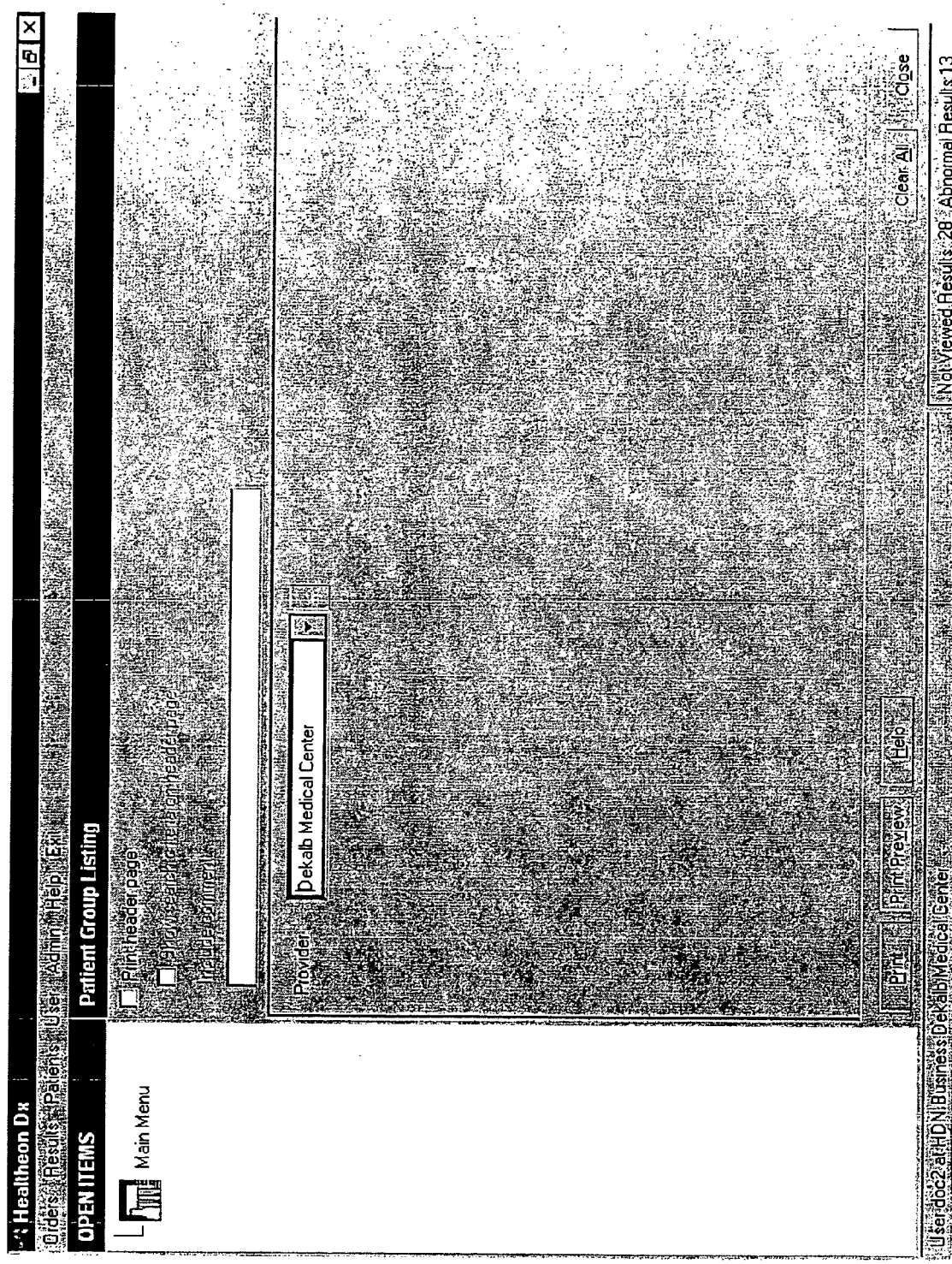
Figure 65:
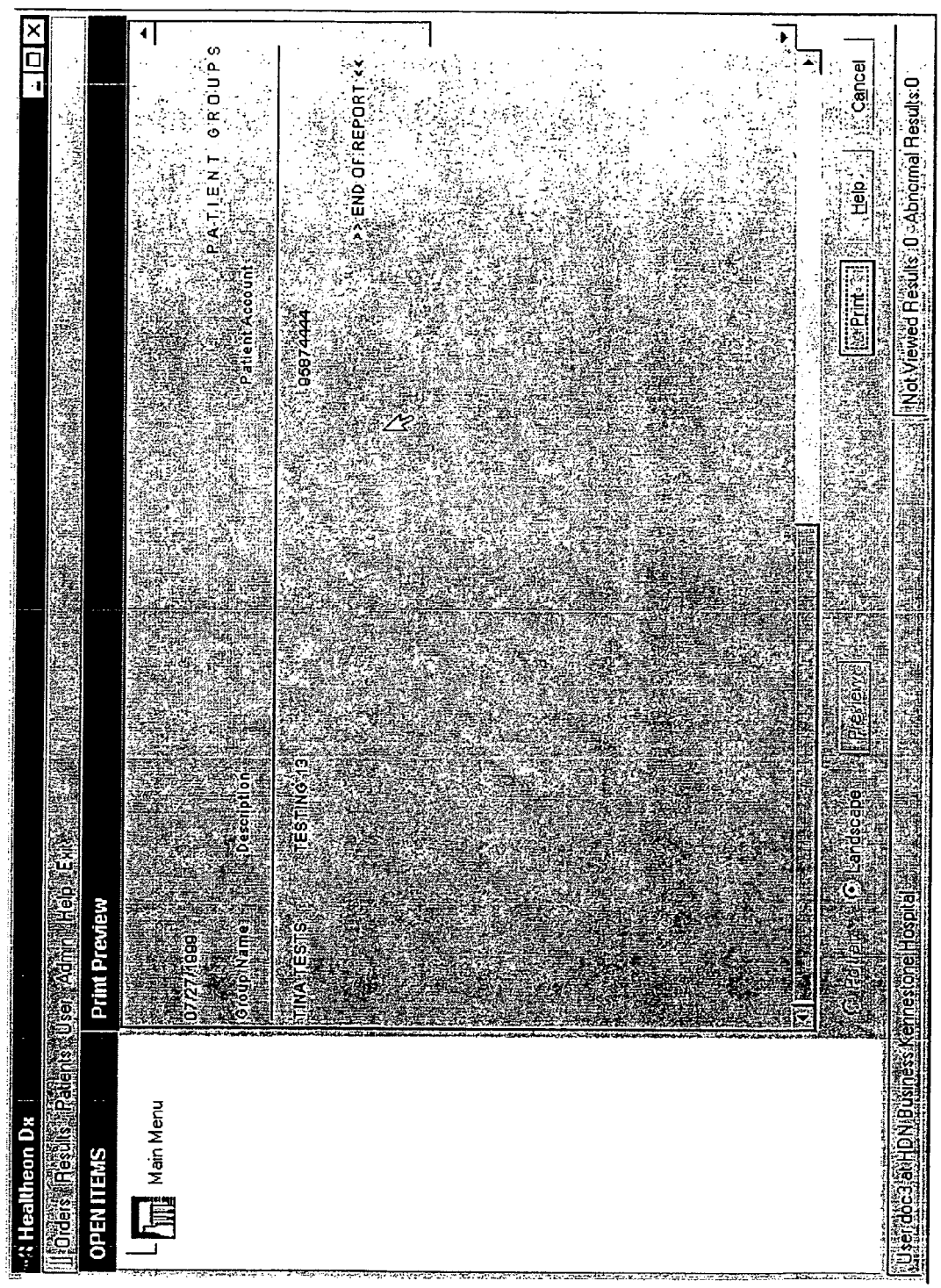

To generate the Patient Group Listing, the user selects Patient Group Listing from the Patients menu. The Patient Group Listing window appears, as shown in FIG. 64. The user then enters criteria for generating a patient group listing. FIG. 65 illustrates a Patient Group Listing Print Preview window for previewing a report.

User Module

Figure 66:
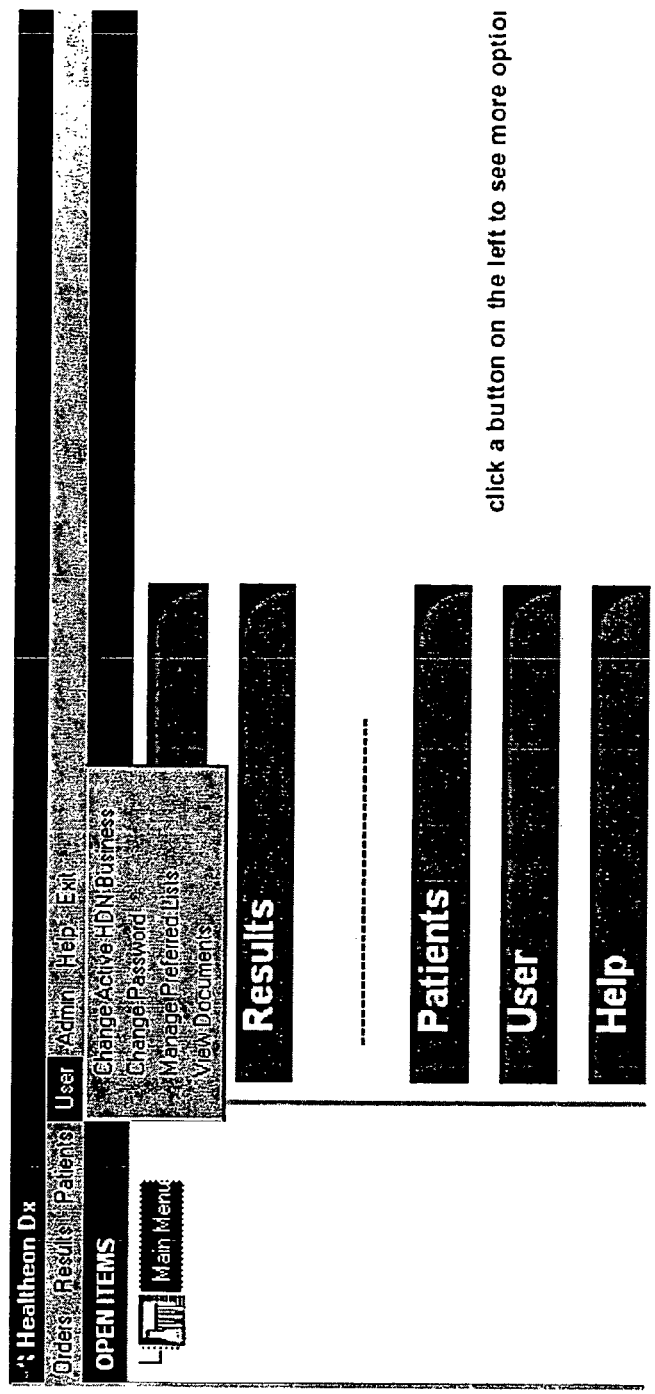

In one embodiment, there are four basic functions to the User module of The system:

Change Active HDN Business
Change Password
Manage Preferred Lists
View Documents These functions are accessed through the User menu, as shown in FIG. 66, or the User desktop menu. The User functions are described below. Before discussing these functions, a brief overview of security considerations is given.

Security Considerations in the System

The system provides the ability to secure information across a large and open network of computers and the people that use them. This network is referred to herein as a Health Data Network, or HDN. The security of this network, including access to it, is critical because the system provides access to confidential patient information, including laboratory test results and medical history.

User Accounts—Before the user can log on to the system, the user must have a user account including a logon name and a password. The user account provides the needed security for controlling access to the HDN and identifies the user while the user is using the system.

HDN Businesses—When the user log on to the system, the user connects to the system on behalf of a Health Data Network (HDN) Business. An HDN Business is any business, including a hospital, clinic, physician office, laboratory, payer, or employer, that participates in the creation and sponsorship of a specific HDN.

Through the user's user account, the user is linked with HDN Businesses. The user may be allowed to log on to the system on behalf of more than one HDN Business. For example, the user's primary HDN Business may be the office in which the user is currently working, but there may also be times when the user may need to access the system on behalf of a hospital where the user has patients in order to check on their status. In this case, the user may be linked to both HDN Businesses, the user's office and the hospital.

Parent-Child HDN Businesses—If the user's practice has more than one location or business unit, and all orders and results are shared throughout the practice, the user's practice may be configured as a single HDN Business. In this case, the practice's data may be stored in a central location and can be accessed by all users who have the appropriate permissions.

However, if the user's practice has more than one location or business unit, and the need exists to keep orders and results isolated within a location or business unit, the practice may be configured in a parent-child HDN Business relationship. This prevents lab orders and results and other data associated with one location or business unit from being accessed by users logged on to other locations or business units of the practice.
  1. A parent HDN Business is created for the entire practice.
  2. Child HDN Businesses are created for each business unit or location. Some business units or locations may actually share a single child, while others may be set up as individual child HDN Businesses.
  3. All child HDN Businesses are linked to the single parent HDN Business.
  4. The user's user account is associated with each child HDN Business where the user are permitted to access the information. The user's account may not be associated with all child HDN Businesses for the practice. Some advanced users may have their account associated with the parent HDN Business so they can carry out global administrative functions.

The data for the user's practice is then stored at two levels:
  1. At the parent-level, the following information is stored and available to all child HDN Businesses of that parent HDN Business:
    Patient records and supporting information, excluding orders and results
    Payers
    Providers and caregivers
    Codes, including diagnosis codes (ICD-9), test codes, analyte codes, report codes and profile codes
    Report groups, patient groups and test groups
    System configuration When the user add any of these items to the system, they are available to all child HDN Businesses associated with the parent HDN Business.
  2. At the child-level, the following information is stored on behalf of and is only available to users logged on to that child HDN Business:
    User preferences
    Orders
    Results originating from orders transmitted on behalf of the child HDN Business The orders, results and user preferences for each child HDN Business are isolated from the other child HDN Businesses. The only way a user can access this information is to log on to the child HDN Business. If the user are logged on to the parent HDN Business and have the appropriate permissions, the user can access all information for the practice, including the orders and results stored specifically for a child HDN Business.

Healtheon Field Service Representatives work with the user's practice to best determine the configuration of the user's system from the perspectives of data management and security.

Permissions, Roles, Operations and Objects

In addition to the ability to log on to the system on behalf of an HDN Business, users also must have permission to actually use the many functions of the system, and need access to the data stored across the HDN. As part of creating the user's permission profile, the user is assigned a role that the user performs when working with the system. This includes information regarding the types of data the user needs to be able to access and the functions the user needs to carry out on that data.

Types of data are referred to as objects and functions are referred to as operations. Patient records, lab requisitions, lab results, test codes, ICD-9 codes, lab profiles and physician profiles are examples of objects. An example of an operation is adding new objects. Viewing, modifying, printing, and deleting existing objects are also examples of operations. The process of searching for existing objects is also considered an operation.

A role defines what objects a user can access and what operations a user is allowed to carry out on each of those objects. For example, one role may allow users to add, view, modify, print and delete lab test requisitions, while another role may only allow users to view and print lab test requisitions.

When a permission profile is defined for the user, it is specific for an HDN Business. If the user belongs to more than one HDN Business, the user may have more than one permission profile. Each of these profiles may be different. For example, the user may have permission to add, view, modify, print, and delete patient records on behalf of one HDN Business, but the user may only have permission to view and print patient records on behalf of another HDN Business.

Effective dates and expiration dates may also be set for each permission profile, creating a limited period of time when that permission profile is in effect. This can be useful, for example, if a first user is going to be temporarily out of the office and the first user needs to be able to allow a second user to do the first user's work while the first user is gone. The permission profile for the second user can be set to begin the first day the first user is out of the office and to expire at the end of the day before the first user returns.

An administrator may work with users to ensure that the permission profiles and roles selected for each user are sufficient to meet the users' job requirements.

User: Change Active HDN Business

When the user logs on to the system, the user is connected to the HDN on behalf of an HDN Business. The user may select a default HDN Business at login time. For example, after entering a username and password, a popup window may appear with a list of HDN Businesses to choose from. Once the user log on to the system, a message at the bottom of the screen displays the name of the user's current HDN Business.

Figure 67:
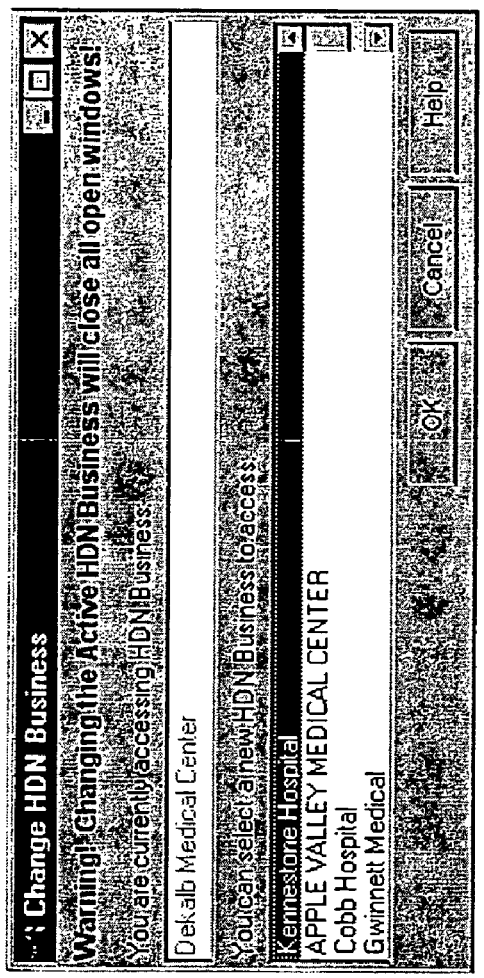
Figure 68:
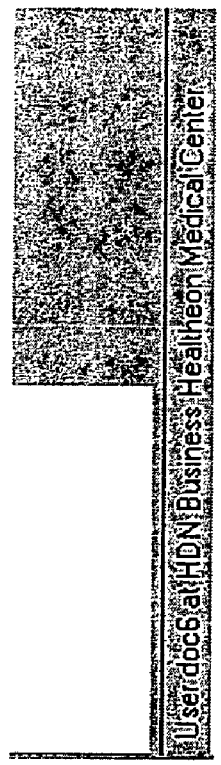

The Change Active HDN Business menu option of the User menu enables the user to select another HDN Business after the user has logged on to the system, provided that the user has permission to access more than one HDN Business. This permission may be set up by an administrator. When the user chooses the Change Active HDN Business menu option, the Change HDN Business dialog box appears, as shown in FIG. 67. The list includes HDN Businesses with which the user is associated but that are not currently active. After switching to another HDN Business, the switch can be confirmed by checking the status bar, as shown in FIG. 68.

User: Change Password

The Change Password menu option of the User menu enables the user to change the user's account password. The Change Password dialog box may impose different criteria for determining whether a password is a valid password, depending on how an organization has configured this function.

User: Manage Preferred Lists

Figure 69:
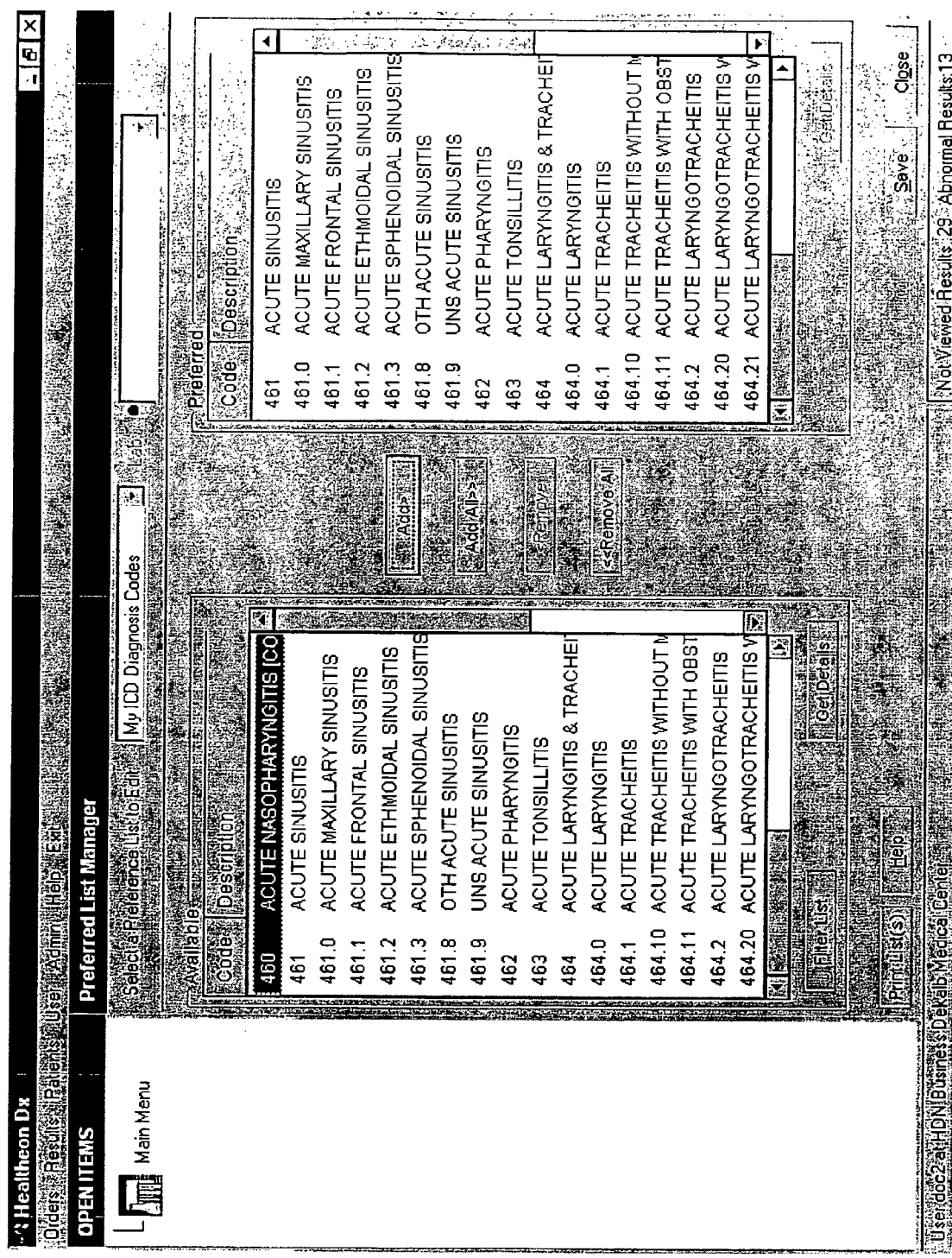

Preferred lists are a time saving feature that enable the user to carry out repetitive tasks more efficiently. The Manage Preferred Lists menu option of the User menu provides a means to carry out various recurrent tasks quickly without having to go through multiple screens and numerous keystrokes. In one embodiment, the system enables the user to set the user's own preferences for:

Caregivers
HDN Businesses
Payers
ICD Diagnosis Codes
ICD Procedure Codes
CPT Codes and
Test Codes The system enables the user to maintain and modify these preference lists to suit the user's own requirements. Setting up preference lists helps the user streamline many tasks the user does within the application. The following is a sample of some common repetitious tasks that the user can be simplified by using preferred lists:

Creating Requisitions
Generating Lab Reports
Entering Insurance Information for a Patient In the Preferred List Manager window, shown in FIG. 69, two separate lists appear side by side. On the left side of the screen, there is a list of Available items. On the right side of the screen, there is a list of Preferred items. New entries can be added to both lists.

From the Manage Preferred Lists menu option the user can:
Retrieve a preferred list.
Add items to a preferred list
Modify items on the user's preferred list
Remove single or multiple items from the user's preferred lists
Apply a Custom Filter to narrow down the user's search results
Get Details on any preferred list item
Print a preferred list
Shared Lists—The user can view the preferences of another user at the user's HDN Business or at another HDN Business and use items from their existing preferred lists to create the user's own list. There are two types of preferences: shared and individual. For example, in the case of caregivers, the user can have a My Caregivers preferred list and a Shared Caregivers preferred list.

Under the My Caregivers preferred list, a user may include those caregivers that only that user uses on a regular basis. Under the Shared Caregivers preferred list, the user may include those caregivers that are accessed by that user as well as other users associated with the active HDN Business. The user can have two types of preferred lists for other categories as well (HDN Businesses, Payers, ICD, CPT and Test Codes, etc).

Each HDN Business can set up its own list of preferences and make this list accessible to all users at that HDN Business. A user can have a different preferred list of items for every HDN Business the user has access to.

When the user displays a preferred list, the shared and individual lists may be combined and sorted in various ways, depending on what type of data the lists contain. For example, lists of caregivers, HDN Businesses, and payers maybe sorted in alphabetical order, whereas lists of ICD, CPT and test codes may be sorted numerically by code. Each item on a list may also have a descriptive comment next to it.

Users may own their preferred lists so that the entries a user makes to the user's preferred lists can be deleted only by that user. The HDN Business user preferences are accessible to all the users at that HDN Business. In one embodiment, they can be modified or deleted by any user at the HDN Business. Preferences may be linked to the user's account rather than to the user's workstation. Thus, the user can view the same preference lists regardless of the workstation used to access the system.

User: View Documents

An HDN business typically sends, receives, and stores many reports and other documents. Although these documents are often generated electronically by the various participants in the delivery of healthcare services for a patient, including health care providers, hospitals, labs and payers, the documents are traditionally printed and distributed by a number of different manual delivery methods, such as inter-office mail, facsimile, US Mail, or some other physical delivery method.

Figure 70:
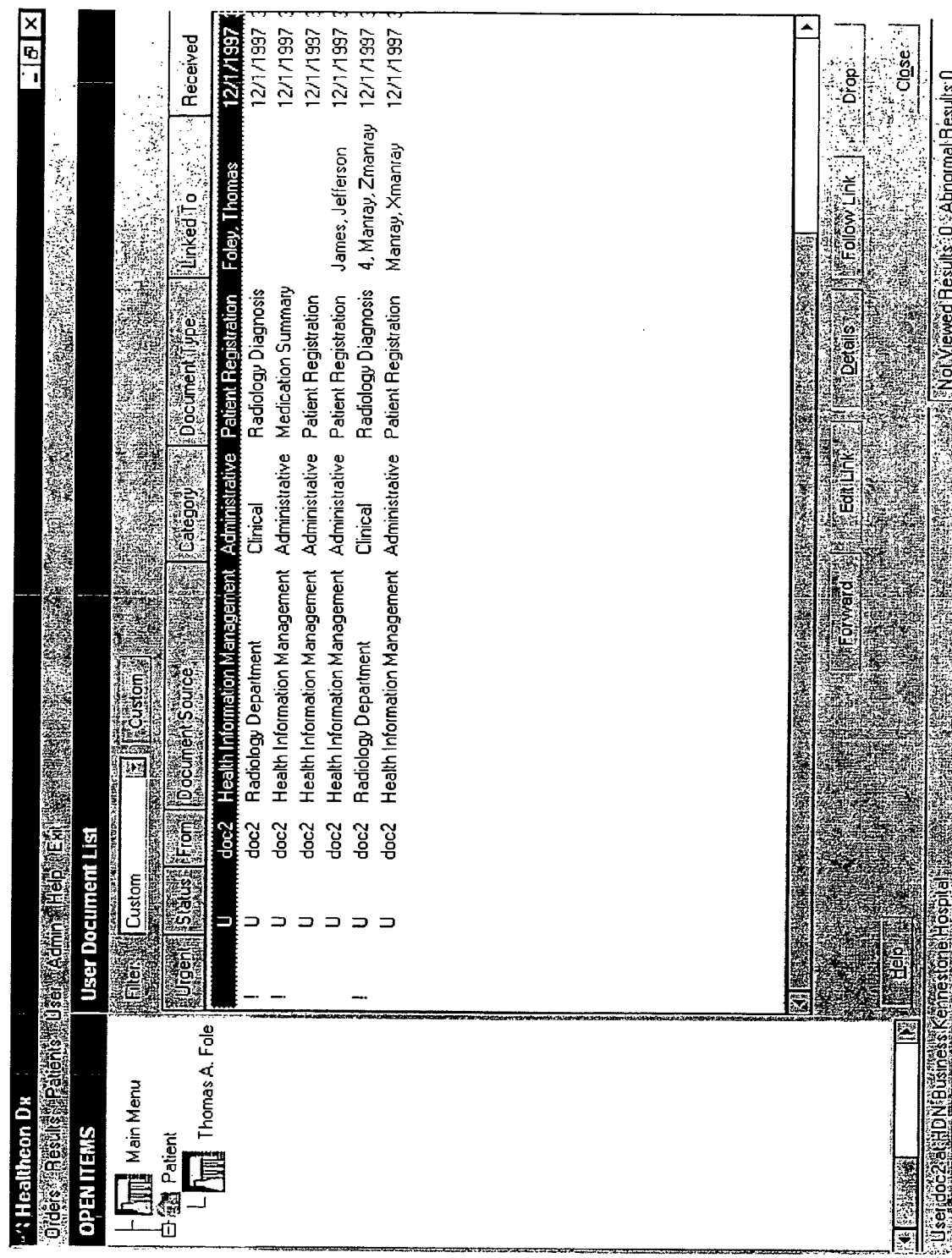

The View Documents menu option of the User menu provides instant, two-way, electronic communication between the various participants in the delivery of healthcare services for a patient. Documents, such as those described previously, can be linked to a user or list of users and then listed on their User Document List, shown in FIG. 70. From the user's User Document List, the user can:

View the document
Link the document to a patient record
Forward the document to another user or group of users Documents that are not generated electronically or are from a source not participating in the Health Data Network (HDN), such as an employer, can be faxed into the user's system and then linked to a user or list of users. The faxed document is then treated like any other document generated electronically within the HDN.

The following table provides definitions for the columns on the User Document List window:

| Column | Description |
| --- | --- |
| Category | The document category |
| Date Created | The date the document was created |
| Document Source | The source of the document |
| Document Type | The type of document |
| From | The user who forwarded the document to the user |
| Linked To | The person to whom the document is linked |
| Status | The read status of the document. A "U" indicates that the document is unread |
| Urgent | An exclamation point ("!") indicates an urgent document |

Figure 71:
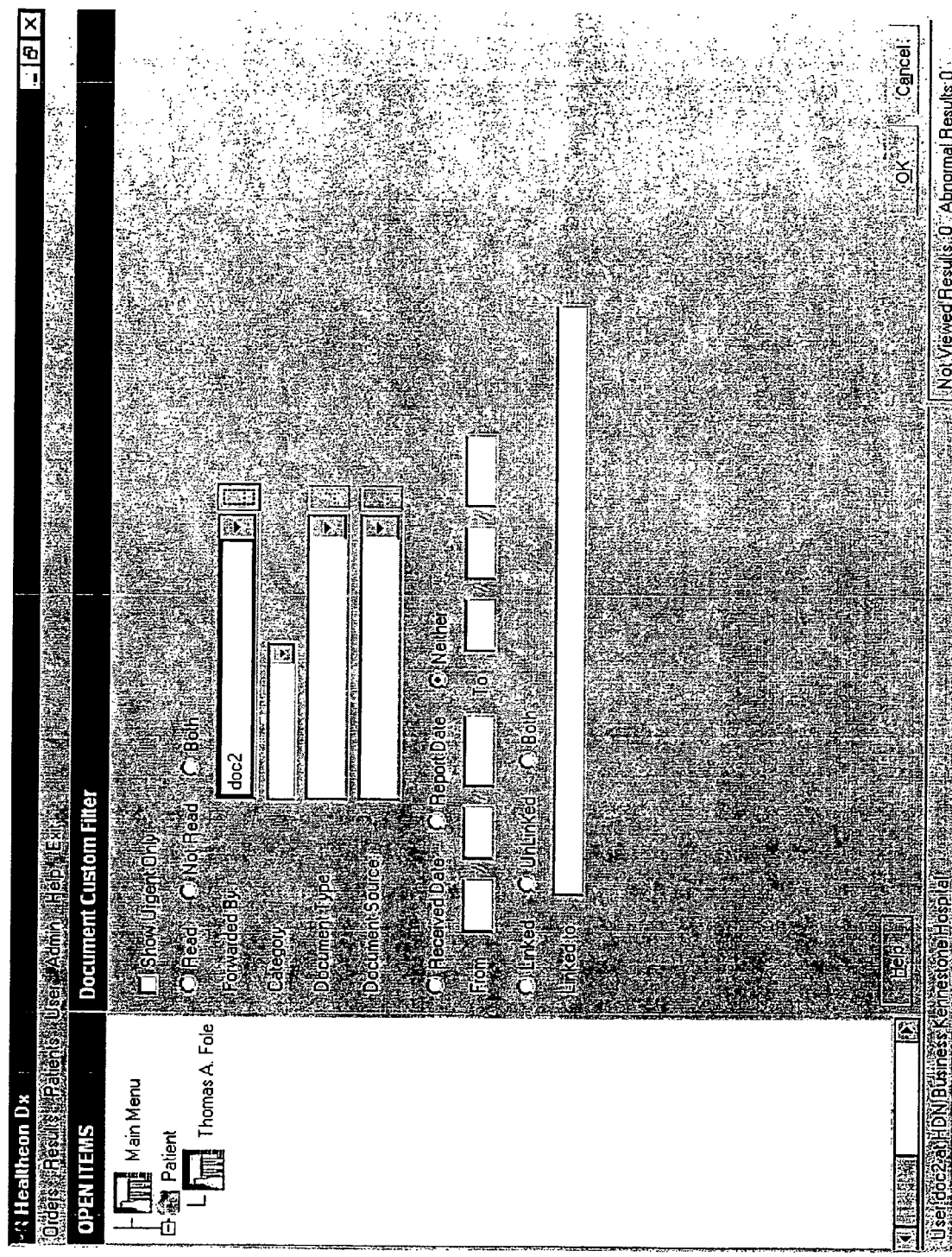

FIG. 71 illustrates a window for applying a custom filter to the User Document List.

Figure 72:
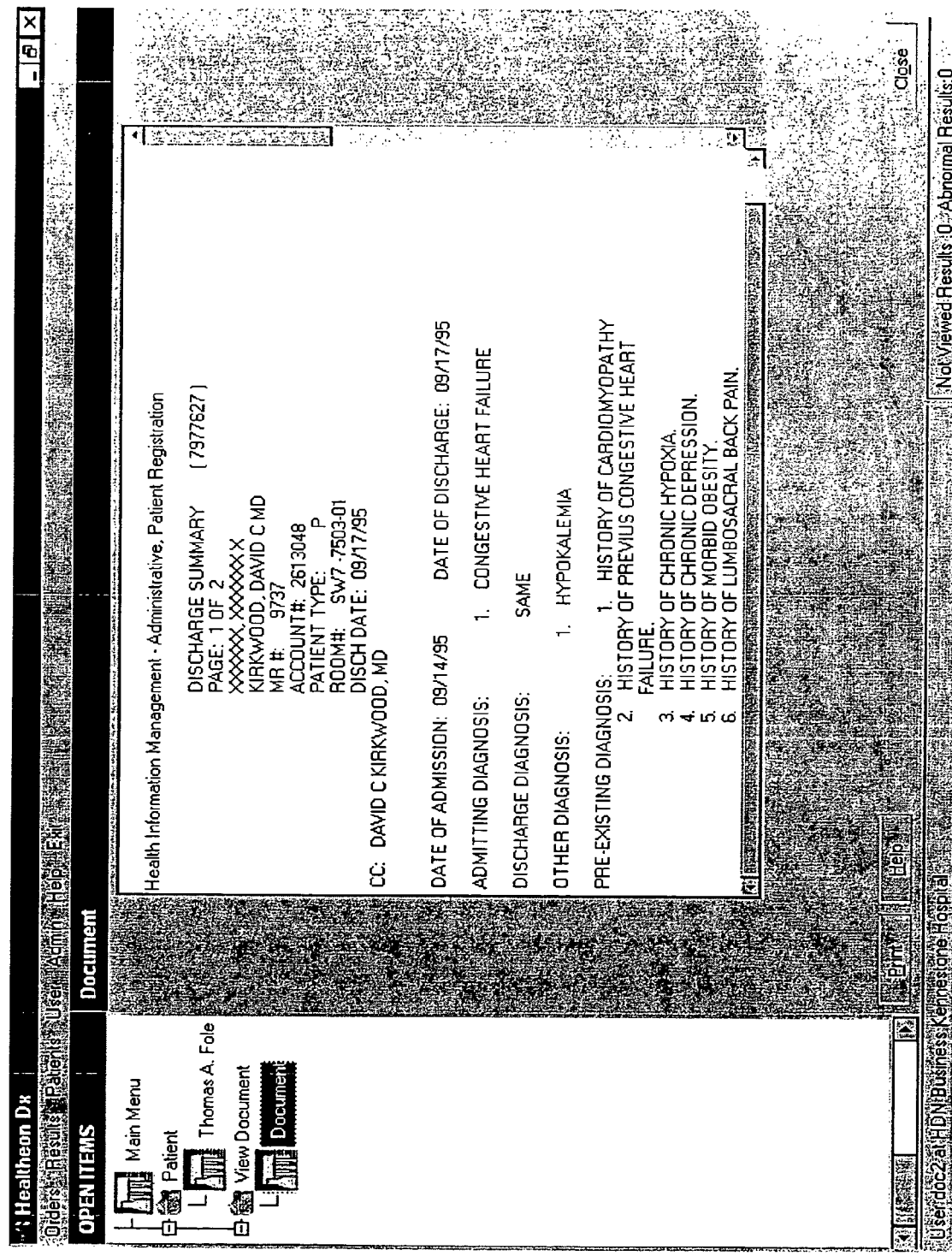

FIG. 72 illustrates a window for viewing a user document.

Figure 73:
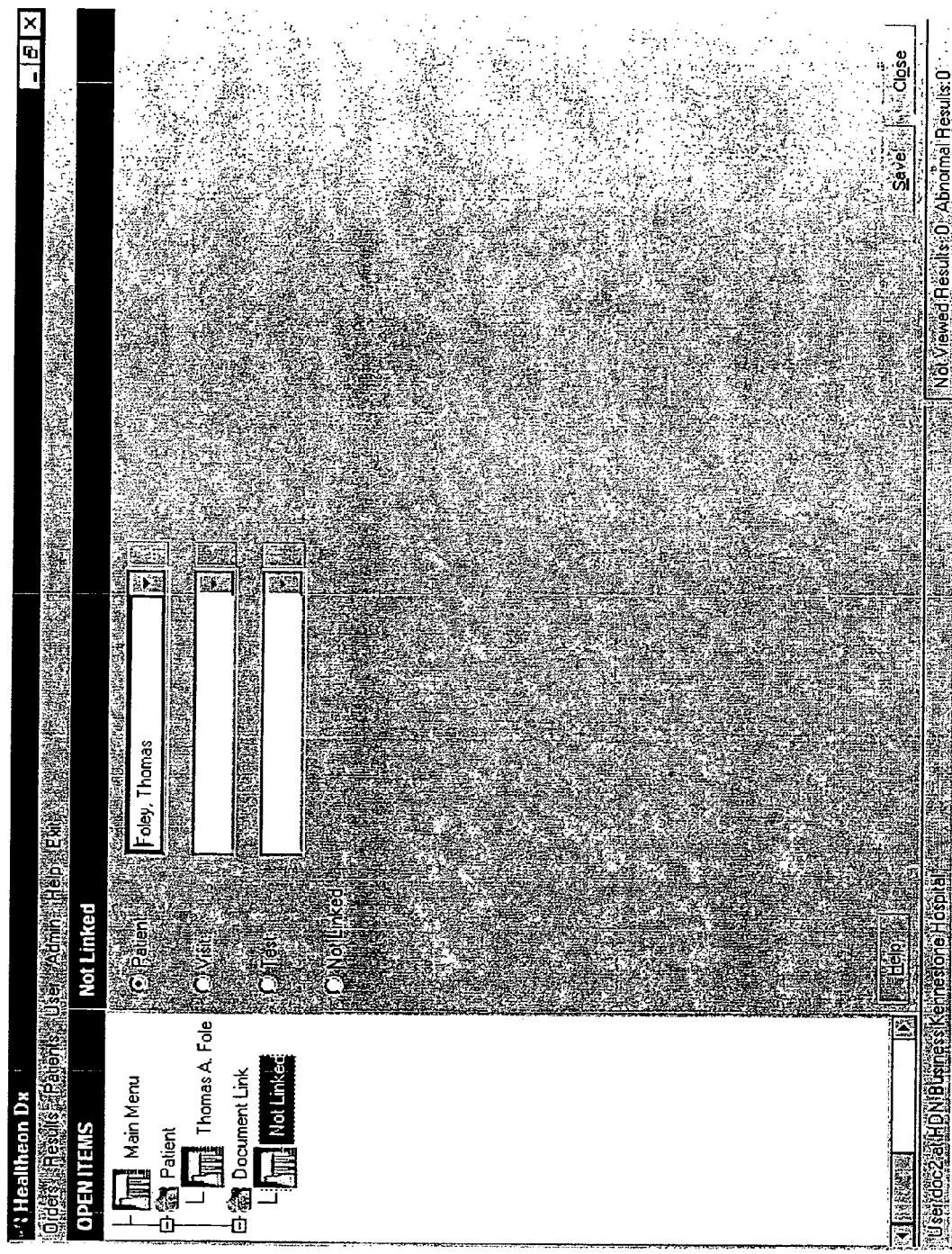

FIG. 73 illustrates a window for editing the link for a user document.

Figure 74:
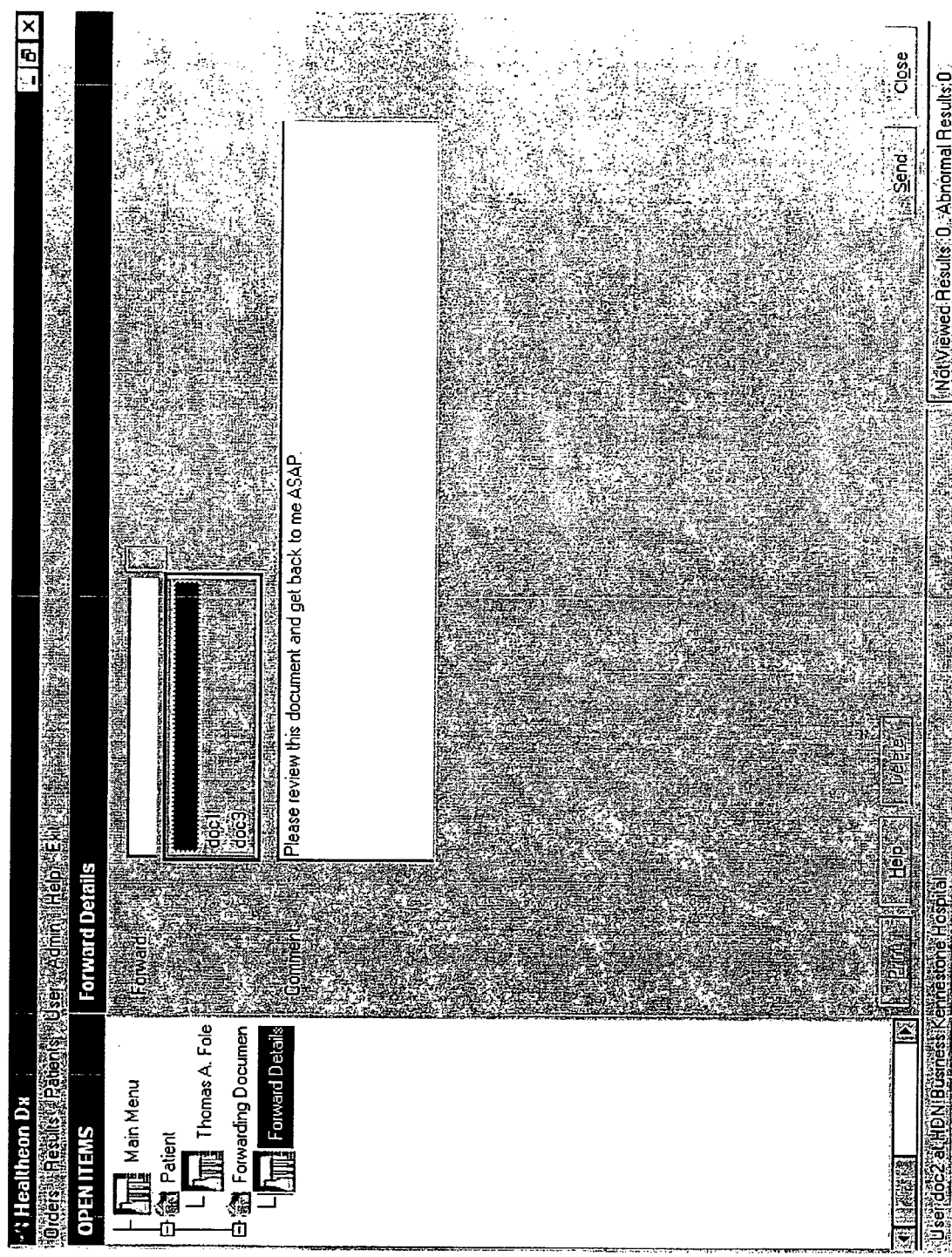

FIG. 74 illustrates a window for forwarding a user document to one or more users.

Admin Module

Figure 75:
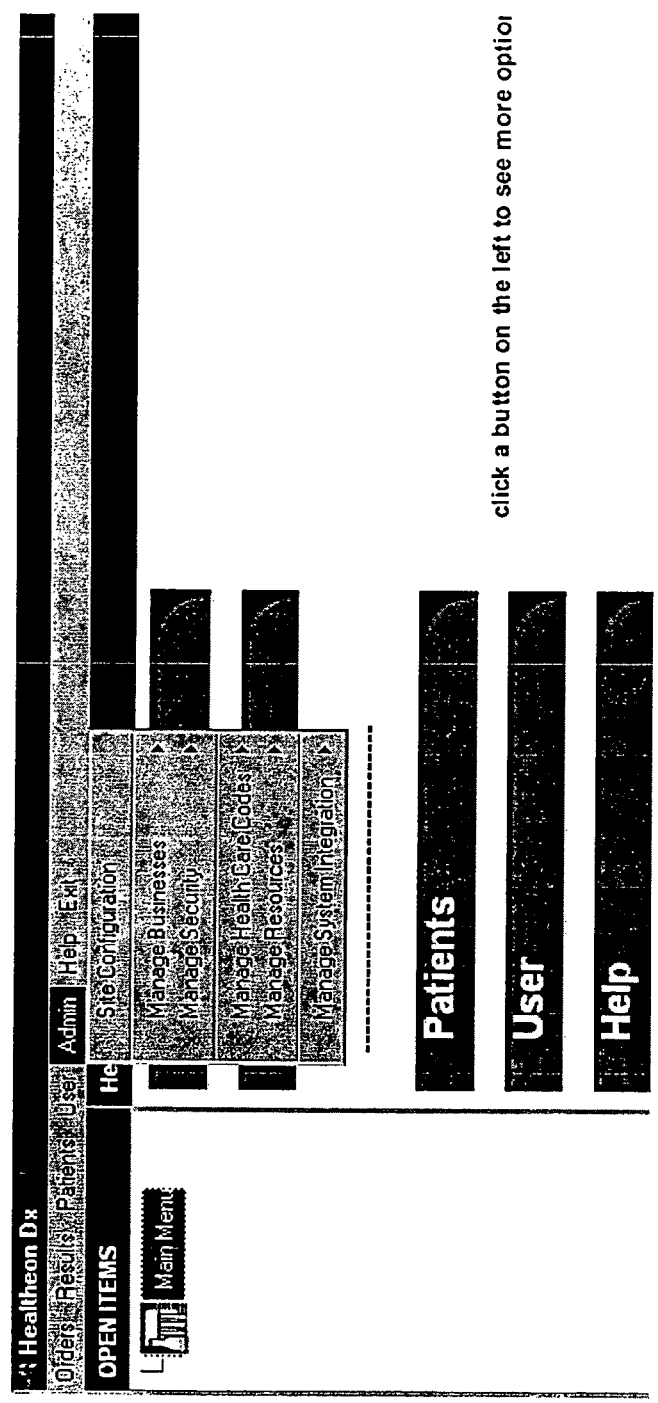

Tasks carried out in the application comprise administrative as well as user tasks. Administrative tasks are found on the Admin menu, as shown in FIG. 75, which includes a Site Configuration option and the following five submenus:

Manage Businesses
Manage Security
Manage Health Care Codes
Manage Resources
Manage System Integration It is noted that some or all of the functions accessible via the Admin menu may be restricted for use only by users with administrative privileges. Thus, in the following descriptions of the Admin menu options and submenus, the term "the user" may refer to administrative users.

Admin: Site Configuration

Before using the Admin menu options to configure the user's site, it is important to have an understanding of Health Data Network (HDN) Businesses, and how they relate to other system components. The user must also understand the concept of parent-child relationships in order to successfully maintain the user's site.

In the preferred embodiment, the system can interface to multiple labs simultaneously and seamlessly. The Site Configuration option in the Admin menu enables the user, e.g., an administrator, to support and manage this feature and provides the user the functionality needed to define relationships between the user's site and several laboratories.

Figure 76:
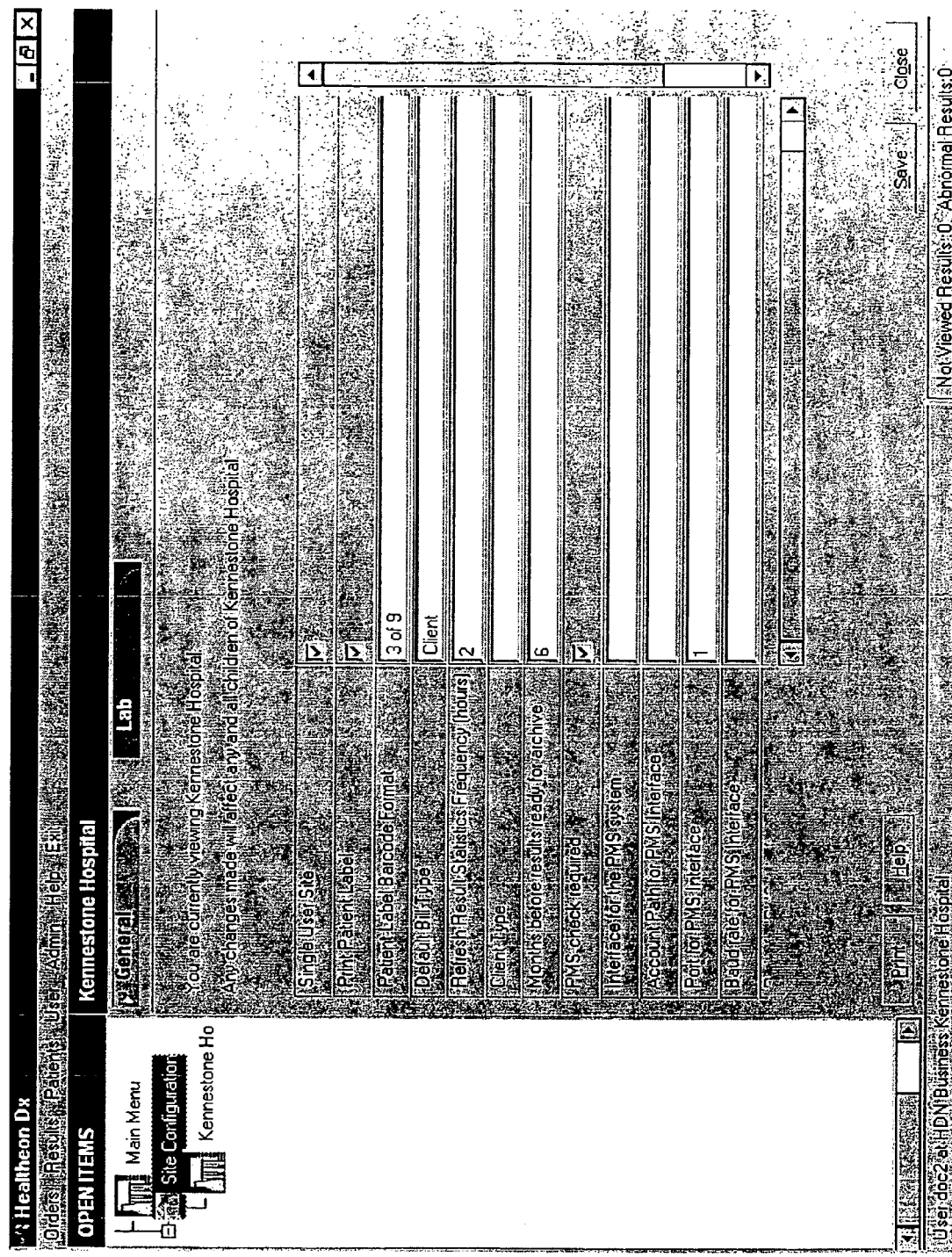

When selected, the Site Configuration window appears with the General page active, as shown in FIG. 76. This page is used to specify HDN Business level interface settings that affect how the system works.

Figure 77:
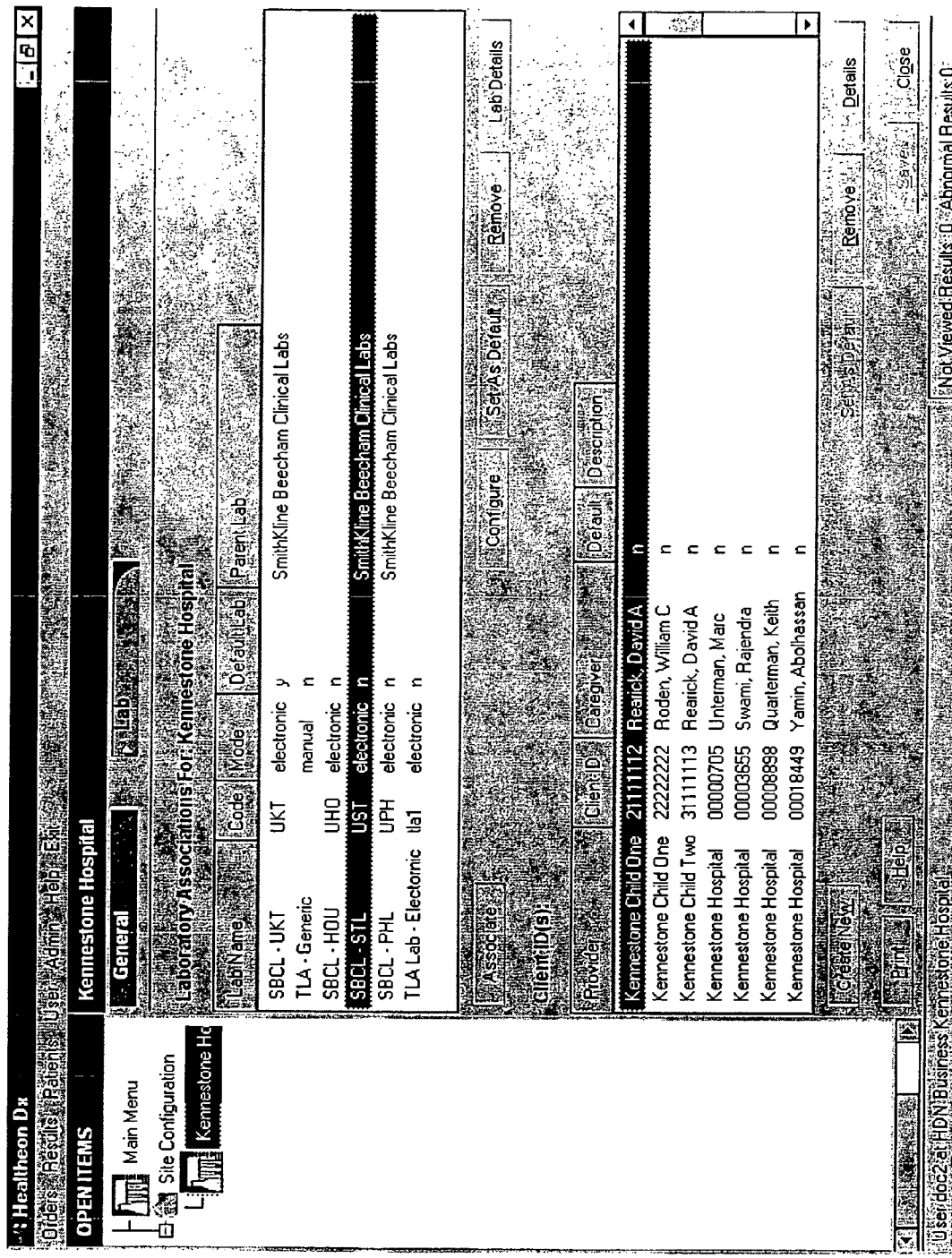

The Lab page, shown in FIG. 77, is used to define and maintain information on provider-lab associations. Before an order can be sent from a Provider HDN Business, that business must have at least one lab association and one client ID for that association. From this page, the user can carry out the following functions:

Create, configure and maintain associations between a provider and multiple labs
View and/or modify detailed lab information
Create Client IDs for each provider-lab association
View and/or modify information on existing Client IDs
Print configuration data, lab association information and Client IDs for a provider Site Configuration—General Page As described above, a user's practice may be configured as a parent-child HDN Business relationship. To modify the configuration data of the table shown in FIG. 76, the user may log in to the parent HDN Business. A message appears at the top of the page in FIG. 76 indicating the name of the HDN Business the user is currently viewing.

When the user views a child HDN Business, the configuration data that appears on the screen may be that of the parent HDN Business. In one embodiment, any configuration data defined at the parent level cannot be modified at the child level. When viewing information for a child business, any parent-specific data may appear grayed out on the configuration table so that the data cannot be modified. As described above, individual HDN Businesses may have their own policies regarding what permissions a user can have. Thus, a Business may define a policy such that only administrators are allowed to define or modify configuration information.

The following table explains the fields on the General page of the Site Configuration Details window:

| Field Name | Definition |
| --- | --- |
| Account Path for PMS Interface | The account path for a Practice Management System (PMS) interface. |
| Baud rate for PMS Interface | The baud rate for the PMS interface. |
| Client Type | The client type. |
| Databits for PMS Interface | The number of databits for the PMS interface. |
| Default Bill Type | The default bill type. Includes drop-down list values of: Client, Patient or Third Party. The value selected appears as the default Bill Type when creating a requisition. |
| Interface for the PMS System | The interface for the PMS system. |
| Months before results | The number of months before results are ready to be archived. |
| Parity for PMS Interface | The parity for the PMS interface. |
| Patient Label Barcode Format | Indicates the method used for encoding information in the patient label bar code. |
| PMS Check Required | This box tells the system to search for patient records in the Practice Management System |
| Port for PMS Interface | The port for the PMS interface. |
| Print Patient Label | Indicates whether patient labels are printed. If this box is selected, a label is printed when a requisition is created, as long as a label printer is attached to the workstation where the requisition is created. Labels are placed on specimens for identification purposes. |
| Refresh Results Statistics Frequency (hours) | The frequency at which the results statistics in the main screen status bar are updated. (Not Viewed Results, Abnormal Results) |
| Single User Site | Indicates if the site is a single user site. |
| Stopbits for PMS Interface | The number of stopbits for the PMS interface. |

Site Configuration—Lab Page (FIG. 77)

Providers can preferably send orders through either parent or child labs, as long as they are orderable labs. Orderable labs are those that a client can directly send orders to. For every set of labs associated with a provider, one of the labs may be setup as the default lab. Each Provider HDN Business may have a set of Labs associated with the Provider and a set of Client IDs linked to the Provider. The Lab page of the Site Configuration window, shown in FIG. 77, includes functions for managing this information.

The Laboratory Associations portion of the Site Configuration Details window allows the user to define and maintain associations between the user's site and various labs. These lab associations must be defined before a Provider HDN Business can send orders to one or more labs. The associations between a Provider HDN Business and a set of orderable labs may be defined at the parent level, and child HDN Businesses may inherit the lab associations of their parent HDN Businesses.

The management and creation of lab detail information may be performed through the Labs subsystem of the Manage Businesses submenu option, as described below. The user can also view and modify lab detail information on labs accessed through the Site Configuration Details window. In the Laboratory Associations section of the Lab page the user carry out the following functions:

Create and configure associations between a site and one or more labs
View and/or modify detailed information on existing labs
Print lab association information To configure a provider-lab association, the user highlights the provider-lab association to configure and clicks Configure. In response, the Lab Association Configuration window appears, as shown in FIG. 78. The user may then modify the fields on the page as needed. The following table explains the fields found on the Lab Association Configuration window:

| Field Name | Definition |
| --- | --- |
| Allow manual requisition | If this box is selected, manual requisition numbers numbers can be entered when creating a requisition. Otherwise, each new requisition uses a number generated by the system. |
| Eligibility results rechecked after delay of (hours) | This field applies primarily to Future requisitions. If eligibility has been verified for a requisition, patient or insurance within the specified number of hours, it will not be re-checked. Otherwise, it will be verified again. |
| Exclude Bill Type | A drop-down list with possible values of Client, Patient or Third Party. If a value is selected then that Bill Type cannot be used when creating a requisition. |
| FDA check required | When this box is selected, if Bill Type is Third Party and the patient has a limited coverage policy, such as Medicare, and a non FDA-compliant test code is used in a requisition, the ABN Dialog box appears. An Advanced Beneficiary Notice (ABN) is a printed statement that includes a list of tests not covered by the payer. |
| HDN Business | The Provider HDN Business being linked to a lab. Also, the currently active HDN Business. This is a read only field and cannot be modified. |
| Lab | The Lab associated with the Provider. This is a read only field and cannot be modified. |
| LCP check required | When this box is selected, if Bill Type is Third Party and the patient has a limited coverage policy, such as Medicare, and a non LCP-compliant test code is used in a requisition, the ABN Dialog box appears. An Advanced Beneficiary Notice (ABN) is a printed statement that includes a list of tests not covered by the payer. |
| Maximum requisition number | This field is used to designate the maximum requisition number that can be entered, regardless of whether manual or automatic requisition numbers are used. |
| Minimum requisition number | This field is used to designate the minimum requisition number that can be entered, regardless of whether manual or automatic requisition numbers are used. |
| Selec Test Only Specificity check required | Accepts one of two possible values, Yes or No. When this box is selected, if a user enters an ICD-9 code in a requisition that has more specific designations or codes, the user is required to select a more specific ICD-9 code instead of the non-specific one. |
| Transfer ID | A unique identifier assigned to each site. This field is used during the process of uploading and downloading results. Multiple client IDs may map to the same transfer ID. |

It is noted that for every set of labs associated with a provider, one lab may be selected as the default lab. The default laboratory may be used for requisitions that have patient or client billing. However, when creating a requisition, a user can send the order to any lab associated with the provider HDN Business, even if another lab has been defined as the default lab.

The Client IDs portion of the Site Configuration Details window allows the user to create and maintain client ID information for the user's site. Client IDs are used for billing and for distributing lab results. Providers must have Client IDs in order for them to be able to send orders to a lab. In addition to the default client ID for the user's site, the user can also have numerous client IDs associated to different caregivers and to the user's site. For businesses that have a parent-child relationship, the workstation client IDs may be linked to child HDN Businesses so that the results ordered can be returned to the originating workstations. To support the proper distribution of results based on client ID, client IDs can be stored at the parent or at the child HDN Business level. For every set of client IDs associated with a provider, one ID may be selected as the default client ID.

Figure 79:
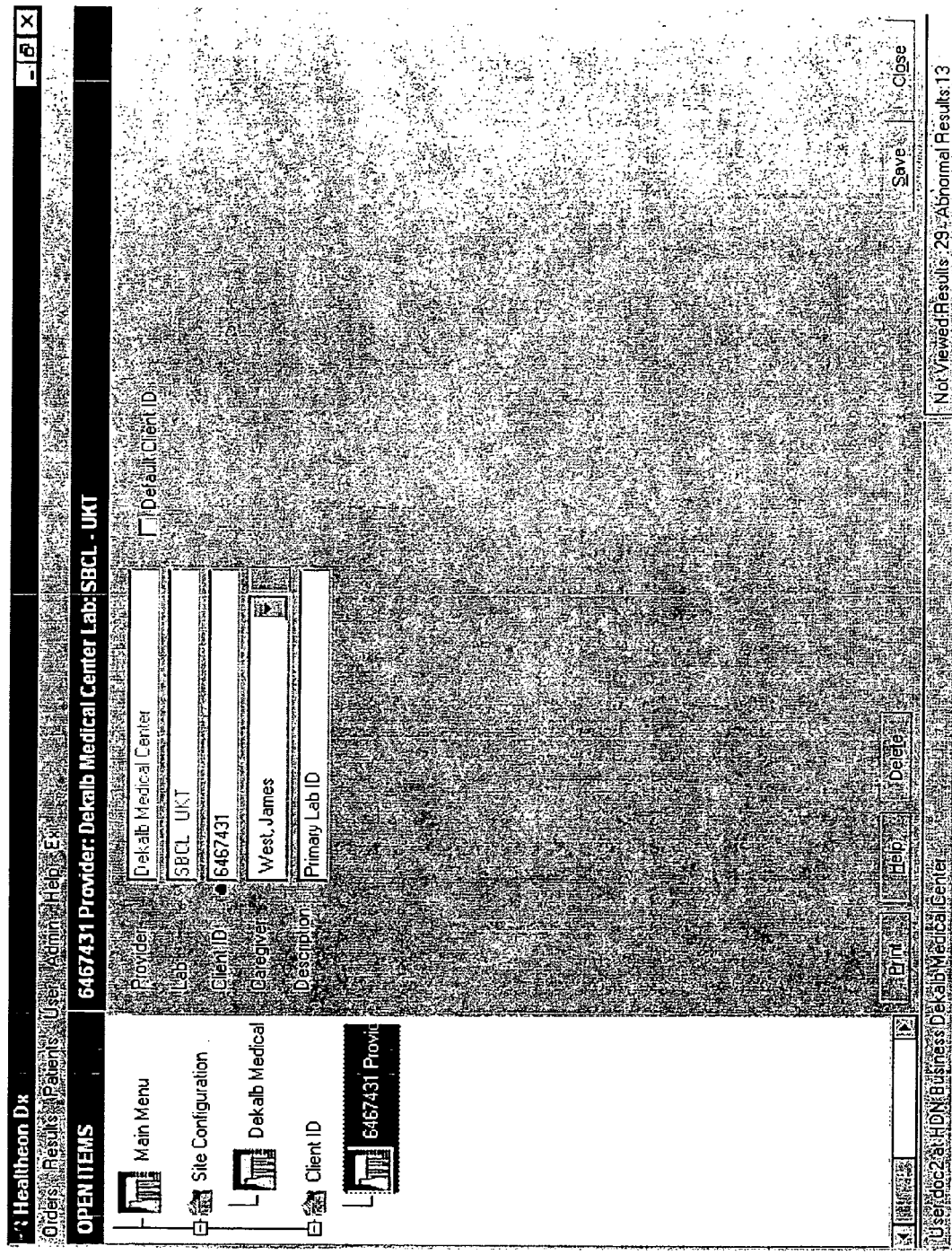

In the Client IDs section. of the Lab page the user can perform the following functions:
    Create Client IDs for each provider-lab association
    View and/or modify information on existing Client IDs
    Print information on Client IDs FIG. 79 illustrates a window for creating or editing a Provider-Lab Client ID. The following table explains the fields found on the Provider-Lab Client ID Details window:

| Field Name | Definition |
| --- | --- |
| Caregiver | This is the name of the physician to whom the provider client ID is assigned. If no physician is selected, the client ID is defined for the provider. |
| Client ID | The lab assigned identifier for the provider. |
| Default Client ID | This check box indicates if the client ID is the default ID for the provider. |
| Description | A description of the associated provider caregiver. |
| Lab | The lab associated with the provider. This field cannot be modified. |
| Provider | The name of the provider to whom the client ID is assigned. This field cannot be modified. |

Admin: Manage Businesses

In a health care delivery system, businesses rarely function as standalone units. Because of the layered business structures that exist in today's health care industry, flexibility is needed to define and manage business units. With the Manage Businesses submenu, the user has the flexibility to manage various types of businesses. These business types may include the following:

| Business Type | Definition |
| --- | --- |
| Employers | A company that the patient, insured party, or guarantor works for. |
| Labs | An organization that provides clinical testing and observation. |
| Payers | A party responsible for paying the lab bill, usually a commercial health insurer or government agency that underwrites or administers programs that pay for health services. |
| Providers | An institution or individual that gives medical care. |

Figure 80:
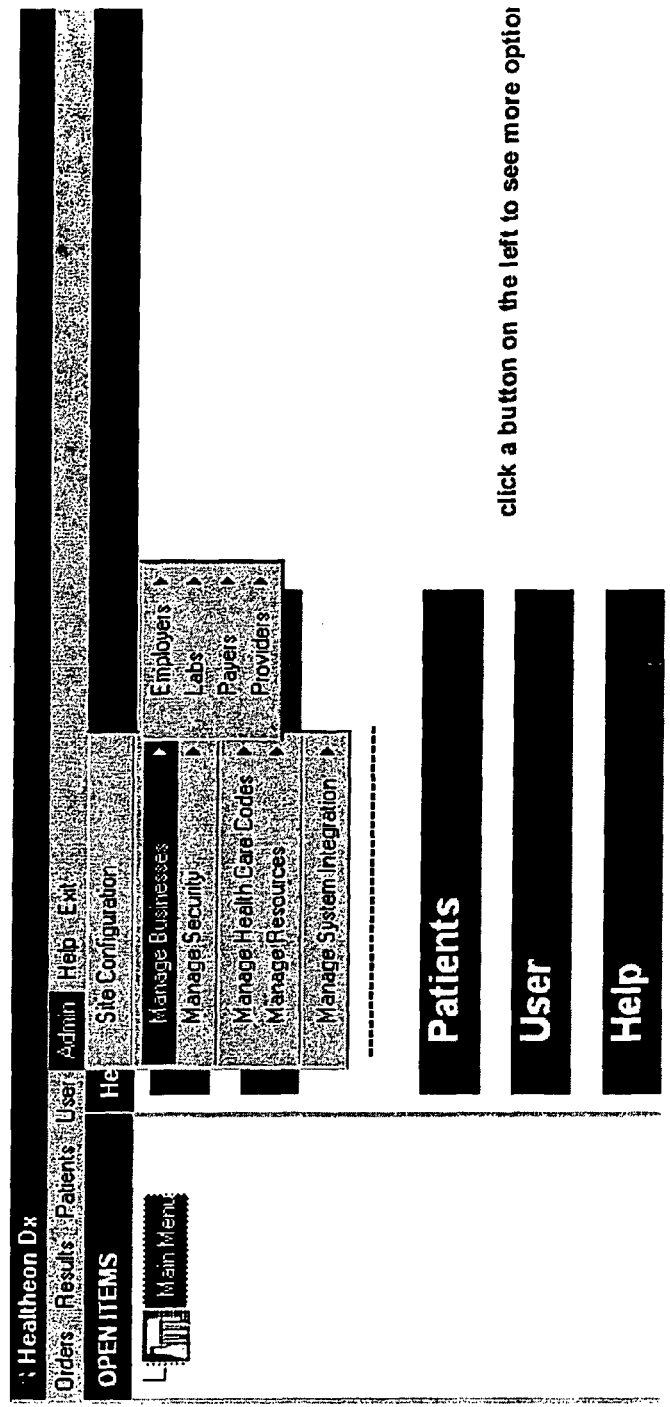

Business subsystems for managing these business types may be accessed through the Manage Businesses option of the Admin menu, as shown in FIG. 80.

Admin: Manage Businesses: Employers

Although the employers of patients, insured parties, and guarantors are not directly involved in the delivery of healthcare, they are part of the business structure. Using the Employer menu option of the Manage Businesses submenu, the user can carry out the following functions:
    Create new employer records
    View and/or modify existing employer records
    Print employer records details
    Delete employer records
    Print lists of employers Once created, employer records can then be linked to patient, insured party and guarantor records.

Admin: Manage Businesses: Labs

A lab may be an organization that provides clinical testing and/or observation services. Using the Labs menu option of the Manage Businesses submenu, the user maintains information on the labs the user does business with. This information may be used by functions accessed via the Orders menu, which include utilities used to prepare and submit requisitions. In the Labs subsystem, the user can carry out the following functions:

- Create new lab records
- View and/or modify existing lab records
- Print lab records details
- Delete lab records
- Print lists of labs In addition to basic demographic information, each lab record may include information shown in the following table:

| Information Type | Definition |
| --- | --- |
| Child Labs | These are the children of a parent lab. Not all labs have child labs. |
| Configuration | These are the configuration settings for the lab. |
| Payers | These are the payers associated with the lab that have electronic eligibility. |

Figure 81:
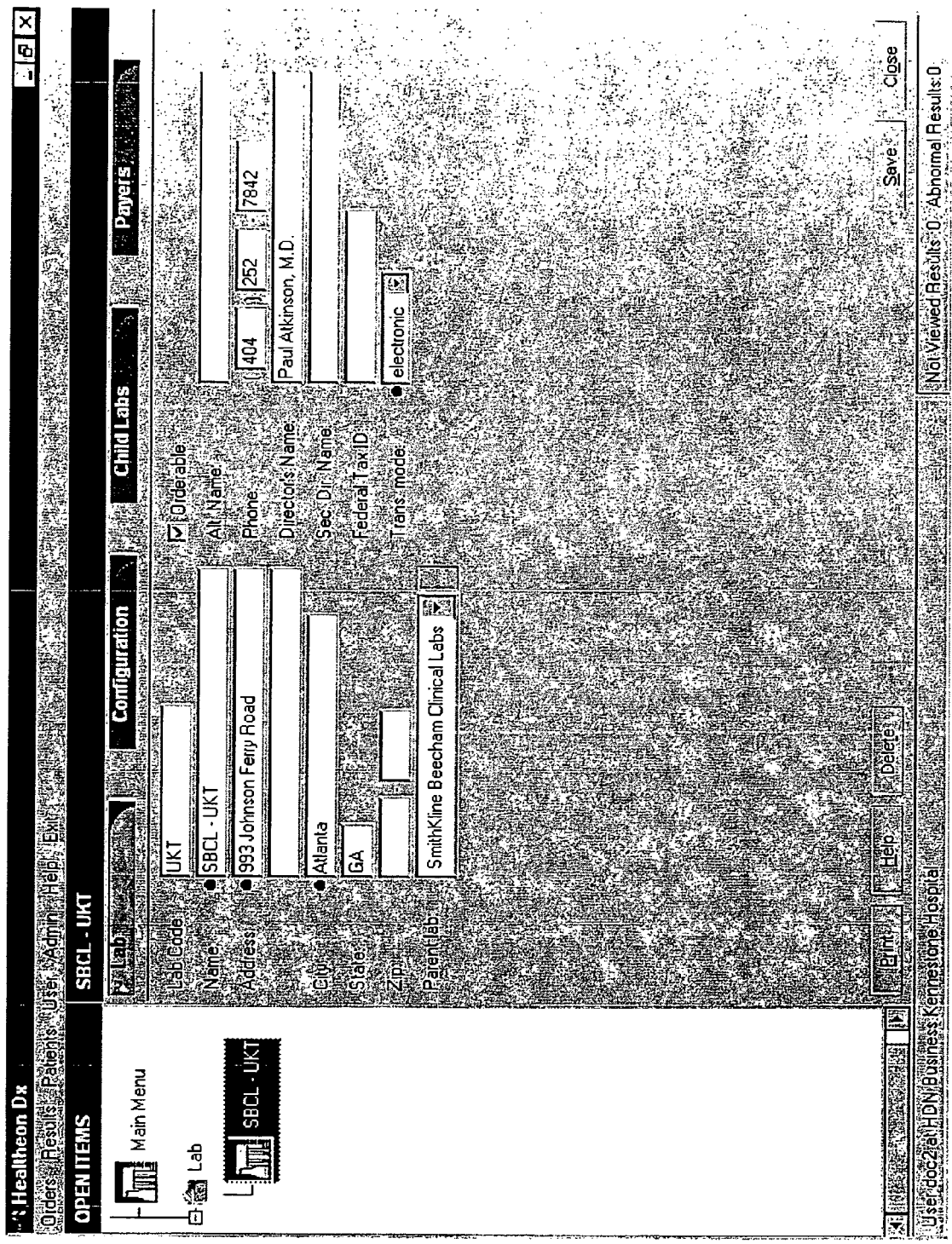

FIG. 81 illustrates the Lab Details window, for creating a new lab or modifying details of an existing lab. The following table explains the fields found on the Lab Details window:

| Field Name | Definition |
| --- | --- |
| Address | The lab address. |
| Alt. Name | An alternative name that identifies the lab. |
| City | The city for the lab mailing address. |
| Director's Name | The name of the lab director. |
| Federal Tax ID | The lab Federal Tax Identification number. |
| Lab Code | A user-defined identifying code for the lab. |
| Name | The complete name of the lab. |
| Orderable | If this box is selected the lab is an orderable lab. An orderable lab is one that a client can directly send orders to regardless of how a Provider HDN Business is setup. |
| Parent lab | If the lab is a child, this field contains the name of the parent lab. |
| Phone | The phone number of the primary contact at the lab. |
| Sec. Dir. Name: | An alternate contact for the lab director. |
| State | The 2-character abbreviation for the name of the State in the lab mailing address. |
| Transmission mode | The transmission mode used by the lab. In general, sponsoring labs use electronic transmission, while generic labs use manual or paper based transmission. |
| Zip | The zip code for the lab address. |

Figure 82:
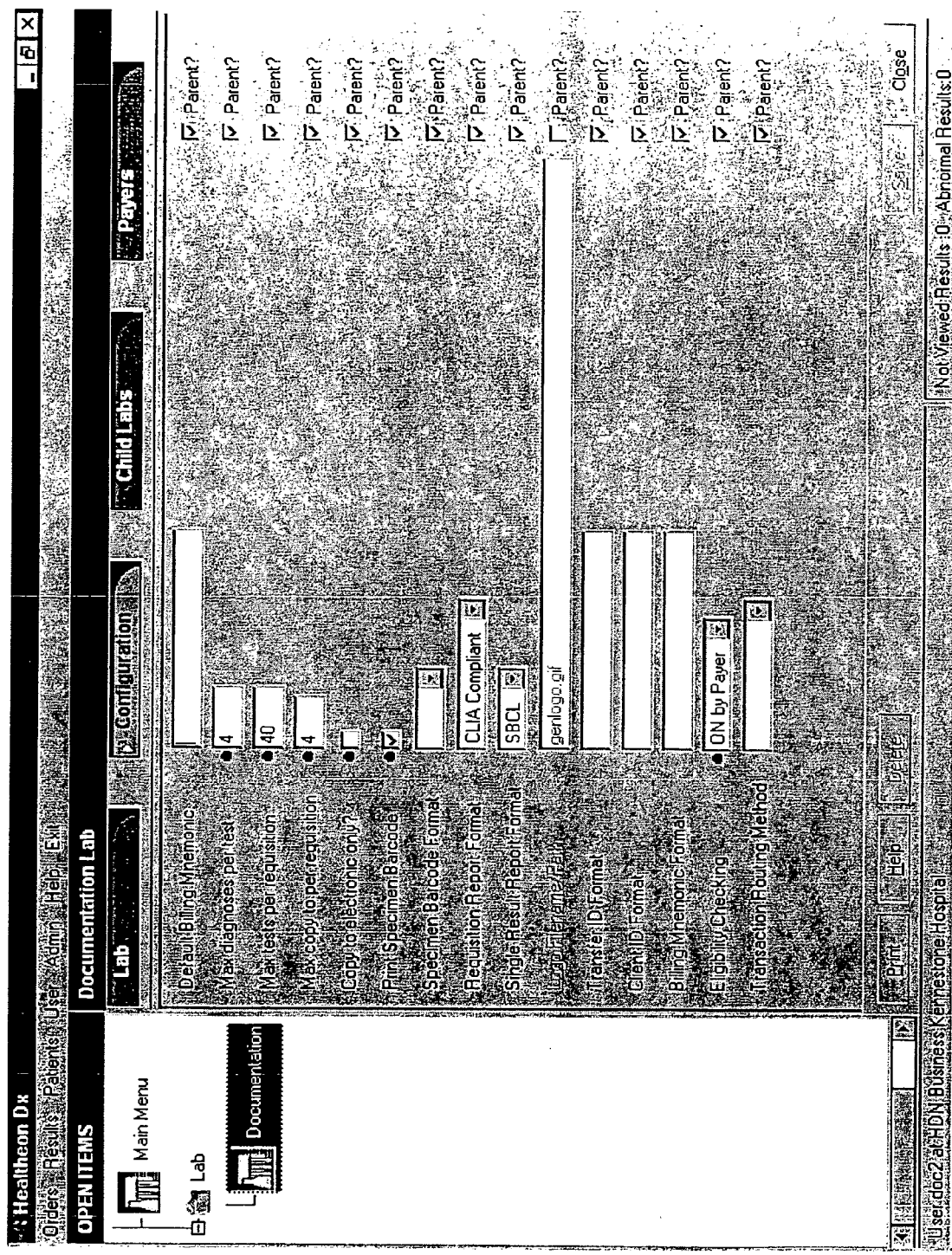

To access the Configuration page, the user clicks Configuration on the Lab Details window. In response, the Configuration Details window appears, as shown in FIG. 82. The Configuration Details window enables the user to define lab level settings for a specific lab. These settings may affect how some of the data is stored in the system, as well as the process of creating requisitions and the use of lab records. They also affect the relationship between labs and payers. From this page the user can define the level of data ownership for a lab: parent only, child only, or a combination of both. This page enables the user to specify what data is stored at the parent level and what data is stored at the child level.

The following table explains the fields found on the Configuration page of the Lab Details window. Note that a Parent? check box appears next to every configuration field. This box indicates the level of ownership, parent or child, for each field. If the Parent? box is checked, this means the setting is defined at the parent level and the children of that lab will inherit that value. The field appears grayed out or disabled when viewed from a child lab. If the Parent? box is unchecked, this means the setting is deferred to the children of that lab. The field is enabled when viewed from a child lab.

| Field Name | Definition |
| --- | --- |
| Default Billing Mnemonic | The default Host System Identifier for a Payer. |
| Max diagnoses per test | The maximum number of diagnosis (ICD-9) codes allowed per test. |
| Max tests per requisition | The maximum number of test codes allowed in a requisition. |
| Max copy to per requisition | The maximum number of Caregivers to receive copies of a requisition. This field affects the list of caregivers in the Additional Info page of a requisition. |
| Copy to electronic only? | This check box affects the physician results list in the Additional Info page of a requisition. If this box is checked, the search only returns caregivers that have Client IDs. Otherwise, the search returns all caregivers that meet the user's search criteria. |
| Print Specimen Barcode | This check box determines whether a specimen bar code is printed when a requisition is created. |
| Specimen Barcode Format | Defines the method used for encoding information in a bar code. A value may be selected from the drop-down list. |
| Requisition Report Format | Defines the requisition report format. A value may be selected from the drop-down list. |
| Single Result Report Format | The format of a typical result report. A value may be selected from the drop-down list. |
| Logo Filename/Path | This is the file name and location of the logo image that appears on a requisition. |
| Transfer ID Format | Specifies the transfer ID format. (X means any alphanumeric character is allowed, N stands for numeric, A stands for alpha, and anything inside quotes is a literal string or code). |
| Client ID Format | Specifies the Client ID format. (X means any alphanumeric character is allowed, N stands for numeric, A stands for alpha, and any text inside quotes is a literal string or code). |
| Billing Mnemonic format | Specifies the Billing Mnemonic format. (X means any alphanumeric character is allowed, N stands for numeric, A stands for alpha, and any text inside quotes is a literal string or code). |
| Eligibility Checking | The eligibility checking mode for the lab. This field may have a value of Always OFF, Always ON, or ON by Payer. (See below.) |
| Transaction Routing Method | The lab Transaction Routing Method. This field affects electronic transmissions. For generic labs, the field can be left blank. |

Eligibility Checking—Some labs prefer to have eligibility checking or enabled for all payers, some labs want this feature disabled all the time, and other labs want to be able to select which payers to perform electronic eligibility checking on. The system may support these different scenarios by providing various settings for checking eligibility. The user may specify these settings through the Eligibility Checking field which appears on the Configuration page of each lab.

In one embodiment, the user can set the Eligibility Checking field to be one of the following: OFF Always; ON Always; or ON by Payer. If the user selects the ON by Payer option, the user can select payers from an existing set of payers that have been globally enabled for electronic eligibility within the system. Eligibility payer lists may be defined at the same lab level (parent or child) that the Eligibility Checking configuration option is defined.

Figure 83:

To access the Child Labs page, the user clicks Child Labs on the Lab Details window. In response, the Child Labs window appears, as shown in FIG. 83. The Child Labs page lists the children of a parent lab. This relationship is established when a Parent lab is selected for a child lab on the Lab page of the Lab Details window. When the user views a parent lab that has children labs, the Child Labs page is active and it includes a list of all the children labs. When the user views a parent lab that has no children labs, the Child Labs page is active, but no labs are listed.

Figure 84:
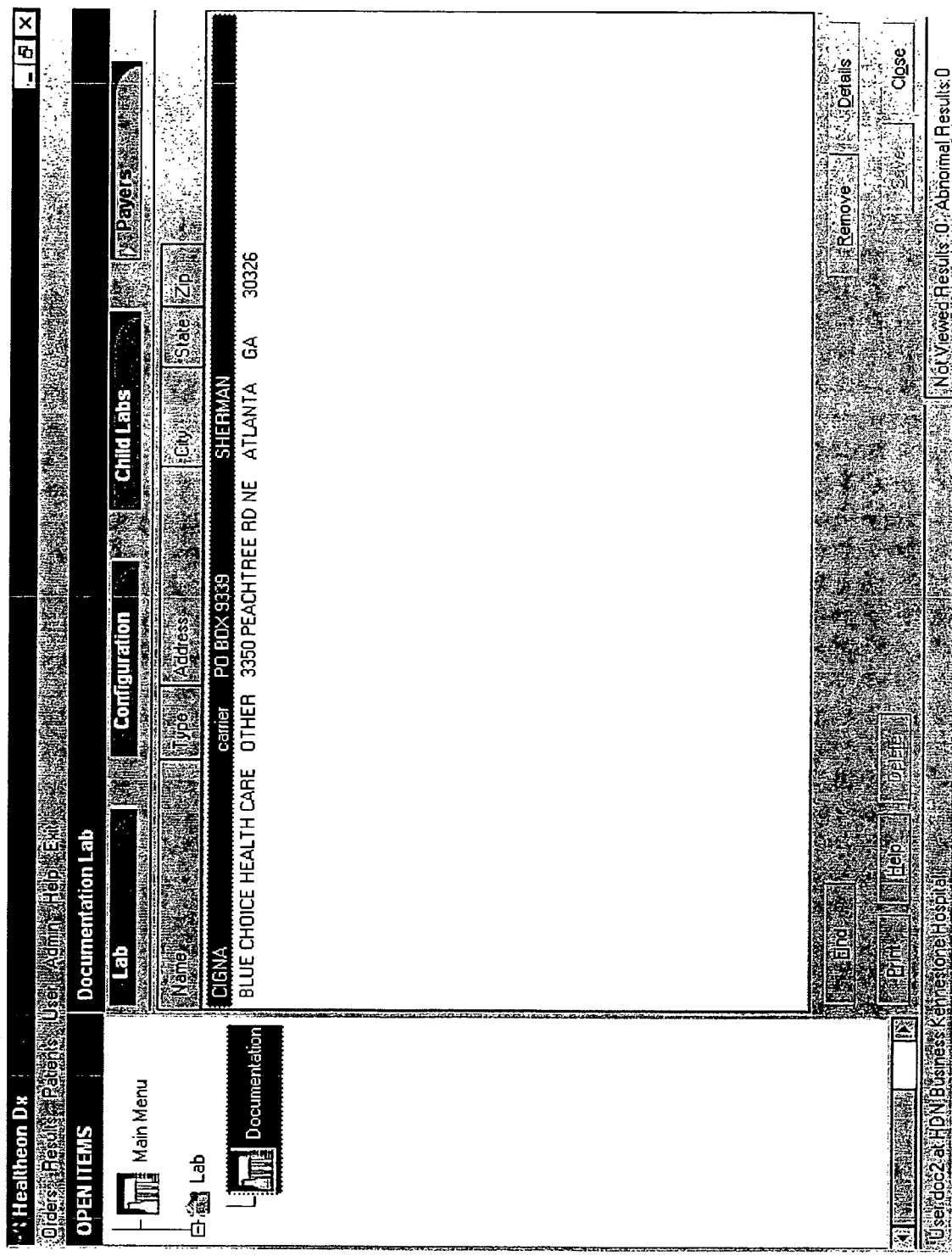

From the Child Labs page, the user can carry out the following tasks:
- View details of existing child labs
- Modify detail information of existing child labs
- Modify the parent-child relationship between two labs To access the Payers page, the user clicks Payers on the Lab Details window. In response, the Payers window appears, as shown in FIG. 84. Payers can have contractual agreements with some labs, wherein if the lab work for a patient is sent to a contracted lab, there is a financial benefit to be gained by the payer. The lab-payer associations are typically defined at the parent lab level, but the system does not restrict it to this level. The association between labs and payers is managed through the Payers page of the Lab Details window. The Payers page includes a list of payers associated with a lab that may be checked for eligibility if electronic eligibility is enabled.

From this page, the user carry out the following tasks:
- Associate existing payers with labs
- View details of existing payers
- Remove existing associations between payers and labs Admin: Manage Businesses: Payers A payer typically refers to an insurance company, but it can mean any organization, such as an employer or government agency, that pays for medical services provided to a patient. A payer is different than a guarantor. The guarantor is the person ultimately responsible for payment of the medical bill. For example, if the insurance company does not cover medical charges, the guarantor, which is usually the patient or the patient's guardian, is responsible for payment.

Using the Payers menu option of the Manage Businesses submenu, the user can carry out the following functions:
- Create new payer records
- View and/or modify existing payer records
- Print payer records details
- Delete payer records
- Print lists of payers In addition to basic demographic information, each payer record may include the following information:

| Information Type | Definition |
| --- | --- |
| Providers | Providers and caregivers for whom the payer will cover medical expenses. |
| Service | Services on the network that the payer participates in. |
| Billing | Lab-defined billing IDs for the payer. |
| Insurance Code | A user defined value used to identify a payer. |
| Labs | The labs for whom the payer will cover medical expenses. |

Because the number of payers stored on the user's system may be very large, the user can create a list of preferred payers as described above. The Preferred List of Payers may include those payers that the user frequently uses, which makes locating a payer much easier and faster. This Preferred List of Payers can be defined through the Manage Preferred Lists option of the User subsystem or by selecting Add to List(s), either Shared List or My List, when carrying out a find function for a payer.

Figure 85:
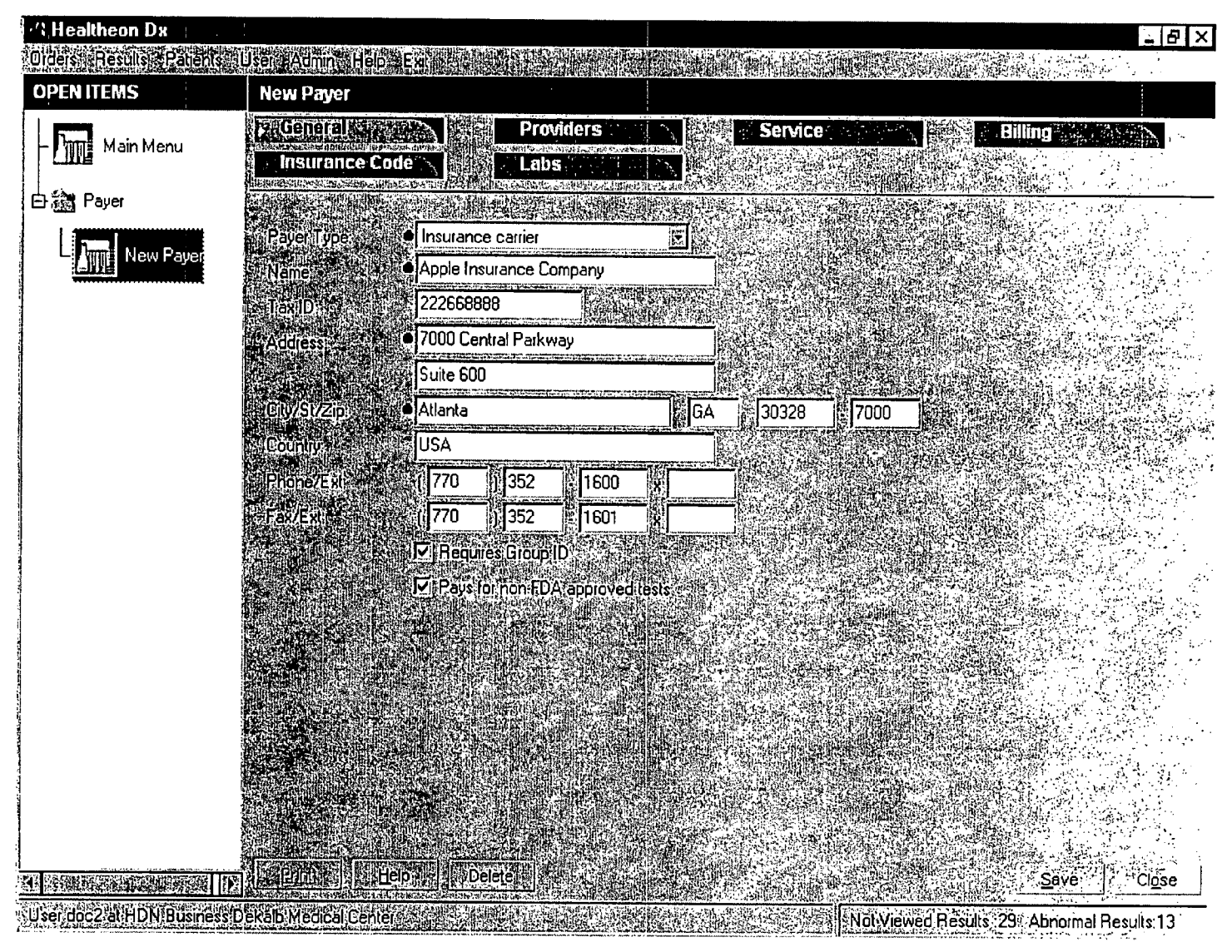

FIG. 85 illustrates the General page of the Payer Details window. The General page includes fields specifying general information regarding a payer.

Figure 86:
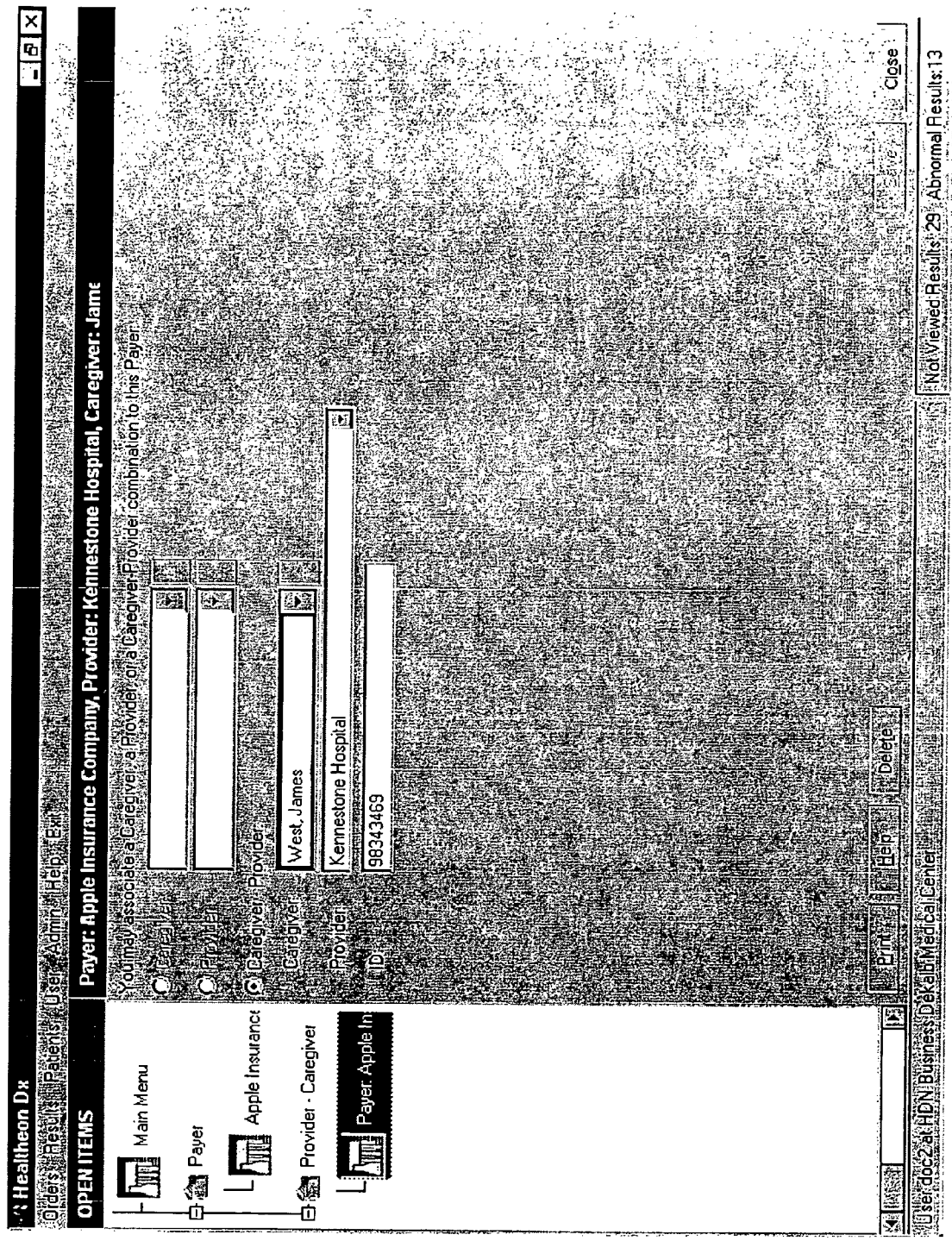

FIG. 86 illustrates the Providers page of the Payer Details window. A provider is any organization that supplies health care-related services, such as a hospital, clinic, lab, and diagnostic center. On the Providers page in the Payer subsystem, the user can view the providers and caregivers for whom the Payer will cover patient expenses. The user may pick either a provider or caregiver to show their identifiers associated with the payer. These providers may be used for assigning IDs used in billing. (i.e., HMO provider ID). Management of payer-providers is carried out through the Providers page of the Payer Details window.

Figure 87:
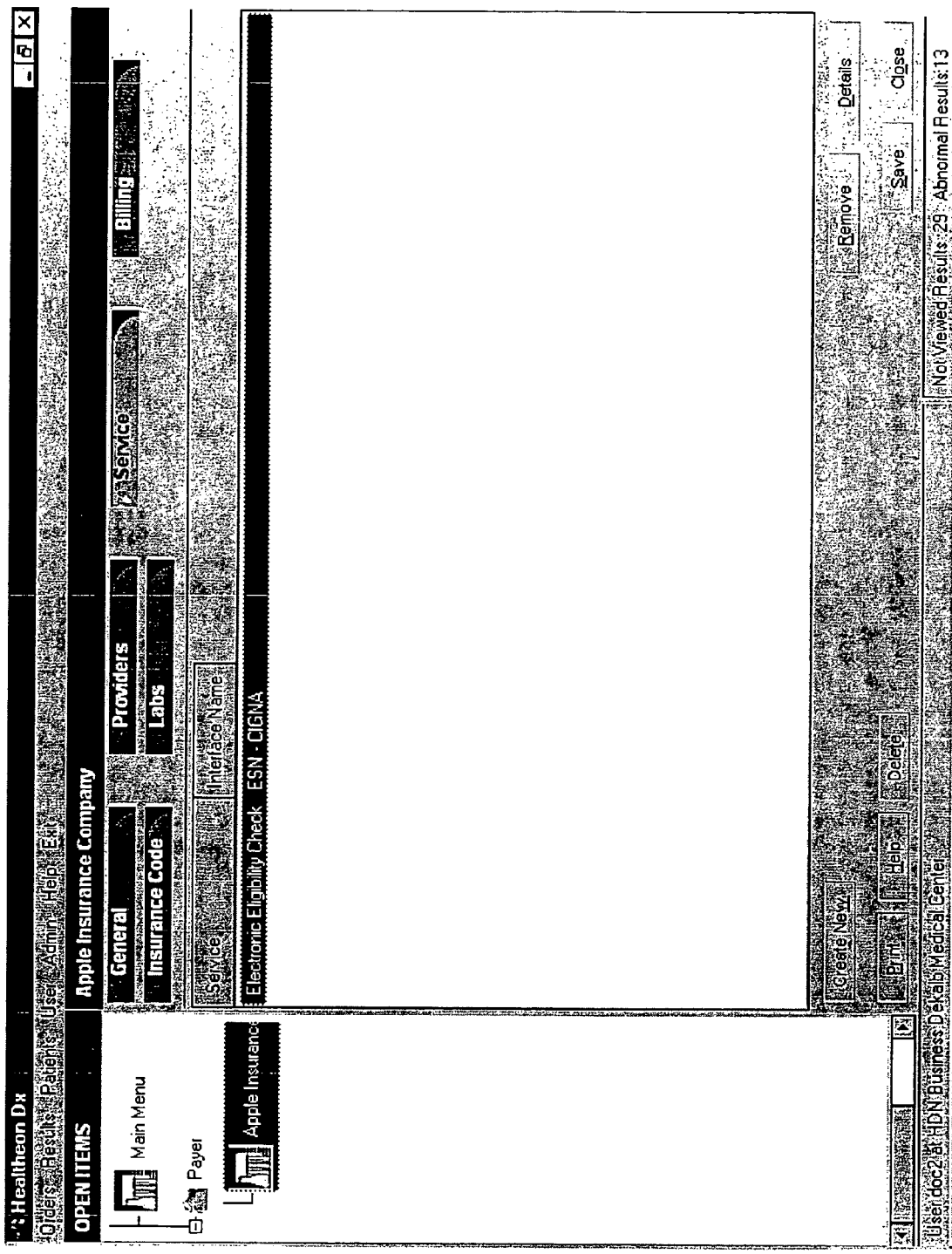

FIG. 87 illustrates the Service page of the Payer Details window. Claims and eligibility verification are examples of payer-related services in the system. The system allows payers to interface with these services. Management of payer-services is carried out through the Service page of the Payer Details window. For each Payer-service definition, the user can link a payer with a service and indicate the interface method used for the service.

Figure 88:
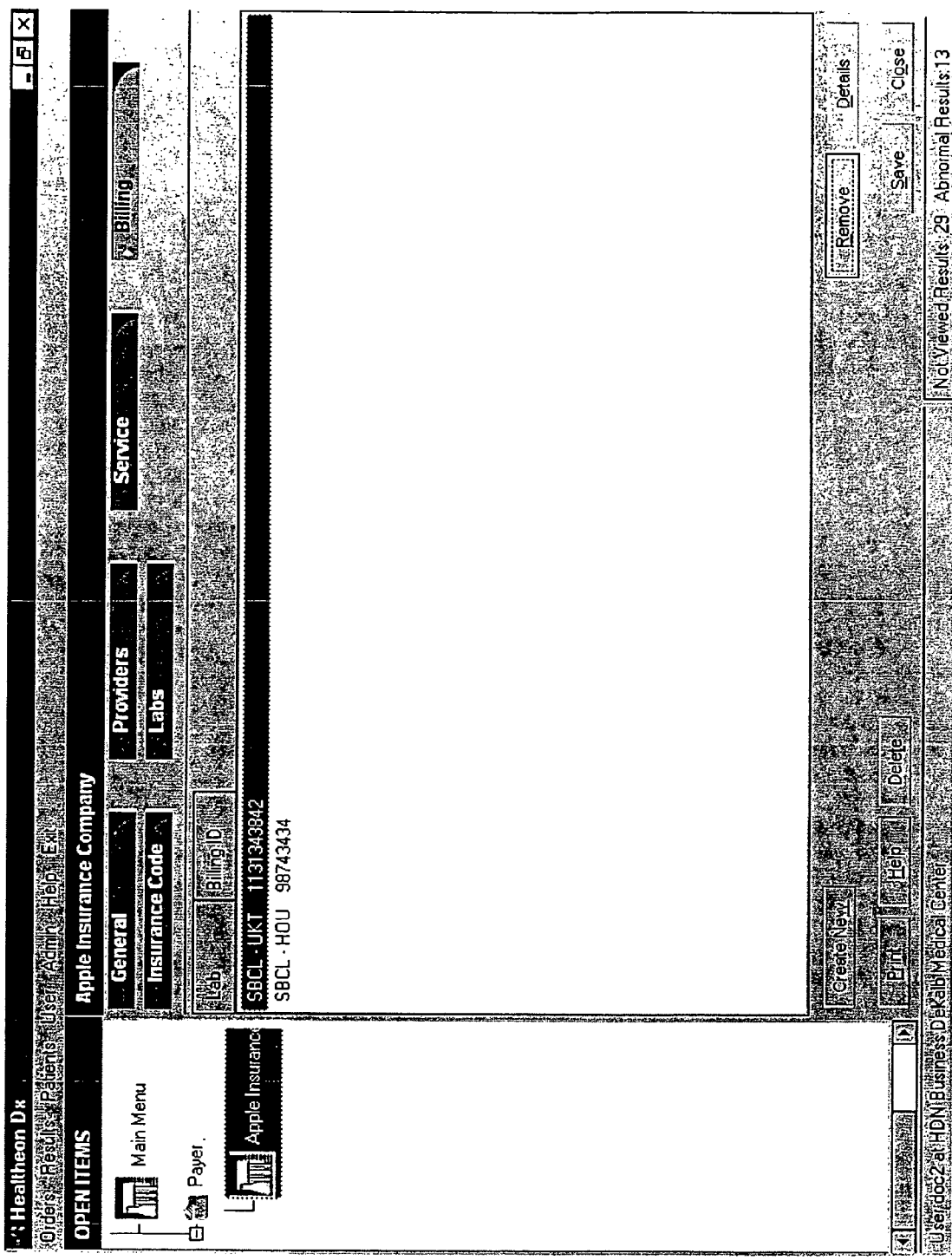

FIG. 88 illustrates the Billing page of the Payer Details window. A lab identifies a payer by a billing ID. If the payer is to be billed for a requisition, the payer's billing ID is sent to the lab with the requisition. The Billing page of the Payers subsystem lists the lab-defined billing IDs for the payer that the user selects. Management of payer-billing identifiers is carried out through the Billing page of the Payer Details window.

Figure 89:
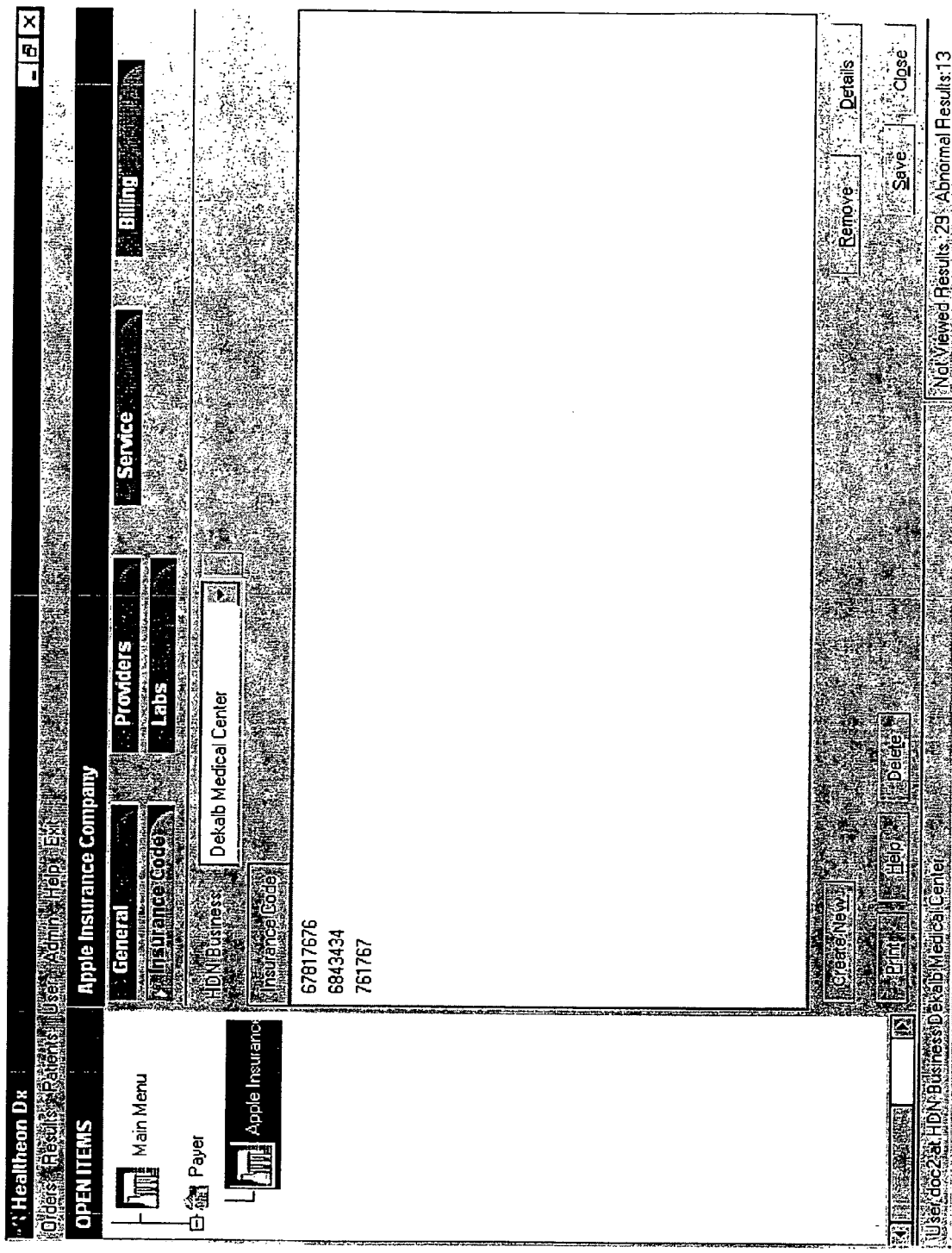

FIG. 89 illustrates the Insurance Code page of the Payer Details window. This page shows the insurance codes for a payer. An insurance code is a user-defined identifier used to designate a payer. Each site can have more than one insurance code to designate the same payer. Management of payer-insurance codes is carried out through the Insurance Code page of the Payer Details window.

Figure 90:
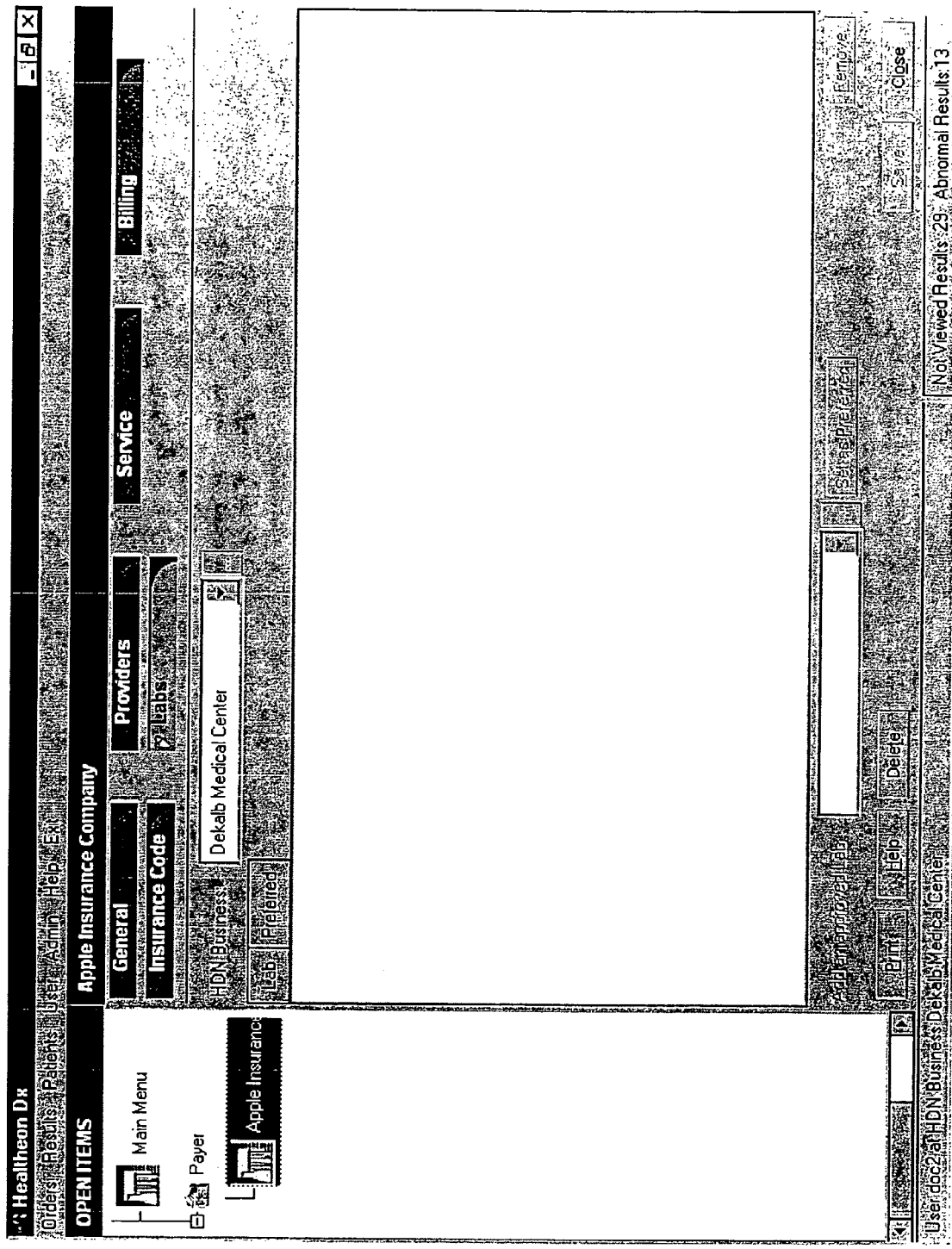

FIG. 90 illustrates the Labs page of the Payer Details window. The Labs page shows all the labs associated with the active payer. These labs are considered payer-approved labs. Payers can have contractual agreements with some labs wherein if the lab work for a patient is sent to a contracted lab, there is a financial benefit to be gained by the payer. For each lab-payer set, each provider HDN Business can specify which lab in the set is their preferred one to use.

When creating a requisition, the user may choose what lab to send the order to. For patient and client billing, the lab may default to the default lab for the ordering provider HDN Business, although a user can choose from any lab associated with the provider. For third party billing, the payer is chosen first then the lab defaults to the payer preferred lab if one exists, then to the HDN Business level default lab if that lab is in the payer-lab list, or to nothing if neither of these conditions apply. Again, the user can choose any of the labs setup for the Provider HDN Business and override any default labs.

The association between labs and payers is managed through the Labs page of the Payer Details window. From this page, the user can carry out the following tasks:
- Associate existing labs with a payer
- Designate a lab-payer combination as preferred
- Remove existing associations between labs and payers Admin: Manage Businesses: Providers A provider is any organization that supplies health care-related services, such as a hospital, clinic, lab, diagnostic center, etc. Using the Providers menu option of the Manage Businesses submenu, the user can maintain information on the Providers in the user's network. In the Provider subsystem, the user can perform the following functions:

Create new provider records
View and/or modify existing provider records
Print provider records details
Delete provider records
Print lists of providers In addition to basic demographic information, each provider record may include the following information:

| Information Type | Definition |
| --- | --- |
| Caregiver | Caregivers associated with the provider |
| Client IDs | Physicians' client IDs for particular labs |
| Specialties | Specialties of the provider |

Figure 91:
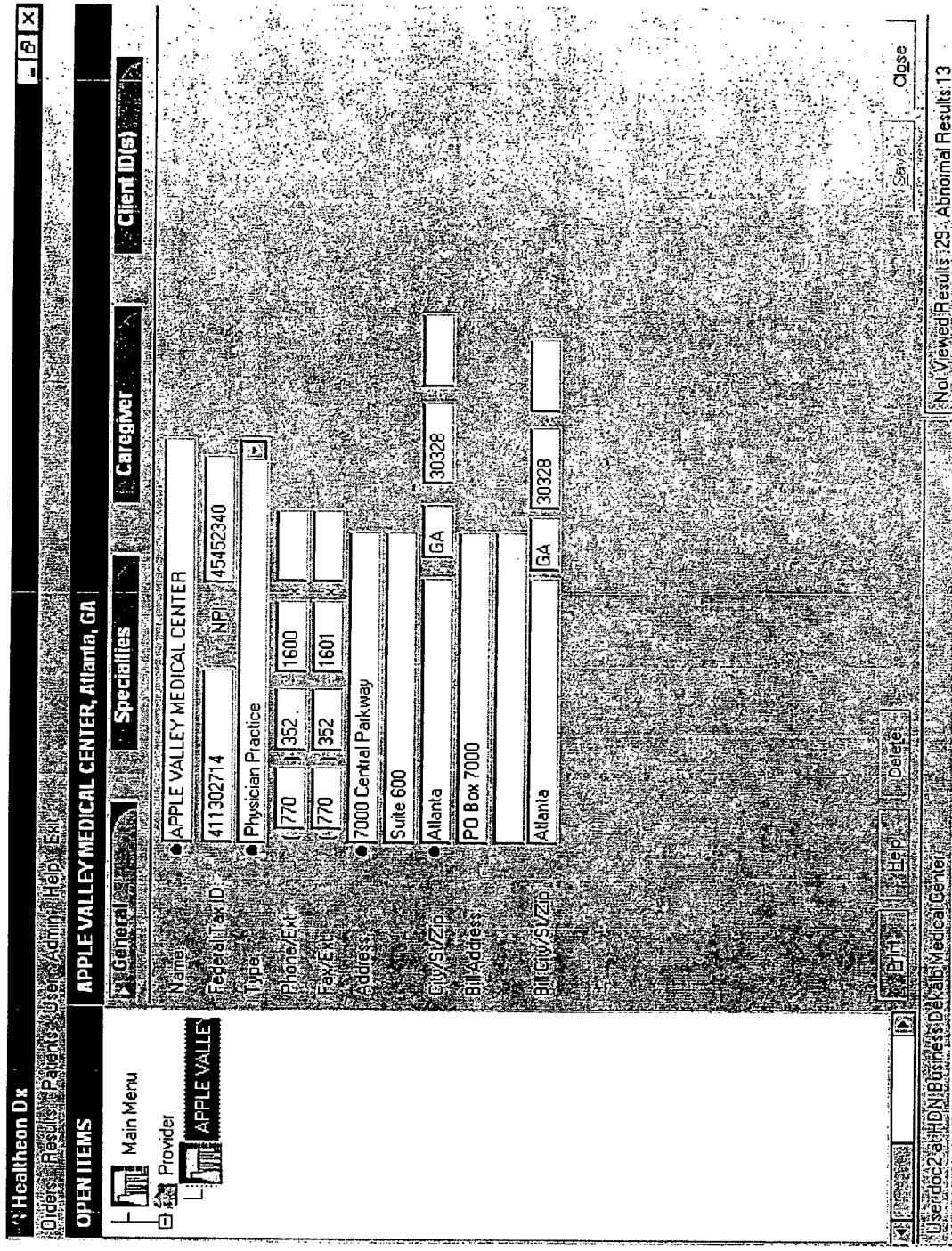

FIG. 91 illustrates the General page of the Provider Details window. The General page includes fields specifying general information regarding a provider.

Figure 92:
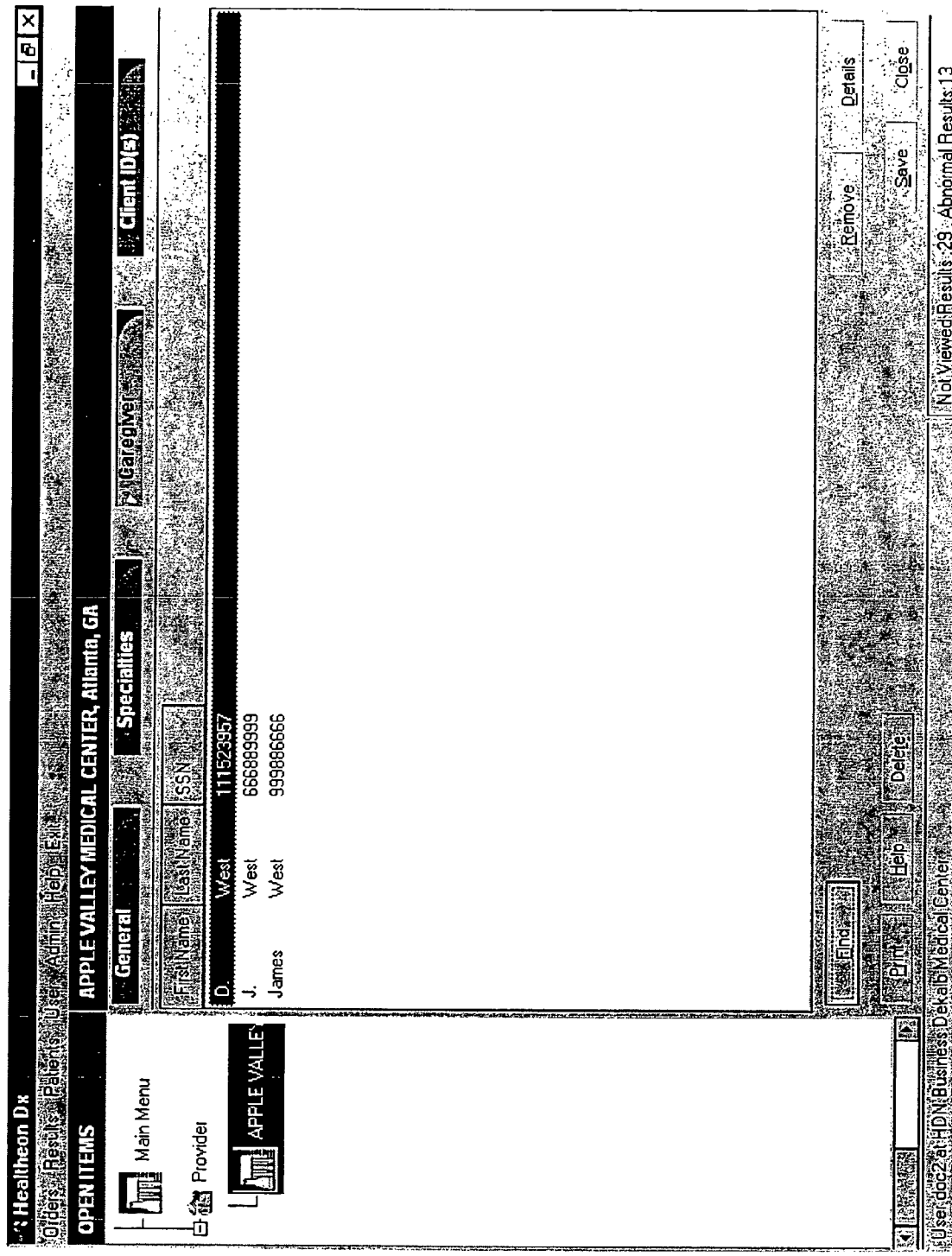

FIG. 92 illustrates the Caregiver page of the Provider Details window. A caregiver is a person who provides health care services to patients. Physicians, nurses, technicians, and physician's assistants are all examples of caregivers. In the business of healthcare, caregivers are typically associated with providers. The management of this association is carried out through the Caregiver page of the Provider Details window. From this page, the user can carry out the following tasks:

Associate existing caregivers with providers
View details of existing caregivers
Remove existing associations between caregivers and providers.

Figure 93:
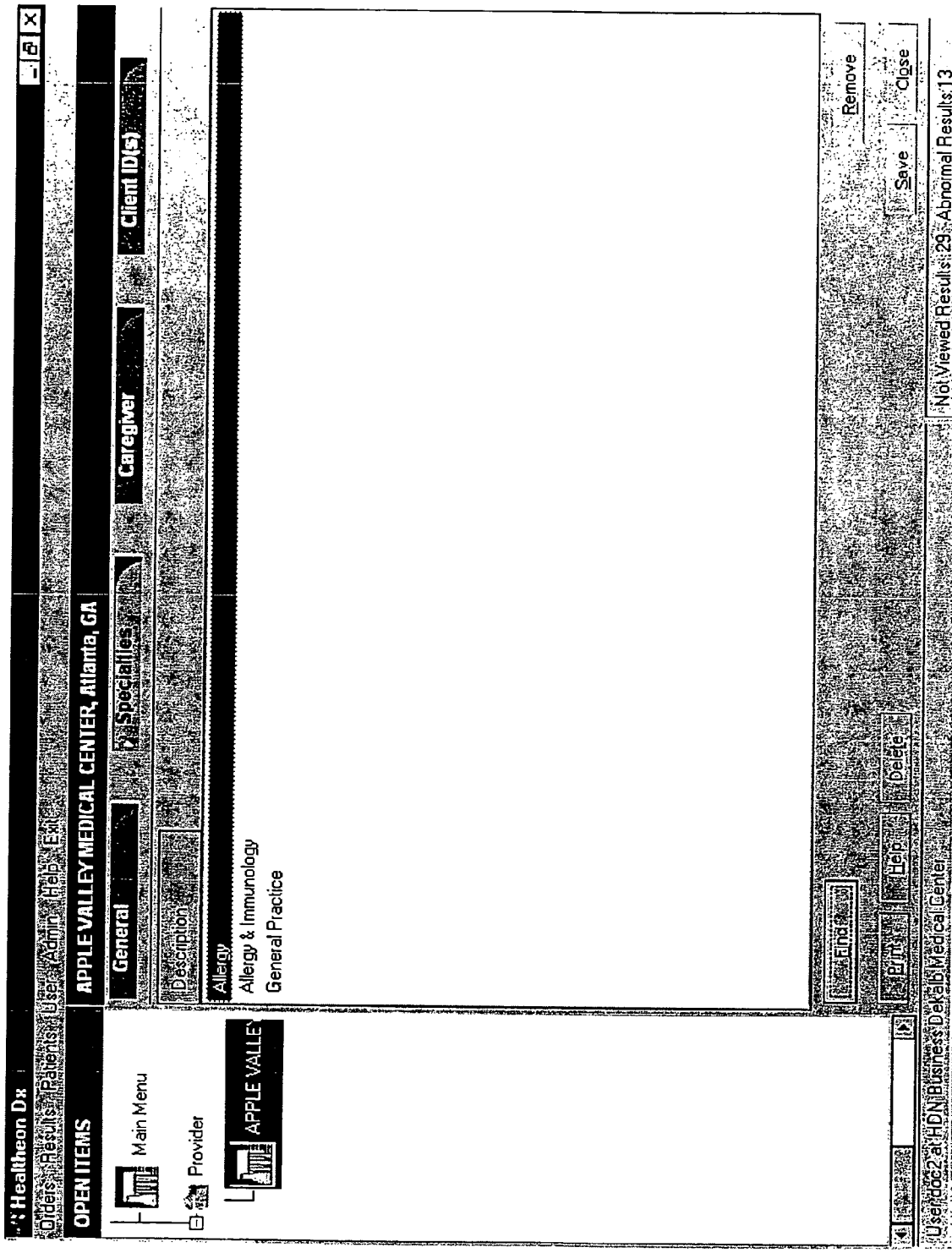

FIG. 93 illustrates the Specialties page of the Provider Details window. A specialty defines a specific area of medicine, such as cardiology, pediatrics, or oncology, that a provider supplies. On the Specialties page of the Providers subsystem, the user can view specialties associated with the selected Provider. Each specialty record includes a description, and the specialties are linked to caregivers. Management of provider specialties is carried out through the Specialties page of the Provider Details window.

Figure 94:
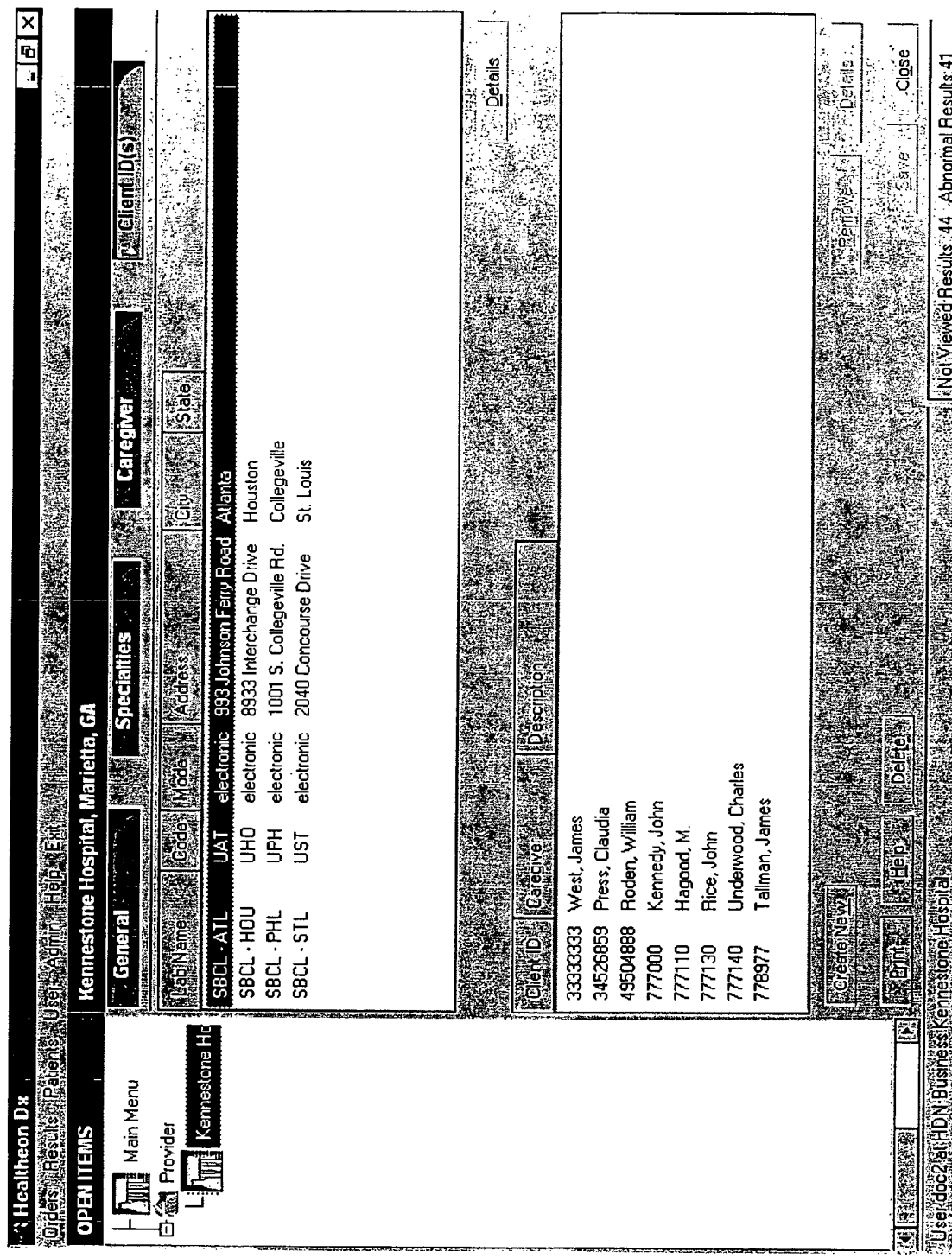

FIG. 94 illustrates the Client IDs page of the Provider Details window. The caregivers listed in the Client IDs page are a subset of those listed in the Caregiver page. The list of caregivers on the Client IDs page is based on the caregivers linked to the selected provider who have been assigned Client IDs by a particular lab. Generally these caregivers are physicians, but any caregiver type can be assigned a Client ID.

A caregiver must have a client ID when he or she submits a requisition to a laboratory. If the caregiver does not have a client ID, he or she uses the default client ID, which is assigned to the caregiver's HDN Business. The default client ID is typically used only when the ordering caregiver does not have a client ID.

Management of provider client identifiers is carried out through the Client IDs page of the Provider Details window. The Client ID page lists physicians, their client IDs, and the labs where they have IDs assigned.

Admin: Manage Security

Security administration involves setting up and maintaining security aspects of the system. Using the Manage Security submenu of the Admin menu, the user, i.e., an administrator, can control user access to confidential patient information stored on the network. For example, the security features may prevent a data record from being viewed or modified by unauthorized users.

Figure 95:
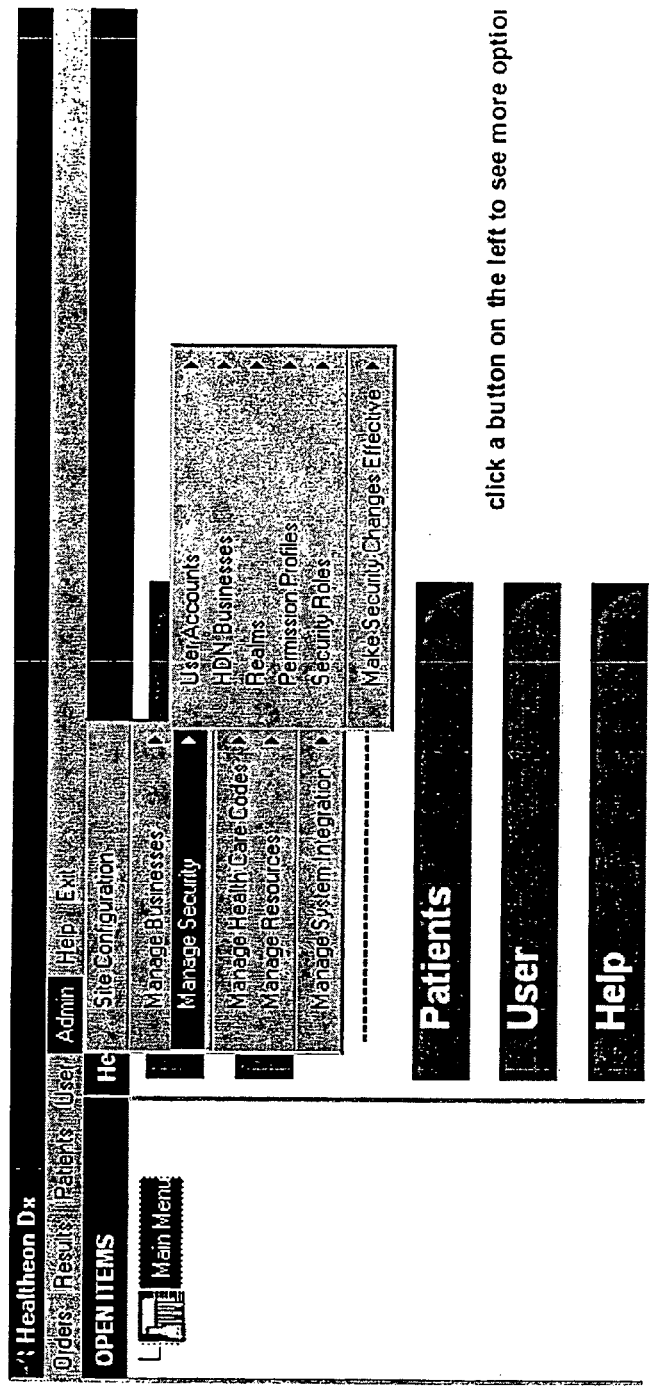

Security functions are accessed through the Manage Security submenu of the Admin menu, as shown in FIG. 95. The Manage Security menu option enables the user to manage key aspects of the system, such as shown in the following table:

| Key Aspect | Description |
| --- | --- |
| User Accounts | Information about the people associated with an HDN Business who access the system. |
| HDN Businesses | Businesses connected to the Health Data Network. |
| Realms | Collection of security roles and permission profiles. |
| Permission Profiles | General grants of access given by an owner to a user. |
| Security Roles | Groups of operations that are typically related to a specific function or position. |

After the user make changes to the security system, the user may update the users and realms through a Make Security Changes Effective menu option.

Security Checks—One important feature of the system is the secure exchange of information across a possibly very large and open network. To accomplish this, the system may check the following aspects of a user account before allowing the user to carry out a function:

| Security checks the . . . | Which is a . . . |
| --- | --- |
| Operation | Task that a user carries out on the data stored on the HDN. Operations may be global to the entire HDN. |
| Security Role | Collection of typically related operations. |
| Permission Profile | Set of parameters for selected roles as they apply to users of an HDN Business. |
| Realm | Collection of roles and permission profiles. |

Roles and Permissions—In the preferred embodiment, the security system is based on roles and permissions. These two concepts, combined with ownership, determine a user's authorization level, or the operations the user can carry out. A role is a group of operations that is typically related to a specific function or position. For example, various roles may be defined for physicians, nurses, office assistants, etc., or for any other function or position that a business desires. Roles limit transaction access to certain groups of users. For example, roles can be used to deny access to transactions related to clinical results except for people whose job requires that they have access. Only people with an approved need to know should be assigned roles that have search and read capabilities on patient information. The system users are classified and their permissions are assigned based on pre-defined security roles.

A permission profile is created from a role. The permission profile specifies the role's clearance level, effective date, expiration date, owner, and what realm it belongs to. A realm refers to a collection of roles and permission profiles. Usually the realm owns the permission profile, but it can also be owned by a user.

Admin: Manage Security: User Accounts

Users are people associated with one or more HDN (Health Data Network) Businesses who access the system, such as caregivers, physicians, staff members, and administrators. The User Accounts menu option of the Manage Security submenu may be used to manage information regarding the HDN Businesses a user is linked to and the permissions assigned to the user for a specific HDN Business.

Prior to adding users or modifying user information, an administrator may initialize the security system by creating a realm, business entity, roles, permissions, etc. Users may then be added and assigned to HDN Businesses with specific permissions. The User Accounts menu option enables access to the following information:

| Select this page... | To see... |
| --- | --- |
| General | User attributes and information used to verify the user's identity |
| HDN Business | Status, active or inactive, of the selected user for the HDN Businesses listed |
| Permissions | Permission profiles for roles assigned to the user |
| Site ID | Healtheon Practice site IDs assigned to the user |

Figure 96:
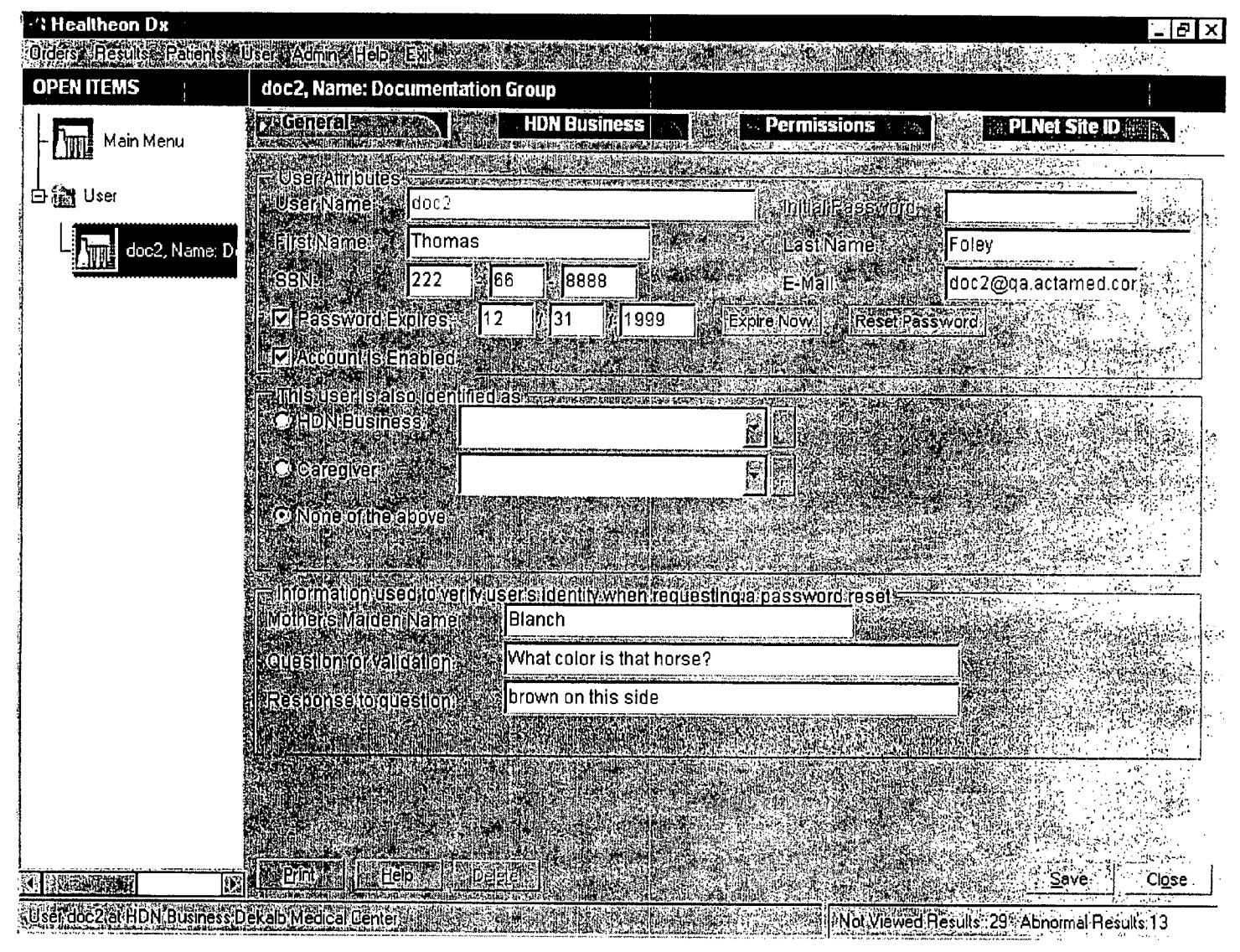

FIG. 96 illustrates the General page of the User Account Details window. The General page includes fields specifying general information regarding a user account.

Figure 97:
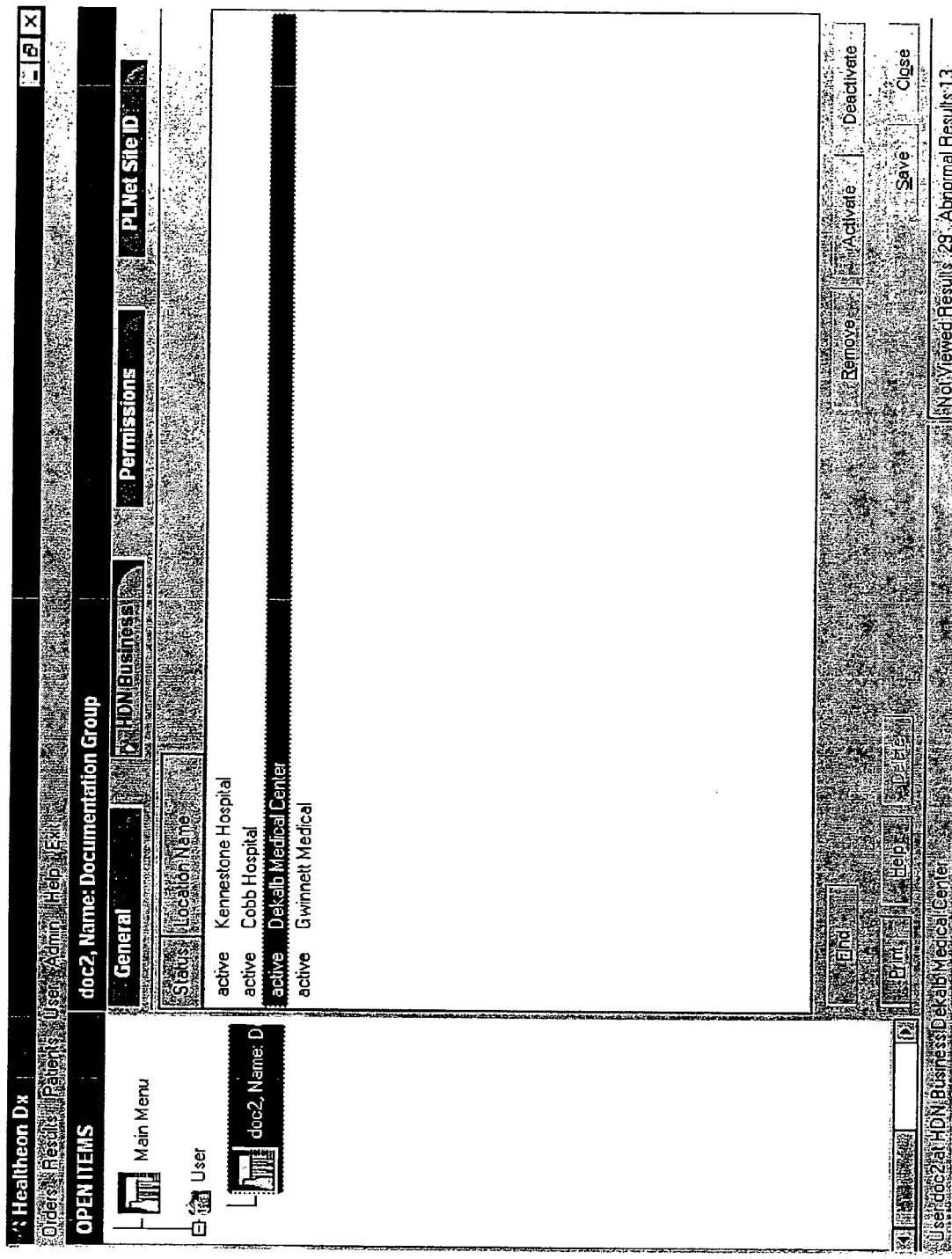

FIG. 97 illustrates the HDN Business page of the User Account Details window. HDN Businesses are associated with a user by clicking Add and then finding an HDN Business. The HDN Businesses page also shows the status (active or inactive) of the selected user for the HDN Businesses listed. To activate an inactive account, the user highlights the account and clicks Activate. To deactivate an active account, highlight the account and click Deactivate.

Figure 98:
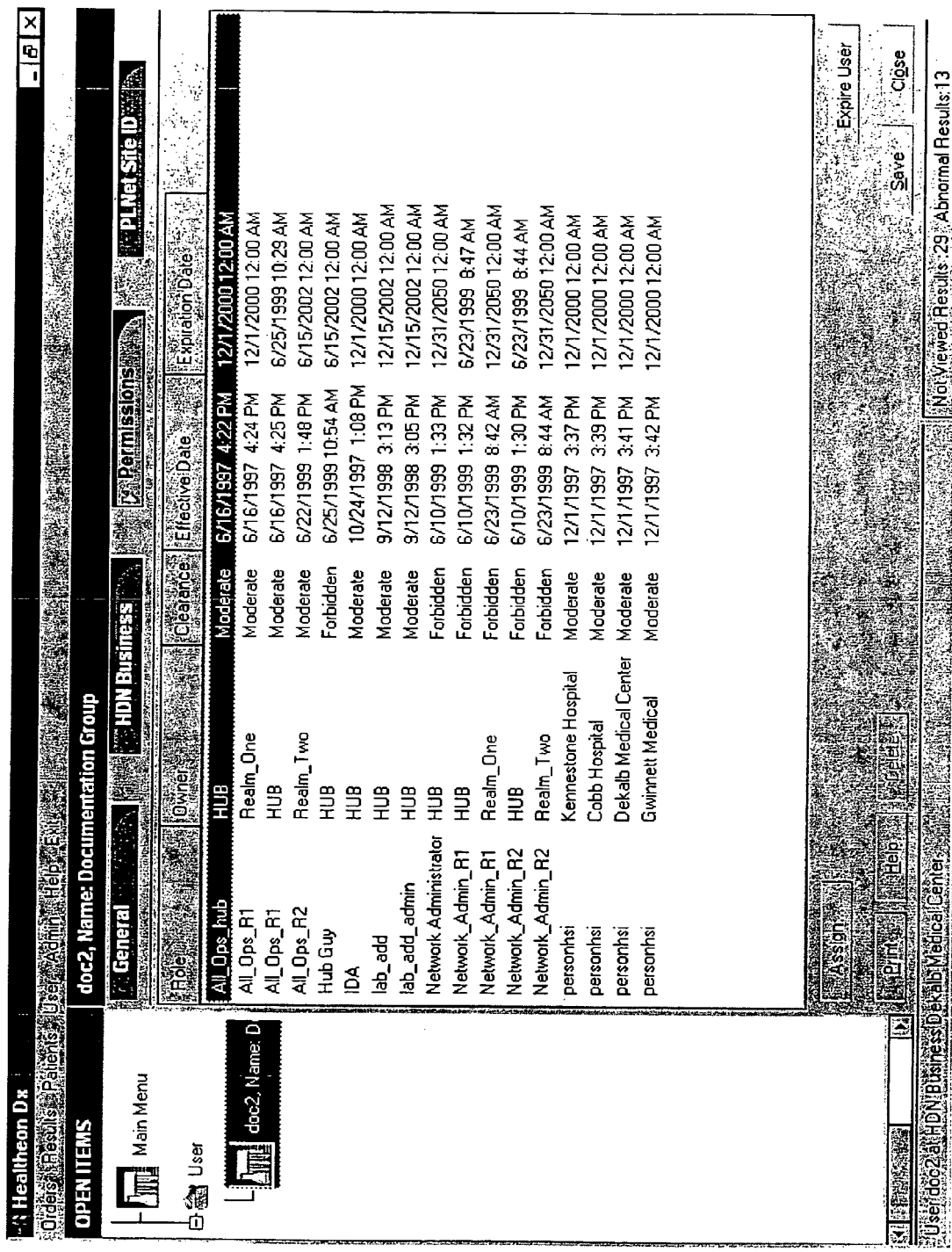

FIG. 98 illustrates the Permissions page of the User Account Details window. A permission is a general grant of access given by an owner to another user. A permission comprises an owner identifier, a user identifier, and a role identifier. Each permission may be mapped to a clearance level.

Permission profiles are assigned to users for a specific HDN Business. Users can have the same or different permission profiles with different HDN Businesses. The Permissions page shows the permission profiles for roles assigned to the selected user.

Figure 99:
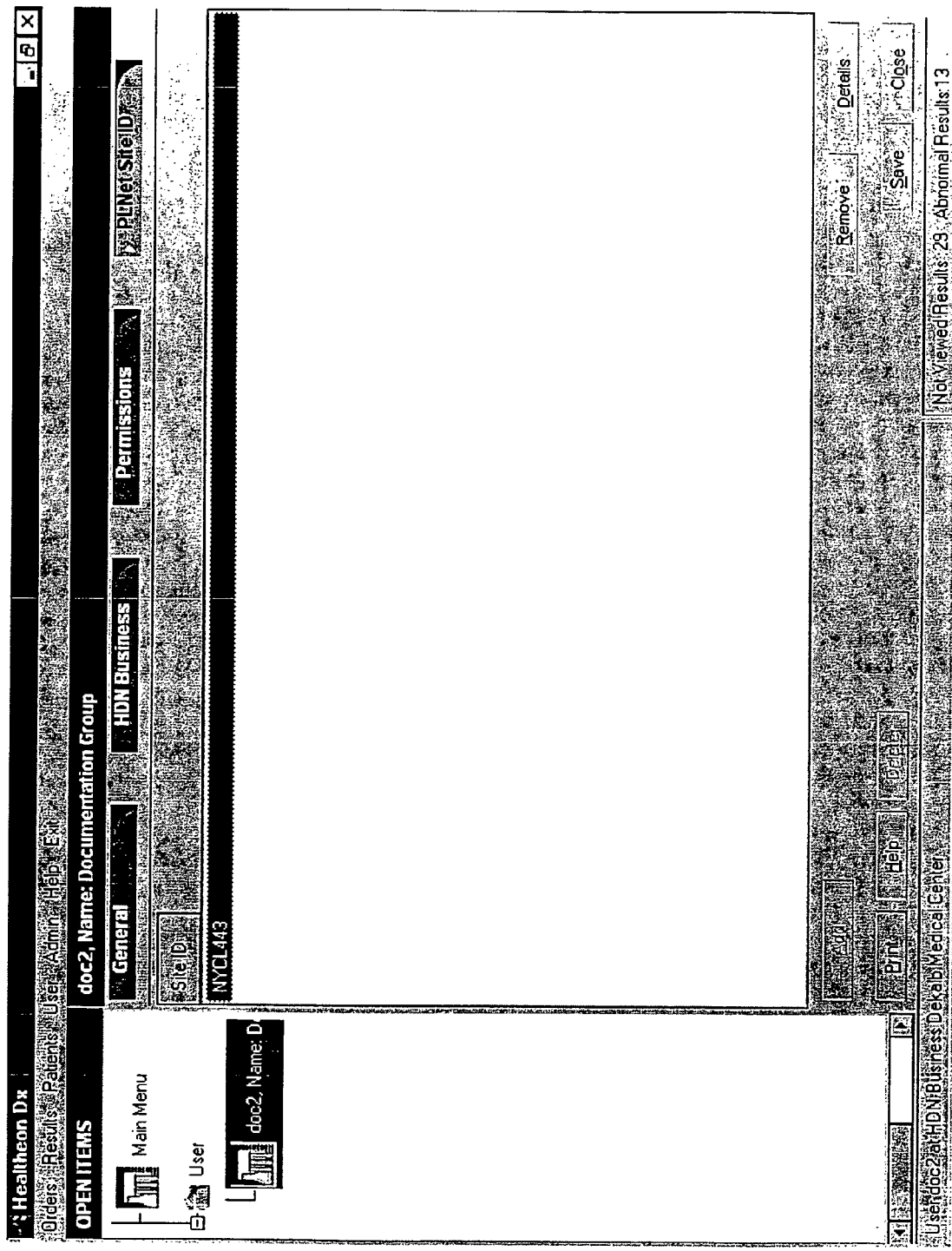

FIG. 99 illustrates the Site ID page of the User Account Details window. A Healtheon Practice site can be any health care entity, such as a caregiver, hospital department, or hospital. The site definition depends on the user's contractual agreement with Healtheon for using the Healtheon Practice system. The Site ID page contains a list of site IDs that the user can assign to the selected user. The user then has access to information at the specified Healtheon Practice site. The user set up the site IDs using the Site ID subsystem of the Manage System Integration option.

Admin: Manage Security: HDN Businesses

A Health Data Network (HDN) Business is any business connected to the Health Data Network. An HDN Business may or may not share data with other HDN Businesses. Using the HDN Businesses menu option of the Manage Security submenu, the information regarding the HDN Businesses in the Health Data Network may be managed. The HDN Business Details window provides access to the following information:

| Select this page... | To see... |
| --- | --- |
| General | Specifics where the business fits in the network |
| Contact | Entity representatives |
| Billing | Reference and tax identification |
| Users | Attributes and identity verification |
| Configuration | Network participation |

When a new HDN Business is created, it may be linked it to a Global Location. This is referred to as assigning a data slice to an HDN Business. There is a field on the HDN Business General page called Data Server. By selecting one of the data servers on the list the user link the HDN Business to a Global Location.

Figure 100:
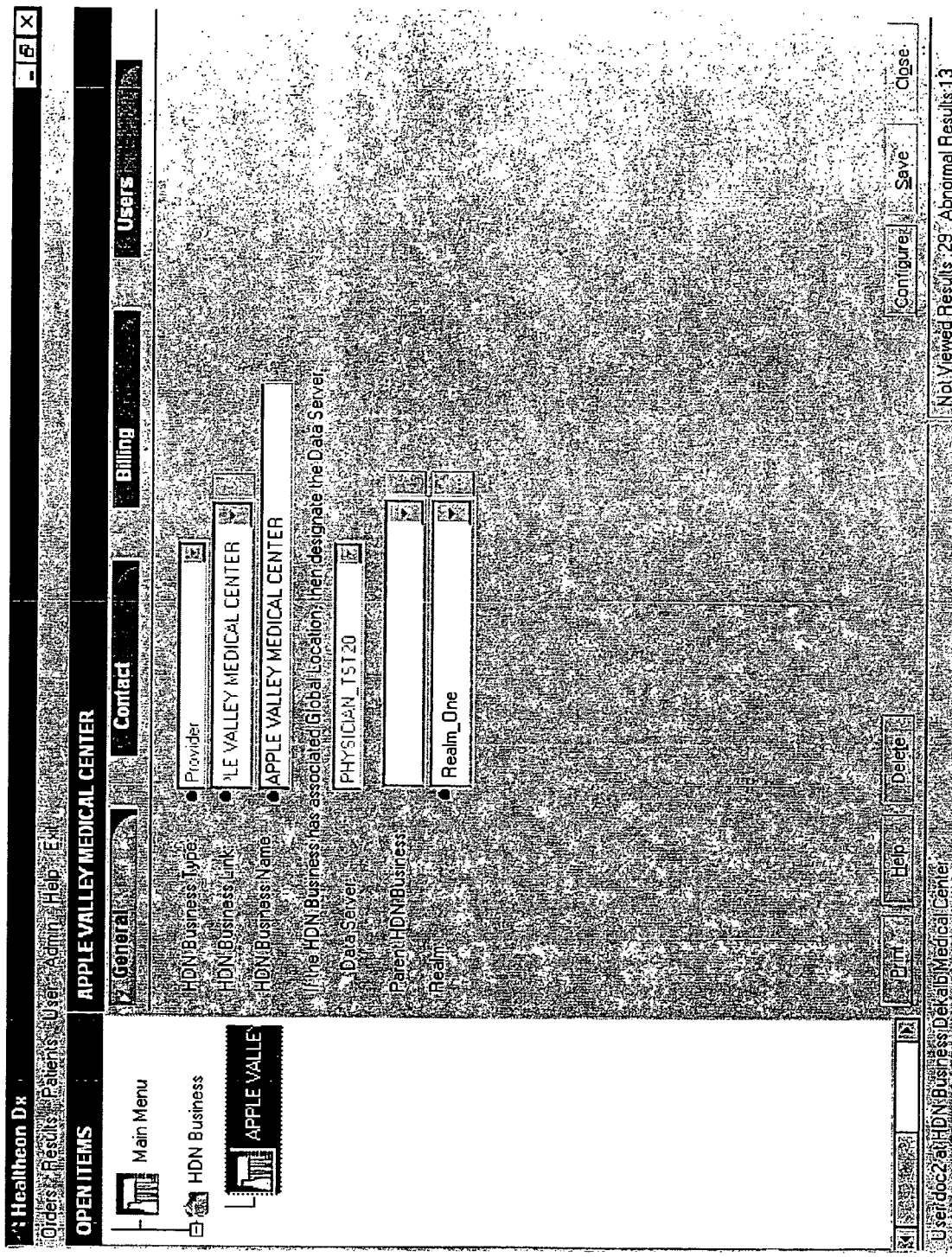

The following table explains the fields on the General page of the HDN Business Details window, shown in FIG. 100:

| Field Name | Definition |
| --- | --- |
| Data Server | The data server where the data for the HDN Business is stored. |
| HDN Business Link | The business that is linked to this HDN Business. The type of business is determined by the value in the HDN Business Type field. On windows and printouts that include an address, such as a Requisition, the address from the linked business is used. |
| HDN Business Name | The name of the HDN Business. |
| HDN Business Type | The type of HDN Business. The value in this field determines which business can be selected in the HDN Business Link field. |
| Parent HDN Business | The parent HDN Business for the HDN Business. |
| Realm | The realm the HDN Business belongs to. |

Other HDN Business pages include a Contact page, a Billing page, and a Users page.

Admin: Manage Security: Realms

A realm is a collection of roles and permission profiles. A user's access to the system is determined by roles and permissions. The purpose of a realm is to specify the roles and permission profiles associated with an HDN Business. Each realm may include one or more HDN Businesses that use the same set of roles and permission profiles. Although a realm can include several HDN Businesses, an HDN Business can be linked to only one realm. Multiple realms may exist, one of which may be the hub realm.

Through the Realms menu option of the Manage Security submenu, the user can maintain the list of HDN Businesses in a realm. In addition, the user can define the roles and permissions for the realm. The Realm menu option enables access to the following information:

| Select this page... | To see... |
| --- | --- |
| General | Realm name and description |
| HDN Businesses | HDN Businesses in the realm |
| Permission Profiles | Permission profiles associated with the realm |
| Roles | Roles associated with the realm |

-continued

| Select this page... | To see... |
|---|---|
| Users Online | Users currently online who have roles associated with a realm |

Figure 101:
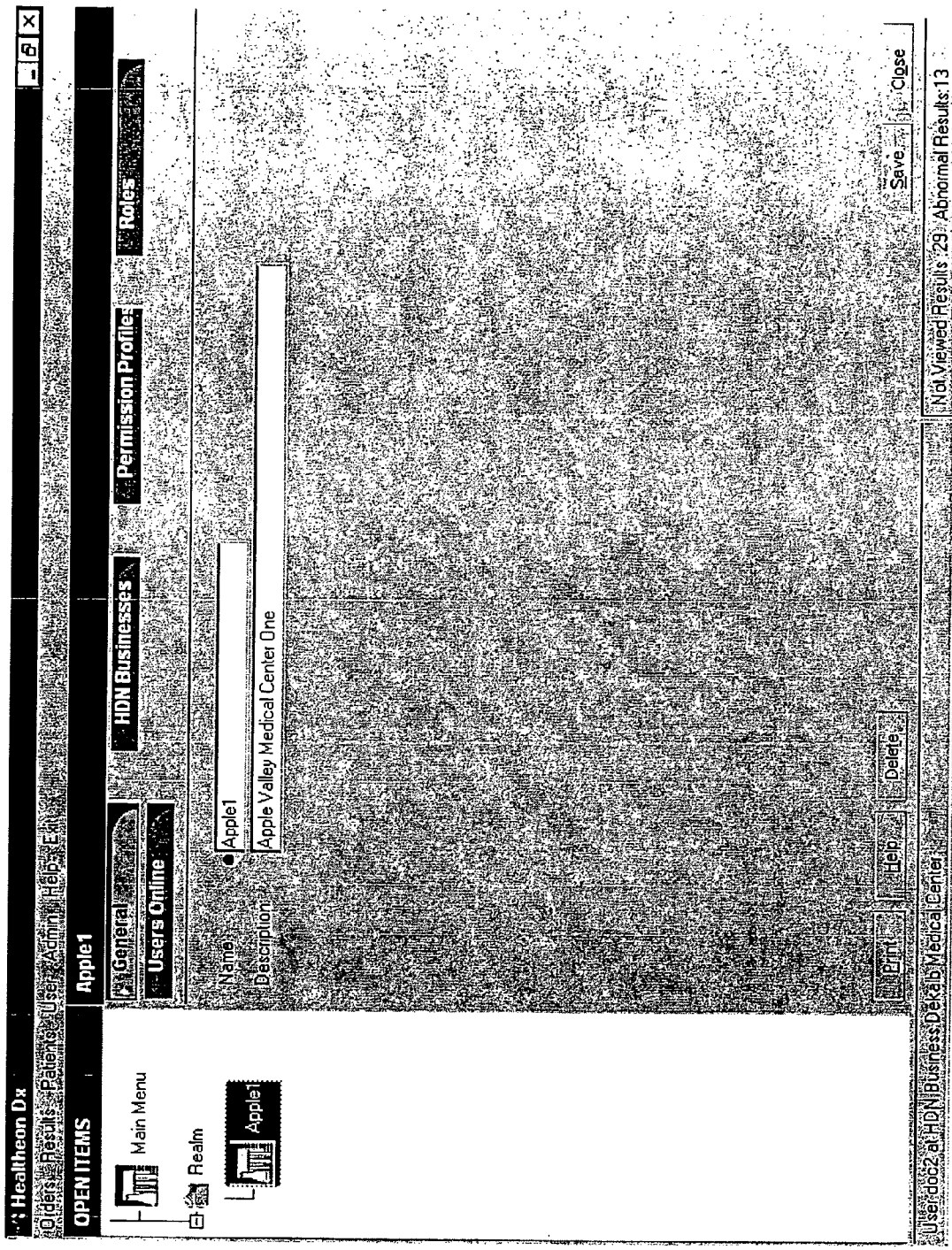

FIG. 101 illustrates the General page of the Realm Details window. The General page includes fields for entering a name and description for a realm.

Figure 102:
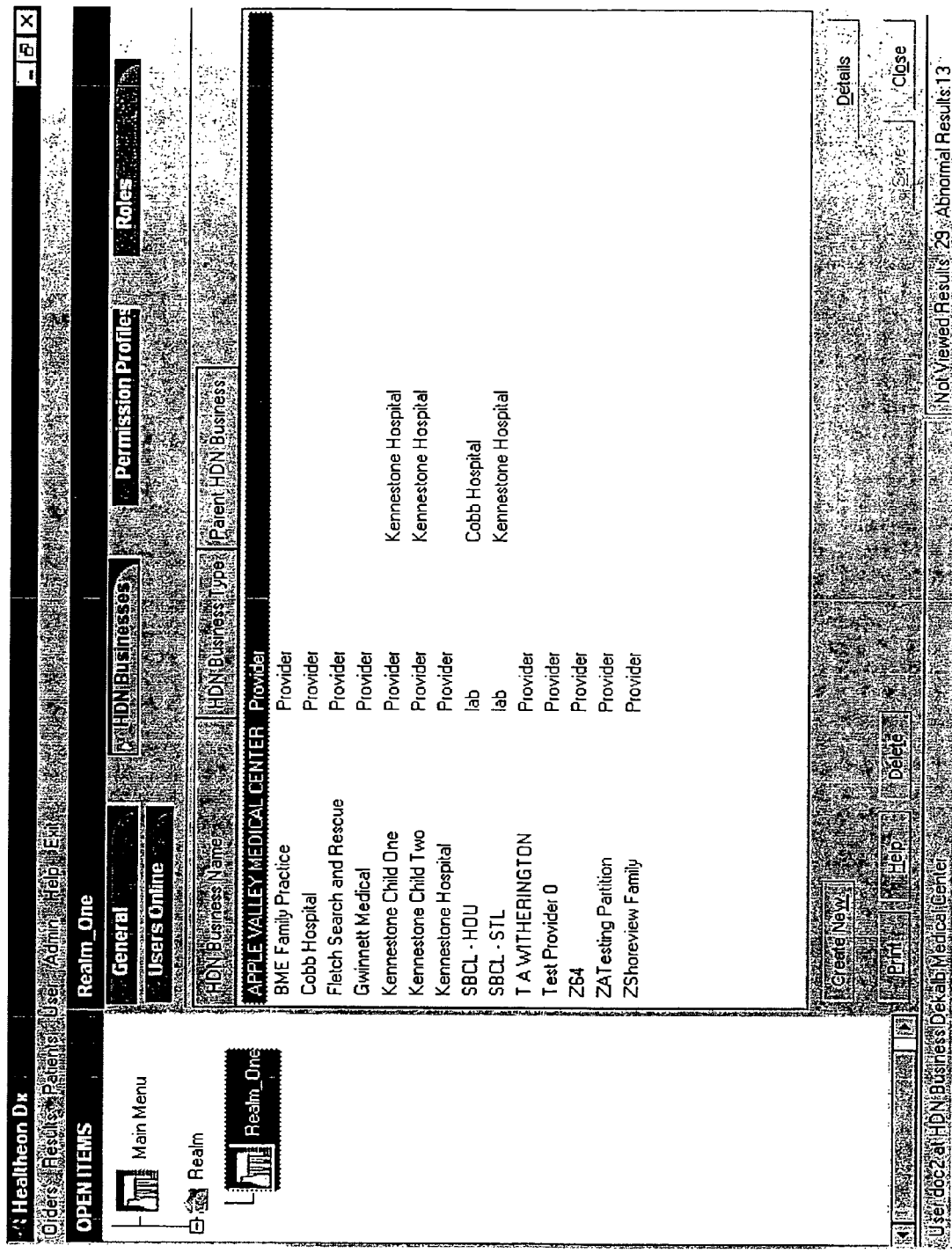
Figure 103:
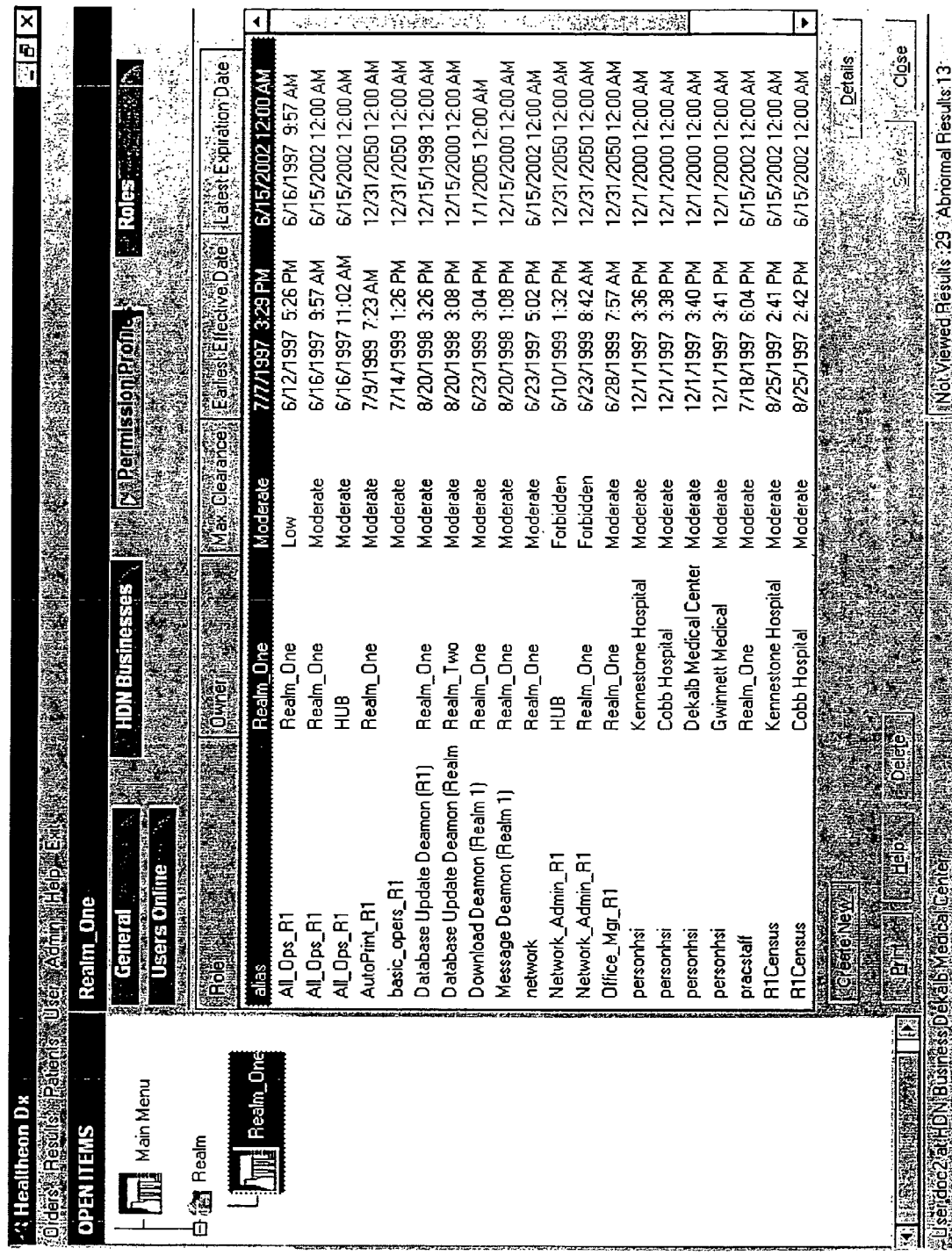
Figure 104:
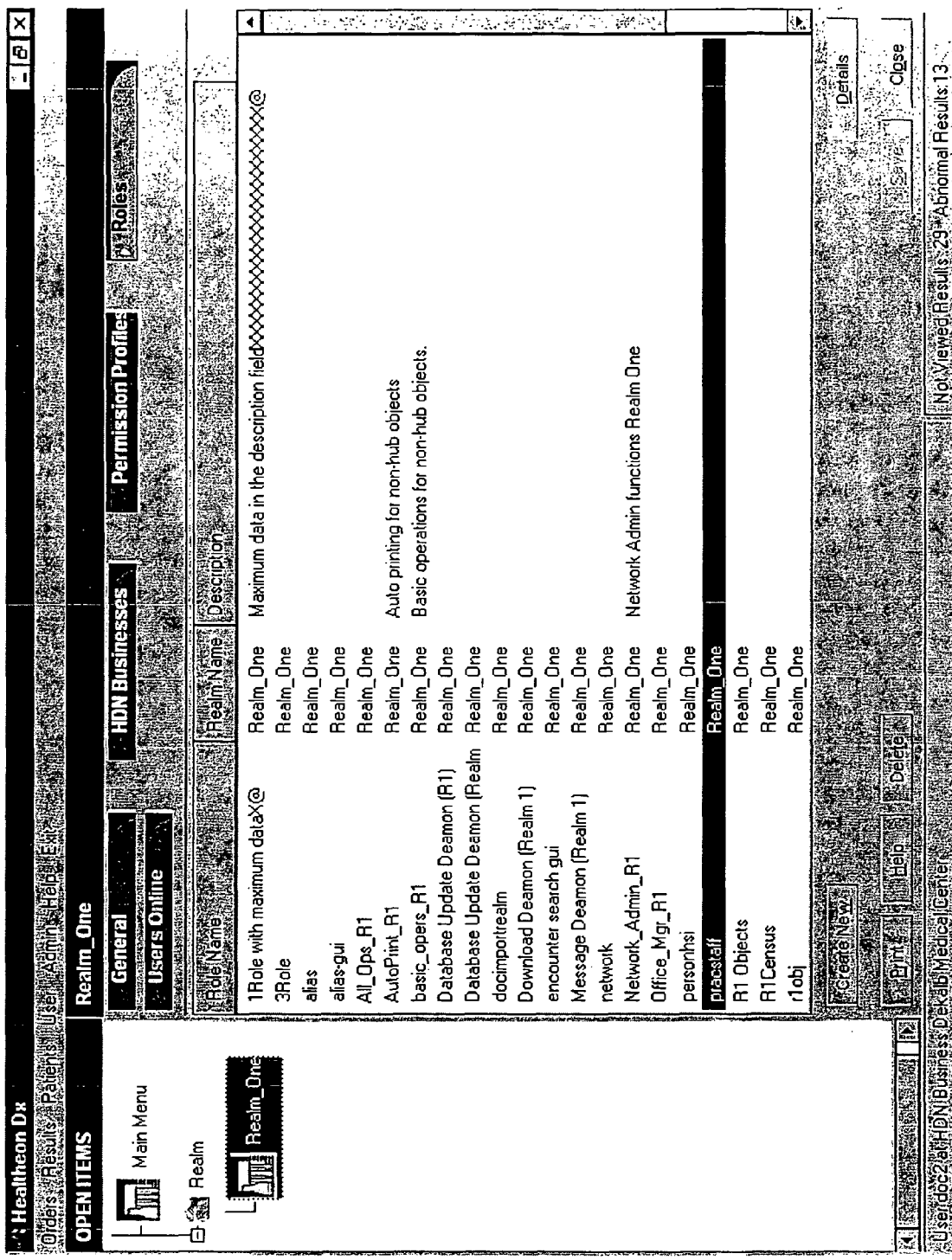

FIG. 102 illustrates the HDN Businesses page of the Realm Details window. The HDN Businesses page lists the HDN Businesses linked to the selected realm. If the HDN Business is a sub-business of another, the parent business entity is also listed. From this window, the user can carry out the following tasks:
  Create New HDN Businesses that are automatically associated with the active realm
  Get Details of an existing HDN Business the is associated with the active realm FIG. 103 illustrates the Permission Profiles page of the Realm Details window. The Permission Profiles lists the permission profiles associated with a realm. From this window, the user can carry out the following tasks:
  Create New permission profiles that are automatically associated with the active realm
  Get Details of an existing permission profile the is associated with the active realm FIG. 104 illustrates the Roles page of the Realm Details window. The Roles page lists the roles associated with a realm. From this window, the user can carry out the following tasks:
  Create New security roles that are automatically associated with the active realm
  Get Details of an existing security roles the is associated with the active realm The Users Online page of the Realms Details window lists the users currently online who have roles associated with the specified realm.

Admin: Manage Security: Permission Profiles

A permission is a general grant of access given by an owner to a user. Usually the realm owns the permission profile, but a user can also be an owner. In one embodiment, a permission comprises a role, an owner, a clearance level, an effective date, and an expiration date. Thus, when a permission profile is assigned to a user, information may be specified, such as the operation the user can perform, the level of clearance entailed, and a beginning and ending date between which the operations can be performed.

Figure 105:
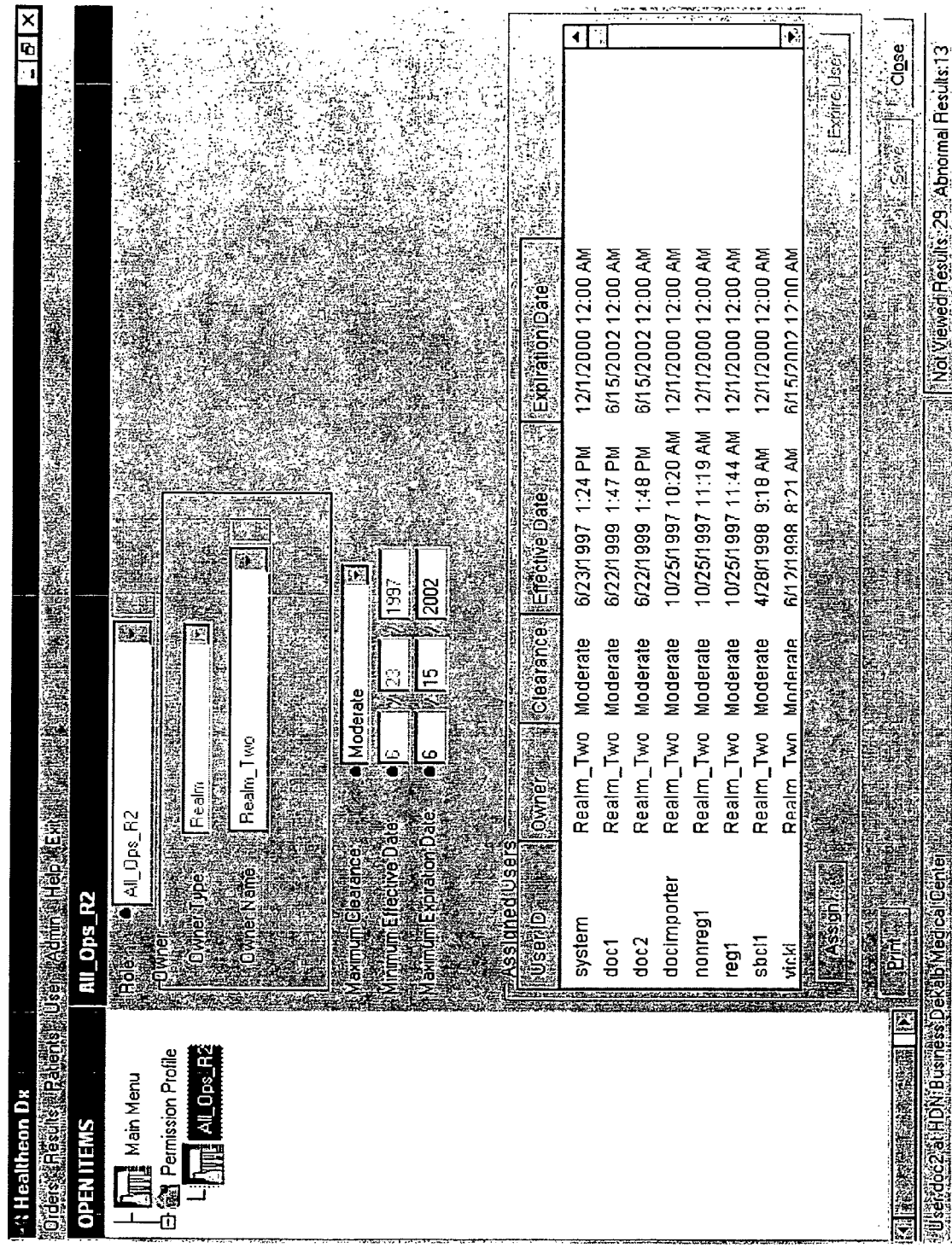

Through the Permission Profiles menu option of the Manage Security submenu, the user, e.g., an administrator, can create permission profiles. The user can then assign the permission profiles to selected users. FIG. 105 illustrates the Permission Profile Details window, which can be used to create or edit permission profiles. The following table describes the fields found on the Permission Profile Details window:

| Field Name | Description |
|---|---|
| Assigned Users | The users that this permission profile has been assigned to. |
| Effective Date | The date the permission profile becomes effective. |

-continued

| Field Name | Description |
|---|---|
| Expiration Date | The date the permission profile expires. |
| Maximum Clearance | The maximum clearance that can be assigned to users for this permission profile. |
| Owner Type | The type of owner for the permission profile. |
| Owner Name | The owner of the permission profile. |
| Realm Name | The realm for which the permission profile is created. |
| Role Name | The role for which the permission profile is defined. |

There are preferably no limitations on the number of permission profiles that can be assigned to users. In one embodiment, permission profiles are limited to one role each, and more than one permission profile may be assigned to a user who has several roles. Also, the same permission profile may be assigned to different users who perform the same role. For example, three different hospital registration clerks could share the same role that allows them to view and modify patient information.

The following procedure may be used to assign a permission to a user.
  1. On the Permission Profile Details window, the user clicks Assign. In response, the first window of the Assign Permission wizard appears.
  2. The user then selects a Clearance level from the drop-down list for the field and clicks Next. The second window of the Assign Permission wizard appears.
  3. The user enters the Effective Date and Expiration Date for the permission assignment and clicks Next. The third window of the Assign Permission wizard appears.
  4. From the list of users, the user selects one or more users to assign the permission profile to.
  5. The user clicks Finish. The system validates the assignment. If the assignment was successful, the Permission Granted dialog box appears. If the assignment was not successful, the Permission NOT Granted dialog box appears.

Admin: Manage Security: Security Roles

As descried above, a role comprises a group of operations that is typically related to a specific function or position. Roles limit transaction access to certain groups of users. For example, roles can be used to deny access to transactions related to clinical results except for people whose job requires that they have access to this information. Only people with an approved need to know should be assigned roles that have search and read capabilities on patient information.

When the user creates a role in the Security Roles subsystem, the user names the role and specifies its realm. The user then selects from a list of available user accounts that are linked to one or more operations. The user can add and remove the user accounts that are associated with the role. The user maintains existing security roles similarly.

Defined roles may be available for permission assignment by any and all realms in the network. Roles defined locally by a realm may be available for permission assignment on that realm only.

Figure 106:
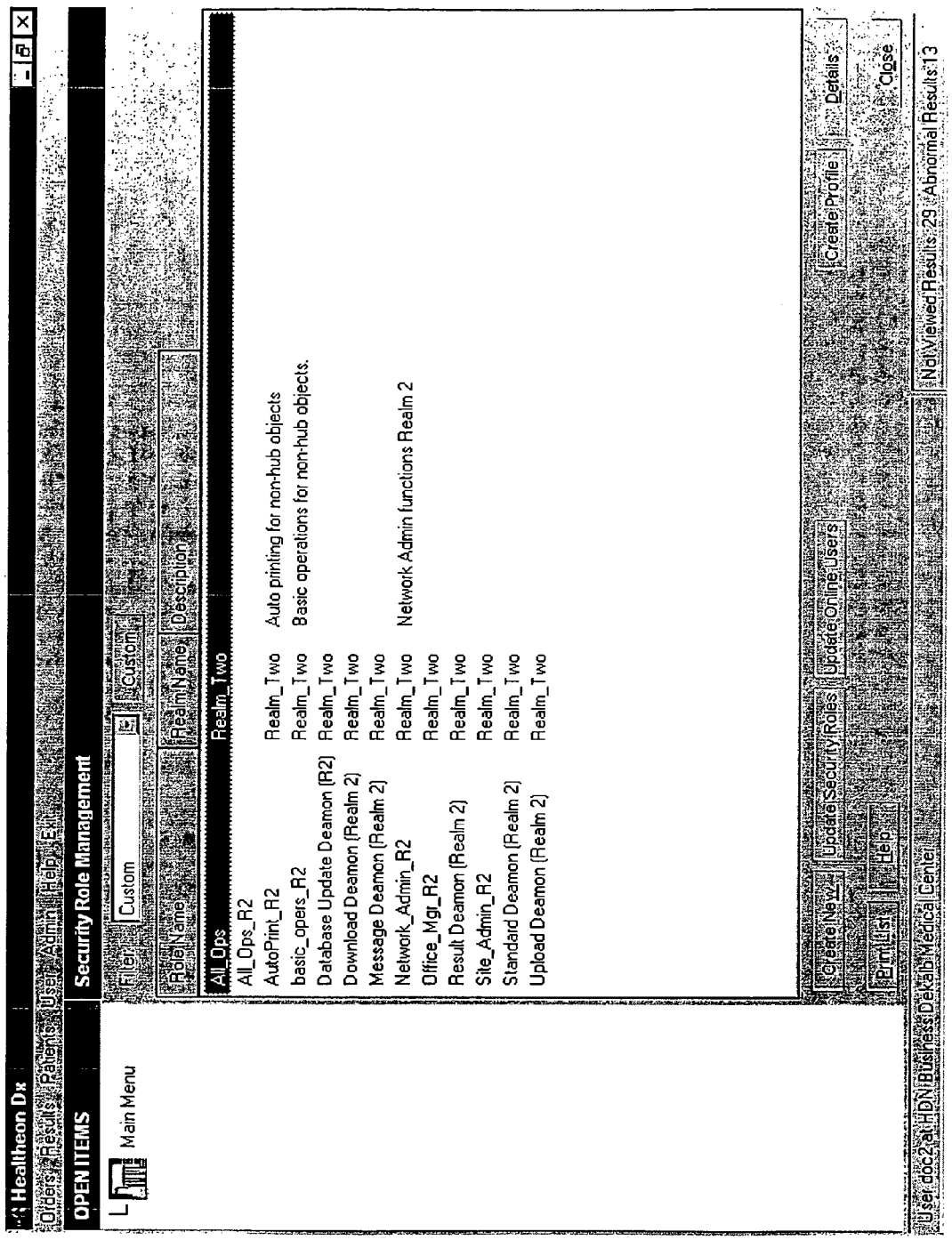
Figure 107:
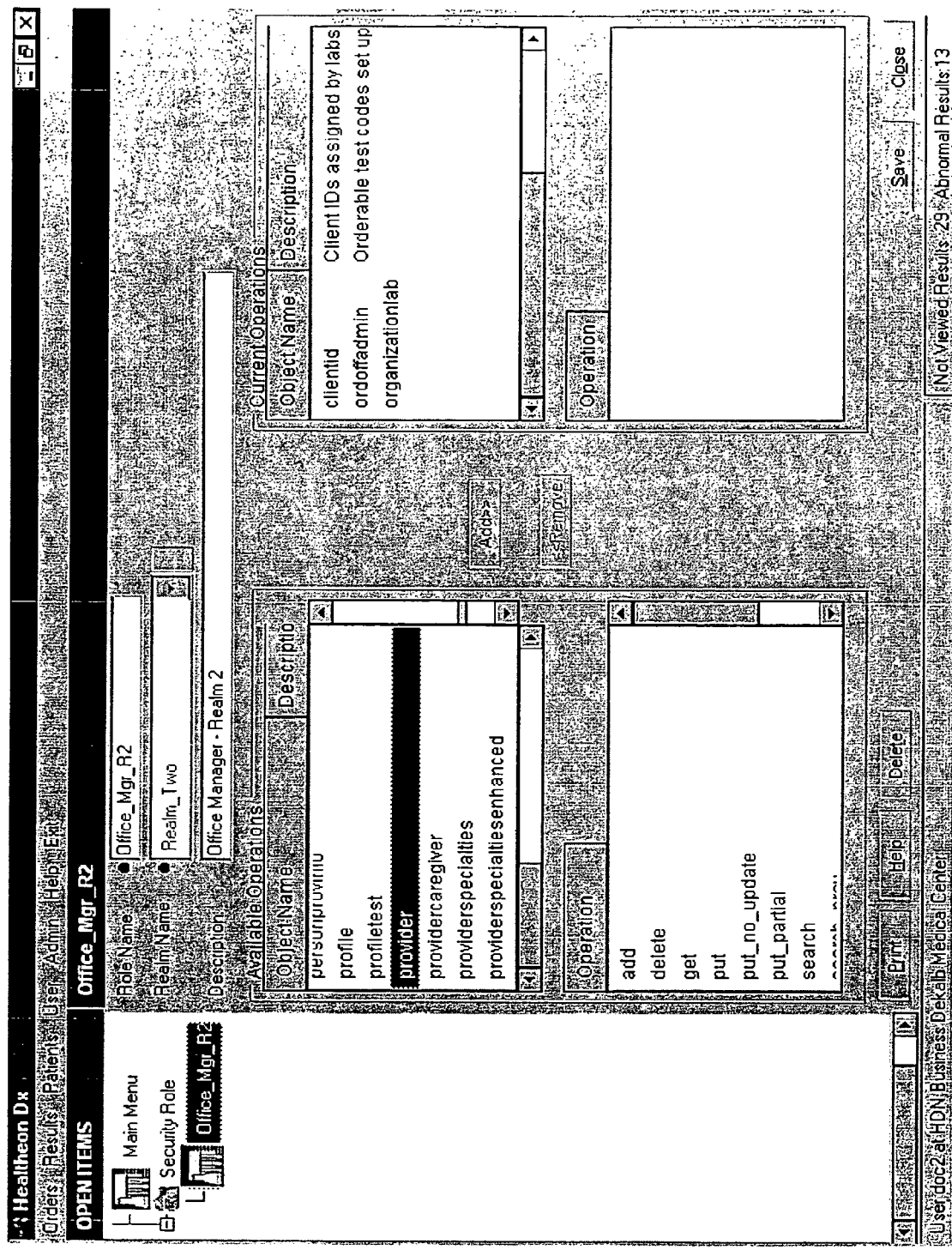

FIG. 106 illustrates the Security Role Management window. From this window the user can:
  filter the Security Role Management list
  print the Security Role Management list
  create a new security role
  display details of an existing security role
  create a permission profile for the highlighted security role
  update the security roles FIG. 107 illustrates the Security Role Details window for specifying or viewing details of a particular role. A security role comprises objects and the operations that can be carried out on those objects. The Security Role Details window has two panels, each with two lists. The top list in the left-hand panel displays all available objects. When the user clicks on an object, the list of operations that can be carried out on those objects appears in the list at the bottom of the panel. The top list in the right-hand panel displays all objects which have been assigned to the security role. When the user clicks on an object, the list of operations which can be carried out on that object that have been assigned to the security role appears on the list at the bottom of the panel.

To assign object-operations to a security role, the user clicks on an object in the Available panel and then selects the desired operations that users with this role should be able to carry out on that object. Clicking Add assigns the object-operations to the security role.

Admin: Manage Security: Make Security Changes Effective

Using the Make Security Changes Effective menu option of the Manage Security submenu, the user updates users and realms with changes that have been made to the security system, such as creating a new user or changing a user password. If this function is not performed, then the next time a user logs on to the system, the changes may occur anyway.

Admin: Manage Health Care Codes

Various sets of health care codes may be used throughout the system, as shown in the following list.
  CPT-4 codes
  ICD-9 codes
  Specialties
  Analyte codes
  Profile codes
  Report codes
  Test codes Code sets are accessed through the Manage Health Care Codes menu option of the Admin menu.

Analyte Codes—An analyte is the smallest unit or component for which a laboratory test is performed. A laboratory test may include multiple analytes. For example, a CBC (complete blood count) is a single test that includes multiple analytes. Analyte codes may be specific to a lab, and may be pre-loaded into the system. As updates become available, these may also be loaded into the system automatically, with no action required on the part of the user. Using the Analyte Codes function, the user can find and print codes. Analyte codes are used for viewing and reporting on results.

CPT4 Codes—Current Procedural Terminology version 4 (CPT-4) codes can be used by physicians to report the services that they provide to their patients. These codes are used for evaluation and management. Because CPT-4 codes have been universally adopted in the healthcare industry, they are not specific to any one lab. These codes may be pre-loaded into the system. As updates become available, these may also be loaded into the system automatically, with no action required on the part of the user. Using the CPT-4 Codes function, the user can find codes and print lists of codes.

Because the number of CPT-4 codes stored on the system may be very large, the user can create a list of preferred codes, i.e., those codes that the user frequently uses. This makes locating a CPT-4 code much easier and faster. When the user selects Preferred from the CPT-4 Code field control menu, the Preferred List of CPT-4 Codes appears with the user's list and the shared list combined. This allows the user to see the list of preferred CPT-4 codes for the entire HDN Business, as well as those that the user have added for the user's own use. Even if the user is a new user, the user still has a Preferred List of CPT-4 Codes that includes codes from the shared list.

ICD-9 Codes—International Classification of Diseases version 9 codes (ICD-9 coding) are used in clinical settings for reporting diagnoses and diseases to U.S. Public Health Service and Health Care Financing Administration programs. Because ICD-9 codes have been universally adopted in the healthcare industry, they are not specific to any one lab. These codes may be pre-loaded into the user's system. As updates become available, these may also be loaded into the system automatically, with no action required on the part of the user. ICD-9 diagnosis codes are used by functions accessed via the Orders subsystem, which includes utilities for preparing and submitting requisitions.

Using the ICD-9 Codes function, the user can find codes and print lists of codes. To simplify locating codes, the system differentiates between diagnosis and procedure codes. The list of ICD-9 codes on which to search is determined by the requirements of the field or list from which the search was initiated. Because the number of ICD-9 codes stored on the user's system may be very large, the user can create lists of preferred diagnosis and procedure codes, i.e., those codes that the user frequently uses. This makes locating an ICD-9 code much easier and faster.

Profile codes—Profile codes are used for both requisitions and for results. In requisitions, a lab profile includes multiple individual tests, which can be ordered collectively as a profile or individually as needed. In results, a lab profile includes multiple report codes and may include a panel, i.e., multiple tests that have the same report code. Profile codes may be specific to a lab, and may be pre-loaded into the system. As updates become available, these may also loaded into the system automatically, with no action required on the part of the user. Using the Profile Codes function, the user can find codes and print lists of codes. Profile codes are used by both functions accessed from the Orders menu and functions accessed from the Results menu.

Report Codes—A report code identifies the results of a laboratory clinical test. It differs from an order code in that an order code is the test code used to send an order, and a report code is the code used to return results. A collective set of multiple report codes is referred to as a lab profile. Report codes may be specific to a lab, and may be pre-loaded into the system. As updates become available, these may also loaded into the system automatically, with no action required on the part of the user. Using the Report Codes function, the user can find codes and print lists of codes. Report codes are used by the functions accessed via the Results menu for viewing and reporting on results.

Specialty List—Specialties define the specific area of medicine or focused approach to health care that a provider or caregiver supplies. Using the Specialty List function, the user may create the specialties that are used throughout the system. Once created, these specialties can then be linked to provider and caregiver records.

Test Codes—A test code is used to specify what tests need to be performed. Test codes may be specific to a lab and may be loaded into the system based on the transmission mode configuration of the lab. If the lab accepts requisitions electronically, the test codes may be pre-loaded into the system. As updates become available, these may also loaded into the system automatically, with no action required on the part of the user. If the lab only accepts requisitions manually, the test codes can be pre-loaded into the system and/or added through the user interface. Using the Test Codes function, the user can carry out the following functions regardless of the transmission mode configuration for the lab: Finding codes; and Printing lists of codes. Because the number of test codes stored on the system may be very large, the user can create a list of preferred codes, i.e., those codes that the user frequently uses. This makes locating a test code much easier and faster.

Admin: Manage Resources

As used herein, resources refer to the manpower, money, facilities, equipment, and supplies used to deliver healthcare services. Using the Manage Resources submenu of the Admin menu, the user can add, remove, and modify these resources as appropriate.

Admin: Manage Resources: Caregivers

A caregiver is a person who provides health care services to a patient. For example, physicians, nurses, technicians, and physician's assistants are all caregivers. Using the Caregiver menu option of the Manage Resources submenu, the user can view the caregivers associated with the HDN Business the user is logged on to. The user can search for a caregiver by identifier or the user can perform a general search. The user can also maintain information regarding the caregivers the user does business with. This includes:

Creating new caregivers
Maintaining information on existing caregivers
Deleting existing caregivers
Printing lists of caregivers Admin: Manage System Integration System Integration refers to a group of settings that affect certain aspects of the system. These settings fall within four main categories that the user can manage using the corresponding menu options in the Manage System Integration submenu:

| System Aspect | Menu Options |
| --- | --- |
| Code Sets | Local Codes |
| | Global Codes |
| | Code Translations |
| System Identifiers | HDN Business-Specific Identifier Types |
| | Site IDs |
| Document Storage | Document Routing Configuration |
| | Documentation Distribution Lists |
| Network Configuration | Network Configuration |

From the Manage System Integration submenu, the user can define and maintain the codes, identifiers, and rules related to these four areas.

Code Sets

The user may define and maintain the user's own code sets, such as groups of values or symbols used to represent information such as a patient's employment status, religion, marital status, etc. These values usually appear in drop-down lists from which the user makes a selection. To handle the code sets, the system may be operable to map and translate global and local codes. Global codes refer to user-defined codes that are used uniformly across the entire network (hub). Local codes refer to user-defined codes that are specific to a certain HDN Business.

Code Translation

The Code Translation function provides a mechanism for translating codes between different HDN Businesses. Using the Code Translation function, the user can map system codes to HDN Business codes. The purpose of code translations is to support network participants having different sets of valid values for the same field and to provide a mapping from one participant's representation to that of another participant's representation.

For example, suppose that two hospitals, A and B, are participants in the same network. Hospital A has three Patient Type codes: IN for inpatient, OU for outpatient, and OT for other. Hospital B has four Patient Type codes: I for inpatient, O for outpatient, E for emergency, and B for Obstetrics. Through the Code Translation function, both participants can maintain their existing coding systems. The system automatically translates and converts codes when data is shared between participants. Code translation lets a participant receive data from another participant and view that data in their own native domain set using their own coding systems, regardless of who owns the data.

The idea behind code translations is to provide for each code type, such as relationship code type and religion code type, a set of:

The system codes
HDN Business codes (if a network participant wants their own set)
Mappings for inbound and outbound translation The Code Translations menu option provides access to the following information:

| Select this page... | To see... |
| --- | --- |
| General | Inbound and outbound translations for the code type that the user select |
| The system Codes | Set of The system codes for the code type that the user select |
| HDN Business Codes | Set of HDN Business codes for the code type that the user select |

The General page of the Code Translations subsystem lists inbound and outbound code translations. Inbound and outbound translations differ based on whether the code is being translated from a system source or HDN Business source. The following table describes these two types of code translation:

| Code Translation | Definition |
| --- | --- |
| Inbound | Mappings from HDN Business codes to system codes |
| Outbound | Mappings from system codes to HDN Business codes |

Each system code may map to exactly one code in each defined HDN Business code set. This makes outbound translation possible. Each HDN Business code may be mapped to exactly one system code value. This makes inbound translation possible. The system set of codes within a code set may include a superset of all possible code descriptions that might be used by any HDN Business set in the network.

The System Codes page of the Code Translations subsystem lists the set of system codes for the code type that the user selects, such as MS for marital status. The system codes then appear in the Outbound section on the General page. For example, the system marital status codes appear on the System Codes page after the user selects MS as the code type. If the user clicks the General page button to see the General page, the system marital status code set appears in the Outbound section of the General page.

The HDN Business Codes page of the Code Translations subsystem lists the set of HDN Business codes for the code type that the user select, such as MS for marital status. The HDN Business codes then appear in the Inbound section on the General page. For example, the system marital status codes appear on the HDN Business page after the user selects MS as the code type. If the user clicks the General page button to see the General page, the HDN Business-specific marital status code set appears in the Inbound section of the General page.

System Identifiers

A system identifier is a string of characters used as a label, such as BAN for Billing Account Number. There are two categories of system identifiers: Caregiver and Patient. The Registration flag is used by the identifier labels Insurance Code and Patient Account. Each HDN Business may define one registration label for each type (Caregiver, Patient or Payer). For example the registration label for Payer type may be Insurance Code and the registration label for Patient Type may be Patient Account. Because identifiers are categorized, only the patient identifiers appear in the Patient subsystem. These categories are used to store IDs originating from external systems such as Practice Management Systems. These identifiers help distinguish between the various types of account numbers. Identifiers might also be used to distinguish between types of payer account numbers or types of caregiver certificate numbers.

Document Storage

Medical personnel and related administrative staff receive many reports and other documents in paper form. Often, these are generated electronically by various systems, then printed and distributed by a manual delivery method. In the preferred embodiment, the system allows its participants to automatically receive electronic images of printed documents that would otherwise have to be received through interoffice mail, fax, US Mail, or some other physical delivery method. The Document Routing Configuration subsystem allows the user to manage and configure the receipt and distribution of documents.

Routing and Distribution—Routing allows the user to map a document recipient to a user. A document's routing specifies its first point of entry into the system. Distribution defines which users should receive the document in addition to the first recipient. For example, a document, such as a patient's insurance statement, might be addressed to a physician, but the document should also go to the claims administrator working in his or her practice. Thus, the document should be routed to the claims administrator. The claims administrator might need to distribute or forward the insurance statement to several clerks. Thus, the document should be routed to the specific clerks.

Document Routing

Routing allows the user to specify a recipient for a document. A routing configuration is the "path" the user wants a document to take from its source to a destination. Through the Document Routing Configuration menu option of the Manage System Integration submenu, the user sets up the rules that determine how and to whom documents are routed. Documents routed by these rules may then be accessed through the View Documents menu option of the User menu. The user can select the Document Routing Configuration menu option to access the following information:

| Select this page . . . | To see . . . |
| --- | --- |
| Routing | Rules for routing the user's documents |
| Sources | Client sources from which the user receives documents |
| Types | Type of documents that the user receive |

Using the Routing page, the user creates the rules for routing the user's documents. The user can set up two types of routing rules: General Routing Rules and Document-Specific Routing Rules.

General routing rules are for documents from a specific source that are to be sent to a single person. For example, if all incoming electronic clinical results documents from an SBCL lab in St. Louis are to be sent to a lab tech in the user's office regardless of to whom the results are addressed, the user can set up a rule that automatically routes documents of that category from the specific source to that person. This is a general routing rule. The user creates general routing rules for a source by selecting a pre-defined category of documents, entering an addressee, and then selecting a user to whom electronic documents of the selected category that are addressed to the addressee are routed.

Document-specific routing rules are for specific types of documents that are to be sent to a single person. For example, if all incoming electronic radiology documents are to be sent to the radiologist in the user's office regardless of to whom the results are addressed, the user can set up a rule that automatically routes documents of that type to that person. This is a document-specific routing rule. The user creates document-specific routing rules for a source by selecting a document type, entering an addressee, and then selecting a user to whom electronic documents of the selected type that are addressed to the addressee are routed.

When the user sets up document routing rules, the user first specifies the source of the document. The Sources page is used to define these sources. The Sources page lists the name and description of each source.

When the user creates document-specific routing rules, the user selects a document type. The Types page is used to define document types. Each document type falls in a system-defined category. The following table lists common document types and their categories:

| Category | Document Type |
| --- | --- |
| Administrative | Patient history |
|  | Patient demographics |
| Clinical | Radiology Diagnosis |
|  | Patient Evaluation |
| Financial | Payments From Patient |
|  | Billing |

Document Distribution Lists

A document distribution is like a document routing in that it uses rules to automatically distribute electronic documents that have been routed to a specific user. Documents distributed by these rules are then accessed through the View Documents function of the User menu. However, unlike a routing, which only allows the user to automatically send a document to a single user, document distribution allows the user to create a list of users to whom a single document is sent.

The Document Distribution Lists function allows the user to create general distribution rules for a "routed to user" by selecting a system-defined category of documents and then selecting users to whom electronic documents of the selected category are distributed. The user can also create document-specific distribution rules for a "routed to user" by selecting a document type and then selecting users to whom electronic documents of the selected type are distributed.

Although the embodiments above have been described in considerable detail, numerous variations and modifications will become apparent to those skilled in the art once the above disclosure is fully appreciated. It is intended that the following claims be interpreted to embrace all such variations and modifications.

We claim:

1. A computer-implemented method comprising:

receiving information about a patient record;

in response to receiving the information about the patient record, performing a search through one or more databases of records for one or more matching records that match the patient record;

for each of the one or more matching records that are found through the search, creating an unconfirmed link between that matching record and the patient record; and in response to input from a user regarding a selected record that is from the group consisting of said patient record and the one or more matching records, converting the unconfirmed link for the selected record to a directional confirmed link identifying which of the selected record and the linked record identified by the unconfirmed link for the selected record is a leader record, wherein the leader record among two linked records is the record among the two linked records that is at least one of most current, most correct, and most proper, wherein receiving information, performing the search, creating unconfirmed links, and converting unconfirmed links is performed by a computer system.

2. The method of claim 1, wherein the information about the patient record is information that is to be stored in a new patient record.

3. The method of claim 1, wherein performing the search through one or more databases for one or more matching records that match the patient record is based on real world primary key information.

4. The method of claim 1, further comprising:

receiving search criteria from the user;

performing a search for records that match to the search criteria;

displaying a list of records that match the search criteria;

receiving user input choosing one of the records from the list of records, wherein the chosen record is said selected record; and receiving user input specifying confirmation information for the unconfirmed link of the selected record.

5. The method of claim 4, further comprising in response to receiving further input at a later time changing the directional confirmed link to a certified link.

6. The method of claim 1, wherein performing the search through one or more databases of records comprises using real world primary key information from the patient record to identify the one or more matching records.

7. The method of claim 6, wherein the real world primary key information includes any of a first name, a last name, a social security number, a gender, and a date of birth for a patient.

8. The method of claim 1, wherein receiving information about a patient record involves receiving information for creating a new record for a patient.

9. The method of claim 1, wherein the record among the two linked records to which the leader record is linked is a trailer and wherein converting the unconfirmed link to a directional confirmed link comprises modifying the leader record based on information in the trailer record.

* * * * *